United States Patent [19]
Pedersen et al.

[11] Patent Number: 5,998,353
[45] Date of Patent: Dec. 7, 1999

[54] LACCASE MUTANTS

[75] Inventors: Anders Hjelholt Pedersen, Lyngby; Allan Svendsen, Birkerød; Palle Schneider, Ballerup; Grethe Rasmussen, Farum; Joel Cherry, Hellerup, all of Denmark

[73] Assignee: Novo Nordisk A/S, Baqsraerd, Denmark

[21] Appl. No.: 08/993,318

[22] Filed: Dec. 18, 1997

Related U.S. Application Data

[60] Provisional application No. 60/035,413, Jan. 23, 1997.

[30] Foreign Application Priority Data

Dec. 19, 1996 [DK] Denmark ................................. 1449/96
Sep. 8, 1997 [DK] Denmark ................................. 1021/97

[51] Int. Cl.$^6$ ............................... C11D 3/48; C11D 7/42; C12N 9/02
[52] U.S. Cl. ............................................ 510/392; 435/189
[58] Field of Search ............................... 435/189; 510/392

[56] References Cited

U.S. PATENT DOCUMENTS 5,480,801 1/1996 Wahleithner et al. ................ 435/254.3

FOREIGN PATENT DOCUMENTS

| WO 92/01046 | 1/1992 | WIPO . |
| WO 95/07988 | 3/1995 | WIPO . |
| WO 95/33836 | 12/1995 | WIPO . |
| WO 95/33837 | 12/1995 | WIPO . |
| WO 96/00290 | 1/1996 | WIPO . |
| WO 96/06930 | 3/1996 | WIPO . |
| WO 96/23874 | 8/1996 | WIPO . |

OTHER PUBLICATIONS

Kojima et al., Cloning, Sequence Analysis, and Expression of Ligninolytic Phenoloxidase Genes of the White–rot Basidiomycete Coriolus hirsutus, J. Biol. Chem., vol. 265, No. 25, Sep. 5, 1990, pp. 15224–15230.

Fems Microbiology Letters, vol. 132, 1995, Soon–ja Kim et al., "Characteristics of a Laccase Over–Secreting Mutant of Coprinus Congregatus", pp. 177–179.

Biochimica et Biophysica Acta, vol. 1292, 1996, Feng Xu et al., "A Study of a Series of Recombinant Fungal Laccases and Bilirubin Oxidase . . . ", p. 303, p. 311, p. 310.

*Primary Examiner*—Robert A. Wax
*Attorney, Agent, or Firm*—Steve T. Zelson; Reza Green

[57] ABSTRACT

The present invention relates to a method of designing laccase mutants with improved stability properties, which method is based on the hitherto unknown three-dimensional structure of *Coprinus cinereus* laccase.

5 Claims, No Drawings

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 539 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

```
Met Phe Lys Asn Leu Leu Ser Phe Ala Leu Leu Ala Ile Ser Val Ala
 1               5                  10                  15

Asn Ala Gln Ile Val Asn Ser Val Asp Thr Met Thr Leu Thr Asn Ala
            20                  25                  30

Asn Val Ser Pro Asp Gly Phe Thr Arg Ala Gly Ile Leu Val Asn Gly
        35                  40                  45

Val His Gly Pro Leu Ile Arg Gly Gly Lys Asn Asp Phe Glu Leu
    50                  55                  60

Asn Val Val Asn Asp Leu Asp Asn Pro Thr Met Leu Arg Pro Thr Ser
65                  70                  75                  80
```

```
Ile His Trp His Gly Leu Phe Gln Arg Gly Thr Asn Trp Ala Asp Gly
             85                  90                  95

Ala Asp Gly Val Asn Gln Cys Pro Ile Ser Pro Gly His Ala Phe Leu
            100                 105                 110

Tyr Lys Phe Thr Pro Ala Gly His Ala Gly Thr Phe Trp Tyr His Ser
            115                 120                 125

His Phe Gly Thr Gln Tyr Cys Asp Gly Leu Arg Gly Pro Met Val Ile
            130                 135                 140

Tyr Asp Asp Asn Asp Pro His Ala Ala Leu Tyr Asp Glu Asp Asp Glu
145                 150                 155                 160

Asn Thr Ile Ile Thr Leu Ala Asp Trp Tyr His Ile Pro Ala Pro Ser
                165                 170                 175

Ile Gln Gly Ala Ala Gln Pro Asp Ala Thr Leu Ile Asn Gly Lys Gly
            180                 185                 190

Arg Tyr Val Gly Gly Pro Ala Ala Glu Leu Ser Ile Val Asn Val Glu
            195                 200                 205

Gln Gly Lys Lys Tyr Arg Met Arg Leu Ile Ser Leu Ser Cys Asp Pro
210                 215                 220

Asn Trp Gln Phe Ser Ile Asp Gly His Glu Leu Thr Ile Ile Glu Val
225                 230                 235                 240

Asp Gly Gln Leu Thr Glu Pro His Thr Val Asp Arg Leu Gln Ile Phe
            245                 250                 255

Thr Gly Gln Arg Tyr Ser Phe Val Leu Asp Ala Asn Gln Pro Val Asp
            260                 265                 270

Asn Tyr Trp Ile Arg Ala Gln Pro Asn Lys Gly Arg Asn Gly Leu Ala
            275                 280                 285

Gly Thr Phe Ala Asn Gly Val Asn Ser Ala Ile Leu Arg Tyr Ala Gly
            290                 295                 300

Ala Ala Asn Ala Asp Pro Thr Thr Ser Ala Asn Pro Asn Pro Ala Gln
305                 310                 315                 320

Leu Asn Glu Ala Asp Leu His Ala Leu Ile Asp Pro Ala Ala Pro Gly
            325                 330                 335

Ile Pro Thr Pro Gly Ala Ala Asp Val Asn Leu Arg Phe Gln Leu Gly
            340                 345                 350

Phe Ser Gly Gly Arg Phe Thr Ile Asn Gly Thr Ala Tyr Glu Ser Pro
            355                 360                 365

Ser Val Pro Thr Leu Leu Gln Ile Met Ser Gly Ala Gln Ser Ala Asn
370                 375                 380

Asp Leu Leu Pro Ala Gly Ser Val Tyr Glu Leu Pro Arg Asn Gln Val
385                 390                 395                 400

Val Glu Leu Val Val Pro Ala Gly Val Leu Gly Gly Pro His Pro Phe
            405                 410                 415

His Leu His Gly His Ala Phe Ser Val Val Arg Ser Ala Gly Ser Ser
            420                 425                 430

Thr Tyr Asn Phe Val Asn Pro Val Lys Arg Asp Val Val Ser Leu Gly
            435                 440                 445

Val Thr Gly Asp Glu Val Thr Ile Arg Phe Val Thr Asp Asn Pro Gly
            450                 455                 460

Pro Trp Phe Phe His Cys His Ile Glu Phe His Leu Met Asn Gly Leu
465                 470                 475                 480

Ala Ile Val Phe Ala Glu Asp Met Ala Asn Thr Val Asp Ala Asn Asn
            485                 490                 495

Pro Pro Val Glu Trp Ala Gln Leu Cys Glu Ile Tyr Asp Asp Leu Pro
            500                 505                 510
```

```
Pro Glu Ala Thr Ser Ile Gln Thr Val Val Arg Arg Ala Glu Pro Thr
        515                 520                 525

Gly Phe Ser Ala Lys Phe Arg Arg Glu Gly Leu
        530                 535

(2) INFORMATION FOR SEQ ID NO: 2:

(i) SEQUENCE CHARACTERISTICS:
        (A) LENGTH: 499 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

Gly Ile Gly Pro Val Ala Asp Leu Thr Ile Thr Asn Ala Ala Val Ser
1               5                   10                  15

Pro Asp Gly Phe Ser Arg Gln Ala Val Val Asn Gly Gly Thr Pro
            20                  25                  30

Gly Pro Leu Ile Thr Gly Asn Met Gly Asp Arg Phe Gln Leu Asn Val
            35                  40                  45

Ile Asp Asn Leu Thr Asn His Thr Met Leu Lys Ser Thr Ser Ile His
 50                  55                  60

Trp His Gly Phe Phe Gln Lys Gly Thr Asn Trp Ala Asp Gly Pro Ala
65                   70                  75                  80

Phe Ile Asn Gln Cys Pro Ile Ser Gly His Ser Phe Leu Tyr Asp
                85                  90                  95

Phe Gln Val Pro Asp Gln Ala Gly Thr Phe Trp Tyr His Ser His Leu
            100                 105                 110

Ser Thr Gln Tyr Cys Asp Gly Leu Arg Gly Pro Phe Val Val Tyr Asp
            115                 120                 125

Pro Asn Asp Pro Ala Ala Asp Leu Tyr Asp Val Asp Asn Asp Thr
            130                 135             140

Val Ile Thr Leu Val Asp Trp Tyr His Val Ala Ala Lys Leu Gly Pro
145                 150                 155                 160

Ala Phe Pro Leu Gly Ala Asp Ala Thr Leu Ile Asn Gly Lys Gly Arg
                165                 170                 175

Ser Pro Ser Thr Thr Thr Ala Asp Leu Ser Val Ile Ser Val Thr Pro
            180                 185                 190

Gly Lys Arg Tyr Arg Phe Arg Leu Val Ser Leu Ser Cys Asp Pro Asn
            195                 200                 205

Tyr Thr Phe Ser Ile Asp Gly His Asn Met Thr Ile Ile Glu Thr Asp
            210                 215                 220

Ser Ile Asn Thr Ala Pro Leu Val Val Asp Ser Ile Gln Ile Phe Ala
225                 230                 235                 240

Ala Gln Arg Tyr Ser Phe Val Leu Glu Ala Asn Gln Ala Val Asp Asn
            245                 250                 255

Tyr Trp Ile Arg Ala Asn Pro Asn Phe Gly Asn Val Gly Phe Thr Gly
            260                 265                 270

Gly Ile Asn Ser Ala Ile Leu Arg Tyr Asp Gly Ala Ala Ala Val Glu
            275                 280                 285

Pro Thr Thr Thr Gln Thr Thr Ser Thr Ala Pro Leu Asn Glu Val Asn
            290                 295                 300

Leu His Pro Leu Val Thr Thr Ala Val Pro Gly Ser Pro Val Ala Gly
305                 310                 315                 320
```

```
Gly Val Asp Leu Ala Ile Asn Met Ala Phe Asn Phe Asn Gly Thr Asn
                325                 330                 335

Phe Phe Ile Asn Gly Ala Ser Phe Thr Pro Pro Thr Val Pro Val Leu
                340                 345                 350

Leu Gln Ile Ile Ser Gly Ala Gln Asn Ala Gln Asp Leu Leu Pro Ser
                355                 360                 365

Gly Ser Val Tyr Ser Leu Pro Ser Asn Ala Asp Ile Glu Ile Ser Phe
                370                 375                 380

Pro Ala Thr Ala Ala Pro Gly Ala Pro His Pro Phe His Leu His
385                 390                 395                 400

Gly His Ala Phe Ala Val Val Arg Ser Ala Gly Ser Thr Val Tyr Asn
                405                 410                 415

Tyr Asp Asn Pro Ile Phe Arg Asp Val Val Ser Thr Gly Thr Pro Ala
                420                 425                 430

Ala Gly Asp Asn Val Thr Ile Arg Phe Arg Thr Asp Asn Pro Gly Pro
                435                 440                 445

Trp Phe Leu His Cys His Ile Asp Phe His Leu Glu Ala Gly Phe Ala
                450                 455                 460

Val Val Phe Ala Glu Asp Ile Pro Asp Val Ala Ser Ala Asn Pro Val
465                 470                 475                 480

Pro Gln Ala Trp Ser Asp Leu Cys Pro Thr Tyr Asp Ala Leu Asp Pro
                485                 490                 495

Ser Asp Gln (2) INFORMATION FOR SEQ ID NO: 3:

(i) SEQUENCE CHARACTERISTICS:
        (A) LENGTH: 499 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

Ala Ile Gly Pro Val Ala Ser Leu Val Val Ala Asn Ala Pro Val Ser
1               5                   10                  15

Pro Asp Gly Phe Leu Arg Asp Ala Ile Val Val Asn Gly Val Val Pro
                20                  25                  30

Ser Pro Leu Ile Thr Gly Lys Lys Gly Asp Arg Phe Gln Leu Asn Val
                35                  40                  45

Val Asp Thr Leu Thr Asn His Ser Met Leu Lys Ser Thr Ser Ile His
        50                  55                  60

Trp His Gly Phe Phe Gln Ala Gly Thr Asn Trp Ala Glu Gly Pro Ala
65                  70                  75                  80

Phe Val Asn Gln Cys Pro Ile Ala Ser Gly His Ser Phe Leu Tyr Asp
                85                  90                  95

Phe His Val Pro Asp Gln Ala Gly Thr Phe Trp Tyr His Ser His Leu
                100                 105                 110

Ser Thr Gln Tyr Cys Asp Gly Leu Arg Gly Pro Phe Val Val Tyr Asp
                115                 120                 125

Pro Lys Asp Pro His Ala Ser Arg Tyr Asp Val Asp Asn Glu Ser Thr
                130                 135                 140

Val Ile Thr Leu Thr Asp Trp Tyr His Thr Ala Ala Arg Leu Gly Pro
145                 150                 155                 160

Lys Phe Pro Leu Gly Ala Asp Ala Thr Leu Ile Asn Gly Leu Gly Arg
                165                 170                 175
```

-continued

```
Ser Ala Ser Thr Pro Thr Ala Ala Leu Ala Val Ile Asn Val Gln His
            180                 185                 190

Gly Lys Arg Tyr Arg Phe Arg Leu Val Ser Ile Ser Cys Asp Pro Asn
            195                 200                 205

Tyr Thr Phe Ser Ile Asp Gly His Asn Leu Thr Val Ile Glu Val Asp
            210                 215                 220

Gly Ile Asn Ser Gln Pro Leu Leu Val Asp Ser Ile Gln Ile Phe Ala
225                 230                 235                 240

Ala Gln Arg Tyr Ser Phe Val Leu Asn Ala Asn Gln Thr Val Gly Asn
            245                 250                 255

Tyr Trp Val Arg Ala Asn Pro Asn Phe Gly Thr Val Gly Phe Ala Gly
            260                 265                 270

Gly Ile Asn Ser Ala Ile Leu Arg Tyr Gln Gly Ala Pro Val Ala Glu
            275                 280                 285

Pro Thr Thr Thr Gln Thr Pro Ser Val Ile Pro Leu Ile Glu Thr Asn
            290                 295                 300

Leu His Pro Leu Ala Arg Met Pro Val Pro Gly Ser Pro Thr Pro Gly
305                 310                 315                 320

Gly Val Asp Lys Ala Leu Asn Leu Ala Phe Asn Phe Asn Gly Thr Asn
            325                 330                 335

Phe Phe Ile Asn Asn Ala Thr Phe Thr Pro Pro Thr Val Pro Val Leu
            340                 345                 350

Leu Gln Ile Leu Ser Gly Ala Gln Thr Ala Gln Asp Leu Leu Pro Ala
            355                 360                 365

Gly Ser Val Tyr Pro Leu Pro Ala His Ser Thr Ile Glu Ile Thr Leu
            370                 375                 380

Pro Ala Thr Ala Leu Ala Pro Gly Ala Pro His Pro Phe His Leu His
385                 390                 395                 400

Gly His Ala Phe Ala Val Val Arg Ser Ala Gly Ser Thr Thr Tyr Asn
            405                 410                 415

Tyr Asn Asp Pro Ile Phe Arg Asp Val Val Ser Thr Gly Thr Pro Ala
            420                 425                 430

Ala Gly Asp Asn Val Thr Ile Arg Phe Gln Thr Asp Asn Pro Gly Pro
            435                 440                 445

Trp Phe Leu His Cys His Ile Asp Phe His Leu Asp Ala Gly Phe Ala
            450                 455                 460

Ile Val Phe Ala Glu Asp Val Asp Val Lys Ala Ala Asn Pro Val
465                 470                 475                 480

Pro Lys Ala Trp Ser Asp Leu Cys Pro Ile Tyr Asp Gly Leu Ser Glu
            485                 490                 495

Ala Asn Gln
```

(2) INFORMATION FOR SEQ ID NO: 4:

(i) SEQUENCE CHARACTERISTICS:
        (A) LENGTH: 548 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Met His Thr Phe Leu Arg Ser Thr Ala Leu Val Val Ala Gly Leu Ser
1               5                   10                  15

Ala Arg Ala Leu Ala Ser Ile Gly Pro Val Thr Asp Phe His Ile Val
```

-continued

```
                    20                  25                  30
Asn Ala Ala Val Ser Pro Asp Gly Phe Ser Arg Gln Ala Val Leu Ala
                35                  40                  45
Glu Gly Val Phe Pro Gly Pro Leu Ile Ala Gly Asn Lys Gly Asp Asn
 50                  55                  60
Phe Gln Ile Asn Val Ile Asp Glu Leu Thr Asn Ala Thr Met Leu Lys
 65                  70                  75                  80
Thr Thr Thr Ile His Trp His Gly Phe Phe Gln His Gly Thr Asn Trp
                85                  90                  95
Ala Asp Gly Pro Ala Phe Ile Asn Gln Cys Pro Ile Ala Ser Gly Asp
            100                 105                 110
Ser Phe Leu Tyr Asn Phe Gln Val Pro Asp Gln Ala Gly Thr Phe Trp
            115                 120                 125
Tyr His Ser His Leu Ser Thr Gln Tyr Cys Asp Gly Leu Arg Gly Pro
    130                 135                 140
Phe Val Val Tyr Asp Pro Ala Asp Pro Tyr Leu Asp Gln Tyr Asp Val
145                 150                 155                 160
Asp Asp Asp Ser Thr Val Ile Thr Leu Ala Asp Trp Tyr His Thr Ala
                165                 170                 175
Ala Arg Leu Gly Ser Pro Phe Pro Ala Ala Asp Thr Thr Leu Ile Asn
            180                 185                 190
Gly Leu Gly Arg Cys Gly Glu Ala Gly Cys Pro Val Ser Asp Leu Ala
            195                 200                 205
Val Ile Ser Val Thr Lys Gly Lys Arg Tyr Arg Phe Arg Leu Val Ser
    210                 215                 220
Ile Ser Cys Asp Ser Phe Phe Thr Phe Ser Ile Asp Gly His Ser Leu
225                 230                 235                 240
Asn Val Ile Glu Val Asp Ala Thr Asn His Gln Pro Leu Thr Val Asp
                245                 250                 255
Glu Leu Thr Ile Tyr Ala Gly Gln Arg Tyr Ser Phe Ile Leu Thr Ala
            260                 265                 270
Asp Gln Asp Val Asp Asn Tyr Trp Ile Arg Ala Asn Pro Gly Ile Gly
    275                 280                 285
Ile Thr Thr Gly Phe Ala Gly Gly Ile Asn Ser Ala Ile Leu Arg Tyr
    290                 295                 300
Asp Gly Ala Asp Val Val Glu Pro Thr Thr Thr Gln Ala Thr Ser Pro
305                 310                 315                 320
Val Val Leu Ser Glu Ser Asn Leu Ala Pro Leu Thr Asn Ala Ala Ala
                325                 330                 335
Pro Gly Leu Pro Glu Val Gly Gly Val Asp Leu Ala Leu Asn Phe Asn
            340                 345                 350
Leu Thr Phe Asp Gly Pro Ser Leu Lys Phe Gln Ile Asn Gly Val Thr
            355                 360                 365
Phe Val Pro Pro Thr Val Pro Val Leu Leu Gln Ile Leu Ser Gly Ala
    370                 375                 380
Gln Ser Ala Ala Asp Leu Leu Pro Ser Gly Ser Val Tyr Ala Leu Pro
385                 390                 395                 400
Ser Asn Ala Thr Ile Glu Leu Ser Leu Pro Ala Gly Ala Leu Gly Gly
                405                 410                 415
Pro His Pro Phe His Leu His Gly His Thr Phe Ser Val Val Arg Pro
            420                 425                 430
Ala Gly Ser Thr Thr Tyr Asn Tyr Val Asn Pro Val Gln Arg Asp Val
            435                 440                 445
```

```
Val Ser Ile Gly Asn Thr Gly Asp Asn Val Thr Ile Arg Phe Asp Thr
450                 455                 460

Asn Asn Pro Gly Pro Trp Phe Leu His Cys His Ile Asp Trp His Leu
465                 470                 475                 480

Glu Ala Ala Leu Pro Leu Ser Ser Leu Arg Thr Ser Leu Thr Leu Arg
                485                 490                 495

Pro Leu Thr Leu Ser Pro Arg Thr Gly Pro Thr Cys Ala Leu Ser Thr
                500                 505                 510

Thr Leu Trp Thr His Leu Ile Thr Ser Gly Phe Ala Ser Ile Ile Gln
                515                 520                 525

Trp Met Met Gly Gly Asn Gly Leu Phe Ala Pro His Ala Leu Ser Phe
        530                 535                 540

Leu Gly Ser Gln
545
```

(2) INFORMATION FOR SEQ ID NO: 5:

(i) SEQUENCE CHARACTERISTICS:
        (A) LENGTH: 529 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

```
Met Leu Ser Ser Ile Thr Leu Leu Pro Leu Leu Ala Ala Val Ser Thr
1               5                   10                  15

Pro Ala Phe Ala Ala Val Arg Asn Tyr Lys Phe Asp Ile Lys Asn Val
                20                  25                  30

Asn Val Ala Pro Asp Gly Phe Gln Arg Ser Ile Val Ser Val Asn Gly
            35                  40                  45

Leu Val Pro Gly Thr Leu Ile Thr Ala Asn Lys Gly Asp Thr Leu Arg
        50                  55                  60

Ile Asn Val Thr Asn Gln Leu Thr Asp Pro Ser Met Arg Arg Ala Thr
65                  70                  75                  80

Thr Ile His Trp His Gly Leu Phe Gln Ala Thr Thr Ala Asp Glu Asp
                85                  90                  95

Gly Pro Ala Phe Val Thr Gln Cys Pro Ile Ala Gln Asn Leu Ser Tyr
                100                 105                 110

Thr Tyr Glu Ile Pro Leu Arg Gly Gln Thr Gly Thr Met Trp Tyr His
            115                 120                 125

Ala His Leu Ala Ser Gln Tyr Val Asp Gly Leu Arg Gly Pro Leu Val
130                 135                 140

Ile Tyr Asp Pro Asn Asp Pro His Lys Ser Arg Tyr Asp Val Asp Asp
145                 150                 155                 160

Ala Ser Thr Val Val Met Leu Glu Asp Trp Tyr His Thr Pro Ala Pro
                165                 170                 175

Val Leu Glu Lys Gln Met Phe Ser Thr Asn Asn Thr Ala Leu Leu Ser
            180                 185                 190

Pro Val Pro Asp Ser Gly Leu Ile Asn Gly Lys Gly Arg Tyr Val Gly
            195                 200                 205

Gly Pro Ala Val Pro Arg Ser Val Ile Asn Val Lys Arg Gly Lys Arg
        210                 215                 220

Tyr Arg Leu Arg Val Ile Asn Ala Ser Ala Ile Gly Ser Phe Thr Phe
225                 230                 235                 240

Ser Ile Glu Gly His Ser Leu Thr Val Ile Glu Ala Asp Gly Ile Leu
```

-continued

```
                        245                 250                 255
His Gln Pro Leu Ala Val Asp Ser Phe Gln Ile Tyr Ala Gly Gln Arg
            260                 265                 270

Tyr Ser Val Ile Val Glu Ala Asn Gln Thr Ala Asn Tyr Trp Ile
        275                 280                 285

Arg Ala Pro Met Thr Val Ala Gly Ala Gly Thr Asn Ala Asn Leu Asp
        290                 295                 300

Pro Thr Asn Val Phe Ala Val Leu His Tyr Glu Gly Ala Pro Asn Ala
305                 310                 315                 320

Glu Pro Thr Thr Glu Gln Gly Ser Ala Ile Gly Thr Ala Leu Val Glu
                325                 330                 335

Glu Asn Leu His Ala Leu Ile Asn Pro Gly Ala Pro Gly Gly Ser Ala
                340                 345                 350

Pro Ala Asp Val Ser Leu Asn Leu Ala Ile Gly Arg Ser Thr Val Asp
                355                 360                 365

Gly Ile Leu Arg Phe Thr Phe Asn Asn Ile Lys Tyr Glu Ala Pro Ser
        370                 375                 380

Leu Pro Thr Leu Leu Lys Ile Leu Ala Asn Asn Ala Ser Asn Asp Ala
385                 390                 395                 400

Asp Phe Thr Pro Asn Glu His Thr Ile Val Leu Pro His Asn Lys Val
                405                 410                 415

Ile Glu Leu Asn Ile Thr Gly Gly Ala Asp His Pro Ile His Leu His
                420                 425                 430

Gly His Val Phe Asp Ile Val Lys Ser Leu Gly Gly Thr Pro Asn Tyr
        435                 440                 445

Val Asn Pro Pro Arg Arg Asp Val Val Arg Val Gly Gly Thr Gly Val
        450                 455                 460

Val Leu Arg Phe Lys Thr Asp Asn Pro Gly Pro Trp Phe Val His Cys
465                 470                 475                 480

His Ile Asp Trp His Leu Glu Ala Gly Leu Ala Leu Val Phe Ala Glu
                485                 490                 495

Ala Pro Ser Gln Ile Arg Gln Gly Val Gln Ser Val Gln Pro Asn Asn
            500                 505                 510

Ala Trp Asn Gln Leu Cys Pro Lys Tyr Ala Ala Leu Pro Pro Asp Leu
        515                 520                 525

Gln (2) INFORMATION FOR SEQ ID NO: 6:

(i) SEQUENCE CHARACTERISTICS:
        (A) LENGTH: 599 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

Met Ala Arg Ser Thr Thr Ser Leu Phe Ala Leu Ser Leu Val Ala Ser
1               5                   10                  15

Ala Phe Ala Arg Val Val Asp Tyr Gly Phe Asp Val Ala Asn Gly Ala
            20                  25                  30

Val Ala Pro Asp Gly Val Thr Arg Asn Ala Val Leu Val Asn Gly Arg
        35                  40                  45

Phe Pro Gly Pro Leu Ile Thr Ala Asn Lys Gly Asp Thr Leu Lys Ile
        50                  55                  60
```

```
Thr Val Arg Asn Lys Leu Ser Asp Pro Thr Met Arg Arg Ser Thr Thr
 65                  70                  75                  80

Ile His Trp His Gly Leu Leu Gln His Arg Thr Ala Glu Glu Asp Gly
                 85                  90                  95

Pro Ala Phe Val Thr Gln Cys Pro Ile Pro Pro Gln Glu Ser Tyr Thr
            100                 105                 110

Tyr Thr Met Pro Leu Gly Glu Gln Thr Gly Thr Tyr Trp Tyr His Ser
        115                 120                 125

His Leu Ser Ser Gln Tyr Val Asp Gly Leu Arg Gly Pro Ile Val Ile
    130                 135                 140

Tyr Asp Pro His Asp Pro Tyr Arg Asn Tyr Tyr Asp Val Asp Asp Glu
145                 150                 155                 160

Arg Thr Val Phe Thr Leu Ala Asp Trp Tyr His Thr Pro Ser Glu Ala
                165                 170                 175

Ile Ile Ala Thr His Asp Val Leu Lys Thr Ile Pro Asp Ser Gly Thr
                180                 185                 190

Ile Asn Gly Lys Gly Lys Tyr Asp Pro Ala Ser Ala Asn Thr Asn Asn
            195                 200                 205

Thr Thr Leu Glu Asn Leu Tyr Thr Leu Lys Val Lys Arg Gly Lys Arg
        210                 215                 220

Tyr Arg Leu Arg Ile Ile Asn Ala Ser Ala Ile Ala Ser Phe Arg Phe
225                 230                 235                 240

Gly Val Gln Gly His Lys Cys Thr Ile Ile Glu Ala Asp Gly Val Leu
                245                 250                 255

Thr Lys Pro Ile Glu Val Asp Ala Phe Asp Ile Leu Ala Gly Gln Arg
                260                 265                 270

Tyr Ser Cys Ile Leu Lys Ala Asp Gln Asp Pro Asp Ser Tyr Trp Ile
        275                 280                 285

Asn Ala Pro Ile Thr Asn Val Leu Asn Thr Asn Val Gln Ala Leu Leu
290                 295                 300

Val Tyr Glu Asp Asp Lys Arg Pro Thr His Tyr Pro Trp Lys Pro Phe
305                 310                 315                 320

Leu Thr Trp Lys Ile Ser Asn Glu Ile Ile Gln Tyr Trp Gln His Lys
                325                 330                 335

His Gly Ser His Gly His Lys Gly Lys Gly His His His Lys Val Arg
            340                 345                 350

Ala Ile Gly Gly Val Ser Gly Leu Ser Ser Arg Val Lys Ser Arg Ala
        355                 360                 365

Ser Asp Leu Ser Lys Lys Ala Val Glu Leu Ala Ala Ala Leu Val Ala
    370                 375                 380

Gly Glu Ala Glu Leu Asp Lys Arg Gln Asn Glu Asp Asn Ser Thr Ile
385                 390                 395                 400

Val Leu Asp Glu Thr Lys Leu Ile Pro Leu Val Gln Pro Gly Ala Pro
                405                 410                 415

Gly Gly Ser Arg Pro Ala Asp Val Val Val Pro Leu Asp Phe Gly Leu
            420                 425                 430

Asn Phe Ala Asn Gly Leu Trp Thr Ile Asn Asn Val Ser Tyr Ser Pro
        435                 440                 445

Pro Asp Val Pro Thr Leu Leu Lys Ile Leu Thr Asp Lys Asp Lys Val
    450                 455                 460

Asp Ala Ser Asp Phe Thr Ala Asp Glu His Thr Tyr Ile Leu Pro Lys
465                 470                 475                 480

Asn Gln Val Val Glu Leu His Ile Lys Gly Gln Ala Leu Gly Ile Val
                485                 490                 495
```

His Pro Leu His Leu His Gly His Ala Phe Asp Val Val Gln Phe Gly
                500                 505                 510

Asp Asn Ala Pro Asn Tyr Val Asn Pro Pro Arg Arg Asp Val Val Gly
            515                 520                 525

Val Thr Asp Ala Gly Val Arg Ile Gln Phe Arg Thr Asp Asn Pro Gly
        530                 535                 540

Pro Trp Phe Leu His Cys His Ile Asp Trp His Leu Glu Glu Gly Phe
545                 550                 555                 560

Ala Met Val Phe Ala Glu Ala Pro Glu Asp Ile Lys Lys Gly Ser Gln
                565                 570                 575

Ser Val Lys Pro Asp Gly Gln Trp Lys Lys Leu Cys Glu Lys Tyr Glu
            580                 585                 590

Lys Leu Pro Glu Ala Leu Gln
            595

(2) INFORMATION FOR SEQ ID NO: 7:

(i) SEQUENCE CHARACTERISTICS:
        (A) LENGTH: 572 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

Met Ala Arg Thr Thr Phe Leu Val Ser Val Ser Leu Phe Val Ser Ala
1               5                   10                  15

Val Leu Ala Arg Thr Val Glu Tyr Asn Leu Lys Ile Ser Asn Gly Lys
            20                  25                  30

Ile Ala Pro Asp Gly Val Glu Arg Asp Ala Thr Leu Val Asn Gly Gly
        35                  40                  45

Tyr Pro Gly Pro Leu Ile Phe Ala Asn Lys Gly Asp Thr Leu Lys Val
    50                  55                  60

Lys Val Gln Asn Lys Leu Thr Asn Pro Asp Met Tyr Arg Thr Thr Ser
65                  70                  75                  80

Ile His Trp His Gly Leu Leu Gln His Arg Asn Ala Asp Asp Asp Gly
                85                  90                  95

Pro Ala Phe Val Thr Gln Cys Pro Ile Val Pro Gln Ala Ser Tyr Thr
            100                 105                 110

Tyr Thr Met Pro Leu Gly Asp Gln Thr Gly Thr Tyr Trp Tyr His Ser
        115                 120                 125

His Leu Ser Ser Gln Tyr Val Asp Gly Leu Arg Gly Pro Leu Val Ile
    130                 135                 140

Tyr Asp Pro Lys Asp Pro His Arg Arg Leu Tyr Asp Ile Asp Asp Glu
145                 150                 155                 160

Lys Thr Val Leu Ile Ile Gly Asp Trp Tyr His Thr Ser Ser Lys Ala
                165                 170                 175

Ile Leu Ala Thr Gly Asn Ile Thr Leu Gln Gln Pro Asp Ser Ala Thr
            180                 185                 190

Ile Asn Gly Lys Gly Arg Phe Asp Pro Asp Asn Thr Pro Ala Asn Pro
        195                 200                 205

Asn Thr Leu Tyr Thr Leu Lys Val Lys Arg Gly Lys Arg Tyr Arg Leu
    210                 215                 220

Arg Val Ile Asn Ser Ser Ala Ile Ala Ser Phe Arg Met Ser Ile Gln
225                 230                 235                 240

-continued

```
Gly His Lys Met Thr Val Ile Ala Ala Asp Gly Val Ser Thr Lys Pro
                245                 250                 255

Tyr Gln Val Asp Ser Phe Asp Ile Leu Ala Gly Gln Arg Ile Asp Ala
                260                 265                 270

Val Val Glu Ala Asn Gln Glu Pro Asp Thr Tyr Trp Ile Asn Ala Pro
                275                 280                 285

Leu Thr Asn Val Ala Asn Lys Thr Ala Gln Ala Leu Leu Ile Tyr Glu
        290                 295                 300

Asp Asp Arg Arg Pro Tyr His Pro Pro Lys Gly Pro Tyr Arg Lys Trp
305                 310                 315                 320

Ser Val Ser Glu Ala Ile Ile Lys Tyr Trp Lys His Lys Gly Arg
                325                 330                 335

Gly Leu Leu Ser Gly His Gly Gly Leu Lys Ala Arg Met Met Glu Gly
                340                 345                 350

Ser Leu His Leu His Gly Arg Arg Asp Ile Val Lys Arg Gln Asn Glu
                355                 360                 365

Thr Thr Thr Val Val Met Asp Glu Thr Lys Leu Val Pro Leu Glu His
        370                 375                 380

Pro Gly Ala Ala Cys Gly Ser Lys Pro Ala Asp Leu Val Ile Asp Leu
385                 390                 395                 400

Thr Phe Gly Val Asn Phe Thr Thr Gly His Trp Met Ile Asn Gly Ile
                405                 410                 415

Pro His Lys Ser Pro Asp Met Pro Thr Leu Leu Lys Ile Leu Thr Asp
                420                 425                 430

Thr Asp Gly Val Thr Glu Ser Asp Phe Thr Gln Pro Glu His Thr Ile
        435                 440                 445

Ile Leu Pro Lys Asn Lys Cys Val Glu Phe Asn Ile Lys Gly Asn Ser
        450                 455                 460

Gly Leu Gly Ile Val His Pro Ile His Leu His Gly His Thr Phe Asp
465                 470                 475                 480

Val Val Gln Phe Gly Asn Asn Pro Pro Asn Tyr Val Asn Pro Pro Arg
                485                 490                 495

Arg Asp Val Val Gly Ala Thr Asp Glu Gly Val Arg Phe Gln Phe Lys
                500                 505                 510

Thr Asp Asn Pro Gly Pro Trp Phe Leu His Cys His Ile Asp Trp His
                515                 520                 525

Leu Glu Glu Gly Phe Ala Met Val Phe Ala Glu Ala Pro Glu Ala Ile
        530                 535                 540

Lys Gly Gly Pro Lys Ser Val Pro Val Asp Arg Gln Trp Lys Asp Leu
545                 550                 555                 560

Cys Arg Lys Tyr Gly Ser Leu Pro Ala Gly Phe Leu
                565                 570
```

(2) INFORMATION FOR SEQ ID NO: 8:

(i) SEQUENCE CHARACTERISTICS:
        (A) LENGTH: 575 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

```
Met Ala Arg Thr Thr Phe Leu Val Ser Val Ser Leu Phe Val Ser Ala
1               5                   10                  15

Val Leu Ala Arg Thr Val Glu Tyr Gly Leu Lys Ile Ser Asp Gly Glu
```

-continued

```
                   20                  25                  30
Ile Ala Pro Asp Gly Val Lys Arg Asn Ala Thr Leu Val Asn Gly Gly
             35                  40                  45
Tyr Pro Gly Pro Leu Ile Phe Ala Asn Lys Gly Asp Thr Leu Lys Val
 50                  55                  60
Lys Val Gln Asn Lys Leu Thr Asn Pro Glu Met Tyr Arg Thr Thr Ser
 65                  70                  75                  80
Ile His Trp His Gly Leu Leu Gln His Arg Asn Ala Asp Asp Asp Gly
                 85                  90                  95
Pro Ser Phe Val Thr Gln Cys Pro Ile Val Pro Arg Glu Ser Tyr Thr
            100                 105                 110
Tyr Thr Ile Pro Leu Asp Asp Gln Thr Gly Thr Tyr Trp Tyr His Ser
            115                 120                 125
His Leu Ser Ser Gln Tyr Val Asp Gly Leu Arg Gly Pro Leu Val Ile
        130                 135                 140
Tyr Pro Lys Asp Pro His Arg Arg Leu Tyr Asp Val Asp Asp Glu Lys
145                 150                 155                 160
Thr Val Leu Ile Ile Gly Asp Trp Tyr His Glu Ser Ser Lys Ala Ile
                165                 170                 175
Leu Ala Ser Gly Asn Ile Thr Arg Gln Arg Pro Val Ser Ala Thr Ile
            180                 185                 190
Asn Gly Lys Gly Arg Phe Asp Pro Asp Asn Thr Pro Ala Asn Pro Asp
        195                 200                 205
Thr Leu Tyr Thr Leu Lys Val Lys Arg Gly Lys Arg Tyr Arg Leu Arg
        210                 215                 220
Val Ile Asn Ser Ser Glu Ile Ala Ser Phe Arg Phe Ser Val Glu Gly
225                 230                 235                 240
His Lys Val Thr Val Ile Ala Ala Asp Gly Val Ser Thr Lys Pro Tyr
                245                 250                 255
Gln Val Asp Ala Phe Asp Ile Leu Ala Gly Gln Arg Ile Asp Cys Val
            260                 265                 270
Val Glu Ala Asn Gln Pro Asp Thr Tyr Trp Ile Asn Ala Pro Leu
        275                 280                 285
Thr Asn Val Pro Asn Lys Thr Ala Gln Ala Leu Leu Val Tyr Glu Glu
        290                 295                 300
Asp Arg Arg Pro Tyr His Pro Pro Lys Gly Pro Tyr Arg Lys Trp Ser
305                 310                 315                 320
Val Ser Glu Ala Ile Ile Lys Tyr Trp Asn His Lys His Lys His Gly
                325                 330                 335
Arg Gly Leu Leu Ser Gly His Gly Leu Lys Ala Arg Met Ile Glu
            340                 345                 350
Gly Ser His His Leu His Ser Arg Ser Val Val Lys Arg Gln Asn Glu
        355                 360                 365
Thr Thr Thr Val Val Met Asp Glu Ser Lys Leu Val Pro Leu Glu Tyr
        370                 375                 380
Pro Gly Ala Ala Cys Gly Ser Lys Pro Ala Asp Leu Val Leu Asp Leu
385                 390                 395                 400
Thr Phe Gly Leu Asn Phe Ala Thr Gly His Trp Met Ile Asn Gly Ile
                405                 410                 415
Pro Tyr Glu Ser Pro Lys Ile Pro Thr Leu Leu Lys Ile Leu Thr Asp
            420                 425                 430
Glu Asp Gly Val Thr Glu Ser Asp Phe Thr Lys Glu Glu His Thr Val
        435                 440                 445
```

```
Ile Leu Pro Lys Asn Lys Cys Ile Glu Phe Asn Ile Lys Gly Asn Ser
            450                 455                 460

Gly Ile Pro Ile Thr His Pro Val His Leu His Gly His Thr Trp Asp
465                     470                 475                 480

Val Val Gln Phe Gly Asn Asn Pro Pro Asn Tyr Val Asn Pro Pro Arg
                    485                 490                 495

Arg Asp Val Val Gly Ser Thr Asp Ala Gly Val Arg Ile Gln Phe Lys
            500                 505                 510

Thr Asp Asn Pro Gly Pro Trp Phe Leu His Cys His Ile Asp Trp His
            515                 520                 525

Leu Glu Glu Gly Phe Ala Met Val Phe Ala Glu Ala Pro Glu Ala Val
530                     535                 540

Lys Gly Gly Pro Lys Ser Val Ala Val Asp Ser Gln Trp Glu Gly Leu
545                 550                 555                 560

Cys Gly Lys Tyr Asp Asn Trp Leu Lys Ser Asn Pro Gly Gln Leu
                565                 570                 575

(2) INFORMATION FOR SEQ ID NO: 9:

(i) SEQUENCE CHARACTERISTICS:
        (A) LENGTH: 616 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

Met Lys Arg Phe Phe Ile Asn Ser Leu Leu Leu Ala Gly Leu Leu
1               5                   10                  15

Asn Ser Gly Ala Leu Ala Ala Pro Ser Thr His Pro Arg Ser Asn Pro
                20                  25                  30

Asp Ile Leu Leu Glu Arg Asp His Ser Leu Thr Ser Arg Gln Gly
            35                  40                  45

Ser Cys His Ser Pro Ser Asn Arg Ala Cys Trp Cys Ser Gly Phe Asp
50                  55                  60

Ile Asn Thr Asp Tyr Glu Thr Lys Thr Pro Asn Thr Gly Val Val Arg
65                  70                  75                  80

Arg Tyr Thr Phe Asp Ile Thr Glu Val Asp Asn Arg Pro Gly Pro Asp
                85                  90                  95

Gly Val Ile Lys Glu Lys Leu Met Leu Ile Asn Asp Lys Leu Leu Gly
                100                 105                 110

Pro Thr Val Phe Ala Asn Trp Gly Asp Thr Ile Glu Val Thr Val Asn
            115                 120                 125

Asn His Leu Arg Thr Asn Gly Thr Ser Ile His Trp His Gly Leu His
130                 135                 140

Gln Lys Gly Thr Asn Tyr His Asp Gly Ala Asn Gly Val Thr Glu Cys
145                 150                 155                 160

Pro Ile Pro Pro Gly Gly Ser Arg Val Tyr Ser Phe Arg Ala Arg Gln
                165                 170                 175

Tyr Gly Thr Ser Trp Tyr His Ser His Phe Ser Ala Gln Tyr Gly Asn
            180                 185                 190

Gly Val Ser Gly Ala Ile Gln Ile Asn Gly Pro Ala Ser Leu Pro Tyr
            195                 200                 205

Asp Ile Asp Leu Gly Val Leu Pro Leu Xaa Asp Trp Tyr Tyr Lys Ser
210                 215                 220

Ala Asp Gln Leu Val Ile Glu Thr Leu Xaa Lys Gly Asn Ala Pro Phe
```

```
            225                 230                 235                 240
Ser Asp Asn Val Leu Ile Asn Gly Thr Ala Lys His Pro Thr Thr Gly
                    245                 250                 255

Glu Gly Glu Tyr Ala Ile Val Lys Leu Thr Pro Asp Lys Arg His Arg
                260                 265                 270

Leu Arg Leu Ile Asn Met Ser Val Glu Asn His Phe Gln Val Ser Leu
            275                 280                 285

Ala Lys His Thr Met Thr Val Ile Ala Asp Met Val Pro Val Asn
        290                 295                 300

Ala Met Thr Val Asp Ser Leu Phe Met Ala Val Gly Gln Arg Tyr Asp
305                 310                 315                 320

Val Thr Ile Asp Ala Ser Gln Ala Val Gly Asn Tyr Trp Phe Asn Ile
                325                 330                 335

Thr Phe Gly Gly Gln Gln Lys Cys Gly Phe Ser His Asn Pro Ala Pro
                340                 345                 350

Ala Ala Ile Phe Arg Tyr Glu Gly Ala Pro Asp Ala Leu Pro Thr Asp
            355                 360                 365

Pro Gly Ala Ala Pro Lys Asp His Gln Cys Leu Asp Thr Leu Asp Leu
        370                 375                 380

Ser Pro Val Val Gln Lys Asn Val Pro Val Asp Gly Phe Val Lys Glu
385                 390                 395                 400

Pro Gly Asn Thr Leu Pro Val Thr Leu His Val Asp Gln Ala Ala Ala
                405                 410                 415

Pro His Val Phe Thr Trp Lys Ile Asn Gly Ser Ala Ala Asp Val Asp
                420                 425                 430

Trp Asp Arg Pro Val Leu Glu Tyr Val Met Asn Asn Asp Leu Ser Ser
            435                 440                 445

Ile Pro Val Lys Asn Asn Ile Val Arg Val Asp Gly Val Asn Glu Trp
        450                 455                 460

Thr Tyr Trp Leu Val Glu Asn Asp Pro Glu Gly Arg Leu Ser Leu Pro
465                 470                 475                 480

His Pro Met His Leu His Gly His Asp Phe Phe Val Leu Gly Arg Ser
                485                 490                 495

Pro Asp Val Ser Pro Asp Ser Glu Thr Arg Phe Val Phe Asp Pro Ala
                500                 505                 510

Val Asp Leu Pro Arg Leu Arg Gly His Asn Pro Val Arg Arg Asp Val
            515                 520                 525

Thr Met Leu Pro Ala Arg Gly Trp Leu Leu Leu Ala Phe Arg Thr Asp
        530                 535                 540

Asn Pro Gly Ala Trp Leu Phe His Cys His Ile Ala Xaa His Val Ser
545                 550                 555                 560

Gly Gly Leu Ser Val Asp Phe Leu Glu Arg Pro Asp Glu Leu Arg Gly
                565                 570                 575

Gln Leu Thr Gly Glu Ser Lys Ala Glu Leu Glu Arg Val Cys Arg Glu
                580                 585                 590

Trp Lys Asp Trp Glu Ala Lys Ser Pro His Gly Lys Ile Asp Ser Gly
            595                 600                 605

Leu Lys Gln Arg Arg Trp Asp Ala
        610                 615

(2) INFORMATION FOR SEQ ID NO: 10:

(i) SEQUENCE CHARACTERISTICS:
        (A) LENGTH: 573 amino acids
        (B) TYPE: amino acid
```

(C) STRANDEDNESS: single
(D) TOPOLOGY: linear (ii) MOLECULE TYPE: protein (xi) SEQUENCE DESCRIPTION: SEQ ID NO: 10:

```
Gln Gln Ser Cys Asn Thr Pro Ser Asn Arg Ala Cys Trp Thr Asp Gly
1               5                   10                  15
Tyr Asp Ile Asn Thr Asp Tyr Glu Val Asp Ser Pro Thr Gly Val
            20                  25                  30
Val Arg Pro Tyr Thr Leu Thr Leu Thr Glu Val Asp Asn Trp Thr Gly
            35                  40                  45
Pro Asp Gly Val Val Lys Glu Lys Val Met Leu Val Asn Asn Ser Ile
50                      55                  60
Ile Gly Pro Thr Ile Phe Ala Asp Trp Gly Asp Thr Ile Gln Val Thr
65                  70                  75                  80
Val Ile Asn Asn Leu Glu Thr Asn Gly Thr Ser Ile His Trp His Gly
                85                  90                  95
Leu His Gln Lys Gly Thr Asn Leu His Asp Gly Ala Asn Gly Ile Thr
                100                 105                 110
Glu Cys Pro Ile Pro Pro Lys Gly Gly Arg Lys Val Tyr Arg Phe Lys
            115                 120                 125
Ala Gln Gln Tyr Gly Thr Ser Trp Tyr His Ser His Phe Ser Ala Gln
130                 135                 140
Tyr Gly Asn Gly Val Val Gly Ala Ile Gln Ile Asn Gly Pro Ala Ser
145                 150                 155                 160
Leu Pro Tyr Asp Thr Asp Leu Gly Val Phe Pro Ile Ser Asp Tyr Tyr
                165                 170                 175
Tyr Ser Ser Ala Asp Glu Leu Val Glu Leu Thr Lys Asn Ser Gly Ala
                180                 185                 190
Pro Phe Ser Asp Asn Val Leu Phe Asn Gly Thr Ala Lys His Pro Glu
            195                 200                 205
Thr Gly Glu Gly Glu Tyr Ala Asn Val Thr Leu Thr Pro Gly Arg Arg
210                 215                 220
His Arg Leu Arg Leu Ile Asn Thr Ser Val Glu Asn His Phe Gln Val
225                 230                 235                 240
Ser Leu Val Asn His Thr Met Cys Ile Ile Ala Ala Asp Met Val Pro
                245                 250                 255
Val Asn Ala Met Thr Val Asp Ser Leu Phe Leu Gly Val Gly Gln Arg
                260                 265                 270
Tyr Asp Val Val Ile Glu Ala Asn Arg Thr Pro Gly Asn Tyr Trp Phe
            275                 280                 285
Asn Val Thr Phe Gly Gly Gly Leu Leu Cys Gly Gly Ser Arg Asn Pro
            290                 295                 300
Tyr Pro Ala Ala Ile Phe His Tyr Ala Gly Ala Pro Gly Gly Pro Pro
305                 310                 315                 320
Thr Asp Glu Gly Lys Ala Pro Val Asp His Asn Cys Leu Asp Leu Pro
                325                 330                 335
Asn Leu Lys Pro Val Val Ala Arg Asp Val Pro Leu Ser Gly Phe Ala
                340                 345                 350
Lys Arg Ala Asp Asn Thr Leu Asp Val Thr Leu Asp Thr Thr Gly Thr
                355                 360                 365
Pro Leu Phe Val Trp Lys Val Asn Gly Ser Ala Ile Asn Ile Asp Trp
370                 375                 380
Gly Arg Ala Val Val Asp Tyr Val Leu Thr Gln Asn Thr Ser Phe Pro
```

-continued

```
385                390                395                400
Pro Gly Tyr Asn Ile Val Glu Val Asn Gly Ala Asp Gln Trp Ser Tyr
            405                410                415

Trp Leu Ile Glu Asn Asp Pro Gly Ala Pro Phe Thr Leu Pro His Pro
            420                425                430

Met His Leu His Gly His Asp Phe Tyr Val Leu Gly Arg Ser Pro Asp
            435                440                445

Glu Ser Pro Ala Ser Asn Glu Arg His Val Phe Asp Pro Ala Arg Asp
            450                455                460

Ala Gly Leu Leu Ser Gly Ala Asn Pro Val Arg Arg Asp Val Ser Met
465                470                475                480

Leu Pro Ala Phe Gly Trp Val Val Leu Ser Phe Arg Ala Asp Asn Pro
            485                490                495

Gly Ala Trp Leu Phe His Cys His Ile Ala Trp His Val Ser Gly Gly
            500                505                510

Leu Gly Val Val Tyr Leu Glu Arg Ala Asp Asp Leu Arg Gly Ala Val
            515                520                525

Ser Asp Ala Asp Ala Asp Asp Leu Asp Arg Leu Cys Ala Asp Trp Arg
            530                535                540

Arg Tyr Trp Pro Thr Asn Pro Tyr Pro Lys Ser Asp Ser Gly Leu Lys
545                550                555                560

His Arg Trp Val Glu Glu Gly Glu Trp Leu Val Lys Ala
            565                570
```

LACCASE MUTANTS

CROSS-REFERENCE TO RELATED APPLICATIONS

This application claims priority under 35 U.S.C. 119 of Danish application nos. 1449/96 filed on Dec. 19, 1996, and 1021/97 filed on Sep. 8, 1997, and of U.S. provisional application no. 60/035,413 filed on Jan. 23, 1997, the contents of which are fully incorporated herein by reference.

FIELD OF THE INVENTION

The present invention relates to a method of designing laccase mutants with improved stability properties, which method is based on the hitherto unknown three-dimensional structure of laccases.

BACKGROUND OF THE INVENTION

Laccase is a polyphenol oxidase (EC 1.10.3.2) which catalyses the oxidation of a variety of inorganic and aromatic compounds, particularly phenols, with the concomitant reduction of molecular oxygen to water.

Laccase belongs to a family of blue copper-containing oxidases which includes ascorbate oxidase and the mammalian plasma protein ceruloplasmin. All these enzymes are multi-copper-containing proteins.

Because laccases are able to catalyze the oxidation of a variety of inorganic and aromatic compounds, laccases have been suggested in many potential industrial applications such as lignin modification, paper strengthening, dye transfer inhibition in detergents, phenol polymerization, hair colouring, and waste water treatment. A major problem with the use of laccases are their poor storage stability at temperatures above room temperature, especially at 40° C.

In Example 1 of the present application we have tested the stability of various laccases at 40° C., and it can be seen that after 2 weeks of storage the laccase activity is down to less than 50% of the initial value, and at low pH the laccase activity after 2 weeks is zero. For many purposes such a decrease is unacceptable, so it is the purpose of the present invention to create laccase variants with improved stability by using the information of a three-dimensional structure of a *Coprinus cinereus* laccase. No three-dimensional structural information has been available for a laccase before.

BRIEF DISCLOSURE OF THE INVENTION

The three-dimensional structure of a laccase has now been elucidated. On the basis of an analysis of said structure it is possible to identify structural parts or specific amino acid residues which from structural or functional considerations appear to be important for the stability of a laccase.

Furthermore, when comparing the three-dimensional structure of the Coprinus laccase structure with known amino acid sequences of various laccases, it has been found that some similarities exist between the sequences. The present invention is based on these findings.

Accordingly, in a first aspect the invention relates to a method of constructing a variant of a parent Coprinus laccase, which variant has laccase activity and improved stability as compared to said parent laccase, which method comprises i) analysing the three-dimensional structure of the parent Coprinus laccase to identify at least one amino acid residue or at least one structural part of the Coprinus laccase structure, which amino acid residue or structural part is believed to be of relevance for altering the stability of the parent Coprinus laccase (as evaluated on the basis of structural or functional considerations), ii) constructing a Coprinus laccase variant, which as compared to the parent Coprinus laccase, has been modified in the amino acid residue or structural part identified in i) so as to alter the stability, and, optionally, iii) testing the resulting Coprinus laccase variant with respect to stability.

In a second aspect the present invention relates to a method of constructing a variant of a parent Coprinus-like laccase, which variant has laccase activity and improved stability as compared to said parent laccase, which method comprises i) comparing the three-dimensional amino acid structure of the Coprinus laccase with an amino acid sequence of a Coprinus-like laccase, ii) identifying a part of the Coprinus-like laccase amino acid sequence which is different from the Coprinus laccase amino acid sequence and which from structural or functional considerations is contemplated to be responsible for differences in the stability of the Coprinus and Coprinus-like laccase, iii) modifying the part of the Coprinus-like laccase identified in ii) whereby a Coprinus-like laccase variant is obtained, which has an improved stability as compared to the parent Coprinus-like laccase, and optionally, iv) testing the resulting Coprinus-like laccase variant with respect to stability.

In still further aspects the invention relates to variants of a Coprinus laccase and of Coprinus-like laccases, DNA encoding such variants and methods of preparing the variants. Finally, the invention relates to the use of the variants for various industrial purposes.

DETAILED DISCLOSURE OF THE INVENTION

The Coprinus-like laccases

A number of laccases produced by different fungi are homologous on the amino acid level. For instance, when using the homology percent obtained from UWGCG program using the GAP program with the default parameters (penalties: gap weight=3.0, length weight=0.1; WISCONSIN PACKAGE Version 8.1-UNIX, August 1995, Genetics Computer Group, 575 Science Drive, Madison, Wis., USA 53711) the following homology was found:

*Coprinus cinereus* laccase comprising the amino acid sequence shown in SEQ ID No. 1:100%;

*Polyporus pinsitus* (I) laccase comprising the amino acid sequence shown in SEQ ID No. 2:74.4%;

*Polyporus pinsitus* (II) laccase comprising the amino acid sequence shown in SEQ ID No. 3: 73.8%;

*Phlebia radiata* laccase comprising the amino acid sequence shown in SEQ ID No. 4:69.9% ;

*Rhizoctonia solani* (I) laccase comprising the amino acid sequence shown in SEQ ID No. 5:64.8%;

*Rhizoctonia solani* (II) laccase comprising the amino acid sequence shown in SEQ ID No. 6:63.0%;

*Rhizoctonia solani* (III) laccase comprising the amino acid sequence shown in SEQ ID No. 7:61.0%;

*Rhizoctonia solani* (IV) laccase comprising the amino acid sequence shown in SEQ ID No. 8:59.7%;

*Scytalidium thermophilum* laccase comprising the amino acid sequence shown in SEQ ID No. 9:57.4%;

*Myceliophthora thermophila* laccase comprising the amino acid sequence shown in SEQ ID No. 10:56.5%.

Because of the homology found between the above mentioned laccases, they are considered to belong to the same class of laccases, namely the class of n"Coprinus-like laccases".

Accordingly, in the present context, the term "Coprinus-like laccase" is intended to indicate a laccase which, on the amino acid level, displays a homology of at least 50% and less than 100% to the *Coprinus cinereus* laccase SEQ ID NO 1, or at least 55% and less than 100% to the *Coprinus cinereus* laccase SEQ ID NO 1, or at least 60% and less than 100% to the *Coprinus cinereus* accase SEQ ID NO 1, or at least 65% and less than 100% to the *Coprinus cinereus* laccase SEQ ID NO 1, or at least 70% and less than 100% to the *Coprinus cinereus* laccase SEQ ID NO 1, or at least 75% and less than 100% to the *Coprinus cinereus* laccase SEQ ID NO 1, or at least 80% and less than 100% to the *Coprinus cinereus* laccase SEQ ID NO 1, or at least 85% and less than 100% to the *Coprinus cinereus* laccase SEQ ID NO 1, or at least 90% and less than 100% to the *Coprinus cinereus* laccase SEQ ID NO 1, or at least 95% and less than 100% to the *Coprinus cinereus* laccase SEQ ID NO 1.

In the present context, "derived from" is intended not only to indicate a laccase produced or producible by a strain of the organism in question, but also a laccase encoded by a DNA sequence isolated from such strain and produced in a host organism containing said DNA sequence. Finally, the term is intended to indicate a laccase which is encoded by a DNA sequence of synthetic and/or cDNA origin and which has the identifying characteristics of the laccase in question.

The three-dimensional Coprinus laccase structure

The Coprinus laccase which was used to elucidate the three-dimensional structure forming the basis for the present invention consists of the 539 amino acids derived from *Coprinus cinereus* laccase IFO 8371 as disclosed in sequence ID No. 1.

The obtained three-dimensional structure is believed to be representative for the structure of any Coprinus-like laccase.

The structure of the laccase was solved in accordance with the principle for X-ray crystallographic methods given in "X-Ray Structure Determination", Stout, G. K. and Jensen, L. H., John Wiley & Sons, inc. N.Y., 1989. The structural coordinates for the solved crystal structure of the laccase at 2.2 Å resolution using the isomorphous replacement method are given in a standard PDB format (Brookhaven Protein Data Base) in Appendix 1. It is to be understood that Appendix 1 forms part of the present application.

In Appendix 1 the amino acid residues of the enzyme are identified by three-letter amino acid code (capitalized letters).

The laccase structure is made up of three plastocyanin-like domains. These three domains all have a similar beta-barrel fold.

3 copper atoms were observed in the three-dimensional structure:

The so-called type 1 copper ion is coordinated by two histidines and one cysteine.

The so-called type 2 copper of the trinuclear centre is missing in the structure disclosed in the present application.

The so-called type 3 copper consists of two type 3 copper atoms (pair of copper atoms) bound to a total of 6 histidine ligands.

When comparing the amino acid sequence of the crystallized three-dimensional structure with *Coprinus cinereus* amino acid sequence ID No. 1 the following four differences are observed: 18 amino acids are missing from the N-terminal of the crystallized protein;

17 amino acids are missing from the C-terminal of the crystallized protein;

Q19 in sequence ID No. 1 is an A1 in the crystallized protein; and

Q243 in sequence ID No. 1 is an E225 in the crystallized protein.

Generality of structure

Because of the homology between the Coprinus laccase and the various Coprinus-like laccases, the solved structure defined by the coordinates of Appendix 1 is believed to be representative for the structure of all Coprinus-like laccases.

A model structure of Coprinus-like laccases may be built on the basis of the coordinates given in Appendix 1 adapted to the laccase in question by use of an alignment between the respective amino acid sequences.

The above identified structurally characteristic parts of the Coprinus laccase structure may be identified in other Coprinus-like laccases on the basis of a model (or solved) structure of the relevant Coprinus-like laccase or simply on the basis of an alignment between the amino acid sequence of the Coprinus-like laccase in question with that of the Coprinus laccase used herein for identifying the amino acid residues of the respective structural elements.

Furthermore, in connection with Coprinus laccase variants of the invention, which are defined by modification of specific amino acid residues of the parent Coprinus laccase, it will be understood that variants of Coprinus-like laccases modified in an equivalent position (as determined from the best possible amino acid sequence alignment between the respective sequences) are intended to be covered as well.

Methods of the invention for design of novel laccase variants

The analysis or comparison performed in step i) of the methods of the invention may be performed by use of any suitable computer programme capable of analysing and/or comparing amino acid sequences.

The structural part which is identified in step i) of the methods of the invention may be composed of one amino acid residue. However, normally the structural part comprises more than one amino acid residue, typically constituting one of the above mentioned parts of the Coprinus structure such as one of the copper centres.

According to the invention useful laccase variants may be modified in one or more amino acid residues present within 15 Å from any copper ion, preferably variants which are modified within 10 Å from any copper ion, in particular variants which are modified within 5 Å from any copper ion.

Determination of residues within 5Å, 10Å and 15Å from the copper ions in the three-dimensional structure: The coordinates from the appendix are read into INSIGHT program provided by BIOSYM technologies. The spatial coordinates are presented showing the bonds between the atoms. The copper atoms are presented as well as the water atoms. The program package contains a part which can be used for creating subsets. This part is used for creating a 5Å, 10Å and 15Å subset around all Cu-ions present in the structure (the command ZONE is used). The found subsets contain all residues having an atom within 5, 10 20 and 15Å from any of the Cu-ions present in the structure. All residues having an atom within this subset are compiled and written out by the LIST MOLECULE command.

The amino acid residues found in this way within a distance of 15 Å from a copper ion in the *Coprinus cinereus* laccase are the following (SEQ ID No 1 numbering):
M27, V46, G51, P52, I54, L64, L76, T79, S80, I81, H82, W83, H84, G85, L86, F87, Q88, R89, T91, N92, W93, A94, D95, G96, A97, D98, G99, V100, N101, Q102, C103, P104, Y113, F115, H120, G122, T123, F124, W125, Y126, H127, S128, H129, F130, G131, T132, Q133, Y134, 30 C135, D136, G137, L138, R139, G140, P141, M142, V143, I144, I164, T165, L166, A167, D168, H170, G179, A180, A181, Q182, P183, L217, I218, S219, L220, S221, C222, D223, P224, N225, W226, E239, V240, D241, G242, Q243, Q254, I255, F256, T257, G258, Q259, R260, Y261, N281, K282, F349, Q350, L351, G352, F353, S354, G356, R357, F358, T359, I360, N361, T363, A364, Y365, E366, S367, P368, P371, T372, L373, P388, S391, V392, L403, V404, V405, P406, A407, G408, V409, L410, G411, G412, P413, H414, P415, F416, H417, L418, H419, G420, H421, A422, F423, A429, K441, R442, D443, V444, V445, S446, L447, G448, V449, T450, D452, V454, I456, F458, N462, G464, P465, W466, F467, F468, H469, C470, H471, I472, E473, F474, H475, L476, M477, N478, G479, L480, A481, I482, V483, F484, A485, E486.

The amino acid residues found within a distance of 10 Å from a copper ion in the *Coprinus cinereus* laccase (SEQ ID No 1) are the following:
S80, I81, H82, W83, H84, G85, L86, D95, G96, A97, D98, V100, N101, F124, W125, Y126, H127, S128, H129, F130, G131, Y134, L138, R139, G140, I218, S219, L220, S221, C222, D223, P224, D241, F256, T257, G258, Q259, R260, K282, L351, G352, F353, F358, T359, V405, V409, L410, G411, G412, P413, H414, P415, F416, H417, L418, H419, G420, D443, V444, V445, S446, L447, G448, V454, I456, F458, W466, F467, F468, H469, C470, H471, I472, E473, F474, H475, L476, M477, N478, G479, L480, A481, I482.

The amino acid residues found within a distance of 5 Å from a copper ion in the *Coprinus cinereus* laccase (SEQ ID No 1) are the following:
H82, H84, W125, H127, H129, G411, H414, P415, H417, H419, F467, H469, C470, H471, I472, H475, L480.

The 15Å/10Å/5Å regions can be found in other laccases by comparison of the modelled structures or by taking the sequence homology numbers.

Modifications

The modification of an amino acid residue or structural part is typically accomplished by suitable modifications of a DNA sequence encoding the parent enzyme in question. The term "modified" as used in the methods according to the invention is intended to have the following meaning: When used in relation to an amino acid residue the term is intended to mean replacement of the amino acid residue in question with another amino acid residue. When used in relation to a structural part, the term is intended to mean: replacement of one or more amino acid residues of said structural part with other amino acid residues, or addition of one or more amino acid residues to said part, or deletion of one or more amino acid residues of said structural part.

The construction of the variant of interest is accomplished by cultivating a microorganism comprising a DNA sequence encoding the variant under conditions which are conducive for producing the variant, and optionally subsequently recovering the variant from the resulting culture broth. This is described in detail further below.

Variants with altered stability

It is contemplated that it is possible to improve the stability of a parent Coprinus laccase or a parent Coprinus-like laccase, wherein said variant is the result of a mutation, i.e. one or more amino acid residues having been deleted from, replaced or added to the parent laccase, the stability test performed as described below.

Preferred positions for mutations are the following:

| MtL: | StL: | CcL: | PpL1: | PpL2: | PrL: | RsL4: | RsL1: | RsL2: | RsL3: |
|------|------|------|-------|-------|------|-------|-------|-------|-------|
| M433 | M483 | — | — | — | — | — | — | — | — |
| W373 | W422 | — | — | — | — | W411 | W411 | W439 | — |
| W136 | W181 | W125 | W107 | W107 | W128 | W125 | W125 | W125 | W126 |
| Y145 | Y190 | Y134 | Y116 | Y116 | Y137 | Y134 | Y134 | Y134 | Y135 |
| M480 | M530 | — | — | — | — | — | — | — | — |
| Y137 | Y182 | Y126 | Y108 | Y108 | Y129 | Y126 | Y126 | Y126 | Y127 |
| Y176 | Y221 | Y170 | Y152 | Y152 | Y137 | Y170 | Y169 | Y170 | Y171 |
| M254 | M300 | — | — | — | — | — | — | — | — |
| — | — | M75 | M57 | M57 | M78 | M75 | M75 | M75 | M76 |
| — | — | M477 | — | | | | | | |
| | | | | M328 | | | | | |
| — | M313 | — | — | | | | | | |
| W507, | | | | | | | | | | wherein
CcL: *Coprinus cinereus* laccase comprising the amino acid sequence shown in SEQ ID No. 1;
PpL1: *Polyporus pinsitus* (I) laccase comprising the amino acid sequence shown in SEQ ID No. 2;
PpL2: *Polyporus pinsitus* (II) laccase comprising the amino acid sequence shown in SEQ ID No. 3;
PrL: *Phlebia radiata* laccase comprising the amino acid sequence shown in SEQ ID No. 4;
RsL3: *Rhizoctonia solani* (I) laccase comprising the amino acid sequence shown in SEQ ID No. 5;
RsL2: *Rhizoctonia solani* (II) laccase comprising the amino acid sequence shown in SEQ ID No. 6;
RsL4: *Rhizoctonia solani* (III) laccase comprising the amino acid sequence shown in SEQ ID No. 7;
RsL1: *Rhizoctonia solani* (IV) laccase comprising the amino acid sequence shown in SEQ ID No. 8;
StL: *Scytalidium thermophilum* laccase comprising the amino acid sequence shown in SEQ ID No. 9; and
MtL: *Myceliophthora thermophila* laccase comprising the amino acid sequence shown in SEQ ID No. 10.

The above shown rows have homologous positions. (–) or ( )=not present in this laccase.

The following variants are preferred:

A variant of a parent Coprinus laccase, which comprises one or more of the following substitutions in SEQ ID No. 1:

| W125 | A, | V, | L, | I, | P, | F, | M, | G, | S, | T, | C, | Y, | N, | Q, | D, | E, | K, | R, | H; |
|------|----|----|----|----|----|----|----|----|----|----|----|----|----|----|----|----|----|----|----|
| Y134 | A, | V, | L, | I, | P, | F, | W, | G, | S, | T, | C, | M, | N, | Q, | D, | E, | K, | R, | H; |
| Y126 | A, | V, | L, | I, | P, | F, | W, | G, | S, | T, | C, | M, | N, | Q, | D, | E, | K, | R, | H; |
| Y170 | A, | V, | L, | I, | P, | F, | W, | G, | S, | T, | C, | M, | N, | Q, | D, | E, | K, | R, | H; |
| M75  | A, | V, | L, | I, | P, | F, | W, | G, | S, | T, | C, | Y, | N, | Q, | D, | E, | K, | R, | H; |
| M477 | A, | V, | L, | I, | P, | F, | W, | G, | S, | T, | C, | Y, | N, | Q, | D, | E, | K, | R, | H. |

In particular a variant of a parent Coprinus laccase, which comprises one or more of the following substitutions in SEQ ID No. 1:

A variant of a parent *Polyporus pinsitus* (I) laccase, which comprises a mutation in a position corresponding to at least one of the following positions in SEQ ID No. 2:

| | | | | | | | | | | | | | | | | | | |
|---|---|---|---|---|---|---|---|---|---|---|---|---|---|---|---|---|---|---|
| W125 | F, H; | | | | | | | | | | | | | | | | | |
| Y134 | F; | | | | | | | | | | | | | | | | | |
| Y126 | F; | | | | | | | | | | | | | | | | | |
| Y170 | F; | | | | | | | | | | | | | | | | | |
| M75 | F, V, I, L, Q; | | | | | | | | | | | | | | | | | |
| M477 | F, V, I, L, Q. | | | | | | | | | | | | | | | | | |

In particular a variant of a parent *Polyporus pinsitus* (I) laccase, which comprises a mutation in a position corresponding to at least one of the following positions in SEQ ID No. 2:

| | | | | | | | | | | | | | | | | | | |
|---|---|---|---|---|---|---|---|---|---|---|---|---|---|---|---|---|---|---|
| W107 | F, H; | | | | | | | | | | | | | | | | | |
| Y116 | F; | | | | | | | | | | | | | | | | | |
| Y108 | F; | | | | | | | | | | | | | | | | | |
| Y152 | F; | | | | | | | | | | | | | | | | | |
| M57 | F, V, I, L, Q; | | | | | | | | | | | | | | | | | |
| M328 | F, V, I, L, Q. | | | | | | | | | | | | | | | | | |

A variant of a parent *Polyporus pinsitus* (II) laccase, which comprises a mutation in a position corresponding to at least one of the following positions in SEQ ID No. 3:

| | | | | | | | | | | | | | | | | | | |
|---|---|---|---|---|---|---|---|---|---|---|---|---|---|---|---|---|---|---|
| W107 | A, | V, | L, | I, | P, | F, | M, | G, | S, | T, | C, | Y, | N, | Q, | D, | E, | K, | R, | H; |
| Y116 | A, | V, | L, | I, | P, | F, | W, | G, | S, | T, | C, | M, | N, | Q, | D, | E, | K, | R, | H; |
| Y108 | A, | V, | L, | I, | P, | F, | W, | G, | S, | T, | C, | M, | N, | Q, | D, | E, | K, | R, | H; |
| Y152 | A, | V, | L, | I, | P, | F, | W, | G, | S, | T, | C, | M, | N, | Q, | D, | E, | K, | R, | H; |
| M57 | A, | V, | L, | I, | P, | F, | W, | G, | S, | T, | C, | Y, | N, | Q, | D, | E, | K, | R, | H. |

In particular a variant of a parent *Polyporus pinsitus* (II) laccase, which comprises a mutation in a position corresponding to at least one of the following positions in SEQ ID No. 3:

A variant of a parent *Phlebia radiata* laccase, which comprises a mutation in a position corresponding to at least one of the following positions in SEQ ID No. 4:

| | | | | | | | | | | | | | | | | | | |
|---|---|---|---|---|---|---|---|---|---|---|---|---|---|---|---|---|---|---|
| W107 | F, H; | | | | | | | | | | | | | | | | | |
| Y116 | F; | | | | | | | | | | | | | | | | | |
| Y108 | F; | | | | | | | | | | | | | | | | | |
| Y152 | F; | | | | | | | | | | | | | | | | | |
| M57 | F, V, I, L, Q. | | | | | | | | | | | | | | | | | |

| | | | | | | | | | | | | | | | | | | |
|---|---|---|---|---|---|---|---|---|---|---|---|---|---|---|---|---|---|---|
| W107 | A, | V, | L, | I, | P, | F, | M, | G, | S, | T, | C, | Y, | N, | Q, | D, | E, | K, | R, | H; |
| Y116 | A, | V, | L, | I, | P, | F, | W, | G, | S, | T, | C, | M, | N, | Q, | D, | E, | K, | R, | H; |
| Y108 | A, | V, | L, | I, | P, | F, | W, | G, | S, | T, | C, | M, | N, | Q, | D, | E, | K, | R, | H; |
| Y152 | A, | V, | L, | I, | P, | F, | W, | G, | S, | T, | C, | M, | N, | Q, | D, | E, | K, | R, | H; |
| M57 | A, | V, | L, | I, | P, | F, | W, | G, | S, | T, | C, | Y, | N, | Q, | D, | E, | K, | R, | H; |
| M328 | A, | V, | L, | I, | P, | F, | W, | G, | S, | T, | C, | Y, | N, | Q, | D, | E, | K, | R, | H. |

| | | | | | | | | | | | | | | | | | | |
|---|---|---|---|---|---|---|---|---|---|---|---|---|---|---|---|---|---|---|
| W128 | A, | V, | L, | I, | P, | F, | M, | G, | S, | T, | C, | Y, | N, | Q, | D, | E, | K, | R, | H; |
| Y137 | A, | V, | L, | I, | P, | F, | W, | G, | S, | T, | C, | M, | N, | Q, | D, | E, | K, | R, | H; |
| Y129 | A, | V, | L, | I, | P, | F, | W, | G, | S, | T, | C, | M, | N, | Q, | D, | E, | K, | R, | H; |
| Y137 | A, | V, | L, | I, | P, | F, | W, | G, | S, | T, | C, | M, | N, | Q, | D, | E, | K, | R, | H; |
| M78 | A, | V, | L, | I, | P, | F, | W, | G, | S, | T, | C, | Y, | N, | Q, | D, | E, | K, | R, | H. |

In particular a variant of a parent *Phlebia radiata* laccase, which comprises a mutation in a position corresponding to at least one of the following positions in SEQ ID No. 4:

| | |
|---|---|
| W128 | F, H; |
| Y137 | F; |
| Y129 | F; |
| Y137 | F; |
| M78 | F, V, I, L, Q. |

A variant of a parent *Rhizoctonia solani* (I) laccase, which comprises a mutation in a position corresponding to at least one of the following positions in SEQ ID No. 5:

| | | | | | | | | | | | | | | | | | | |
|---|---|---|---|---|---|---|---|---|---|---|---|---|---|---|---|---|---|---|
| W126 | A, | V, | L, | I, | P, | F, | M, | G, | S, | T, | C, | Y, | N, | Q, | D, | E, | K, | R, | H; |
| Y135 | A, | V, | L, | I, | P, | F, | W, | G, | S, | T, | C, | M, | N, | Q, | D, | E, | K, | R, | H; |
| Y127 | A, | V, | L, | I, | P, | F, | W, | G, | S, | T, | C, | M, | N, | Q, | D, | E, | K, | R, | H; |
| Y171 | A, | V, | L, | I, | P, | F, | W, | G, | S, | T, | C, | M, | N, | Q, | D, | E, | K, | R, | H; |
| M76 | A, | V, | L, | I, | P, | F, | W, | G, | S, | T, | C, | Y, | N, | Q, | D, | E, | K, | R, | H. |

In particular a variant of a parent *Rhizoctonia solani* (I) laccase, which comprises a mutation in a position corresponding to at least one of the following positions in SEQ ID No. 5:

| | |
|---|---|
| W126 | F, H; |
| Y135 | F; |
| Y127 | F; |
| Y171 | F; |
| M76 | F, V, I, L, Q. |

A variant of a parent *Rhizoctonia solani* (II) laccase, which comprises a mutation in a position corresponding to at least one of the following positions in SEQ ID No. 6:

| | | | | | | | | | | | | | | | | | | |
|---|---|---|---|---|---|---|---|---|---|---|---|---|---|---|---|---|---|---|
| W439 | A, | V, | L, | I, | P, | F, | M, | G, | S, | T, | C, | Y, | N, | Q, | D, | E, | K, | R, | H; |
| W125 | A, | V, | L, | I, | P, | F, | M, | G, | S, | T, | C, | Y, | N, | Q, | D, | E, | K, | R, | H; |
| Y134 | A, | V, | L, | I, | P, | F, | W, | G, | S, | T, | C, | M, | N, | Q, | D, | E, | K, | R, | H; |
| Y126 | A, | V, | L, | I, | P, | F, | W, | G, | S, | T, | C, | M, | N, | Q, | D, | E, | K, | R, | H; |
| Y170 | A, | V, | L, | I, | P, | F, | W, | G, | S, | T, | C, | M, | N, | Q, | D, | E, | K, | R, | H; |
| M75 | A, | V, | L, | I, | P, | F, | W, | G, | S, | T, | C, | Y, | N, | Q, | D, | E, | K, | R, | H. |

In particular a variant of a parent *Rhizoctonia solani* (II) laccase, which comprises a mutation in a position corre-sponding to at least one of the following positions in SEQ ID No. 6:

| | |
|---|---|
| W439 | F, H; |
| W125 | F, H; |
| Y134 | F; |
| Y126 | F; |
| Y170 | F; |
| M75 | F, V, I, L, Q. |

A variant of a parent *Rhizoctonia solani* (III) laccase, which comprises a mutation in a position corresponding to at least one of the following positions in SEQ ID No. 7:

| | | | | | | | | | | | | | | | | | | |
|---|---|---|---|---|---|---|---|---|---|---|---|---|---|---|---|---|---|---|
| W411 | A, | V, | L, | I, | P, | F, | M, | G, | S, | T, | C, | Y, | N, | Q, | D, | E, | K, | R, | H; |
| W125 | A, | V, | L, | I, | P, | F, | M, | G, | S, | T, | C, | Y, | N, | Q, | D, | E, | K, | R, | H; |
| Y134 | A, | V, | L, | J, | P, | F, | W, | G, | S, | T, | C, | M, | N, | Q, | D, | E, | K, | R, | H; |
| Y126 | A, | V, | L, | I, | P, | F, | W, | G, | S, | T, | C, | M, | N, | Q, | D, | E, | K, | R, | H; |
| Y170 | A, | V, | L, | I, | P, | F, | W, | G, | S, | T, | C, | M, | N, | Q, | D, | E, | K, | R, | H; |
| M75 | A, | V, | L, | I, | P, | F, | W, | G, | S, | T, | C, | Y, | N, | Q, | D, | E, | K, | R, | H. |

In particular a variant of a parent Rhizoctonia solani (III) laccase, which comprises a mutation in a position corresponding to at least one of the following positions in SEQ ID No. 7:

| | |
|---|---|
| W411 | F, H; |
| W125 | F, H; |
| Y134 | F; |
| Y126 | F; |
| Y170 | F; |
| M75 | F, V, I, L,

| M433 | A, | V, | L, | I, | P, | F, | W, | G, | S, | T, | C, | Y, | N, | Q, | D, | E, | K, | R, | H; |
|------|----|----|----|----|----|----|----|----|----|----|----|----|----|----|----|----|----|----|----|
| W373 | A, | V, | L, | I, | P, | F, | M, | G, | S, | T, | C, | Y, | N, | Q, | D, | E, | K, | R, | H; |
| W136 | A, | V, | L, | I, | P, | F, | M, | G, | S, | T, | C, | Y, | N, | Q, | D, | E, | K, | R, | H; |
| Y145 | A, | V, | L, | I, | P, | F, | W, | G, | S, | T, | C, | M, | N, | Q, | D, | E, | K, | R, | H; |
| M480 | A, | V, | L, | I, | P, | F, | W, | G, | S, | T, | C, | Y, | N, | Q, | D, | E, | K, | R, | H; |
| Y137 | A, | V, | L, | I, | P, | F, | W, | G, | S, | T, | C, | M, | N, | Q, | D, | E, | K, | R, | H; |
| Y176 | A, | V, | L, | I, | P, | F, | W, | G, | S, | T, | C, | M, | N, | Q, | D, | E, | K, | R, | H; |
| M254 | A, | V, | L, | I, | P, | F, | W, | G, | S, | T, | C, | Y, | N, | Q, | D, | E, | K, | R, | H; |

In particular a variant of a parent *Myceliophthora thermophila* laccase, which comprises a mutation in a position corresponding to at least one of the following positions in SEQ ID No. 10:

```
M433 F, V, I, L, Q;
W373 F, H;
W136 F, H;
Y145 F;
M480 F, V, I, L, Q;
Y137 F;
Y176 F;
M254 F, V, I, L, Q.
```

Methods of preparing laccase variants

Several methods for introducing mutations into genes are known in the art. After a brief discussion of the cloning of laccase-encoding DNA sequences, methods for generating mutations at specific sites within the laccase-encoding sequence will be discussed.

Cloning a DNA sequence encoding a laccase

The DNA sequence encoding a parent laccase may be isolated from any cell or microorganism producing the laccase in question, using various methods well known in the art. First, a genomic DNA and/or cDNA library should be constructed using chromosomal DNA or messenger RNA from the organism that produces the laccase to be studied. Then, if the amino acid sequence of the laccase is known, homologous, labelled oligonucleotide probes may be synthesized and used to identify laccase-encoding clones from a genomic library prepared from the organism in question. Alternatively, a labelled oligonucleotide probe containing sequences homologous to a known laccase gene could be used as a probe to identify laccase-encoding clones, using hybridization and washing conditions of lower stringency.

A method for identifying laccase-encoding clones involves inserting cDNA into an expression vector, such as a plasmid, transforming laccase-negative fungi with the resulting cDNA library, and then plating the transformed fungi onto agar containing a substrate for laccase, thereby allowing clones expressing the laccase to be identified.

Alternatively, the DNA sequence encoding the enzyme may be prepared synthetically by established standard methods, e.g. the phosphoroamidite method. In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers.

Site-directed mutagenesis

Once a laccase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the laccase-encoding sequence, is created in a vector carrying the laccase gene. Then the synthetic nucleotide, bearing the desired mutation, is annealed to a homologous portion of the single-stranded DNA. The remaining gap is then filled in with T7 DNA polymerase and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method of introducing mutations into laccase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random mutagenesis

The random mutagenesis of a DNA sequence encoding a parent laccase may conveniently be performed by use of any method known in the art.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents.

The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the laccase enzyme by any published technique, using e.g. PCR, LCR or any DNA polymerase and ligase.

When PCR-generated mutagenesis is used, either a chemically treated or non-treated gene encoding a parent laccase enzyme is subjected to PCR under conditions that increase the mis-incorporation of nucleotides (Deshler 1992; Leung et al., Technique, Vol.1, 1989, pp. 11–15).

A mutator strain of *E. coli* (Fowler et al., Molec. Gen. Genet., 133, 1974, pp. 179–191), *S. cereviseae* or any other microbial organism may be used for the random mutagenesis of the DNA encoding the laccase enzyme by e.g. transforming a plasmid containing the parent enzyme into the mutator strain, growing the mutator strain with the plasmid and isolating the mutated plasmid from the mutator strain. The mutated plasmid may subsequently be transformed into the expression organism.

The DNA sequence to be mutagenized may conveniently be present in a genomic or cDNA library prepared from an organism expressing the parent laccase enzyme. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to the expression step or the screening step being performed. Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenizing agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are fungal hosts such as *Aspergillus niger* or *Aspergillus oryzae*.

The mutated DNA sequence may further comprise a DNA sequence encoding functions permitting expression of the mutated DNA sequence.

Localized random mutagenesis

The random mutagenesis may advantageously be localized to a part of the parent laccase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized random mutagenesis is conveniently performed by use of PCR-generated mutagenesis techniques as described above or any other suitable technique known in the art.

Alternatively, the DNA sequence encoding the part of the DNA sequence to be modified may be isolated, e.g. by being inserted into a suitable vector, and said part may subsequently be subjected to mutagenesis by use of any of the mutagenesis methods discussed above.

With respect to the screening step in the above-mentioned method of the invention, this may conveniently be performed by use of aa filter assay based on the following principle:

A microorganism capable of expressing the mutated laccase enzyme of interest is incubated on a suitable medium and under suitable conditions for the enzyme to be secreted, the medium being provided with a double filter comprising a first protein-binding filter and on top of that a second filter exhibiting a low protein binding capability. The microorganism is located on the second filter. Subsequent to the incubation, the first filter comprising enzymes secreted from the microorganisms is separated from the second filter comprising the microorganisms. The first filter is subjected to screening for the desired enzymatic activity and the corresponding microbial colonies present on the second filter are identified.

The filter used for binding the enzymatic activity may be any protein binding filter e.g. nylon or nitrocellulose. The top filter carrying the colonies of the expression organism may be any filter that has no or low affinity for binding proteins e.g. cellulose acetate or Durapore™. The filter may be pretreated with any of the conditions to be used for screening or may be treated during the detection of enzymatic activity.

The enzymatic activity may be detected by a dye, fluorescence, precipitation, pH indicator, IR-absorbance or any other known technique for detection of enzymatic activity.

The detecting compound may be immobilized by any immobilizing agent, e.g., agarose, agar, gelatine, polyacrylamide, starch, filter paper, cloth; or any combination of immobilizing agents.

Testing of variants of the invention

The storage stability of Coprinus variants or Coprinus-like variants should be investigated at 40° C. for 2 weeks at pH 5, 8 and 9.3, respectively. The stability of the parent laccase and the variants may be tested both in a liquid buffer formulation and in a lyophilized form.

According to the invention the residual activity of the variants following two weeks of incubation are then compared to the residual activity of the parent laccase, and variants with an improved stability at either pH 5, 8 or 9.3 are selected.

Laccase activity

In the context of this invention, the laccase activity was measured using 10-(2-hydroxyethyl)-phenoxazine (HEPO) as substrate for the various laccases. HEPO was synthesized using the same procedure as described for 10-(2-hydroxyethyl)-phenothiazine, (G. Cauquil in Bulletin de la Society Chemique de France, 1960, p. 1049). In the presence of oxygen laccases (E.C. 1.10.3.2) oxidize HEPO to a HEPO radical that can be monitored photometrically at 528 nm.

The *Coprinus cinereus* laccase was measured using 0.4 mM HEPO in 50 mM sodium acetate, pH 5.0, 0.05% TWEEN-20 at 30° C. The absorbance at 528 nm was followed for 200 s and the rate calculated from the linear part of the progress curve.

The *Myceliophthora thermophila* laccase was measured using 0.4 mM HEPO in 25 mM Tris-HCl, pH 7.5, 0.05% Tween-20 at 30° C. The absorbance at 528 nm was followed for 200 s and the rate calculated from the linear part of the progress curve.

The *Polyporus pinsitus* laccase was measured using 0.4 mM HEPO in 50 mM MES-NaOH, pH 5.5. The absorbance at 528 nm was followed for 200 s and the rate calculated from the linear part of the progress curve.

Expression of laccase variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding a laccase variant of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding a laccase variant of the invention, especially in a fungal host, are those derived from the gene encoding A. oryzae TAKA amylase, Rhizomucor miehei aspartic proteinase, A. niger neutral α-amylase, A. niger acid stable α-amylase, A. niger glucoamylase, Rhizomucor miehei lipase, A. oryzae alkaline protease, A. oryzae triose phosphate isomerase or A. nidulans acetamidase.

The expression vector of the invention may also comprise a suitable transcription terminator and, in eukaryotes, polyadenylation sequences operably connected to the DNA sequence encoding the laccase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMBI and pIJ702.

The vector may also comprise a selectable marker, e.g. a gene, the product of which complements a defect in the host cell, such as one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g. as described in WO 91/17243.

The procedures used to ligate the DNA construct of the invention encoding a laccase variant, the promoter, terminator and other elements, respectively, and to insert them into suitable vectors containing the information necessary for replication, are well known to persons skilled in the art (cf., for instance, Sambrook et al. (1989)).

The cell of the invention, either comprising a DNA construct or an expression vector of the invention as defined above, is advantageously used as a host cell in the recombinant production of a laccase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells. The cell of the invention may be a cell of a higher organism such as a mammal or an insect, but is preferably a microbial cell, e.g. a fungal cell.

The filamentous fungus may advantageously belong to a species of Aspergillus, e.g. Aspergillus oryzae or Aspergillus niger. Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method of producing a laccase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the laccase variant of the invention. Suitable media are available from commercial suppliers or may be prepared according to published recipes (e.g. as described in catalogues of the American Type Culture Collection).

The laccase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Industrial Applications

The laccase variants of this invention possesses valuable properties allowing for various industrial applications, in particular lignin modification, paper strengthening, dye transfer inhibition in detergents, phenol polymerization, hair dyeing, bleaching of textiles (in particular bleaching of denim as described in WO 96/12845 and WO 96/12846) and waste water treatment. Any detergent composition normally used for enzymes may be used, e.g., the detergent compositions disclosed in WO The invention is further illustrated in the following examples, which are not intended to be in any way limiting to the scope of the invention as claimed.

EXAMPLE 1

Storage stability of the wild type Myceliophthora thermophila and the Polyporus pinsitus laccases.

The storage stability of the Myceliophthora thermophila and the Polyporus pinsitus laccases was tested for 2 weeks at 40° C. at pH 5, 8 and 9.3, respectively.

The laccase (1 mg/ml) was dialyzed against 0.1 M sodium acetate, pH 5, or 0.1 M Tris-maleate, pH 8, or 0.1 M Tris-maleate, pH 9.3. Following dialysis the different preparations were poured into two sets of glass vials with screw caps: one for the liquid formulation and the other one for the lyophilized form. After two weeks of incubation the enzyme activity was measured as described above and the residual activity of the enzymes was calculated in percentage using a preparation of *Myceliophthora thermophila* and *Polyporus pinsitus* kept at 4° C. as references. The results are given below in Table 1 and 2.

TABLE 1

Storage stability of *Myceliophthora thermophila*

| | Liquid formulation | | Lyophilized form | |
|---|---|---|---|---|
| pH | Residual (%) | activity | Residual (%) | activity |
| 5.0 | <5 | | <5 | |
| 8.0 | <5 | | <5 | |
| 9.3 | 35 | | 30 | |

TABLE 2

Storage stability of *Polyporus pinsitus*

| | Liquid formulation | | Lyophilized form | |
|---|---|---|---|---|
| pH | Residual (%) | activity | Residual (%) | activity |
| 5.0 | <5 | | n.d. | |
| 8.0 | 35 | | n.d. | |
| 9.3 | n.d.* | | n.d. | |

*not determined

EXAMPLE 2
Homology building of the Polyporus pinsitus 3D-structure

Using sequence homology of *Coprinus cinereus* (CcL) to other sequences, e.g., *Polyporus pinsitus,* Coprinus-like 3 D-structures can be found.

In comparison with the *Coprinus cinereus,* used for elucidating the structure, *Polyporus pinsitus* differs in a number of residues. The model may be built using the HOMOLOGY program from BIOSYM. The program substitutes the amino acids in the *Coprinus cinereus* with amino acids from *Polyporus pinsitus* in the homologous positions defined in the program as structurally conserved regions (SCR). The residues in between are built using the LOOP option with GENERATE. Using these steps a crude model may be obtained which gives information of spatial interactions.

The structure can be refined using the method described in the HOMOLOGY package.

EXAMPLE 3
Storage stability of *Myceliophthora thermophila* variants Laccase activity:

In this Example the *Myceliophthora thermophila* laccase variants were measured using 0.4 mM HEPO in 0.1 M Tris-maleate, pH 7.5, 0.05% TWEEN-20 at 30° C. The absorbance at 528 nm was followed for 200 s and the rate calculated from the linear part of the progress curve.

The storage stability of the *Myceliophthora thermophila* variants were tested for 4 weeks at 40° C. at pH 5, 7, and 9.3, respectively. The laccase (1 mg/ml) was dialyzed against 0.1 M Tris-maleate, pH 5 or 0.1 M Tris-maleate, pH 7 or 0.1 M Tris-maleate, pH 9.3. Following dialysis the different preparations were poured into two set of glass vials with screw caps: one for the liquid formulation and the other set of glasses for lyophilization. Following two and four weeks of incubation the enzyme activity was measured as described above and the residual activity of the variants were calculated in percentage using a preparation kept at 4° C. as reference.

TABLE 3

Storage stability of *Myceliophthora thermophila* variants, lyophilized formulation

| | Residual activity, pH 5 | | Residual activity, pH 7 | | Residual activity, pH 9.2 | |
|---|---|---|---|---|---|---|
| | 2 weeks | 4 weeks | 2 weeks | 4 weeks | 2 weeks | 4 weeks |
| wt | 18 | 18 | 55 | 36 | 59 | 38 |
| W136F | <5 | <5 | 76 | 64 | 88 | 77 |
| Y137F | 12 | <5 | 58 | 41 | 64 | 49 |
| Y145F | <5 | <5 | 53 | 20 | 45 | 51 |
| W373F | 14 | 14 | 33 | 19 | 51 | 36 |
| M433I | 7 | <5 | 57 | 43 | 74 | 35 |
| M480L | 33 | 18 | 65 | 32 | 72 | 52 |
| W507F | 18 | <5 | 72 | 51 | 68 | 71 |

In lyophilized form none of the tested variants have improved stability at pH 5. At pH 7 and pH 9.2 both W136F and W507F have increased stability. At pH 9.2 M480L is also better than wt.

TABLE 4

Storage stability to *Myceliophthora thermophila* variants, liquid formulation

| | Residual activity, 5, 2 weeks | Residual pH activity, pH 7, 2 weeks | Residual activity, pH 9.2, 2 weeks |
|---|---|---|---|
| wt | <5 | 5 | 20 |
| W136F | 5 | 28 | 55 |
| Y137F | <5 | <5 | <5 |
| Y145F | <5 | <5 | <5 |
| W373F | <5 | 40 | <5 |
| M433I | 8 | 40 | 65 |
| M480L | <5 | <5 | 15 |
| W507F | <5 | <5 | 22 |

Also in the liquid formulation none of the tested variants have improved stability at pH 5. At pH 7 and pH 9.2 both W136F and M433I has increased stability. At pH7 W373F has better stability than wt but the variant looses the stability completely at pH 9.2.

Of the tested variants only W136F has increased stability in both formulations.

Appendix 1:
SEQRES 1 A 504 GLN ILE VAL ASN SER VAL ASP THR MET THR LEU THR ASN
SEQRES 2 A 504 ALA ASN VAL SER PRO ASP GLY PHE THR ARG ALA GLY ILE
SEQRES 3 A 504 LEU VAL ASN GLY VAL HIS GLY PRO LEU ILE ARG GLY GLY
SEQRES 4 A 504 LYS ASN ASP ASN PHE GLU LEU ASN VAL VAL ASN ASP LEU
SEQRES 5 A 504 ASP ASN PRO THR MET LEU ARG PRO THR SER ILE HIS TRP
SEQRES 6 A 504 HIS GLY LEU PHE GLN ARG GLY THR ASN TRP ALA ASN GLY
SEQRES 7 A 504 ALA ASP GLY VAL ASN GLN CYS PRO ILE SER PRO GLY HIS
SEQRES 8 A 504 ALA PHE LEU TYR LYS PHE THR PRO ALA GLY HIS ALA GLY
SEQRES 9 A 504 THR PHE TRP TYR HIS SER HIS PHE GLY THR GLN TYR CYS SEQRES 10 A 504 ASP GLY LEU ARG GLY PRO MET VAL ILE TYR
ASP ASP ASN
SEQRES 11 A 504 ASP PRO HIS ALA ALA LEU TYR ASP GLU ASP
ASP GLU ASN
SEQRES 12 A 504 THR ILE ILE THR LEU ALA ASP TRP TYR HIS
ILE PRO ALA
SEQRES 13 A 504 PRO SER ILE GLN GLY ALA ALA GLN PRO ASP
ALA THR LEU
SEQRES 14 A 504 ILE ASN GLY LYS GLY ARG TYR VAL GLY GLY
PRO ALA ALA
SEQRES 15 A 504 GLU LEU SER ILE VAL ASN VAL GLU GLN GLY
LYS LYS TYR
SEQRES 16 A 504 ARG MET ARG LEU ILE SER LEU SER CYS ASP
PRO ASN TRP
SEQRES 17 A 504 GLN PHE SER ILE ASP GLY HIS GLU LEU THR
ILE ILE GLU
SEQRES 18 A 504 VAL ASP GLY ASN LEU THR GLU PRO HIS THR
VAL ASP ARG
SEQRES 19 A 504 LEU GLN ILE PHE THR GLY GLN ARG TYR SER
PHE VAL LEU
SEQRES 20 A 504 ASP ALA ASN GLN PRO VAL ASP ASN TYR TRP
ILE ARG ALA
SEQRES 21 A 504 GLN PRO ASN LYS GLY ARG ASN GLY LEU ALA
GLY THR PHE
SEQRES 22 A 504 ALA ASN GLY VAL ASN SER ALA ILE LEU ARG
TYR ALA GLY
SEQRES 23 A 504 ALA ALA ASN ALA ASP PRO THR THR SER ALA
ASN PRO ASN
SEQRES 24 A 504 PRO ALA GLN LEU ASN GLU ALA ASP LEU HIS
ALA LEU ILE
SEQRES 25 A 504 ASP PRO ALA ALA PRO GLY ILE PRO THR PRO
GLY ALA ALA
SEQRES 26 A 504 ASN VAL ASN LEU ARG PHE GLN LEU GLY PHE
SER GLY GLY
SEQRES 27 A 504 ARG PHE THR ILE ASN GLY THR ALA TYR GLU
SER PRO SER
SEQRES 28 A 504 VAL PRO THR LEU LEU GLN ILE MET SER GLY
ALA GLN SER
SEQRES 29 A 504 ALA ASN ASP LEU LEU PRO ALA GLY SER VAL
TYR GLU LEU
SEQRES 30 A 504 PRO ARG ASN GLN VAL VAL GLU LEU VAL VAL
PRO ALA GLY
SEQRES 31 A 504 VAL LEU GLY GLY PRO HIS PRO PHE HIS LEU
HIS GLY HIS
SEQRES 32 A 504 ALA PHE SER VAL VAL ARG SER ALA GLY SER
SER THR TYR
SEQRES 33 A 504 ASN PHE VAL ASN PRO VAL LYS ARG ASP VAL
VAL SER LEU
SEQRES 34 A 504 GLY VAL THR GLY ASP GLU VAL THR ILE ARG
PHE VAL THR
SEQRES 35 A 504 ASP ASN PRO GLY PRO TRP PHE PHE HIS CYS
HIS ILE GLU
SEQRES 36 A 504 PHE HIS LEU MET ASN GLY LEU ALA ILE VAL
PHE ALA GLU
SEQRES 37 A 504 ASP MET ALA ASN THR VAL ASP ALA ASN ASN
PRO PRO VAL
SEQRES 38 A 504 GLU TRP ALA GLN LEU CYS GLU ILE TYR ASP
ASP LEU PRO
SEQRES 39 A 504 PRO GLU ALA THR SER ILE GLN THR VAL VAL
SSBOND 1 CYS 85 CYS 487
SSBOND 2 CYS 117 CYS 204
CRYST 45.390 85.720 143.070 90.00 90.00 90.00 P212121
SCALE1 0.02203 0.00000 0.00000 0.00000
SCALE2 0.00000 0.01167 0.00000 0.00000
SCALE3 0.00000 0.00000 0.00699 0.00000
ATOM 1 N ALA A 1 0 18.748 34.495 5.326 1.00 36.36
ATOM 2 CA ALA A 1 0 19.554 35.757 5.185 1.00 35.87
ATOM 3 C ALA A 1 0 19.785 36.380 6.558 1.00 34.53
ATOM 4 O ALA A 1 0 19.248 35.884 7.577 1.00 35.40
ATOM 5 CB ALA A 1 0 19.050 36.675 4.107 1.00 36.65
ATOM 6 N ILE A 2 0 20.844 37.201 6.659 1.00 31.00
ATOM 7 CA ILE A 2 0 21.310 37.654 7.963 1.00 27.71
ATOM 8 C ILE A 2 0 21.368 39.165 8.117 1.00 25.19
ATOM 9 O ILE A 2 0 21.789 39.861 7.192 1.00 23.77
ATOM 10 CB ILB A 2 0 22.744 37.107 8.206 1.00 28.28
ATOM 11 CG1 ILE A 2 0 22.790 35.590 8.022 1.00 28.54
ATOM 12 CG2 ILE A 2 0 23.285 37.557 9.554 1.00 27.91
ATOM 13 CD1 ILE A 2 0 23.334 34.738 9.130 1.00 29.32
ATOM 14 N VAL A 3 0 20.986 39.659 9.283 1.00 22.31
ATOM 15 CA VAL A 3 0 21.093 41.092 9.540 1.00 22.78
ATOM 16 C VAL A 3 0 22.246 41.297 10.524 1.00 22.62
ATOM 17 O VAL A 3 0 22.460 40.556 11.467 1.00 21.74
ATOM 18 CB VAL A 3 0 19.801 41.849 9.799 1.00 23.54
ATOM 19 CG1 VAL A 3 0 18.537 40.985 9.684 1.00 21.30
ATOM 20 CG2 VAL A 3 0 19.760 42.709 11.055 1.00 21.32
ATOM 21 N ASN A 4 0 23.122 42.261 10.209 1.00 23.39
ATOM 22 CA ASN A 4 0 24.303 42.520 11.021 1.00 23.45
ATOM 23 C ASN A 4 0 24.002 43.517 12.126 1.00 24.44
ATOM 24 O ASN A 4 0 22.928 44.112 12.160 1.00 23.05
ATOM 25 CB ASN A 4 0 25.477 42.965 10.149 1.00 24.77
ATOM 26 CG ASN A 4 0 25.726 41.991 9.021 1.00 26.62
ATOM 27 OD1 ASN A 4 0 25.668 42.388 7.849 1.00 30.29
ATOM 28 ND2 ASN A 4 0 25.923 40.719 9.324 1.00 27.59
ATOM 29 N SER A 5 0 24.960 43.707 13.040 1.00 24.28
ATOM 30 CA SER A 5 0 24 702 44.636 14.143 1 00 25.77
ATOM 31 C SER A 5 0 24.595 46.090 13.701 1.00 24.41
ATOM 32 O SER A 5 0 23.973 46.862 14.452 1.00 23.55
ATOM 33 CB SER A 5 0 25.741 44.405 15.240 1.00 26.18
ATOM 34 OG SER A 5 0 26.976 44.750 14.641 1.00 27.89
ATOM 35 N VAL A 6 0 25.104 46.517 12.539 1.00 24.01
ATOM 36 CA VAL A 6 0 24.770 47.863 12.096 1.00 25.06
ATOM 37 C VAL A 6 0 24.131 47.617 10.731 1.00 25.57
ATOM 38 O VAL A 6 0 24.778 47.030 9.874 1.00 28.07
ATOM 39 CB VAL A 6 0 25.722 49.032 12.155 1.00 26.65
ATOM 40 CG1 VAL A 6 0 26.937 48.759 13.025 1.00 26.73
ATOM 41 CG2 VAL A 6 0 26.098 49.614 10.801 1.00 25.50
ATOM 42 N ASP A 7 0 22.848 47.952 10.605 1.00 23.82
ATOM 43 CA ASP A 7 0 22.173 47.543 9.369 1.00 24.07
ATOM 44 C ASP A 7 0 20.794 48.170 9.276 1.00 23.66
ATOM 45 O ASP A 7 0 20.342 48.845 10.204 1.00 23.47
ATOM 46 CB ASP A 7 0 21.996 46.012 9.444 1.00 23.43
ATOM 47 CG ASP A 7 0 22.017 45.317 8.111 1.00 23.78
ATOM 48 OD1 ASP A 7 0 21.805 45.937 7.055 1.00 23.74
ATOM 49 OD2 ASP A 7 0 22.255 44.089 8.099 1.00 24.62
ATOM 50 N THR A 8 0 20.155 47.881 8.158 1.00 23.88
ATOM 51 CA THR A 8 0 18.799 48.359 7.928 1.00 24.45
ATOM 52 C THR A 8 0 17.813 47.189 7.950 1.00 22.49
ATOM 53 O THR A 8 0 18.143 46.142 7.377 1.00 22.56
ATOM 54 CB THR A 8 0 18.694 49.108 6.579 1.00 25.75
ATOM 55 OG1 THR A 8 0 19.573 50.242 6.719 1.00 28.53
ATOM 56 CG2 THR A 8 0 17.295 49.656 6.339 1.00 25.55
ATOM 57 N MET A 9 0 16.677 47.364 8.602 1.00 19.10
ATOM 58 CA MET A 9 0 15.650 46.311 8.616 1.00 20.47
ATOM 59 C MET A 9 0 14.392 46.863 7.925 1.00 21.97
ATOM 60 O MET A 9 0 13.638 47.638 8.544 1.00 19.49
ATOM 61 CB MET A 9 0 15.308 45.871 10.022 1.00 20.49
ATOM 62 CG MET A 9 0 16.351 44.982 10.682 1.00 22.11
ATOM 63 SD MET A 9 0 16.192 44.917 12.482 1.00 24.71
ATOM 64 CE MET A 9 0 14.640 44.024 12.635 1.00 22.61
ATOM 65 N THR A 10 0 14.246 46.516 6.641 1.00 21.81
ATOM 66 CA THR A 10 0 13.073 47.064 5.926 1.00 23.43
ATOM 67 C THR A 10 0 11.912 46.081 6.046 1.00 22.90
ATOM 68 O THR A 10 0 12.056 44.890 5.719 1.00 23.55
ATOM 69 CB THR A 10 0 13.390 47.384 4.459 1.00 24.69
ATOM 70 OG1 THR A 10 0 14.533 48.261 4.456 1.00 26.08
ATOM 71 CG2 THR A 10 0 12.216 48.028 3.742 1.00 23.95
ATOM 72 N LEU A 11 0 10.820 46.600 6.583 1.00 21.13
ATOM 73 CA LEU A 11 0 9.615 45.836 6.846 1.00 21.10
ATOM 74 C LEU A 11 0 8.607 45.957 5.709 1.00 24.58
ATOM 75 O LEU A 11 0 8.124 47.056 5.358 1.00 23.89
ATOM 76 CB LEU A 11 0 9.045 46.411 8.129 1.00 21.29
ATOM 77 CG LEU A 11 0 9.474 45.955 9.508 1.00 22.26
ATOM 78 CD1 LEU A 11 0 10.952 45.742 9.692 1.00 22.42
ATOM 79 CD2 LEU A 11 0 8.978 46.931 10.583 1.00 22.75
ATOM 80 N THRA 12 0 8.272 44.836 5.057 1.00 24.01
ATOM 81 CA THRA 12 0 7.302 44.851 3.980 1.00 24.33
ATOM 82 C THRA 12 0 6.322 43.677 4.123 1.00 25.34
ATOM 83 O THRA 12 0 6.480 42.740 4.913 1.00 25.62
ATOM 84 CB THRA 12 0 7.882 44.776 2.560 1.00 25.12
ATOM 85 OG1 THR A 12 0 8.575 43.548 2.377 1.00 24.05
ATOM 86 CG2 THR A 12 0 8.847 45.905 2.217 1.00 25.26
ATOM 87 N ASN A 13 0 5.261 43.760 3.335 1.00 24.09
ATOM 88 CA ASN A 13 0 4.232 42.722 3.299 1.00 22.87
ATOM 89 C ASN A 13 0 4.422 41.954 1.989 1.00 22.13
ATOM 90 O ASN A 13 0 4.809 42.600 1.023 1.00 22.32
ATOM 91 CB ASN A 13 0 2.852 43.355 3.311 1.00 21.58
ATOM 92 CG ASN A 13 0 2.526 44.060 4.607 1.00 22.50
ATOM 93 OD1 ASN A 13 0 2.187 45.245 4.648 1.00 22.20
ATOM 94 ND2 ASN A 13 0 2.615 43.306 5.705 1.00 21.81
ATOM 95 N ALA A 14 0 4.218 40.655 1.985 1.00 21.00
ATOM 96 CA ALA A 14 0 4.270 39.869 0.762 1.00 21.93
ATOM 97 C ALA A 14 0 3.571 38.533 1.078 1.00 20.77
ATOM 98 O ALA A 14 0 3.292 38.309 2.259 1.00 20.45
ATOM 99 CB ALA A 14 0 5.676 39.618 0.248 1.00 23.72

-continued

```
ATOM 100 N ASN A 15 0 3.366 37.695 0.072 1.00 18.88
ATOM 101 CA ASN A 15 0 2.748 36.412 0.337 1.00 19.67
ATOM 102 C ASN A 15 0 3.798 35.457 0.873 1.00 19.19
ATOM 103 O ASN A 15 0 4.891 35.474 0.338 1.00 19.57
ATOM 104 CB ASN A 15 0 2.114 35.721 −0.875 1.00 21.13
ATOM 105 CG ASN A 15 0 0.839 36.457 −1.284 1.00 21.15
ATOM 106 OD1 ASN A 15 0 0.343 37.207 −0.472 1.00 20.87
ATOM 107 ND2 ASN A 15 0 0.379 36.284 −2.501 1.00 20.00
ATOM 108 N VAL A 16 0 3.358 34.614 1.772 1.00 19.11
ATOM 109 CA VAL A 16 0 4.322 33.628 2.342 1.00 18.90
ATOM 110 C VAL A 16 0 3.626 32.293 2.345 1.00 19.25
ATOM 111 O VAL A 16 0 2.386 32.281 2.406 1.00 16.71
ATOM 112 CB VAL A 16 0 4.612 34.317 3.691 1.00 19.95
ATOM 113 CG1 VAL A 16 0 3.990 33.749 4.937 1.00 18.58
ATOM 114 CG2 VAL A 16 0 6.091 34.603 3.814 1.00 21.38
ATOM 115 N SER A 17 0 4.312 31.157 2.303 1.00 18.57
ATOM 116 CA SER A 17 0 3.678 29.869 2.410 1.00 20.90
ATOM 117 C SER A 17 0 4.608 28.866 3.065 1.00 21.12
ATOM 118 O SER A 17 0 5.106 27.939 2.448 1.00 21.24
ATOM 119 CB SER A 17 0 3.186 29.285 1.080 1.00 23.95
ATOM 120 OG SER A 17 0 4.204 29.399 0.125 1.00 26.79
ATOM 121 N PRO A 18 0 4.834 29.051 4.358 1.00 20.78
ATOM 122 CA PRO A 18 0 5.703 28.216 5.141 1.00 20.02
ATOM 123 C PRO A 18 0 5.197 26.793 5.376 1.00 19.74
ATOM 124 O PRO A 18 0 5.978 25.920 5.753 1.00 17.97
ATOM 125 CB PRO A 18 0 5.889 28.954 6.481 1.00 19.27
ATOM 126 CG PRO A 18 0 4.701 29.832 6.536 1.00 21.41
ATOM 127 CD PRO A 18 0 4.249 30.153 5.128 1.00 20.70
ATOM 128 N ASP A 19 0 3.899 26.534 5.241 1.00 18.82
ATOM 129 CA ASP A 19 0 3.323 25.227 5.475 1.00 16.87
ATOM 130 C ASP A 19 0 2.548 24.823 4.237 1.00 17.28
ATOM 131 O ASP A 19 0 1.713 23.929 4.337 1.00 17.84
ATOM 132 CB ASP A 19 0 2.419 25.207 6.701 1.00 16.54
ATOM 133 CG ASP A 19 0 1.192 26.120 6.596 1.00 16.67
ATOM 134 OD1 ASP A 19 0 1.032 26.935 5.654 1.00 14.17
ATOM 135 OD2 ASP A 19 0 0.360 26.045 7.529 1.00 14.56
ATOM 136 N GLY A 20 0 2.782 25.469 3.100 1.00 17.87
ATOM 137 CA GLY A 20 0 2.079 25.091 1.890 1.00 19.40
ATOM 138 C GLY A 20 0 0.732 25.789 1.699 1.00 22.52
ATOM 139 O GLY A 20 0 0.158 25.619 0.628 1.00 22.87
ATOM 140 N PHE A 21 0 0.240 26.587 2.631 1.00 21.35
ATOM 141 CA PHE A 21 0 −0.913 27.443 2.534 1.00 20.39
ATOM 142 C PHE A 21 0 −0.348 28.855 2.322 1.00 21.23
ATOM 143 O PHE A 21 0 0.475 29.316 3.122 1.00 21.26
ATOM 144 CB PHE A 21 0 −1.742 27.472 3.814 1.06 20.80
ATOM 145 CG PHE A 21 0 −3.059 28.180 3.695 1.00 21.91
ATOM 146 CD1 PRE A 21 0 −3.171 29.527 3.963 1.00 22.49
ATOM 147 CD2 PHE A 21 0 −4.207 27.470 3.327 1.00 22.51
ATOM 148 CE1 PHE A 21 0 −4.370 30.207 3.845 1.00 22.27
ATOM 149 CE2 PHE A 21 0 −5.419 28.128 3.203 1.00 22.79
ATOM 150 CZ PHE A 21 0 −5.498 29.497 3.474 1.00 23.34
ATOM 151 N THR A 22 0 −0.638 29.514 1.225 1.00 20.20
ATOM 152 C A THR A 22 0 −0.143 30.850 0.977 1.00 21.36
ATOM 153 C THR A 22 0 −1.083 31.939 1.488 1.00 21.79
ATOM 154 O THR A 22 0 −2.271 31.952 1.162 1.00 21.19
ATOM 155 CB THR A 22 0 0.045 31.012 −0.553 1.00 21.46
ATOM 156 OG1 THR A 22 0 0.838 29.881 −0.934 1.00 20.09
ATOM 157 CG2 THR A 22 0 0.693 32.353 −0.891 1.00 20.94
ATOM 158 N ARG A 23 0 −0.562 32.871 2.257 1.00 20.80
ATOM 159 CA ARG A 23 0 −1.230 34.008 2.844 1.00 20.78
ATOM 160 C ARG A 23 0 −0.257 35.189 2.960 1.00 21.15
ATOM 161 O ARG A 23 0 0.954 35.018 2.740 1.00 20.42
ATOM 162 CB ARG A 23 0 −1.874 33.685 4.172 1.00 20.47
ATOM 163 CG ARG A 23 0 −0.964 33.152 5.295 1.00 21.52
ATOM 164 CD ARG A 23 0 −0.552 34.357 6.113 1.00 22.75
ATOM 165 NE ARG A 23 0 −0.905 34.419 7.477 1.00 21.60
ATOM 166 CZ ARG A 23 0 −0.870 35.283 8.464 1.00 19.89
ATOM 167 NH1 ARG A 23 0 −0.526 36.565 8.453 1.00 20.19
ATOM 168 NH2 ARG A 23 0 −1.249 34.744 9.610 1.00 18.64
ATOM 169 N ALA A 24 0 −0.784 36.389 3.199 1.00 20.05
ATOM 170 CA ALA A 24 0 0.140 37.541 3.243 1.00 22.03
ATOM 171 C ALA A 24 0 0.786 37.561 4.635 1.00 21.09
ATOM 172 O ALA A 24 0 0.200 37.124 5.637 1.00 21.16
ATOM 173 CB ALA A 24 0 −0.578 38.836 2.902 1.00 22.98
ATOM 174 N GLY A 25 0 2.042 37.984 4.683 1.00 20.28
ATOM 175 CA GLY A 25 0 2.786 37.993 5.950 1.00 20.29
ATOM 176 C GLY A 25 0 3.649 39.254 5.979 1.00 21.38
ATOM 177 O GLY A 25 0 3.465 40.229 5.238 1.00 21.06
ATOM 178 N ILE A 26 0 4.604 39.221 6.897 1.00 20.33
ATOM 179 CA ILE A 26 0 5.475 40.365 7.145 1.00 20.64
ATOM 180 C ILE A 26 0 6.903 39.886 6.932 1.00 20.00
ATOM 181 O ILE A 26 0 7.247 38.851 7.485 1.00 21.34
ATOM 182 CB ILE A 26 0 5.278 40.933 8.564 1.00 20.38
ATOM 183 CG1 ILE A 26 0 3.883 41.536 8.667 1.00 20.72
ATOM 184 CG2 ILE A 26 0 6.333 42.007 8.821 1.00 22.34
ATOM 185 CD1 ILE A 26 0 3.310 41.822 10.024 1.00 20.76
ATOM 186 N LEU A 27 0 7.644 40.551 6.079 1.00 19.10
ATOM 187 CA LEU A 27 0 9.005 40.168 5.739 1.00 19.67
ATOM 188 C LEU A 27 0 9.964 41.226 6.280 1.00 19.85
ATOM 189 0 LEU A 27 0 9.591 42.407 6.356 1.00 19.19
ATOM 190 CB LEU A 27 0 9.138 40.172 4.219 1.00 20.26
ATOM 191 CG LEU A 27 0 9.046 38.883 3.415 1.00 22.65
ATOM 192 CD1 LEU A 27 0 8.127 37.835 3.989 1.00 21.10
ATOM 193 CD2 LEU A 27 0 8.738 39.198 1.963 1.00 22.01
ATOM 194 N VAL A 28 0 11.162 40.804 6.630 1.00 18.03
ATOM 195 CA VAL A 28 0 12.199 41.723 7.088 1.00 17.24
ATOM 196 C VAL A 28 0 13.289 41.573 6.040 1.00 18.99
ATOM 197 0 VAL A 28 0 13.791 40.453 5.863 1.00 20.36
ATOM 198 CB VAL A 28 0 12.762 41.415 8.491 1.00 16.50
ATOM 199 CG1 VAL A 28 0 13.899 42.361 8.845 1.00 15.41
ATOM 200 CG2 VAL A 28 0 11.681 41.517 9.558 1.00 15.42
ATOM 201 N ASN A 29 0 13.575 42.601 5.256 1.00 20.78
ATOM 202 CA ASN A 29 0 14.567 42.579 4.198 1.00 20.46
ATOM 203 C ASN A 29 0 14.316 41.435 3.226 1.00 23.05
ATOM 204 0 ASN A 29 0 15.247 40.675 2.880 1.00 23.62
ATOM 205 CB ASN A 29 0 15.982 42.446 4.764 1.00 21.06
ATOM 206 CG ASN A 29 0 16.475 43.654 5.522 1.00 22.44
ATOM 207 OD1 ASN A 29 0 15.870 44.722 5.434 1.00 23.47
ATOM 208 ND2 ASN A 29 0 17.560 43.507 6.288 1.00 22.23
ATOM 209 N GLY A 30 0 13.053 41.215 2.878 1.00 23.18
ATOM 210 CA GLY A 30 0 12.662 40.181 1.922 1.00 23.36
ATOM 211 C GLY A 30 0 12.723 38.757 2.436 1.00 23.85
ATOM 212 O GLY A 30 0 12.707 37.814 1.633 1.00 25.17
ATOM 213 N VAL A 31 0 12.832 38.585 3.755 1.00 21.85
ATOM 214 CA VAL A 31 0 12.999 37.276 4.352 1.00 20.55
ATOM 215 C VAL A 31 0 12.031 37.190 5.548 1.00 19.91
ATOM 216 O VAL A 31 0 11.796 38.172 6.269 1.00 17.50
ATOM 217 CB VAL A 31 0 14.436 37.020 4.856 1.00 21.36
ATOM 218 CG1 VAL A 31 0 14.556 35.709 5.626 1.00 20.79
ATOM 219 CG2 VAL A 31 0 15.495 37.005 3.757 1.00 21.84
ATOM 220 N HIS A 32 0 11.489 35.984 5.698 1.00 17.05
ATOM 221 CA HIS A 32 0 10.592 35.729 6.797 1.00 18.61
ATOM 222 C HIS A 32 0 11.417 35.499 8.050 1.00 17.67
ATOM 223 0 HIS A 32 0 11.873 34.385 8.216 1.00 18.72
ATOM 224 CB HIS A 32 0 9.676 34.543 6.493 1.00 21.00
ATOM 225 CG HIS A 32 0 8.639 34.208 7.517 1.00 23.80
ATOM 226 ND1 HIS A 32 0 7.744 33.174 7.332 1.00 25.14
ATOM 227 CD2 HIS A 32 0 8.331 34.720 8.735 1.00 25.32
ATOM 228 CE1 HIS A 32 0 6.942 33.061 8.385 1.00 25.36
ATOM 229 NE2 HIS A 32 0 7.271 33.986 9.260 1.00 26.23
ATOM 230 N GLY A 33 0 11.522 36.446 8.960 1.00 16.23
ATOM 231 CA GLY A 33 0 12.276 36.252 10.198 1.00 16.97
ATOM 232 C GLY A 33 0 13.740 35.869 10.083 1.00 15.54
ATOM 233 O GLY A 33 0 14.228 34.885 10.609 1.00 15.13
ATOM 234 N PRO A 34 0 14.555 36.734 9.475 1.00 15.75
ATOM 235 CA PRO A 34 0 16.012 36.561 9.359 1.00 14.70
ATOM 236 C PRO A 34 0 16.734 36.660 10.701 1.00 14.02
ATOM 237 O PRO A 34 0 16.241 37.252 11.673 1.00 10.44
ATOM 238 CB PRO A 34 0 16.491 37.699 8.435 1.00 14.40
ATOM 239 CG PRO A 34 0 15.441 38.742 8.783 1.00 15.11
ATOM 240 CD PRO A 34 0 14.113 38.005 8.905 1.00 13.69
ATOM 241 N LEU A 35 0 17.925 36.049 10.767 1.00 13.60
ATOM 242 CA LEU A 35 0 18.748 36.022 11.963 1.00 14.35
ATOM 243 C LEU A 35 0 19.462 37.359 12.161 1.00 16.25
ATOM 244 O LEU A 35 0 20.015 37.902 11.210 1.00 14.10
ATOM 245 CB LEU A 35 0 19.834 34.916 11.862 1.00 15.33
ATOM 246 CG LEU A 35 0 20.958 34.943 12.911 1.00 17.74
ATOM 247 CD1 LEU A 35 0 20.486 34.698 14.348 1.00 16.30
ATOM 248 CD2 LEU A 35 0 22.052 33.934 12.575 1.00 16.60
ATOM 249 N ILE A 36 0 19.471 37.855 13.384 1.00 16.71
ATOM 250 CA ILE A 36 0 20.265 39.027 13.738 1.00 16.66
ATOM 251 C ILE A 36 0 21.403 38.487 14.620 1.00 17.92
ATOM 252 O ILE A 36 0 21.183 37.732 15.573 1.00 17.20
ATOM 253 CB ILE A 36 0 19.560 40.129 14.533 1.00 16.60
ATOM 254 CG1 ILE A 36 0 18.389 40.771 13.771 1.00 16.09
ATOM 255 CG2 ILE A 36 0 20.565 41.226 14.917 1.00 17.67
ATOM 256 CD1 ILE A 36 0 17.590 41.754 14.629 1.00 15.88
ATOM 257 N ARG A 37 0 22.647 38.829 14.288 1.00 18.72
ATOM 258 CA ARG A 37 0 23.754 38.315 15.091 1.00 19.94
ATOM 259 C ARG A 37 0 24.839 39.369 15.280 1.00 20.08
```

-continued

```
ATOM 260 O   ARG A 37  0 24.979 40.249 14.450 1.00 20.52
ATOM 261 CB  ARG A 37  0 24.395 37.077 14.465 1.00 21.72
ATOM 262 CG  ARG A 37  0 25.102 37.393 13.171 1.00 24.46
ATOM 263 CD  ARG A 37  0 26.113 36.339 12.762 1.00 26.90
ATOM 264 NE  ARG A 37  0 26.584 36.571 11.381 1.00 29.30
ATOM 265 CZ  ARG A 37  0 26.838 35571  10.528 1.00 31.29
ATOM 266 NH1 ARG A 37  0 26.711 34.283 10.851 1.00 31.37
ATOM 267 NH2 ARG A 37  0 27.252 35.827  9.291 1.00 31.66
ATOM 268 N   GLY A 38  0 25.587 39.223 16.361 1.00 20.22
ATOM 269 CA  GLY A 38  0 26.716 40.121 16.611 1.00 18.98
ATOM 270 C   GLY A 38  0 27.533 39.545 17.765 1.00 18.08
ATOM 271 O   GLY A 38  0 27.259 38.421 18.225 1.00 15.92
ATOM 272 N   GLY A 39  0 28.436 40.412 18.238 1.00 17.65
ATOM 273 CA  GLY A 39  0 29.322 40.026 19.351 1.00 16.23
ATOM 274 C   GLY A 39  0 28.861 40.774 20.592 1.00 17.21
ATOM 275 O   GLY A 39  0 28.157 41.784 20.489 1.00 17.27
ATOM 276 N   LYS A 40  0 29.276 40.328 21.764 1.00 16.58
ATOM 277 CA  LYS A 40  0 28.839 40.805 23.057 1.00 18.03
ATOM 278 C   LYS A 40  0 29.185 42.267 23.348 1.00 20.44
ATOM 279 O   LYS A 40  0 28.562 42.878 24.221 1.00 19.42
ATOM 280 CB  LYS A 40  0 29.394 39.933 24.185 1.00 16.74
ATOM 281 CG  LYS A 40  0 30.892 39.997 24.370 1.00 17.98
ATOM 282 CD  LYS A 40  0 31.333 39.170 25.569 1.00 20.66
ATOM 283 CE  LYS A 40  0 32.809 38.768 25.493 1.00 21.70
ATOM 284 NZ  LYS A 40  0 33.227 38.111 26.757 1.00 23.11
ATOM 285 N   ASN A 41  0 30.181 42.780 22.645 1.00 21.43
ATOM 286 CA  ASN A 41  0 30.536 44.171 22.840 1.00 25.14
ATOM 287 C   ASN A 41  0 30.092 44.976 21.644 1.00 24.05
ATOM 288 O   ASN A 41  0 30.409 46.161 21.655 1.00 25.66
ATOM 289 CB  ASN A 41  0 32.052 44.326 23.111 1.00 27.02
ATOM 290 CG  ASN A 41  0 32.434 43.606 24.404 1.00 29.76
ATOM 291 OD1 ASN A 41  0 33.398 42.832 24.431 1.00 31.54
ATOM 292 ND2 ASN A 41  0 31.663 43.825 25.473 1.00 30.13
ATOM 293 N   ASP A 42  0 29.424 44.447 20.631 1.00 23.80
ATOM 294 CA  ASP A 42  0 29.073 45.325 19.506 1.00 24.12
ATOM 295 C   ASP A 42  0 28.169 46.484 19.891 1.00 24.24
ATOM 296 O   ASP A 42  0 27.420 46.428 20.872 1.00 22.42
ATOM 297 CB  ASP A 42  0 28.388 44.528 18.392 1.00 26.65
ATOM 298 CG  ASP A 42  0 29.404 43.599 17.773 1.00 28.94
ATOM 299 OD1 ASP A 42  0 30.603 43.754 18.056 1.00 31.45
ATOM 300 OD2 ASP A 42  0 29.026 42.708 17.009 1.00 31.69
ATOM 301 N   ASN A 43  0 28.258 47.547 19.090 1.00 24.72
ATOM 302 CA  ASN A 43  0 27.316 48.660 19.255 1.00 26.50
ATOM 303 C   ASN A 43  0 26.293 48.430 18.128 1.00 26.23
ATOM 304 O   ASN A 43  0 26.723 48.420 16.979 1.00 25.02
ATOM 305 CB  ASN A 43  0 27.934 50.047 19.128 1.00 28.45
ATOM 306 CG  ASN A 43  0 28.858 50.244 20.323 1.00 31.09
ATOM 307 OD1 ASN A 43  0 30.041 50.502 20.106 1.00 33.11
ATOM 308 ND2 ASN A 43  0 28.364 50.055 21.531 1.00 31.18
ATOM 309 N   PHE A 44  0 25.039 48.155 18.468 1.00 24.63
ATOM 310 CA  PHE A 44  0 24.083 47.897 17.393 1.00 23.28
ATOM 311 C   PHE A 44  0 23.450 49.191 16.916 1.00 22.36
ATOM 312 O   PHE A 44  0 23.024 50.008 17.735 1.00 21.07
ATOM 313 CB  PHE A 44  0 22.959 46.965 17.853 1.00 22.04
ATOM 314 CG  PHE A 44  0 23.376 45.525 17.955 1.00 22.96
ATOM 315 CD1 PHE A 44  0 22.779 44.562 17.153 1.00 23.91
ATOM 316 CD2 PHE A 44  0 24.330 45.120 18.869 1.00 22.03
ATOM 317 CE1 PHE A 44  0 23.131 43.230 17.253 1.00 24.42
ATOM 318 CE2 PHE A 44  0 24.689 43.797 18.974 1.00 23.25
ATOM 319 CZ  PHE A 44  0 24.095 42.837 18.168 1.00 24.02
ATOM 320 N   GLU A 45  0 23.350 49.343 15.604 1.00 22.78
ATOM 321 CA  GLU A 45  0 22.611 50.482 15.054 1.00 24.47
ATOM 322 C   GLU A 45  0 21.619 49.884 14.055 1.00 23.79
ATOM 323 O   GLU A 45  0 22.017 49.587 12.924 1.00 24.40
ATOM 324 CB  GLU A 45  0 23.543 51.473 14.368 1.00 27.07
ATOM 325 CG  GLU A 45  0 24.474 52.130 15.374 1.00 31.60
ATOM 326 CD  GLU A 45  0 25.380 53.179 14.772 1.00 33.90
ATOM 327 OE1 GLU A 45  0 25.354 53.438 13.559 1.00 35.62
ATOM 328 OE2 GLU A 45  0 26.155 53.748 15.565 1.00 36.42
ATOM 329 N   LEU A 46  0 20.369 49.684 14.465 1.00 22.18
ATOM 330 CA  LEU A 46  0 19.419 49.044 13.556 1.00 21.22
ATOM 331 C   LEU A 46  0 18.348 50.001 13.077 1.00 21.27
ATOM 332 O   LEU A 46  0 17.464 50.429 13.812 1.00 21.60
ATOM 333 CB  LEU A 46  0 18.837 47.811 14.262 1.00 20.72
ATOM 334 CG  LEU A 46  0 19.827 46.658 14.403 1.00 21.28
ATOM 335 CD1 LEU A 46  0 19.334 45.621 15.397 1.00 20.83
ATOM 336 CD2 LEU A 46  0 20.148 46.034 13.052 1.00 18.33
ATOM 337 N   ASN A 47  0 18.438 50.403 11.823 1.00 21.09
ATOM 338 CA  ASN A 47  0 17.498 51.344 11.252 1.00 22.37
ATOM 339 C   ASN A 47  0 16.273 50.558 10.803 1.00 22.18
ATOM 340 O   ASN A 47  0 16.390 49.810  9.847 1.00 23.41
ATOM 341 CB  ASN A 47  0 18.131 52.104 10.066 1.00 24.01
ATOM 342 CG  ASN A 47  0 17.226 53.243  9.615 1.00 25.54
ATOM 343 OD1 ASN A 47  0 16.443 53.772 10.413 1.00 26.53
ATOM 344 ND2 ASN A 47  0 17.332 53.612  8.346 1.00 26.01
ATOM 345 N   VAL A 48  0 15.147 50.692 11.475 1.00 22.04
ATOM 346 CA  VAL A 48  0 13.918 49.995 11.140 1.00 21.99
ATOM 347 C   VAL A 48  0 13.026 50.879 10.269 1.00 21.82
ATOM 348 O   VAL A 48  0 12.532 51.910 10.699 1.00 20.61
ATOM 349 CB  VAL A 48  0 13.176 49.579 12.430 1.00 22.64
ATOM 350 CG1 VAL A 48  0 11.819 48.931 12.148 1.00 21.99
ATOM 351 CG2 VAL A 48  0 14.098 48.631 13.216 1.00 21.68
ATOM 352 N   VAL A 49  0 12.931 50.512  9.009 1.00 21.79
ATOM 353 CA  VAL A 49  0 12.164 51.167  7.966 1.00 21.34
ATOM 354 C   VAL A 49  0 10.816 50.460  7.795 1.00 21.12
ATOM 355 O   VAL A 49  0 10.703 49.308  7.365 1.00 19.76
ATOM 356 CB  VAL A 49  0 12.983 51.189  6.665 1.00 22.02
ATOM 357 CG1 VAL A 49  0 12.267 51.913  5.519 1.00 21.70
ATOM 358 CG2 VAL A 49  0 14.312 51.933  6.906 1.00 21.47
ATOM 359 N   ASN A 50  0  9.767 51.112  8.257 1.00 20.26
ATOM 360 CA  ASN A 50  0  8.424 50.611  8.215 1.00 22.70
ATOM 361 C   ASN A 50  0  7.751 50.899  6.869 1.00 25.99
ATOM 362 O   ASN A 50  0  7.043 51.925  6.735 1.00 27.06
ATOM 363 CB  ASN A 50  0  7.549 51.230  9.318 1.00 21.92
ATOM 364 CG  ASN A 50  0  6.198 50.569  9.471 1.00 22.44
ATOM 365 OD1 ASN A 50  0  5.818 49.801  8.572 1.00 24.19
ATOM 366 ND2 ASN A 50  0  5.435 50.833 10.526 1.00 20.19
ATOM 367 N   ASP A 51  0  7.915 49.959  5.926 1.00 26.42
ATOM 368 CA  ASP A 51  0  7.208 50.071  4.641 1.00 26.35
ATOM 369 C   ASP A 51  0  5.951 49.200  4.600 1.00 24.86
ATOM 370 O   ASP A 51  0  5.542 48.810  3.511 1.00 25.19
ATOM 371 CB  ASP A 51  0  8.126 49.698  3.481 1.00 26.75
ATOM 372 CG  ASP A 51  0  9.152 50.761  3.158 1.00 29.77
ATOM 373 OD1 ASP A 51  0  8.944 51.904  3.617 1.00 31.03
ATOM 374 OD2 ASP A 51  0 10.166 50.509  2.465 1.00 30.42
ATOM 375 N   LEU A 52  0  5.332 48.801  5.700 1.00 25.05
ATOM 376 CA  LEUA 52  0  4.172 47.911  5.640 1.00 25.44
ATOM 377 C   LEU A 52  0  2.934 48.624  5.094 1.00 26.65
ATOM 378 O   LEU A 52  0  2.553 49.696  5.586 1.00 24.56
ATOM 379 CB  LEUA 52  0  3.837 47.374  7.029 1.00 24.19
ATOM 380 CG  LEU A 52  0  4.896 46.503  7.699 1.00 24.60
ATOM 381 CD1 LEU A 52  0  4.611 46.424  9.196 1.00 24.05
ATOM 382 CD2 LEU A 52  0  4.891 45.119  7.061 1.00 23.49
ATOM 383 N   ASP A 53  0  2.242 47.980  4.169 1.00 28.79
ATOM 384 CA  ASP A 53  0  1.049 48.602  3.581 1.00 29.91
ATOM 385 C   ASP A 53  0 -0.135 47.658  3.492 1.00 29.90
ATOM 386 O   ASP A 53  0 -1.152 48.082  2.951 1.00 30.40
ATOM 387 CB  ASP A 53  0  1.367 49.190  2.197 1.00 29.26
ATOM 388 CG  ASP A 53  0  1.838 48.140  1.218 1.00 31.28
ATOM 389 OD1 ASP A 53  0  1.865 46.926  1.540 1.00 31.64
ATOM 390 OD2 ASP A 53  0  2.233 48.474  0.074 1.00 32.42
ATOM 391 N   ASN A 54  0 -0.060 46.437  4.014 1.00 29.44
ATOM 392 CA  ASN A 54  0 -1.237 45.554  3.983 1.00 26.89
ATOM 393 C   ASN A 54  0 -2.089 45.832  5.192 1.00 27.37
ATOM 394 O   ASN A 54  0 -1.772 45.528  6.350 1.00 27.99
ATOM 395 CB  ASN A 54  0 -0.831 44.095  3.913 1.00 25.11
ATOM 396 CG  ASN A 54  0 -1.978 43.141  3.690 1.00 24.20
ATOM 397 OD1 ASN A 54  0 -1.874 42.344  2.746 1.00 25.13
ATOM 398 ND2 ASN A 54  0 -3.030 43.182  4.481 1.0023.26
ATOM 399 N   PRO A 55  0 -3.337 46.256  4.961 1.00 28.44
ATOM 400 CA  PRO A 55  0 -4.286 46.589  6.014 1.00 26.57
ATOM 401 C   PRO A 55  0 -4.909 45.414  6.721 1.00 27.10
ATOM 402 O   PRO A 55  0 -5.671 45.624  7.687 1.00 26.05
ATOM 403 CB  PRO A 55  0 -5.368 47.465  5.334 1.00 28.18
ATOM 404 CG  PRO A 55  0 -5.249 47.049  3.899 1.00 27.50
ATOM 405 CD  PRO A 55  0 -3.844 46.564  3.625 1.00 27.56
ATOM 406 N   THR A 56  0 -4.603 44.160  6.345 1.00 25.55
ATOM 407 CA  THR A 56  0 -5.214 43.024  7.065 1.00 25.52
ATOM 408 C   THR A 56  0 -4.446 42.647  8.326 1.00 24.87
ATOM 409 O   THR A 56  0 -4.766 41.764  9.115 1.00 23.97
ATOM 410 CB  THR A 56  0 -5.393 41.807  6.154 1.00 25.10
ATOM 411 OG1 THR A 56  0 -4.100 41.345  5.763 1.00 24.26
ATOM 412 CG2 THR A 56  0 -6.178 42.123  4.861 1.00 25.63
ATOM 413 N   MET A 57  0 -3.317 43.311  8.558 1.00 26.01
ATOM 414 CA  MET A 57  0 -2.553 43.099  9.801 1.00 26.57
ATOM 415 C   MET A 57  0 -2.026 44.475 10.201 1.00 25.88
ATOM 416 O   MET A 57  0 -2.026 45.416  9.397 1.00 25,18
ATOM 417 CB  MET A 57  0 -1.561 41.939  9.698 1.00 25.42
ATOM 418 CG  MET A 57  0 -0.639 41.868  8.554 1.00 24.37
ATOM 419 SD  MET A 57  0 -0.034 40.288  7.916 1.00 22.34
```

```
ATOM 420 CE  MET A 57  0  -0.275 40.640  6.167 1.00 19.23
ATOM 421 N   LEU A 58  0  -1.694 44.601 11.476 1.00 25.98
ATOM 422 CA  LEU A 58  0  -1.180 45.850 12.036 1.00 25.57
ATOM 423 C   LEU A 58  0  -0.053 46.425 11.195 1.00 24.52
ATOM 424 O   LEU A 58  0   0.824 45.739 10.638 1.00 23.63
ATOM 425 CB  LEU A 58  0  -0.757 45.535 13.463 1.00 26.67
ATOM 426 CG  LEU A 58  0  -1.628 45.817 14.657 1.00 28.97
ATOM 427 CD1 LEU A 58  0  -3.107 45.995 14.312 1.00 30.99
ATOM 428 CD2 LEU A 58  0  -1.488 44.756 15.736 1.00 28.36
ATOM 429 N   ARG A 59  0  -0.078 47.741 11.030 1.00 24.96
ATOM 430 CA  ARG A 59  0   0.918 48.434 10.231 1.00 26.92
ATOM 431 C   ARG A 59  0   1.932 49.229 11.014 1.00 26.31
ATOM 432 O   ARG A 59  0   3.120 49.198 10.699 1.00 28.82
ATOM 433 CB  ARG A 59  0   0.260 49.277  9.132 1.00 28.35
ATOM 434 CG  ARG A 59  0  -0.252 48.385  7.986 1.00 29.50
ATOM 435 CD  ARG A 59  0  -0.986 49.274  6.996 1.00 30.33
ATOM 436 NE  ARG A 59  0  -2.333 49.604  7.459 1.00 32.26
ATOM 437 CZ  ARG A 59  0  -3.121 50.525  6.883 1.00 33.24
ATOM 438 NH1 ARG A 59  0  -2.679 51.233  5.845 1.00 32.27
ATOM 439 NH2 ARG A 59  0  -4.340 50.712  7.389 1.00 32.65
ATOM 440 N   PRO A 60  0   1.542 49.961 12.020 1.00 26.30
ATOM 441 CA  PRO A 60  0   2.460 50.669 12.916 1.00 26.19
ATOM 442 C   PRO A 60  0   3.312 49.591 13.595 1.00 25.29
ATOM 443 O   PRO A 60  0   2.879 48.432 13.668 1.00 24.63
ATOM 444 CB  PRO A 60  0   1.623 51.464 13.925 1.00 25.93
ATOM 445 CG  PRO A 60  0   0.235 51.357 13.325 1.00 26.19
ATOM 446 CD  PRO A 60  0   0.165 50.073 12.508 1.00 26.23
ATOM 447 N   THR A 61  0   4.544 49.932 13.976 1.00 24.60
ATOM 448 CA  THR A 61  0   5.365 48.871 14.587 1.00 23.49
ATOM 449 C   THR A 61  0   6.204 49.400 15.743 1.00 22.83
ATOM 450 O   THR A 61  0   6.390 50.601 15.921 1.00 20.77
ATOM 451 CB  THR A 61  0   6.245 48.170 13.535 1.00 22.69
ATOM 452 OG1 THR A 61  0   6.668 46.918 14.096 1.00 23.55
ATOM 453 CG2 THR A 61  0   7.444 48.976 13.119 1.00 20.92
ATOM 454 N   SER A 62  0   6.702 48.449 16.507 1.00 22.38
ATOM 455 CA  SER A 62  0   7.599 48.672 17.633 1.00 22.47
ATOM 456 C   SER A 62  0   8.381 47.380 17.893 1.00 22.12
ATOM 457 O   SER A 62  0   7.763 46.331 18.124 1.00 20.53
ATOM 458 CB  SER A 62  0   6.784 49.033 18.882 1.00 22.02
ATOM 459 OG  SER A 62  0   7.666 49.570 19.832 1.00 21.19
ATOM 460 N   ILE A 63  0   9.716 47.451 17.806 1.00 21.17
ATOM 461 CA  ILE A 63  0  10.513 46.240 17.960 1.00 18.32
ATOM 462 C   ILE A 63  0  11.095 46.034 19.354 1.00 18.28
ATOM 463 O   ILE A 63  0  11.832 46.909 19.826 1.00 19.63
ATOM 464 CB  ILE A 63  0  11.642 46.234 16.924 1.00 16.68
ATOM 465 CG1 ILE A 63  0  11.166 46.509 15.508 1.00 18.51
ATOM 466 CG2 ILE A 63  0  12.319 44.848 16.906 1.00 16.78
ATOM 467 CD1 ILB A 63  0  10.055 45.625 14.994 1.00 18.25
ATOM 468 N   HIS A 64  0  10.880 44.890 19.985 1.00 15.18
ATOM 469 CA  HIS A 64  0  11.478 44.539 21.261 1.00 15.51
ATOM 470 C   HIS A 64  0  12.648 43.559 21.029 1.00 16.73
ATOM 471 O   HIS A 64  0  12.491 42.591 20.279 1.00 16.85
ATOM 472 CB  HIS A 64  0  10.512 43.912 22.239 1.00 14.37
ATOM 473 CG  HIS A 64  0  11.033 43.420 23.546 1.00 14.47
ATOM 474 ND1 HIS A 64  0  11.763 44.191 24.410 1.00 12.89
ATOM 475 CD2 HIS A 64  0  10.883 42.223 24.193 1.00 14.85
ATOM 476 CE1 HIS A 64  0  12.067 43.518 25.498 1.00 11.53
ATOM 477 NE2 HIS A 64  0  11.547 42.325 25.423 1.00 13.63
ATOM 478 N   TRP A 65  0  13.761 43.781 21.723 1.00 14.37
ATOM 479 CA  TRP A 65  0  14.966 42.926 21.577 1.00 13.92
ATOM 480 C   TRP A 65  0  14.987 42.084 22.840 1.00 13.50
ATOM 481 O   TRP A 65  0  15.482 42.538 23.901 1.00 12.84
ATOM 482 CB  TRP A 65  0  16.189 43.825 21.371 1.00 13.50
ATOM 483 CG  TRP A 65  0  15.890 45.020 20.492 1.00 13.19
ATOM 484 CD1 TRP A 65  0  15.453 46.247 20.913 1.00 12.42
ATOM 485 CD2 TRP A 65  0  15.908 45.087 19.068 1.00 13.61
ATOM 486 NE1 TRP A 65  0  15.234 47.067 19.862 1.00 11.49
ATOM 487 CE2 TRP A 65  0  15.511 46.390 18.710 1.00 13.77
ATOM 488 CE3 TRP A 65  0  16.251 44.174 18.061 1.00 14.35
ATOM 489 CZ2 TRP A 65  0  15.439 46.815 17.378 1.00 14.99
ATOM 490 CZ3 TRP A 65  0  16.169 44.572 16.735 1.00 13.99
ATOM 491 CH2 TRP A 65  0  15.756 45.869 16.411 1.00 15.82
ATOM 492 N   HIS A 66  0  14.295 40.941 22.747 1.00 10.39
ATOM 493 CA  HIS A 66  0  13.939 40.200 23.966 1.00 12.00
ATOM 494 C   HIS A 66  0  15.158 39.653 24.698 1.00 11.34
ATOM 495 O   HIS A 66  0  15.889 38.859 24.130 1.00 11.51
ATOM 496 CB  HIS A 66  0  12.923 39.069 23.629 1.00 10.76
ATOM 497 CG  HIS A 66  0  12.418 38.308 24.808 1.00 11.26
ATOM 498 ND1 HIS A 66  0  11.106 38.085 25.092 1.00 13.10
ATOM 499 CD2 HIS A 66  0  13.050 37.676 25.824 1.00 13.49
ATOM 500 CE1 HIS A 66  0  10.919 37.407 26.191 1.00 12.50
ATOM 501 NE2 HIS A 66  0  12.116 37.146 26.683 1.00 13.71
ATOM 502 N   GLY A 67  0  15.345 39.971 25.948 1.00 12.84
ATOM 503 CA  GLY A 67  0  16.492 39.469 26.719 1.00 13.36
ATOM 504 C   GLY A 67  0  17.596 40.500 26.914 1.00 13.11
ATOM 505 O   GLY A 67  0  18.435 40.289 27.788 1.00 13.36
ATOM 506 N   LEU A 68  0  17.641 41.558 26.131 1.00 12.89
ATOM 507 CA  LEU A 68  0  18.659 42.598 26.300 1.00 15.22
ATOM 508 C   LEU A 68  0  18.235 43.501 27.448 1.00 16.14
ATOM 509 O   LEU A 68  0  17.029 43.842 27.505 1.00 16.50
ATOM 510 CB  LEU A 68  0  18.929 43.320 24.988 1.00 15.98
ATOM 511 CG  LEU A 68  0  20.002 42.638 24.114 1.00 19.57
ATOM 512 CD1 LEU A 68  0  19.719 41.185 23.809 1.00 20.39
ATOM 513 CD2 LEU A 68  0  20.188 43.316 22.758 1.00 19.59
ATOM 514 N   PHE A 69  0  19.125 43.848 28.386 1.00 13.24
ATOM 515 CA  PHE A 69  0  18.700 44.657 29.526 1.00 13.85
ATOM 516 C   PHE A 69  0  18.499 46.128 29.205 1.00 14.34
ATOM 517 O   PHE A 69  0  17.806 46.879 29.895 1.00 15.02
ATOM 518 CB  PHE A 69  0  19.770 44.579 30.637 1.00 16.02
ATOM 519 CG  PHE A 69  0  20.112 43.187 31.072 1.00 16.45
ATOM 520 CD1 PHE A 69  0  19.172 42.162 31.026 1.00 16.68
ATOM 521 CD2 PHE A 69  0  21.381 42.927 31.578 1.00 16.78
ATOM 522 CE1 PHE A 69  0  19.504 40.883 31.448 1.00 18.86
ATOM 523 CE2 PHE A 69  0  21.717 41.652 32.001 1.00 17.34
ATOM 524 CZ  PHE A 69  0  20.782 40.628 31.932 1.00 18.09
ATOM 525 N   GLN A 70  0  19.081 46.611 28.130 1.00 12.22
ATOM 526 CA  GLN A 70  0  18.919 47.990 27.708 1.00 15.20
ATOM 527 C   GLN A 70  0  19.242 49.004 28.799 1.00 16.76
ATOM 528 O   GLN A 70  0  18.555 50.016 28.919 1.00 16.08
ATOM 529 CB  GLN A 70  0  17.488 48.115 27.232 1.00 15.52
ATOM 530 CG  GLN A 70  0  17.168 47.303 26.003 1.00 17.37
ATOM 531 CD  GLN A 70  0  17.781 47.744 24.709 1.00 17.70
ATOM 532 OE1 GLN A 70  0  17.557 47.090 23.676 1.00 21.63
ATOM 533 NE2 GLN A 70  0  18.549 48.805 24.620 1.00 16.79
ATOM 534 N   ARG A 71  0  20.338 48.804 29.518 1.00 16.49
ATOM 535 CA  ARG A 71  0  20.765 49.712 30.588 1.00 18.41
ATOM 536 C   ARG A 71  0  21.239 51.011 29.970 1.00 15.19
ATOM 537 O   ARG A 71  0  22.059 50.998 29.027 1.00 14.48
ATOM 538 CB  ARG A 71  0  21.827 48.942 31.382 1.00 22.65
ATOM 539 CG  ARG A 71  0  22.273 49.589 32.671 1.00 29.50
ATOM 540 CD  ARG A 71  0  23.286 48.756 33.457 1.00 32.92
ATOM 541 NE  ARG A 71  0  22.712 47.550 34.035 1.00 38.11
ATOM 542 CZ  ARG A 71  0  22.551 46.358 33.452 1.00 40.14
ATOM 543 NH1 ARG A 71  0  22.939 46.138 32.190 1.00 41.23
ATOM 544 NH2 ARG A 71  0  22.022 45.333 34.130 1.00 40.89
ATOM 545 N   GLY A 72  0  20.613 52.145 30.311 1.00 14.82
ATOM 546 CA  GLY A 72  0  20.981 53.414 29.676 1.00 14.51
ATOM 547 C   GLY A 72  0  20.268 53.606 28.338 1.00 15.55
ATOM 548 O   GLY A 72  0  20.401 54.706 27.777 1.00 16.32
ATOM 549 N   THR A 73  0  19.503 52.651 27.804 1.00 12.12
ATOM 550 CA  THR A 73  0  18.857 52.781 26.516 1.00 12.50
ATOM 551 C   THR A 73  0  17.418 52.252 26.621 1.00 13.98
ATOM 552 O   THR A 73  0  16.890 51.534 25.776 1.00 13.81
ATOM 553 CB  THR A 73  0  19.577 52.086 25.346 1.00 12.21
ATOM 554 OG1 THR A 73  0  19.854 50.711 25.666 1.00 12.83
ATOM 555 CG2 THR A 73  0  20.944 52.711 25.000 1.00  9.81
ATOM 556 N   ASN A 74  0  16.744 52.617 27.708 1.00 12.97
ATOM 557 CA  ASN A 74  0  15.354 52.273 27.951 1.00 14.93
ATOM 558 C   ASN A 74  0  14.469 52.718 26.784 1.00 15.92
ATOM 559 O   ASN A 74  0  13.501 52.030 26.455 1.00 16.56
ATOM 560 CB  ASN A 74  0  14.851 52.821 29.271 1.00 13.06
ATOM 561 CG  ASN A 74  0  13.385 52.519 29.556 1.00 15.47
ATOM 562 OD1 ASN A 74  0  12.557 53.250 29.021 1.00 13.99
ATOM 563 ND2 ASN A 74  0  13.063 51.500 30.367 1.00 13.91
ATOM 564 N   TRP A 75  0  14.806 53.765 26.041 1.00 16.16
ATOM 565 CA  TRP A 75  0  14.036 54.262 24.917 1.00 16.49
ATOM 566 C   TRP A 75  0  14.050 53.345 23.701 1.00 17.29
ATOM 567 O   TRP A 75  0  13.235 53.529 22.776 1.00 16.34
ATOM 568 CB  TRP A 75  0  14.516 55.657 24.509 1.00 15.90
ATOM 569 CG  TRP A 75  0  15.990 55.705 24.207 1.00 16.04
ATOM 570 CD1 TRP A 75  0  17.011 55.972 25.072 1.00 14.90
ATOM 571 CD2 TRP A 75  0  16.584 55.475 22.916 1.00 15.94
ATOM 572 NE1 TRP A 75  0  18.210 55.917 24.384 1.00 15.89
ATOM 573 CE2 TRP A 75  0  17.977 55.624 23.076 1.00 15.80
ATOM 574 CE3 TRP A 75  0  16.060 55.171 21.656 1.00 14.88
ATOM 575 CZ2 TRP A 75  0  18.867 55.459 22.016 1.00 17.60
ATOM 576 CZ3 TRP A 75  0  16.928 55.025 20.603 1.00 16.64
ATOM 577 CH2 TRP A 75  0  18.321 55.153 20.785 1.00 18.16
ATOM 578 N   ALA A 76  0  14.962 52.372 23.675 1.00 15.12
ATOM 579 CA  ALA A 76  0  15.075 51.430 22.578 1.00 14.61
```

-continued

```
ATOM 580 C ALA A 76 0 14.569 50.047 22.971 1.00 13.98
ATOM 581 O ALA A 76 0 14.617 49.132 22.159 1.00 14.20
ATOM 582 CB ALA A 76 0 16.554 51.354 22.157 1.00 13.68
ATOM 583 N ASP A 77 0 13.941 49.885 24.121 1.00 14.47
ATOM 584 CA ASP A 77 0 13.409 48.605 24.586 1.00 14.23
ATOM 585 C ASP A 77 0 12.198 48.167 23.762 1.00 15.04
ATOM 586 O ASP A 77 0 11.982 46.946 23.638 1.00 13.78
ATOM 587 CB ASP A 77 0 13.112 48.567 26.072 1.00 13.41
ATOM 588 CG ASP A 77 0 12.945 47.155 26.612 1.00 14.93
ATOM 589 OD1 ASP A 77 0 11.943 46.986 27.345 1.00 15.07
ATOM 590 OD2 ASP A 77 0 13.744 46.217 26.334 1.00 13.73
ATOM 591 N GLY A 78 0 11.458 49.095 23.160 1.00 13.63
ATOM 592 CA GLY A 78 0 10.442 48.686 22.210 1.00 14.96
ATOM 593 C GLY A 78 0 9.040 48.309 22.631 1.00 16.75
ATOM 594 O GLY A 78 0 8.276 47.865 21.755 1.00 16.49
ATOM 595 N ALA A 79 0 8.631 48.436 23.886 1.00 15.34
ATOM 596 CA ALA A 79 0 7.252 48.176 24.270 1.00 14.70
ATOM 597 C ALA A 79 0 6.490 49.495 24.084 1.00 17.51
ATOM 598 O ALA A 79 0 6.690 50.486 24.807 1.00 17.05
ATOM 599 CB ALA A 79 0 7.145 47.70125.708 1.00 14.78
ATOM 600 N ASP A 80 0 5.641 49.536 23.053 1.00 18.56
ATOM 601 CA ASP A 80 0 4.859 50.741 22.798 1.00 19.52
ATOM 602 C ASP A 80 0 3.959 50.963 24.010 1.00 17.61
ATOM 603 O ASP A 80 0 3.530 49.999 24.664 1.00 16.72
ATOM 604 CB ASP A 80 0 4.044 50.714 21.510 1.00 24.02
ATOM 605 CG ASP A 80 0 3.003 49.607 21.549 1.00 28.13
ATOM 606 OD1 ASP A 80 0 3.410 48.417 21.541 1.00 30.66
ATOM 607 OD2 ASP A 80 0 1.803 49.959 21.603 1.00 30.61
ATOM 608 N GLY A 81 0 3.776 52.242 24.337 1.00 15.85
ATOM 609 CA GLY A 81 0 2.991 52.566 25.532 1.00 16.27
ATOM 610 C GLY A 81 0 3.846 52.615 26.784 1.00 18.72
ATOM 611 O GLY A 81 0 3.405 52.983 27.890 1.00 20.61
ATOM 612 N VAL A 82 0 5.108 52.173 26.725 1.00 19.11
ATOM 613 CA VAL A 82 0 5.978 52.119 27.890 1.00 19.14
ATOM 614 C VAL A 82 0 7.288 52.851 27.590 1.00 18.41
ATOM 615 O VAL A 82 0 7.594 53.839 28.242 1.00 16.79
ATOM 616 CB VAL A 82 0 6.266 50.697 28.390 1.00 19.82
ATOM 617 CG1 VAL A 82 0 7.059 50.741 29.710 1.00 21.37
ATOM 618 CG2 VAL A 82 0 4.995 49.894 28.640 1.00 19.27
ATOM 619 N ASN A 83 0 7.982 52.408 26.551 1.00 17.90
ATOM 620 CA ASN A 83 0 9.271 52.926 26.147 1.00 16.94
ATOM 621 C ASN A 83 0 9.226 53.778 24.886 1.00 18.32
ATOM 622 O ASN A 83 0 10.175 54.551 24.634 1.00 20.58
ATOM 623 CB ASN A 83 0 10.249 51.747 25.937 1.00 15.23
ATOM 624 CG ASN A 83 0 10.112 50.745 27.063 1.00 16.00
ATOM 625 OD1 ASN A 83 0 9.493 49.676 26.879 1.00 14.98
ATOM 626 ND2 ASN A 83 0 10.583 51.131 28.249 1.00 13.17
ATOM 627 N GLN A 84 0 8.183 53.668 24.066 1.00 16.40
ATOM 628 CA GLN A 84 0 8.080 54.464 22.867 1.00 16.34
ATOM 629 C GLN A 84 0 6.658 54.465 22.309 1.00 17.95
ATOM 630 O GLN A 84 0 5.816 53.679 22.728 1.00 17.69
ATOM 631 CB GLN A 84 0 8.995 53.953 21.754 1.00 17.98
ATOM 632 CG GLN A 84 0 8.456 52.654 21.127 1.00 16.63
ATOM 633 CD GLN A 84 0 9.272 52.225 19.938 1.00 18.17
ATOM 634 OE1 GLN A 84 0 8.994 52.601 18.792 1.00 20.91
ATOM 635 NE2 GLN A 84 0 10.279 51.385 20.096 1.00 18.70
ATOM 636 N CYS A 85 0 6.419 55.350 21.365 1.00 18.60
ATOM 637 CA CYS A 85 0 5.140 55.344 20.622 1.00 20.25
ATOM 638 C CYS A 85 0 5.512 54.555 19.375 1.00 19.55
ATOM 639 O CYS A 85 0 6.690 54.546 18.995 1.00 18.92
ATOM 640 CB CYS A 85 0 4.772 56.786 20.228 1.00 22.20
ATOM 641 SG CYS A 85 0 3.899 57.783 21.481 1.00 24.65
ATOM 642 N PRO A 86 0 4.589 53.951 18.674 1.00 21.19
ATOM 643 CA PRO A 86 0 4.869 53.152 17.498 1.00 20.78
ATOM 644 C PRO A 86 0 5.560 53.930 16.394 1.00 21.46
ATOM 645 O PRO A 86 0 5.453 55.137 16.298 1.00 23.08
ATOM 646 CB PRO A 86 0 3.530 52.555 17.028 1.00 19.94
ATOM 647 CG PRO A 86 0 2.667 52.720 18.252 1.00 19.59
ATOM 648 CD PRO A 86 0 3.174 53.872 19.062 1.00 20.46
ATOM 649 N ILE A 87 0 6.318 53.259 15.550 1.00 20.95
ATOM 650 CA ILE A 87 0 6.907 53.773 14.337 1.00 22.43
ATOM 651 C ILE A 87 0 5.768 53.641 13.292 1.00 22.80
ATOM 652 O ILE A 87 0 5.148 52.562 13.228 1.00 21.61
ATOM 653 CB ILE A 87 0 8.105 52.954 13.844 1.00 21.99
ATOM 654 CG1 ILE A 87 0 9.130 52.696 14.944 1.00 24.18
ATOM 655 CG2 ILE A 87 0 8.773 53.656 12.674 1.00 22.91
ATOM 656 CD1 ILE A 87 0 10.256 51.776 14.514 1.00 23.87
ATOM 657 N SER A 88 0 5.464 54.702 12.570 1.00 22.64
ATOM 658 CA SER A 88 0 4.338 54.709 11.647 1.00 22.85
ATOM 659 C SER A 88 0 4.751 54.268 10.249 1.00 23.35
ATOM 660 O SER A 88 0 5.870 54.489 9.764 1.00 23.30
ATOM 661 CB SER A 88 0 3.767 56.137 11.518 1.00 24.00
ATOM 662 OG SER A 88 0 3.379 56.770 12.720 1.00 23.93
ATOM 663 N PRO A 89 0 3.778 53.752 9.514 1.00 23.60
ATOM 664 CA PRO A 89 0 3.955 53.382 8.116 1.00 25.19
ATOM 665 C PRO A 89 0 4.579 54.556 7.361 1.00 26.58
ATOM 666 O PRO A 89 0 4.177 55.699 7.585 1.00 26.66
ATOM 667 CB PRO A 89 0 2.566 53.065 7.555 1.00 23.59
ATOM 668 CG PRO A 89 0 1.740 52.856 8.798 1.00 22.37
ATOM 669 CD PRO A 89 0 2.415 53.513 9.970 1.00 23.25
ATOM 670 N GLY A 90 0 5.588 54.311 6.550 1.00 27.73
ATOM 671 CA GLY A 90 0 6.223 55.338 5.748 1.00 30.55
ATOM 672 C GLY A 90 0 7.384 56.032 6.438 1.00 32.38
ATOM 673 O GLY A 90 0 8.050 56.894 5.879 1.00 32.53
ATOM 674 N HIS A 91 0 7.639 55.693 7.702 1.00 32.77
ATOM 675 CA HIS A 91 0 8.691 56.283 8.494 1.00 32.55
ATOM 676 C HIS A 91 0 9.649 55.179 8.982 1.00 32.36
ATOM 677 O HIS A 91 0 9.381 53.972 8.961 1.00 31.30
ATOM 678 CB HIS A 91 0 8.118 57.016 9.722 1.00 33.75
ATOM 679 CG HIS A 91 0 7.147 58.073 9.295 1.00 34.64
ATOM 680 ND1 HIS A 91 0 7.519 59.381 9.072 1.00 34.41
ATOM 681 CD2 HIS A 91 0 5.822 57.977 9.002 1.00 34.89
ATOM 682 CE1 HIS A 91 0 6.450 60.050 8.679 1.00 34.87
ATOM 683 NE2 HIS A 91 0 5.410 59.233 8.628 1.00 35.14
ATOM 684 N ALA A 92 0 10.786 55.668 9.437 1.00 29.57
ATOM 685 CA ALA A 92 0 11.895 54.898 9.937 1.00 27.71
ATOM 686 C ALA A 92 0 12.316 55.347 11.337 1.00 27.41
ATOM 687 O ALA A 92 0 12.076 56.484 11.741 1.00 26.12
ATOM 688 CB ALA A 92 0 13.051 55.057 8.967 1.00 25.23
ATOM 689 N PHE A 93 0 12.931 54.418 12.081 1.00 26.87
ATOM 690 CA PHE A 93 0 13.441 54.760 13.405 1.00 25.87
ATOM 691 C PHE A 93 0 14.746 54.008 13.632 1.00 25.21
ATOM 692 O PHE A 93 0 14.797 52.810 13.347 1.00 2580
ATOM 693 CB PHE A 93 0 12.457 54.456 14.526 1.00 25.30
ATOM 694 CG PHE A 93 0 12.964 54.955 15.847 1.00 25.41
ATOM 695 CD1 PHE A 93 0 13.154 56.309 16.061 1.00 25.36
ATOM 696 CD2 PHE A 93 0 13.276 54.057 16.853 1.00 25.31
ATOM 697 CE1 PHE A 93 0 13.637 56.753 17.285 1.00 26.54
ATOM 698 CE2 PHE A 93 0 13.754 54.503 18.078 1.00 25.39
ATOM 699 CZ PHE A 93 0 13.935 55.857 18.302 1.00 25.01
ATOM 700 N LEU A 94 0 15.756 54.699 14.136 1.00 23.39
ATOM 701 CA LEU A 94 0 17.046 54.058 14.361 1.00 23.35
ATOM 702 C LEU A 94 0 17.191 53.611 15.804 1.00 23.22
ATOM 703 O LEU A 94 0 17.261 54.431 16.714 1.00 23.47
ATOM 704 CB LEU A 94 0 18.186 54.994 13.943 1.00 24.96
ATOM 705 CG LEU A 94 0 19.630 54.555 14.170 1.00 26.28
ATOM 706 CD1 LEU A 94 0 19.979 53.313 13.352 1.00 25.99
ATOM 707 CD2 LEU A 94 0 20.627 55.678 13.887 1.00 26.06
ATOM 708 N TYR A 95 0 17.261 52.293 16.023 1.00 21.81
ATOM 709 CA TYR A 95 0 17.481 51.780 17.379 1.00 19.72
ATOM 710 C TYR A 95 0 18.991 51.663 17.585 1.00 20.90
ATOM 711 O TYR A 95 0 19.690 51.248 16.656 1.00 20.74
ATOM 712 CB TYR A 95 0 16.831 50.448 17.609 1.00 17.86
ATOM 713 CG TYR A 95 0 15.329 50.411 17.691 1.00 16.35
ATOM 714 CD1 TYR A 95 0 14.541 50.288 16.535 1.00 16.89
ATOM 715 CD2 TYR A 95 0 14.701 50.442 18.911 1.00 15.71
ATOM 716 CE1 TYR A 95 0 13.157 50.205 16.621 1.00 17.21
ATOM 717 CE2 TYR A 95 0 13.325 50.362 19.033 1.00 16.25
ATOM 718 CZ TYR A 95 0 12.568 50.266 17.874 1.00 17.97
ATOM 719 OH TYR A 95 0 11.205 50.189 18.001 1.00 18.61
ATOM 720 N LYS A 96 0 19.475 52.105 18.752 1.00 20.56
ATOM 721 CA LYS A 96 0 20.917 52.058 18.975 1.00 21.77
ATOM 722 C LYS A 96 0 21.139 51.519 20.386 1.00 20.91
ATOM 723 O LYS A 96 0 20.558 52.122 21.286 1.00 21.98
ATOM 724 CB LYS A 96 0 21.565 53.427 18.960 1.00 22.89
ATOM 725 CG LYS A 96 0 21.857 54.046 17.609 1.00 26.39
ATOM 726 CD LYS A 96 0 22.749 55.251 17.923 1.00 30.80
ATOM 727 CE LYS A 96 0 22.732 56.348 16.884 1.00 32.90
ATOM 728 NZ LYS A 96 0 23.767 57.378 17.277 1.00 36.06
ATOM 729 N PHE A 97 0 21.871 50.437 20.520 1.00 18.14
ATOM 730 CA PHE A 97 0 22.062 49.863 21.854 1.00 18.19
ATOM 731 C PHE A 97 0 23.276 48.928 21.805 1.00 16.76
ATOM 732 O PHE A 97 0 23.870 48.700 20.747 1.00 14.19
ATOM 733 CB PHE A 97 0 20.816 49.067 22.307 1.00 17.34
ATOM 734 CG PHE A 97 0 20.379 48.026 21.304 1.00 17.56
ATOM 735 CD1 PHE A 97 0 20.873 46.732 21.348 1.00 16.27
ATOM 736 CD2 PHE A 97 0 19.451 48.343 20.326 1.00 18.65
ATOM 737 CE1 PHE A 97 0 20.476 45.801 20.398 1.00 17.76
ATOM 738 CE2 PHE A 97 0 19.026 47.408 19.386 1.00 18.64
ATOM 739 CZ PHE A 97 0 19.546 46.120 19.416 1.00 17.55
```

-continued

```
ATOM 740 N   THR A 98  0 23.552 48.348 22.971 1.00 17.45
ATOM 741 CA  THR A 98  0 24.644 47.359 22.992 1.00 17.00
ATOM 742 C   THR A 98  0 24.304 46.333 24.042 1.00 16.63
ATOM 743 O   THR A 98  0 23.725 46.631 25.090 1.00 15.86
ATOM 744 CB  THR A 98  0 26.028 47.990 23.256 1.00 17.53
ATOM 745 OG1 THR A 98  0 27.017 46.924 23.372 1.00 19.01
ATOM 746 CG2 THR A 98  0 26.088 48.807 24.525 1.00 14.85
ATOM 747 N   PRO A 99  0 24.740 45.097 23.831 1.00 15.98
ATOM 748 CA  PRO A 99  0 24.601 44.019 24.787 1.00 15.11
ATOM 749 C   PRO A 99  0 25.445 44.270 26.020 1.00 15.99
ATOM 750 O   PRO A 99  0 25.260 43.633 27.064 1.00 15.94
ATOM 751 CB  PRO A 99  0 25.025 42.717 24.098 1.00 15.83
ATOM 752 CG  PRO A 99  0 25.042 43.140 22.644 1.00 17.12
ATOM 753 CD  PRO A 99  0 25.362 44.627 22.601 1.00 15.68
ATOM 754 N   ALA A 100 0 26.452 45.149 25.932 1.00 17.29
ATOM 755 CA  ALA A 100 0 27.316 45.501 27.050 1.00 16.88
ATOM 756 C   ALA A 100 0 27.919 44.293 27.754 1.00 16.16
ATOM 757 O   ALA A 100 0 27.779 44.187 28.977 1.00 18.13
ATOM 758 CB  ALA A 100 0 26.498 46.292 28.084 1.00 14.96
ATOM 759 N   GLY A 101 0 28.474 43.360 27.033 1.00 16.41
ATOM 760 CA  GLY A 101 0 29.063 42.172 27.599 1.00 17.49
ATOM 761 C   GLY A 101 0 28.130 40.994 27.769 1.00 16.15
ATOM 762 O   GLY A 101 0 28.593 39.930 28.137 1.00 16.57
ATOM 763 N   HIS A 102 0 26.838 41.120 27.521 1.00 17.58
ATOM 764 CA  HIS A 102 0 25.858 40.058 27.804 1.00 15.77
ATOM 765 C   HIS A 102 0 25.707 39.165 26.600 1.00 15.28
ATOM 766 O   HIS A 102 0 25.087 39.641 25.662 1.00 17.64
ATOM 767 CB  HIS A 102 0 24.498 40.666 28.186 1.00 17.95
ATOM 768 CG  HIS A 102 0 23.432 39.661 28.493 1.00 20.00
ATOM 769 ND1 HIS A 102 0 22.099 40.005 28.547 1.00 20.59
ATOM 770 CD2 HIS A 102 0 23.475 38.323 28.772 1.00 20.09
ATOM 771 CE1 HIS A 102 0 21.398 38.937 28.866 1.00 20.77
ATOM 772 NE2 HIS A 102 0 22.201 37.896 29.016 1.00 20.56
ATOM 773 N   ALA A 103 0 26.277 37.958 26.584 1.00 13.32
ATOM 774 CA  ALA A 103 0 26.141 37.127 25.415 1.00 13.99
ATOM 775 C   ALA A 103 0 24.974 36.156 25.649 1.00 13.43
ATOM 776 O   ALA A 103 0 24.571 35.905 26.784 1.00 11.81
ATOM 777 CB  ALA A 103 0 27.418 36.329 25.151 1.00 16.36
ATOM 778 N   GLY A 104 0 24.459 35.610 24.554 1.00 12.38
ATOM 779 CA  GLY A 104 0 23.381 34.632 24.778 1.00 12.85
ATOM 780 C   GLY A 104 0 22.480 34.451 23.581 1.00 11.06
ATOM 781 O   GLY A 104 0 22.674 35.057 22.515 1.00 10.91
ATOM 782 N   THR A 105 0 21.442 33.650 23.794 1.00 10.14
ATOM 783 CA  THR A 105 0 20.490 33.394 22.704 1.00 10.04
ATOM 784 C   THR A 105 0 19.238 34.236 22.989 1.00 9.52
ATOM 785 O   THR A 105 0 18.738 34.194 24.125 1.00 7.52
ATOM 786 CB  THR A 105 0 20.114 31.913 22.665 1.00 12.67
ATOM 787 OG1 THR A 105 0 21.273 31.075 22.593 1.00 13.47
ATOM 788 CG2 THR A 105 0 19.381 31.684 21.468 1.00 12.75
ATOM 789 N   PHE A 106 0 18.842 35.065 22.044 1.00 7.76
ATOM 790 CA  PHE A 106 0 17.731 35.992 22.243 1.00 10 15
ATOM 791 C   PHE A 106 0 16.756 35.910 21.068 1.00 8.42
ATOM 792 O   PHE A 106 0 16.941 35.083 20.166 1.00 8.33
ATOM 793 CB  PHE A 106 0 18.283 37.460 22.369 1.00 10.19
ATOM 794 CG  PHE A 106 0 19.291 37.577 23.506 1.00 12.95
ATOM 795 CD1 PHE A 106 0 18.905 37.443 24.815 1.00 11.44
ATOM 796 CD2 PHE A 106 0 20.654 37.775 23.220 1.00 12.37
ATOM 797 CE1 PHE A 106 0 19.855 37.531 25.822 1.00 14.20
ATOM 798 CE2 PHE A 106 0 21.574 37.857 24.273 1.00 11.56
ATOM 799 CZ  PHE A 106 0 21.202 37.733 25.599 1.00 9.45
ATOM 800 N   TRP A 107 0 15.869 36.887 20.917 1.00 6.61
ATOM 801 CA  TRP A 107 0 15.062 36.977 19.713 1.00 10.20
ATOM 802 C   TRP A 107 0 14.511 38.398 19.625 1.00 10.63
ATOM 803 O   TRP A 107 0 14.463 39.036 20.657 1.00 13.71
ATOM 804 CB  TRP A 107 0 13.928 35.966 19.636 1.00 7.49
ATOM 805 CG  TRP A 107 0 12.945 35.916 20.755 1.00 9.41
ATOM 806 CD1 TRP A 107 0 13.136 35.804 22.106 1.00 10.53
ATOM 807 CD2 TRP A 107 0 11.509 36.004 20.581 1.00 9.17
ATOM 808 NE1 TRP A 107 0 11.929 35.784 22.768 1.00 10.63
ATOM 809 CE2 TRP A 107 0 10.924 35.926 21.842 1.00 9.90
ATOM 810 CE3 TRP A 107 0 10.698 36.144 19.444 1.00 8.77
ATOM 811 CZ2 TRP A 107 0 9.538  35.947 22.025 1.00 10.01
ATOM 812 CZ3 TRP A 107 0 9.336  36.167 19.613 1.00 8.60
ATOM 813 CH2 TRP A 107 0 8.774  36.061 20.890 1.00 10.09
ATOM 814 N   TYR A 108 0 14.117 38.847 18.464 1.00 10.72
ATOM 815 CA  TYR A 108 0 13.498 40.148 18.302 1.00 12.19
ATOM 816 C   TYR A 108 0 12.030 39.869 17.875 1.00 13.62
ATOM 817 O   TYR A 108 0 11.752 38.837 17.245 1.00 13.85
ATOM 818 CB  TYR A 108 0 14.182 40.994 17.259 1.00 11.05
ATOM 819 CG  TYR A 108 0 14.176 40.413 15.857 1.00 13.89
ATOM 820 CD1 TYR A 108 0 15.087 39.464 15.423 1.00 12.99
ATOM 821 CD2 TYR A 108 0 13.257 40.897 14.920 1.00 14.94
ATOM 822 CE1 TYR A 108 0 15.064 38.979 14.130 1.00 13.64
ATOM 823 CE2 TYR A 108 0 13.216 40.409 13.624 1.00 15.34
ATOM 824 CZ  TYR A 108 0 14.123 39.443 13.236 1.00 14.99
ATOM 825 OH  TYR A 108 0 14.063 38.960 11.946 1.00 16.68
ATOM 826 N   HIS A 109 0 11.123 40.752 18.254 1.00 12.81
ATOM 827 CA  HIS A 109 0 9.735  40.630 17.826 1.00 14.92
ATOM 828 C   HIS A 109 0 9.057  41.988 17.991 1.00 15.96
ATOM 829 O   HIS A 109 0 9.392  42.800 18.875 1.00 15.67
ATOM 830 CB  HIS A 109 0 8.903  39.566 18.550 1.00 12.30
ATOM 831 CG  HIS A 109 0 8.804  39.727 20.036 1.00 12.30
ATOM 832 ND1 HIS A 109 0 7.788  40.429 20.666 1.00 9.89
ATOM 833 CD2 HIS A 109 0 9.614  39.264 21.034 1.00 10.76
ATOM 834 CE1 HIS A 109 0 7.982  40.379 21.971 1.00 8.49
ATOM 835 NE2 HIS A 109 0 9.086  39.679 22.224 1.00 7.92
ATOM 836 N   SER A 110 0 8.070  42.203 17.122 1.00 16.26
ATOM 837 CA  SER A 110 0 7.244  43.404 17.300 1.00 14.55
ATOM 838 C   SER A 110 0 6.548  43.283 18.646 1.00 13.56
ATOM 839 O   SER A 110 0 6.219  42.191 19.140 1.00 13.54
ATOM 840 CB  SER A 110 0 6.219  43.543 16.159 1.00 16.69
ATOM 841 OG  SER A 110 0 5.212  44.481 16.508 1.00 15.32
ATOM 842 N   HIS A 111 0 6.396  44.395 19.359 1.00 14.60
ATOM 843 CA  HIS A 111 0 5.724  44.397 20.645 1.00 16.23
ATOM 844 C   HIS A 111 0 4.349  45.070 20.478 1.00 18.61
ATOM 845 O   HIS A 111 0 3.713  45.391 21.473 1.00 21.72
ATOM 846 CB  HIS A 111 0 6.478  45.166 21.721 1.00 14.37
ATOM 847 CG  HIS A 111 0 6.392  44.519 23.077 1.00 15.33
ATOM 848 ND1 HIS A 111 0 5.341  44.660 23.947 1.00 14.55
ATOM 849 CD2 HIS A 111 0 7.265  43.676 23.680 1.00 14.72
ATOM 850 CE1 HIS A 111 0 5.589  43.936 25.040 1.00 16.29
ATOM 851 NE2 HIS A 111 0 6.773  43.326 24.920 1.00 15.35
ATOM 852 N   PHE A 112 0 3.950  45.382 19.258 1.00 18.67
ATOM 853 CA  PHE A 112 0 2.725  46.139 19.037 1.00 19.61
ATOM 854 C   PHE A 112 0 1.540  45.219 18.777 1.00 19.06
ATOM 855 O   PHE A 112 0 1.521  44.630 17.707 1.00 17.50
ATOM 856 CB  PHE A 112 0 2.971  47.113 17.875 1.00 21.16
ATOM 857 CG  PHE A 112 0 1.798  48.019 17.611 1.00 23.12
ATOM 858 CD1 PHE A 112 0 1.456  49.007 18.509 1.00 24.59
ATOM 859 CD2 PHE A 112 0 1.034  47.886 16.466 1.00 24.82
ATOM 860 CE1 PHE A 112 0 0.387  49.852 18.312 1.00 24.29
ATOM 861 CE2 PHE A 112 0 -0.063 48.714 16.243 1.00 25.87
ATOM 862 CZ  PHE A 112 0 -0.378 49.698 17.161 1.00 25.17
ATOM 863 N   GLY A 113 0 0.599  45.092 19.707 1.00 18.05
ATOM 864 CA  GLY A 113 0 -0.554 44.236 19.433 1.00 19.69
ATOM 865 C   GLY A 113 0 -0.085 42.819 19.096 1.00 22.25
ATOM 866 O   GLY A 113 0 0.937  42.333 19.593 1.00 20.55
ATOM 867 N   THR A 114 0 -0.817 42.173 18.186 1.00 20.91
ATOM 868 CA  THR A 114 0 -0.493 40.816 17.749 1.00 20.85
ATOM 869 C   THR A 114 0 0.296  40.774 16.471 1.00 18.04
ATOM 870 O   THR A 114 0 0.243  39.783 15.743 1.00 18.26
ATOM 871 CB  THR A 114 0 -1.847 40.095 17.487 1.00 23.93
ATOM 872 OG1 THR A 114 0 -2.609 40.910 16.554 1.00 25.68
ATOM 873 CG2 THR A 114 0 -2.571 39.928 18.792 1.00 23.72
ATOM 874 N   GLN A 115 0 1.023  41.819 16.095 1.00 17.04
ATOM 875 CA  GLN A 115 0 1.792  41.842 14.853 1.00 16.88
ATOM 876 C   GLN A 115 0 2.881  40.775 14.744 1.00 17.94
ATOM 877 O   GLN A 115 0 3.203  40.263 13.649 1.00 17.18
ATOM 878 CB  GLN A 115 0 2.391  43.244 14.757 1.00 17.55
ATOM 879 CG  GLN A 115 0 3.026  43.601 13.418 1.00 17.65
ATOM 880 CD  GLN A 115 0 3.558  45.024 13.418 1.00 17.73
ATOM 881 OE1 GLN A 115 0 3.257  45.782 12.482 1.00 19.19
ATOM 882 NE2 GLN A 115 0 4.334  45.421 14.422 1.00 14.70
ATOM 883 N   TYR A 116 0 3.515  40.416 15.881 1.00 16.32
ATOM 884 CA  TYR A 116 0 4.561  39.386 15.859 1.00 15.92
ATOM 885 C   TYR A 116 0 3.935  38.042 15.479 1.00 17.17
ATOM 886 O   TYR A 116 0 4.584  37.258 14.786 1.00 16.70
ATOM 887 CB  TYR A 116 0 5.411  39.312 17.096 1.00 13.45
ATOM 888 CG  TYR A 116 0 5.209  38.487 18.314 1.00 10.97
ATOM 889 CD1 TYR A 116 0 5.581  37.146 18.394 1.00 11.02
ATOM 890 CD2 TYR A 116 0 4.665  39.052 19.460 1.00 12.18
ATOM 891 CE1 TYR A 116 0 5.364  36.399 19.532 1.00 10.02
ATOM 892 CE2 TYR A 116 0 4.491  38.345 20.642 1.00 12.25
ATOM 893 CZ  TYR A 116 0 4.838  36.996 20.649 1.00 11.73
ATOM 894 OH  TYR A 116 0 4.642  36.295 21.821 1.00 12.72
ATOM 895 N   CYS A 117 0 2.654  37.829 15.842 1.00 17.70
ATOM 896 CA  CYS A 117 0 1.965  36.617 15.424 1.00 18.01
ATOM 897 C   CYS A 117 0 1.883  36.496 13.911 1.00 17.55
ATOM 898 O   CYS A 117 0 1.796  35.352 13.450 1.00 17.50
ATOM 899 CB  CYS A 117 0 0.565  36.528 16.042 1.00 17.90
```

-continued

```
ATOM  900  SG  CYS A 117 0  0.463 36.895 17.810 1.00 19.72
ATOM  901  N   ASP A 118 0  2.001 37.568 13.136 1.00 15.51
ATOM  902  CA  ASP A 118 0  1.953 37.509 11.696 1.00 17.74
ATOM  903  C   ASP A 228 0  3.341 37.445 11.061 1.00 18.72
ATOM  904  O   ASP A 118 0  3.494 37.770  9.865 1.00 17.47
ATOM  905  CB  ASP A 118 0  1.142 38.696 11.131 1.00 18.61
ATOM  906  CG  ASP A 118 0 -0.356 38.448 11.378 1.00 21.44
ATOM  907  OD1 ASP A 118 0 -0.826 37.331 11.0821.00 21.55
ATOM  908  OD2 ASP A 118 0 -1.064 39.333 11.885 1.00 21.54
ATOM  909  N   GLY A 119 0  4.355 37.095 11.882 1.00 18.19
ATOM  910  C   AGLY A 119 0 5.671 36.889 11.313 1.00 19.00
ATOM  911  C   GLY A 119 0  6.751 37.898 11.590 1.00 19.79
ATOM  912  O   GLY A 119 0  7.909 37.640 11.213 1.00 19.97
ATOM  913  N   LEU A 120 0  6.445 39.011 12.280 1.00 18.24
ATOM  914  CA  LEU A 120 0  7.484 39.991 12.569 1.00 16.08
ATOM  915  C   LEU A 120 0  8.210 39.565 13.848 1.00 16.53
ATOM  916  O   LEU A 120 0  7.933 40.051 14.939 1.00 15.31
ATOM  917  CB  LEU A 120 0  6.918 41.389 12.654 1.00 16.22
ATOM  918  CG  LEU A 120 0  7.916 42.540 12.830 1.00 17.73
ATOM  919  CD1 LEU A 120 0  9.188 42.293 12.043 1.00 17.73
ATOM  920  CD2 LEU A 120 0  7.302 43.880 12.448 1.00 16.66
ATOM  921  N   ARG A 121 0  9.144 38.622 13.682 1.00 14.23
ATOM  922  CA  ARG A 121 0  9.859 37.985 14.773 1.00 14.19
ATOM  923  C   ARG A 121 0 11.00  7 37.152 14.159 1.00 14.09
ATOM  924  O   ARG A 121 0 10.936 36.787 12.978 1.00 13.72
ATOM  925  CB  ARG A 121 0  8.934 37.061 15.581 1.00 12.30
ATOM  926  CG  ARG A 121 0  8.253 35.999 14.728 1.00 12.44
ATOM  927  CD  ARG A 121 0  7.303 35.098 15.518 1.00 11.94
ATOM  928  NE  ARG A 121 0  6.507 34.269 14.604 1.00 12.92
ATOM  929  CZ  ARG A 121 0  5.413 33.570 14.933 1.00 10.55
ATOM  930  NH1 ARG A 121 0  4.897 33.483 16.137 1.00  8.12
ATOM  931  NH2 ARG A 121 0  4.803 32.946 13.930 1.00 10.40
ATOM  932  N   GLY A 122 0 12.045 36.848 14.937 1.00 12.29
ATOM  933  CA  GLY A 122 0 13.162 36.078 14.364 1.00 11.42
ATOM  934  C   GLY A 122 0 14.185 35.918 15.486 1.00 12.42
ATOM  935  O   GLY A 122 0 14.095 36.604 16.509 1.00 11.47
ATOM  936  N   PRO A 123 0 15.164 35.075 15.246 1.00 11.82
ATOM  937  CA  PRO A 123 0 16.226 34.778 16.190 1.00 12.81
ATOM  938  C   PRO A 123 0 17.288 35.857 16.258 1.00 12.41
ATOM  939  O   PRO A 123 0 17.565 36.580 15.302 1.00 12.03
ATOM  940  CB  PRO A 123 0 16.833 33.416 15.713 1.00 12.34
ATOM  941  CG  PRO A 123 0 16.567 33.494 14.223 1.00 12.19
ATOM  942  CD  PRO A 123 0 15.283 34.289 14.021 1.00 11.35
ATOM  943  N   MET A 124 0 17.903 36.027 17.431 1.00 14.30
ATOM  944  CA  MET A 124 0 18.959 37.024 17.628 1.00 14.19
ATOM  945  C   MET A 124 0 20.040 36.414 18.528 1.00 15.37
ATOM  946  O   MET A 124 0 19.788 36.067 19.690 1.00 15.41
ATOM  947  CB  MET A 124 0 18.411 38.290 18.242 1.00 15.94
ATOM  948  CG  MET A 124 0 19.464 39.345 18.604 1.00 19.30
ATOM  949  SD  MET A 124 0 18.646 40.875 19.164 1.00 21.94
ATOM  950  CE  MET A 124 0 19.918 42.061 18.729 1.00 23.64
ATOM  951  N   VAL A 125 0 21.212 36.178 17.939 1.00 13.74
ATOM  952  CA  VAL A 125 0 22.282 35.479 18.658 1.00 13.87
ATOM  953  C   VAL A 125 0 23.478 36.390 18.872 1.00 13.68
ATOM  954  O   VAL A 125 0 24.004 36.976 17.945 1.00 14.01
ATOM  955  CB  VAL A 125 0 22.672 34.139 18.005 1.00 12.58
ATOM  956  CG1 VAL A 125 0 23.787 33.383 18.749 1.00 11.23
ATOM  957  CG2 VAL A 125 0 21.448 33.212 18.033 1.00 12.14
ATOM  958  N   ILE A 126 0 23.860 36.535 20.135 1.00 14.48
ATOM  959  CA  ILE A 126 0 25.016 37.295 20.557 1.00 14.53
ATOM  960  C   ILE A 126 0 26.131 36.348 21.054 1.00 13.58
ATOM  961  O   ILE A 126 0 26.061 35.791 22.154 1.00 12.93
ATOM  962  CB  ILE A 126 0 24.649 38.295 21.662 1.00 14.95
ATOM  963  CG1 ILE A 126 0 23.563 39.302 21.254 1.00 15.29
ATOM  964  CG2 ILE A 126 0 25.901 39.014 22.174 1.00 14.24
ATOM  965  CD1 ILE A 126 0 23.703 39.905 19.896 1.00 15.84
ATOM  966  N   TYR A 127 0 27.142 36.146 20.236 1.00 13.66
ATOM  967  CA  TYR A 127 0 28.278 35.258 20.529 1.00 14.62
ATOM  968  C   TYR A 127 0 29.328 35.778 21.507 1.00 15.97
ATOM  969  O   TYR A 127 0 29.626 36.977 21.669 1.00 15.27
ATOM  970  CB  TYR A 127 0 28.965 34.939 19.176 1.00 14.97
ATOM  971  CG  TYR A 127 0 28.057 34.136 18.272 1.00 16.10
ATOM  972  CD1 TYR A 127 0 27.823 32.782 18.496 1.00 14.96
ATOM  973  CD2 TYR A 127 0 27.428 34.753 17.177 1.00 16.64
ATOM  974  CE1 TYR A 127 0 26.995 32.057 17.650 1.00 16.16
ATOM  975  CE2 TYR A 127 0 26.576 34.039 16.356 1.00 17.32
ATOM  976  CZ  TYR A 127 0 26.374 32.692 16.592 1.00 18.16
ATOM  977  OH  TYR A 127 0 25.540 31.971 15.756 1.00 20.32
ATOM  978  N   ASP A 128 0 29.892 34.895 22.312 1.00 14.36
ATOM  979  CA  ASP A 128 0 30.825 35.269 23.365 1.00 16.80
ATOM  980  C   ASP A 128 0 32.222 34.863 22.939 1.00 20.11
ATOM  981  O   ASP A 128 0 32.508 33.656 22.777 1.00 21.41
ATOM  982  CB  ASP A 128 0 30.398 34.568 24.649 1.00 16.65
ATOM  983  CG  ASP A 128 0 31.136 35.055 25.874 1.00 18.36
ATOM  984  OD1 ASP A 128 0 32.194 35.708 25.750 1.00 18.72
ATOM  985  OD2 ASP A 128 0 30.710 34.819 27.024 1.00 20.03
ATOM  986  N   ASP A 129 0 33.148 35.798 22.771 1.00 22.30
ATOM  987  CA  ASP A 129 0 34.511 35.389 22.377 1.00 24.39
ATOM  988  C   ASP A 129 0 35.282 34.740 23.509 1.00 22.47
ATOM  989  O   ASP A 129 0 36.275 34.096 23.209 1.00 23.18
ATOM  990  CB  ASP A 129 0 35.298 36.490 21.707 1.00 28.46
ATOM  991  CG  ASP A 129 0 35.372 37.764 22.516 1.00 31.10
ATOM  992  OD1 ASP A 129 0 35.254 37.652 23.747 1.00 32.87
ATOM  993  OD2 ASP A129 0 35.553 38.824 21.891 1.00 34.70
ATOM  994  N   ASN A 130 0 34.829 34.684 24.736 1.00 21.92
ATOM  995  CA  ASN A 130 0 35.368 34.015 25.874 1.00 23.74
ATOM  996  C   ASN A 130 0 34.382 32.976 26.417 1.00 23.02
ATOM  997  O   ASN A 130 0 34.352 32.684 27.616 1.00 20.14
ATOM  998  CB  ASN A130 0 35.686 35.002 27.028 1.00 26.41
ATOM  999  CG  ASN A 130 0 36.583 36.127 26.550 1.00 30.99
ATOM 1000  OD1 ASN A 130 0 36.187 37.309 26.486 1.00 33.20
ATOM 1000  ND2 ASN A 130 0 37.818 35.769 26.175 1.00 30.96
ATOM 1002  N   ASP A 131 0 33.533 32.401 25.561 1.00 23.32
ATOM 1003  CA  ASP A 131 0 32.476 31.543 26.127 1.00 21.63
ATOM 1004  C   ASP A 131 0 33.010 30.514 27.103 1.00 19.56
ATOM 1005  O   ASP A 131 0 33.704 29.569 26.766 1.00 19.71
ATOM 1006  CB  ASP A 131 0 31.594 30.877 25.063 1.00 22.97
ATOM 1007  CG  ASP A 131 0 30.220 30.487 25.591 1.00 24.48
ATOM 1008  OD1 ASP A 131 0 30.181 29.525 26.397 1.00 26.42
ATOM 1009  OD2 ASP A 131 0 29.166 31.051 25.212 1.00 22.66
ATOM 1010  N   PRO A 132 0 32.491 30.548 28.315 1.00 18.77
ATOM 1011  CA  PRO A 132 0 32.759 29.611 29.381 1.00 19.41
ATOM 1012  C   PRO A 132 0 32.523 28.141 29.031 1.00 20.89
ATOM 1013  O   PRO A 132 0 33.112 27.250 29.672 1.00 19.99
ATOM 1014  CB  PRO A 132 0 31.799 29.990 30.531 1.00 18.42
ATOM 1015  CG  PRO A 132 0 31.589 31.470 30.263 1.00 16.87
ATOM 1016  CD  PRO A 132 0 31.645 31.673 28.778 1.00 16.73
ATOM 1017  N   HIS A 133 0 31.668 27.836 28.063 1.00 19.47
ATOM 1018  CA  HIS A 133 0 31.331 26.465 27.700 1.00 18.79
ATOM 1019  C   HIS A 133 0 31.887 26.014 26.372 1.00 19.35
ATOM 1020  O   HIS A 133 0 31.503 24.954 25.826 1.00 18.60
ATOM 1021  CB  HIS A 133 0 29.789 26.428 27.536 1.00 18.91
ATOM 1022  CG  HIS A 133 0 29.065 26.242 28.815 1.00 18.13
ATOM 1023  ND1 HIS A 133 0 29.566 25.551 29.877 1.00 19.52
ATOM 1024  CD2 HIS A 133 0 27.817 26.625 29.183 1.00 19.38
ATOM 1025  CE1 HIS A 133 0 28.679 25.530 30.855 1.00 20.08
ATOM 1026  NE2 HIS A 133 0 27.587 26.180 30.457 1.00 19.60
ATOM 1027  N   ALA A 134 0 32.840 26.801 25.852 1.00 19.40
ATOM 1028  CA  ALA A 134 0 33.413 26.465 24.552 1.00 21.88
ATOM 1029  C   ALA A 134 0 34.080 25.107 24.525 1.00 21.69
ATOM 1030  O   ALA A 134 0 34.120 24.514 23.439 1.00 21.61
ATOM 1031  CB  ALA A 134 0 34.418 27.548 24.128 1.00 22.55
ATOM 1032  N   ALA A 135 0 34.582 24.527 25.622 1.00 21.96
ATOM 1033  CA  ALA A 135 0 35.178 23.192 25.483 1.00 23.53
ATOM 1034  C   ALA A 135 0 34.144 22.096 25.232 1.00 24.47
ATOM 1035  O   ALA A 135 0 34.488 20.936 24.989 1.00 24.77
ATOM 1036  CB  ALA A 135 0 35.910 22.820 26.776 1.00 21.92
ATOM 1037  N   LEU A 136 0 32.862 22.375 25.457 1.00 24.95
ATOM 1038  CA  LEU A 136 0 31.800 21.376 25.404 1.00 23.15
ATOM 1039  C   LEU A 136 0 31.284 21.076 24.016 1.00 20.31
ATOM 1040  O   LEU A 136 0 30.609 20.054 23.924 1.00 19.62
ATOM 1041  CB  LEU A 136 0 30.665 21.845 26.318 1.00 24.43
ATOM 1042  CG  LEU A 136 0 30.501 21.211 27.686 1.00 27.55
ATOM 1043  CD1 LEU A 136 0 31.803 20.721 28.285 1.00 25.75
ATOM 1044  CD2 LEU A 136 0 29.747 22.129 28.644 1.00 26.92
ATOM 1045  N   TYR A 137 0 31.565 21.888 22.998 1.00 17.05
ATOM 1046  CA  TYR A 137 0 31.085 21.612 21.662 1.00 16.65
ATOM 1047  C   TYR A 137 0 32.076 22.054 20.599 1.00 17.99
ATOM 1048  O   TYR A 137 0 32.965 22.891 20.794 1.00 18.69
ATOM 1049  CB  TYR A 137 0 29.724 22.319 21.402 1.00 16.73
ATOM 1050  CG  TYR A 137 0 29.711 23.760 21.857 1.00 16.24
ATOM 1051  CD1 TYR A 137 0 29.302 24.108 23.150 1.00 16.00
ATOM 1052  CD2 TYR A 137 0 30.159 24.754 21.001 1.00 14.76
ATOM 1053  CE1 TYR A 137 0 29.355 25.448 23.551 1.00 15.32
ATOM 1054  CE2 TYR A 137 0 30.165 26.081 21.396 1.00 15.52
ATOM 1055  CZ  TYR A 137 0 29.759 26.410 22.675 1.00 15.61
ATOM 1056  OH  TYR A 137 0 29.782 27.731 23.055 1.00 17.56
ATOM 1057  N   ASP A 138 0 31.903 21.549 19.393 1.00 19.04
ATOM 1058  CA  ASP A 138 0 32.733 21.859 18.253 1.00 20.02
ATOM 1059  C   ASP A 138 0 32.139 22.933 17.364 1.00 21.05
```

-continued

```
ATOM   1060  O    ASP A 138   0   32.911 23.553 16.631  1.00 21.98
ATOM   1061  CB   ASP A 138   0   32.836 20.628 17.315  1.00 20.66
ATOM   1062  CG   ASP A 138   0   33.355 19.455 18.089  1.00 22.79
ATOM   1063  OD1  ASP A 138   0   32.744 18.404 18.318  1.00 24.88
ATOM   1064  OD2  ASP A 138   0   34.481 19.675 18.581  1.00 25.34
ATOM   1065  N    GLU A 139   0   30.825 22.957 17.184  1.00 19.73
ATOM   1066  CA   GLU A 139   0   30.223 23.865 16.213  1.00 21.27
ATOM   1067  C    GLU A 139   0   29.086 24.668 16.825  1.00 18.97
ATOM   1068  O    GLU A 139   0   28.306 24.143 17.608  1.00 16.95
ATOM   1069  CB   GLU A 139   0   29.617 23.164 15.000  1.00 24.71
ATOM   1070  CG   GLU A 139   0   30.509 22.149 14.311  1.00 30.89
ATOM   1071  CD   GLU A 139   0   31.633 22.868 13.587  1.00 34.42
ATOM   1072  OE1  GLU A 139   0   31.340 23.869 12.898  1.00 36.87
ATOM   1073  OE2  GLU A 139   0   32.794 22.457 13.705  1.00 37.60
ATOM   1074  N    ASP A 140   0   29.057 25.933 16.408  1.00 19.38
ATOM   1075  CA   ASP A 140   0   28.026 26.847 16.912  1.00 17.89
ATOM   1076  C    ASP A 140   0   27.858 27.901 15.837  1.00 18.87
ATOM   1077  O    ASP A 140   0   28.705 28.780 15.768  1.00 21.31
ATOM   1078  CB   ASP A 140   0   28.438 27.399 18.268  1.00 16.26
ATOM   1079  CG   ASP A 140   0   27.445 28.399 18.858  1.00 16.73
ATOM   1080  OD 1 ASP A 140   0   27.854 29.143 19.781  1.00 14.86
ATOM   1081  OD 2 ASP A 140   0   26.287 28.446 18.401  1.00 13.82
ATOM   1082  N    ASP A 141   0   26.862 27.844 14.972  1.00 17.34
ATOM   1083  CA   ASP A 141   0   26.750 28.859 13.937  1.00 19.52
ATOM   1084  C    ASP A 141   0   25.301 29.031 13.520  1.00 19.33
ATOM   1085  O    ASP A 141   0   24.342 28.513 14.115  1.00 17.91
ATOM   1086  CB   ASP A 141   0   27.681 28.509 12.772  1.00 21.66
ATOM   1087  CG   ASP A 141   0   27.384 27.151 12.153  1.00 24.87
ATOM   1088  OD1  ASP A 141   0   28.280 26.521 11.567  1.00 28.90
ATOM   1089  OD2  ASP A 141   0   26.271 26.604 12.302  1.00 25.89
ATOM   1090  N    GLU A 142   0   25.102 29.688 12.387  1.00 19.21
ATOM   1091  CA   GLU A 142   0   23.775 29.945 11.880  1.00 20.84
ATOM   1092  C    GLU A 142   0   23.052 28.636 11.592  1.00 19.95
ATOM   1093  O    GLU A 142   0   21.844 28.656 11.665  1.00 18.73
ATOM   1094  CB   GLU A 142   0   23.771 30.894 10.699  1.00 23.40
ATOM   1095  CG   GLU A 142   0   24.295 30.301  9.407  1.00 27.22
ATOM   1096  CD   GLU A 142   0   25.718 30.826  9.221  1.00 32.36
ATOM   1097  OE1  GLU A 142   0   26.513 30.920 10.206  1.00 31.87
ATOM   1098  OE2  GLU A 142   0   25.968 31.136  8.023  1.00 35.76
ATOM   1099  N    ASN A 143   0   23.723 27.508 11.378  1.00 20.40
ATOM   1100  CA   ASN A 143   0   23.066 26.227 11.151  1.00 19.61
ATOM   1101  C    ASN A 143   0   22.785 25.468 12.421  1.00 18.35
ATOM   1102  O    ASN A 143   0   22.317 24.337 12.325  1.00 15.65
ATOM   1103  CB   ASN A 143   0   24.024 25.401 10.229  1.00 23.57
ATOM   1104  CG   ASN A 143   0   24.133 26.067  8.857  1.00 26.63
ATOM   1105  OD1  ASN A 143   0   25.220 26.376  8.356  1.00 29.89
ATOM   1106  ND2  ASN A 143   0   23.049 26.342  8.175  1.00 25.46
ATOM   1107  N    THR A 144   0   23.067 25.974 13.632  1.00 16.76
ATOM   1108  CA   THR A 144   0   22.678 25.257 14.825  1.00 15.40
ATOM   1109  C    THR A 144   0   21.556 25.976 15.577  1.00 15.58
ATOM   1110  O    THR A 144   0   21.361 25.776 16.789  1.00 17.88
ATOM   1111  CB   THR A 144   0   23.848 25.018 15.785  1.00 16.43
ATOM   1112  OG1  THR A 144   0   24.296 26.270 16.297  1.00 14.82
ATOM   1113  CG2  THR A 144   0   24.935 24.215 15.104  1.00 15.98
ATOM   1114  N    ILE A 145   0   20.821 26.834 14.898  1.00 13.92
ATOM   1115  CA   ILE A 145   0   19.697 27.550 15.500  1.00 14.31
ATOM   1116  C    ILE A 145   0   18.392 26.835 15.139  1.00 13.84
ATOM   1117  O    ILE A 145   0   18.127 26.478 13.996  1.00 12.32
ATOM   1118  CB   ILE A 145   0   19.641 29.016 15.011  1.00 15.15
ATOM   1119  CG1  ILE A 145   0   20.881 29.726 15.608  1.00 16.27
ATOM   1120  CG2  ILE A 145   0   18.346 29.736 15.375  1.00 13.14
ATOM   1121  CD1  ILE A 145   0   21.256 31.00  14.892  1.00 16.72
ATOM   1122  N    ILE A 146   0   17.550 26.644 16.141  1.00 13.54
ATOM   1123  CA   ILE A 146   0   16.263 25.983 15.926  1.00 13.70
ATOM   1124  C    ILE A 146   0   15.167 26.899 16.494  1.00 12.67
ATOM   1125  O    ILE A 146   0   15.155 27.082 17.714  1.00 10.09
ATOM   1126  CB   ILE A 146   0   16.183 24.580 16.553  1.00 15.97
ATOM   1127  CG1  ILE A 146   0   17.280 23.621 16.012  1.00 17.29
ATOM   1128  CG2  ILE A 146   0   14.831 23.937 16.207  1.00 14.52
ATOM   1129  CD1  ILE A 146   0   17.359 22.340 16.832  1.00 18.45
ATOM   1130  N    THR A 147   0   14.360 27.507 15.610  1.00 10.81
ATOM   1131  CA   THR A 147   0   13.240 28.310 16.102  1.00 12.54
ATOM   1132  C    THR A 147   0   11.912 27.526 15.988  1.00 13.55
ATOM   1133  O    THR A 147   0   11.655 26.724 15.076  1.00 12.65
ATOM   1134  CB   THR A 147   0   13.078 29.642 15.351  1.00 12.37
ATOM   1135  OG1  THR A 147   0   12.728 29.311 14.005  1.00 10.17
ATOM   1136  CG2  THR A 147   0   14.381 30.479 15.402  1.00 11.93
ATOM   1137  N    LEU A 148   0   11.062 27.715 16.972  1.00 12.48
ATOM   1138  CA   LEU A 148   0    9.719 27.171 17.039  1.00 13.90
ATOM   1139  C    LEU A 148   0    8.719 28.350 16.916  1.00 15.44
ATOM   1140  O    LEU A 148   0    8.860 29.383 17.579  1.00 15.28
ATOM   1141  CB   LEU A 148   0    9.501 26.419 18.340  1.00 12.83
ATOM   1142  CG   LEU A 148   0   10.502 25.293 18.669  1.00 12.45
ATOM   1143  CD1  LEU A 148   0   10.154 24.669 19.997  1.00 11.49
ATOM   1144  CD2  LEU A 148   0   10.552 24.203 17.597  1.00 11.82
ATOM   1145  N    ALA A 149   0    7.726 28.241 16.053  1.00 14.08
ATOM   1146  CA   ALA A 149   0    6.725 29.256 15.825  1.00 15.37
ATOM   1147  C    ALA A 149   0    5.336 28.658 15.521  1.00 16.78
ATOM   1148  O    ALA A 149   0    5.198 27.637 14.841  1.00 15.78
ATOM   1149  CB   ALA A 149   0    7.068 30.127 14.628  1.00 13.22
ATOM   1150  N    ASP A 150   0    4.337 29.344 16.065  1.00 16.39
ATOM   1151  CA   ASP A 150   0    2.941 28.995 15.864  1.00 15.96
ATOM   1152  C    ASP A 150   0    2.515 29.758 14.624  1.00 16.53
ATOM   1153  O    ASP A 150   0    2.960 30.905 14.483  1.00 18.17
ATOM   1154  CB   ASP A 150   0    2.066 29.440 17.027  1.00 16.78
ATOM   1155  CG   ASP A 150   0    2.345 30.836 17.561  1.00 18.15
ATOM   1156  OD1  ASP A 150   0    3.410 31.472 17.347  1.00 16.29
ATOM   1157  OD2  ASP A 150   0    1.414 31.311 18.264  1.00 17.83
ATOM   1158  N    TRP A 151   0    1.776 29.157 13.726  1.00 15.62
ATOM   1159  CA   TRP A 151   0    1.366 29.828 12.499  1.00 14.37
ATOM   1160  C    TRP A 151   0   -0.140 29.688 12.226  1.00 14.78
ATOM   1161  O    TRP A 151   0   -0.679 28.607 12.425  1.00 13.41
ATOM   1162  CB   TRP A 151   0    2.229 29.239 11.373  1.00 13.56
ATOM   1163  CG   TRP A 151   0    2.046 30.004 10.097  1.00 13.31
ATOM   1164  CD1  TRP A 151   0    1.385 29.545  8.991  1.00 13.60
ATOM   1165  CD2  TRP A 151   0    2.484 31.316  9.806  1.00 15.46
ATOM   1166  NE1  TRP A 151   0    1.412 30.497  8.017  1.00 14.49
ATOM   1167  CE2  TRP A 151   0    2.061 31.605  8.473  1.00 15.53
ATOM   1168  CE3  TRP A 151   0    3.189 32.294 10.522  1.00 16.28
ATOM   1169  CZ2  TRP A 151   0    2.306 32.822  7.846  1.00 16.57
ATOM   1170  CZ3  TRP A 151   0    3.436 33.505  9.881  1.00 18.22
ATOM   1171  CH2  TRP A 151   0    3.003 33.766  8.560  1.00 18.00
ATOM   1172  N    TYR A 152   0   -0.818 30.745 11.812  1.00 15.59
ATOM   1173  CA   TYR A 152   0   -2.266 30.813 11.614  1.00 17.47
ATOM   1174  C    TYR A 152   0   -2.556 31.086 10.149  1.00 18.79
ATOM   1175  O    TYR A 152   0   -1.830 31.856  9.521  1.00 19.15
ATOM   1176  CB   TYR A 152   0   -2.981 31.930 12.434  1.00 16.37
ATOM   1177  CG   TYR A 152   0   -2.539 31.776 13.887  1.00 16.24
ATOM   1178  CD1  TYR A 152   0   -1.313 32.303 14.318  1.00 15.22
ATOM   1179  CD2  TYR A 152   0   -3.267 30.998 14.767  1.00 15.29
ATOM   1180  CE1  YRA 152   0   -0.889 32.135 15.626  1.00 14.67
ATOM   1181  CE2  TYR A 152   0   -2.831 30.799 16.054  1.00 16.52
ATOM   1182  CZ   TYR A 152   0   -1.632 31.369 16.474  1.00 16.12
ATOM   1183  OH   TYR A 152   0   -1.219 31.139 17.771  1.00 16.36
ATOM   1184  N    HIS A 153   0   -3.590 30.445  9.599  1.00 20.39
ATOM   1185  CA   HIS A 153   0   -3.899 30.683  8.181  1.00 21.90
ATOM   1186  C    HIS A 153   0   -4.642 31.988  7.952  1.00 21.94
ATOM   1187  O    HIS A 153   0   -4.750 32.386  6.784  1.00 22.32
ATOM   1188  CB   HIS A 153   0   -4.592 29.483  7.549  1.00 22.29
ATOM   1189  CG   HIS A 153   0   -3.651 28.319  7.385  1.00 24.52
ATOM   1190  ND1  HIS A 153   0   -4.071 27.022  7.258  1.00 24.25
ATOM   1191  CD2  HIS A 153   0   -2.286 28.274  7.338  1.00 23.32
ATOM   1192  CE1  HIS A 153   0   -3.034 26.220  7.124  1.00 24.15
ATOM   1193  NE2  HIS A 153   0   -1.956 26.965  7.178  1.00 24.30
ATOM   1194  N    ILE A 154   0   -5.084 32.718  8.972  1.00 21.86
ATOM   1195  CA   ILE A 154   0   -5.611 34.046  8.686  1.00 24.39
ATOM   1196  C    ILE A 154   0   -4.904 35.051  9.597  1.00 22.15
ATOM   1197  O    ILE A 154   0   -4.517 34.732 10.698  1.00 20.15
ATOM   1198  CB   ILE A 154   0   -7.120 34.281  8.693  1.00 26.43
ATOM   1199  CG1  ILE A 154   0   -7.682 34.498 10.099  1.00 27.66
ATOM   1200  CG2  ILE A 154   0   -7.947 33.251  7.928  1.00 26.60
ATOM   1201  CD1  ILE A 154   0   -7.312 33.468 11.125  1.00 28.86
ATOM   1202  N    PRO A 155   0   -4.723 36.255  9.105  1.00 23.79
ATOM   1203  CA   PRO A 155   0   -4.108 37.361  9.816  1.00 23.66
ATOM   1204  C    PRO A 155   0   -4.604 37.435 11.252  1.00 24.59
ATOM   1205  O    PRO A 155   0   -5.814 37.317 11.539  1.00 24.53
ATOM   1206  CB   PRO A 155   0   -4.546 38.634  9.077  1.00 24.20
ATOM   1207  CG   PRO A 155   0   -4.990 38.162  7.733  1.00 23.40
ATOM   1208  CD   PRO A 155   0   -5.207 36.672  7.776  1.00 23.41
ATOM   1209  N    ALA A 156   0   -3.704 37.776 12.178  1.00 24.03
ATOM   1210  CA   ALA A 156   0   -4.066 37.806 13.588  1.00 25.45
ATOM   1211  C    ALA A156    0   -5.262 38.667 13.992  1.00 24.85
ATOM   1212  O    ALA A 156   0   -6.083 38.217 14.798  1.00 22.79
ATOM   1213  CB   ALA A 156   0   -2.866 38.045 14.492  1.00 24.30
ATOM   1214  N    PRO A 157   0   -5.393 39.873 13.518  1.00 25.98
ATOM   1215  CA   PRO A 157   0   -6.521 40.741 13.807  1.00 28.77
ATOM   1216  C    PRO A 157   0   -7.840 40.092 13.406  1.00 30.78
ATOM   1217  O    PRO A 157   0   -8.798 40.416 14.105  1.00 34.62
ATOM   1218  CB   PRO A 157   0   -6.324 42.071 13.068  1.00 26.56
ATOM   1219  CG   PRO A 157   0   -4.859 42.013 12.762  1.00 25.98
```

-continued

```
ATOM 1220 CD  PRO A 157 0 -4.480  40.547 12.585 1.00 25.96
ATOM 1221 N   SER A 158 0 -7.950  39.207 12.430 1.00 30.95
ATOM 1222 CA  SER A 158 0 -9.174  38.549 12.047 1.00 31.32
ATOM 1223 C   SER A 158 0 -9.450  37.288 12.851 1.00 33.61
ATOM 1224 O   SER A 158 0 -10.472 36.633 12.575 1.00 34.71
ATOM 1225 CB  SER A 158 0 -9.176  38.118 10.577 1.00 30.14
ATOM 1226 OG  SER A 158 0 -8.942  39.187 9.665  1.00 31.20
ATOM 1227 N   ILE A 159 0 -8.588  36.875 13.773 1.00 34.23
ATOM 1228 CA  ILE A 159 0 -8.918  35.642 14.491 1.00 36.40
ATOM 1229 C   ILE A 159 0 -10.189 35.896 15.309 1.00 39.20
ATOM 1230 O   ILE A 159 0 -10.294 36.875 16.046 1.00 39.00
ATOM 1231 CB  ILE A 159 0 -7.769  35.121 15.360 1.00 35.56
ATOM 1232 CG1 ILE A 159 0 -6.713  34.408 14.485 1.00 35.58
ATOM 1233 CG2 ILE A 159 0 -8.262  34.184 16.452 1.00 34.97
ATOM 1234 CD1 ILE A 159 0 -5.388  34.268 15.212 1.00 34.91
ATOM 1235 N   GLN A 160 0 -11.137 34.969 15.196 1.00 41.53
ATOM 1236 CA  GLN A 160 0 -12.398 35.056 15.946 1.00 42.57
ATOM 1237 C   GLN A 160 0 -12.466 33.914 16.949 1.00 40.51
ATOM 1238 O   GLN A 160 0 -12.308 32.741 16.585 1.00 41.96
ATOM 1239 CB  GLN A 160 0 -13.542 35.062 14.937 1.00 45.52
ATOM 1240 CG  GLN A 160 0 -14.814 34.319 15.267 1.00 48.48
ATOM 1241 CD  GLN A 160 0 -15.570 33.799 14.055 1.00 50.12
ATOM 1242 OE1 GLN A 160 0 -16.204 32.737 14.118 1.00 50.77
ATOM 1243 NE2 GLN A 160 0 -15.504 34.520 12.940 1.00 51.22
ATOM 1244 N   GLY A 161 0 -12.667 34.191 18.225 1.00 37.10
ATOM 1245 CA  GLY A 161 0 -12.722 33.112 19.208 1.00 34.91
ATOM 1246 C   GLY A 161 0 -11.305 32.826 19.696 1.00 34.13
ATOM 1247 O   GLY A 161 0 -10.412 33.648 19.451 1.00 32.40
ATOM 1248 N   ALA A 162 0 -11.158 31.738 20.433 1.00 33.01
ATOM 1249 CA  ALA A 162 0 -9.864  31.355 20.988 1.00 32.39
ATOM 1250 C   ALA A 162 0 -8.927  30.902 19.880 1.00 31.53
ATOM 1251 O   ALA A 162 0 -9.285  30.132 19.013 1.00 30.73
ATOM 1252 CB  ALA A 162 0 -10.058 30.263 22.010 1.00 34.12
ATOM 1253 N   ALA A 163 0 -7.731  31.475 19.851 1.00 32.06
ATOM 1254 CA  ALA A 163 0 -6.740  31.202 18.814 1.00 30.85
ATOM 1255 C   ALA A 163 0 -6.219  29.774 18.897 1.00 29.40
ATOM 1256 O   ALA A 163 0 -5.967  29.223 19.965 1.00 30.49
ATOM 1257 CB  ALA A 163 0 -5.607  32.217 18.911 1.00 30.29
ATOM 1258 N   GLN A 164 0 -6.101  29.130 17.754 1.00 28.69
ATOM 1259 CA  GLN A 164 0 -5.616  27.769 17.612 1.00 28.24
ATOM 1260 C   GLN A 164 0 -4.720  27.744 16.370 1.00 25.02
ATOM 1261 O   GLN A 164 0 -5.157  28.046 15.260 1.00 23.64
ATOM 1262 CB  GLN A 164 0 -6.732  26.756 17.361 1.00 31.99
ATOM 1263 CG  GLN A 164 0 -7.885  26.640 18.319 1.00 36.24
ATOM 1264 CD  GLN A 164 0 -7.535  25.809 19.540 1.00 40.95
ATOM 1265 OE1 GLN A 164 0 -7.863  26.166 20.684 1.00 43.34
ATOM 1266 NE2 GLN A 164 0 -6.864  24.672 19.328 1.00 41.86
ATOM 1267 N   PRO A 165 0 -3.446  27.406 16.549 1.00 22.68
ATOM 1268 CA  PRO A 165 0 -2.501  27.360 15.463 1.00 20.43
ATOM 1269 C   PRO A 165 0 -2.856  26.294 14.429 1.00 18.89
ATOM 1270 O   PRO A 165 0 -3.286  25.176 14.715 1.00 18.00
ATOM 1271 CB  PRO A 165 0 -1.126  27.075 16.088 1.00 20.83
ATOM 1272 CG  PRO A 165 0 -1.476  26.651 17.479 1.00 22.05
ATOM 1273 CD  PRO A 165 0 -2.873  27.081 17.851 1.00 21.57
ATOM 1274 N   ASP A 166 0 -2.667  26.608 13.169 1.00 17.50
ATOM 1275 CA  ASP A 166 0 -2.829  25.677 12.059 1.00 19.82
ATOM 1276 C   ASP A 166 0 -1.591  24.788 11.930 1.00 19.47
ATOM 1277 O   ASP A 166 0 -1.692  23.649 11.506 1.00 19.38
ATOM 1278 CB  ASP A 166 0 -3.005  26.413 10.727 1.00 19.75
ATOM 1279 CG  ASP A 166 0 -4.347  27.162 10.728 1.00 21.69
ATOM 1280 OD1 ASP A 166 0 -5.376  26.480 10.593 1.00 22.24
ATOM 1281 OD2 ASP A 166 0 -4.384  28.392 10.885 1.00 22.13
ATOM 1282 N   ALA A 167 0 -0.435  25.386 12.231 1.00 18.54
ATOM 1283 CA  ALA A 167 0 0.806   24.614 12.142 1.00 18.74
ATOM 1284 C   ALA A 167 0 1.867   25.056 13.148 1.00 17.69
ATOM 1285 O   ALA A 167 0 1.874   26.147 13.715 1.00 15.83
ATOM 1286 CB  ALA A 167 0 1.387   24.767 10.735 1.00 17.32
ATOM 1287 N   THR A 168 0 2.826   24.166 13.335 1.00 18.40
ATOM 1288 CA  THR A 168 0 4.087   24.402 14.027 1.00 14.85
ATOM 1289 C   THR A 168 0 5.180   24.553 12.955 1.00 15.24
ATOM 1290 O   THR A 168 0 5.402   23.737 12.071 1.00 12.99
ATOM 1291 CB  THR A 168 0 4.530   23.235 14.900 1.00 14.31
ATOM 1292 OG1 THR A 168 0 3.558   23.068 15.920 1.00 12.30
ATOM 1293 CG2 THR A 168 0 5.921   23.516 15.524 1.00 13.60
ATOM 1294 N   LEU A 169 0 5.867   25.686 12.973 1.00 16.69
ATOM 1295 CA  LEU A 169 0 6.976   26.002 12.071 1.00 14.74
ATOM 1296 C   LEU A 169 0 8.285   25.747 12.833 1.00 14.34
ATOM 1297 O   LEU A 169 0 8.497   26.259 13.942 1.00 12.34
ATOM 1298 CB  LEU A 169 0 6.890   27.471 11.652 1.00 14.90
ATOM 1299 CG  LEU A 169 0 6.071   27.845 10.428 1.00 17.83
ATOM 1300 CD1 LEU A 169 0 4.978   26.825 10.133 1.00 15.89
ATOM 1301 CD2 LEU A 169 0 5.500   29.254 10.443 1.00 16.43
ATOM 1302 N   ILE A 170 0 9.141   24.923 12.255 1.00 14.06
ATOM 1303 CA  ILE A 170 0 10.472  24.659 12.819 1.00 14.01
ATOM 1304 C   ILE A 170 0 11.397  25.312 11.784 1.00 15.19
ATOM 1305 O   ILE A 170 0 11.307  25.009 10.585 1.00 14.73
ATOM 1306 CB  ILE A 170 0 10.807  23.179 13.025 1.00 14.75
ATOM 1307 CG1 ILE A 170 0 9.849   22.605 14.069 1.00 13.74
ATOM 1308 CG2 ILE A 170 0 12.268  22.983 13.468 1.00 13.47
ATOM 1309 CD1 ILE A 170 0 9.915   21.134 14.385 1.00 15.26
ATOM 1310 N   ASN A 171 0 12.166  26.317 12.208 1.00 13.13
ATOM 1311 CA  ASN A 171 0 12.992  27.042 11.250 1.00 13.74
ATOM 1312 C   ASN A 171 0 12.163  27.517 10.083 1.00 13.71
ATOM 1313 O   ASN A 171 0 12.562  27.381 8.921  1.00 13.20
ATOM 1314 CB  ASN A 171 0 14.220  26.209 10.793 1.00 14.42
ATOM 1315 CG  ASN A 171 0 15.236  26.157 11.940 1.00 16.29
ATOM 1316 OD1 ASN A 171 0 15.123  26.983 12.875 1.00 16.78
ATOM 1317 ND2 ASN A 171 0 16.203  25.259 11.964 1.00 14.32
ATOM 1318 N   GLY A 172 0 10.967  28.074 10.337 1.00 14.17
ATOM 1319 CA  GLY A 172 0 10.157  28.619 9.270  1.00 11.74
ATOM 1320 C   GLY A 172 0 9.387   27.636 8.433  1.00 14.40
ATOM 1321 O   GLY A 172 0 8.783   28.064 7.441  1.00 15.60
ATOM 1322 N   LYS A 173 0 9.430   26.319 8.669  1.00 13.84
ATOM 1323 CA  LYS A 173 0 8.777   25.363 7.794  1.00 13.67
ATOM 1324 C   LYS A 173 0 8.038   24.303 8.589  1.00 13.59
ATOM 1325 O   LYS A 173 0 8.445   24.027 9.723  1.00 11.70
ATOM 1326 CB  LYS A 173 0 9.775   24.645 6.875  1.00 17.03
ATOM 1327 CG  LYS A 173 0 10.704  25.577 6.118  1.00 17.63
ATOM 1328 CD  LYS A 173 0 11.508  24.796 5.094  1.00 20.84
ATOM 1329 CE  LYS A 173 0 12.213  25.821 4.198  1.00 22.63
ATOM 1330 NZ  LYS A 173 0 13.304  25.087 3.499  1.00 28.08
ATOM 1331 N   GLY A 174 0 6.922   23.821 8.014  1.00 12.28
ATOM 1332 CA  GLY A 174 0 6.178   22.768 8.753  1.00 11.45
ATOM 1333 C   GLY A 174 0 4.958   22.409 7.896  1.00 13.55
ATOM 1334 O   GLY A 174 0 4.823   22.877 6.760  1.00 13.37
ATOM 1335 N   ARG A 175 0 4.042   21.619 8.432  1.00 14.54
ATOM 1336 CA  ARG A 175 0 2.859   21.201 7.687  1.00 16.62
ATOM 1337 C   ARG A 175 0 1.598   21.336 8.541  1.00 17.67
ATOM 1338 O   ARG A 175 0 1.727   21.264 9.769  1.00 18.41
ATOM 1339 CB  ARG A 175 0 2.985   19.718 7.292  1.00 16.05
ATOM 1340 CG  ARG A 175 0 3.894   19.472 6.116  1.00 16.55
ATOM 1341 CD  ARG A 175 0 4.358   18.009 6.108  1.00 17.70
ATOM 1342 NE  ARG A 175 0 5.421   17.861 5.097  1.00 17.74
ATOM 1343 CZ  ARG A 175 0 5.971   16.667 4.792  1.00 17.63
ATOM 1344 NH1 ARG A 175 0 6.918   16.665 3.866  1.00 17.25
ATOM 1345 NH2 ARG A 175 0 5.594   15.538 5.375  1.00 14.80
ATOM 1346 N   TYR A 176 0 0.429   21.438 7.908  1.00 18.08
ATOM 1347 CA  TYR A 176 0 -0.800  21.481 8.746  1.00 18.67
ATOM 1348 C   TYR A 176 0 -1.613  20.200 8.509  1.00 18.24
ATOM 1349 O   TYR A 176 0 -1.417  19.534 7.483  1.00 17.67
ATOM 1350 CB  TYR A 176 0 -1.635  22.709 8.462  1.00 17.21
ATOM 1351 CG  TYR A 176 0 -2.102  22.931 7.053  1.00 16.36
ATOM 1352 CD1 TYR A 176 0 -1.246  23.433 6.089  1.00 14.84
ATOM 1353 CD2 TYR A 176 0 -3.441  22.676 6.677  1.00 17.26
ATOM 1354 CE1 TYR A 176 0 -1.640  23.686. 4.796  1.00 16.01
ATOM 1355 CE2 TYR A 176 0 -3.862  22.908 5.361  1.00 16.65
ATOM 1356 CZ  TYR A 176 0 -2.967  23.407 4.432  1.00 17.65
ATOM 1357 OH  TYR A 176 0 -3.347  23.678 3.131  1.00 17.81
ATOM 1358 N   VAL A 177 0 -2.427  19.815 9.464  1.00 18.46
ATOM 1359 CA  VAL A 177 0 -3.200  18.571 9.303  1.00 21.18
ATOM 1360 C   VAL A 177 0 -4.090  18.639 8.073  1.00 21.50
ATOM 1361 O   VAL A 177 0 -4.788  19.620 7.858  1.00 21.85
ATOM 1362 CB  VAL A 177 0 -4.072  18.306 10.532 1.00 22.29
ATOM 1363 CG1 VAL A 177 0 -4.802  16.974 10.370 1.00 21.70
ATOM 1364 CG2 VAL A 177 0 -3.205  18.289 11.784 1.00 22.43
ATOM 1365 N   GLY A 178 0 -3.989  17.707 7.142  1.00 21.84
ATOM 1366 CA  GLY A 178 0 -4.761  17.742 5.918  1.00 20.35
ATOM 1367 C   GLY A 178 0 -4.047  18.602 4.900  1.00 22.84
ATOM 1368 O   GLY A 178 0 -4.576  18.673 3.774  1.00 23.86
ATOM 1369 N   GLY A 179 0 -2.887  19.220 5.210  1.00 21.49
ATOM 1370 CA  GLY A 179 0 -2.291  20.060 4.149  1.00 19.94
ATOM 1371     GLY A 179 0 -1.389  19.250 3.242  1.00 18.86
ATOM 1372 O   GLY A 179 0 -1.192  18.052 3.399  1.00 19.35
ATOM 1373 N   PRO A 180 0 -0.800  19.905 2.268  1.00 19.42
ATOM 1374 CA  PRO A 180 0 0.150   19.328 1.335  1.00 19.92
ATOM 1375 C   PRO A 180 0 1.430   18.922 2.041  1.00 20.56
ATOM 1376 O   PRO A 180 0 1.731   19.399 3.145  1.00 20.66
ATOM 1377 CB  PRO A 180 0 0.503   20.399 0.298  1.00 19.52
ATOM 1378 CG  PRO A 180 0 -0.144  21.639 0.829  1.00 19.70
ATOM 1379 CD  PRO A 180 0 -0.930  21.356 2.081  1.00 19.79
```

-continued

```
ATOM 1380 N   ALA A 181  0  2.213 18.059  1.403 1.00 21.19
ATOM 1381 CA  ALA A 181  0  3.489 17.644  2.007 1.00 23.04
ATOM 1382 C   ALA A 181  0  4.548 18.723  1.772 1.00 21.24
ATOM 1383 O   ALA A 181  0  5.465 18.522  0.986 1.00 23.93
ATOM 1384 CB  ALA A 181  0  3.928 16.305  1.435 1.00 21.73
ATOM 1385 N   ALA A 182  0  4.398 19.905  2.315 1.00 19.30
ATOM 1386 CA  ALA A 182  0  5.357 20.987  2.183 1.00 18.39
ATOM 1387 C   ALA A 182  0  6.706 20.549  2.791 1.00 17.36
ATOM 1388 O   ALA A 182  0  6.858 19.712  3.701 1.00 16.16
ATOM 1389 CB  ALA A 182  0  4.826 22.209  2.932 1.00 17.68
ATOM 1390 N   GLU A 183  0  7.739 21.103  2.210 1.00 18.23
ATOM 1391 CA  GLU A 183  0  9.134 20.882  2.599 1.00 20.90
ATOM 1392 C   GLU A 183  0  9.381 21.078  4.093 1.00 18.87
ATOM 1393 O   GLU A 183  0  8.976 22.073  4.699 1.00 17.80
ATOM 1394 CB  GLU A 183  0  9.990 21.875  1.820 1.00 25.16
ATOM 1395 CG  GLU A 183  0 11.508 21.760  1.962 4.00 31.31
ATOM 1396 CD  GLU A 183  0 12.075 22.803  0.998 1.00 34.38
ATOM 1397 OE1 GLU A 183  0 11.901 22.609 -0.229 1.00 36.88
ATOM 1398 OE2 GLU A 183  0 12.619 23.809  1.484 1.00 36.18
ATOM 1399 N   LEU A 184  0 10.010 20.093  4.691 1.00 17.33
ATOM 1400 CA  LEU A 184  0 10.388 20.155  6.098 1.00 18.77
ATOM 1401 C   LEU A 184  0 11.780 20.743  6.255 1.00 19.44
ATOM 1402 O   LEU A 184  0 12.582 20.687  5.314 1.00 20.95
ATOM 1403 CB  LEU A 184  0 10.331 18.735  6.673 1.00 18.11
ATOM 1404 CG  LEU A 184  0  8.915 18.125  6.577 1.00 19.10
ATOM 1405 CD1 LEU A 184  0  8.887 16.734  7.178 1.00 18.87
ATOM 1406 CD2 LEU A 184  0  7.868 19.026  7.229 1.00 18.69
ATOM 1407 N   SER A 185  0 12.054 21.342  7.398 1.00 19.18
ATOM 1408 CA  SER A 185  0 13.366 21.883  7.699 1.00 17.73
ATOM 1409 C   SER A 185  0 14.298 20.699  8.018 1.00 16.95
ATOM 1410 O   SER A 185  0 13.883 19.710  8.629 1.00 15.84
ATOM 1411 CB  SER A 185  0 13.303 22.786  8.934 1.00 17.34
ATOM 1412 OG  SER A 185  0 12.846 24.073  8.560 1.00 18.09
ATOM 1413 N   ILE A 186  0 15.533 20.845  7.587 1.00 16.43
ATOM 1414 CA  ILE A 186  0 16.595 19.858  7.821 1.00 16.85
ATOM 1415 C   ILE A 186  0 17.725 20.491  8.626 1.00 15.86
ATOM 1416 O   ILE A 186  0 18.178 21.605  8.387 1.00 11.67
ATOM 1417 CB  ILE A 186  0 17.193 19.390  6.471 1.00 18.77
ATOM 1418 CG1 ILE A 186  0 16.048 18.895  5.557 1.00 19.78
ATOM 1419 CG2 ILE A 186  0 18.167 18.241  6.697 1.00 18.53
ATOM 1420 CD1 ILE A 186  0 16.464 18.731  4.110 1.00 22.35
ATOM 1421 N   VAL A 187  0 18.114 19.840  9.703 1.00 16.18
ATOM 1422 CA  VAL A 187  0 19.243 20.287 10.505 1.00 16.63
ATOM 1423 C   VAL A 187  0 20.362 19.239 10.231 1.00 17.36
ATOM 1424 O   VAL A 187  0 20.158 18.046 10.505 1.00 15.19
ATOM 1425 CB  VAL A 187  0 18.928 20.323 11.984 1.00 16.68
ATOM 1426 CG1 VAL A 187  0 20.198 20.622 12.796 1.00 16.82
ATOM 1427 CG2 VAL A 187  0 17.874 21.375 12.275 1.00 17.07
ATOM 1428 N   ASN A 188  0 21.449 19.695  9.634 1.00 16.45
ATOM 1429 CA  ASN A 188  0 22.528 18.766  9.272 1.00 19.84
ATOM 1430 C   ASN A 188  0 23.598 18.597 10.349 1.00 19.41
ATOM 1431 O   ASN A 188  0 24.051 19.618 10.862 1.00 21.31
ATOM 1432 CB  ASN A 188  0 23.209 19.246  7.976 1.00 18.78
ATOM 1433 CG  ASN A 188  0 22.249 19.186  6.797 1.00 20.77
ATOM 1434 OD1 ASN A 188  0 21.734 20.201  6.305 1.00 21.70
ATOM 1435 ND2 ASN A 188  0 21.995 17.985  6.286 1.00 20.52
ATOM 1436 N   VAL A 189  0 24.024 17.389 10.681 1.00 17.35
ATOM 1437 CA  VAL A 189  0 25.098 17.164 11.617 1.00 17.93
ATOM 1438 C   VAL A 189  0 26.091 16.135 11.046 1.00 19.82
ATOM 1439 O   VAL A 189  0 25.773 15.392 10.109 1.00 18.90
ATOM 1440 CB  VAL A 189  0 24.660 16.684 13.009 1.00 18.43
ATOM 1441 CG1 VAL A 189  0 23.931 17.796 13.766 1.00 18.89
ATOM 1442 CG2 VAL A 189  0 23.760 15.449 12.965 1.00 15.94
ATOM 1443 N   GLU A 190  0 27.242 15.993 11.688 1.00 21.48
ATOM 1444 CA  GLU A 190  0 28.220 14.972 11.274 1.00 24.63
ATOM 1445 C   GLU A 190  0 28.514 14.065 12.469 1.00 23.06
ATOM 1446 O   GLU A 190  0 28.797 14.650 13.522 1.00 21.04
ATOM 1447 CB  GLU A 190  0 29.569 15.551 10.860 1.00 26.79
ATOM 1448 CG  GLU A 190  0 29.571 16.355  9.567 1.00 32.24
ATOM 1449 CD  GLU A 190  0 30.951 16.990  9.351 1.00 34.67
ATOM 1450 OE1 GLU A 190  0 31.927 16.199  9.305 1.00 35.41
ATOM 1451 OE2 GLU A 190  0 30.999 18.236  9.264 1.00 35.78
ATOM 1452 N   GLN A 191  0 28.490 12.752 12.256 1.00 21.94
ATOM 1453 CA  GLN A 191  0 28.768 11.824 13.357 1.00 21.92
ATOM 1454 C   GLN A 191  0 30.121 12.151 13.984 1.00 22.68
ATOM 1455 O   GLN A 191  0 31.052 12.516 13.251 1.00 23.08
ATOM 1456 CB  GLN A 191  0 28.797 10.400 12.820 1.00 22.01
ATOM 1457 CG  GLN A 191  0 28.795  9.347 13.917 1.00 23.87
ATOM 1458 CD  GLN A 191  0 28.846  7.966 13.259 1.00 26.64
ATOM 1459 OE1 GLN A 191  0 29.745  7.761 12.427 1.00 28.86
ATOM 1460 NE2 GLN A 191  0 27.909  7.080 13.563 1.00 26.40
ATOM 1461 N   GLY A 192  0 30.224 12.119 15.290 1.00 21.84
ATOM 1462 CA  GLY A 192  0 31.418 12.469 15.996 1.00 22.91
ATOM 1463 C   GLY A 192  0 31.564 13.910 16.446 1.00 23.87
ATOM 1464 O   GLY A 192  0 32.394 14.174 17.322 1.00 25.80
ATOM 1465 N   LYS A 193  0 30.839 14.867 15.922 1.00 23.54
ATOM 1466 CA  LYS A 193  0 30.899 16.259 16.362 1.00 22.84
ATOM 1467 C   LYS A 193  0 29.840 16.584 17.404 1.00 21.67
ATOM 1468 O   LYS A 193  0 28.826 15.882 17.538 1.00 20.99
ATOM 1469 CB  LYS A 193  0 30.682 17.155 15.143 1.00 24.53
ATOM 1470 CG  LYS A 193  0 31.900 17.149 14.217 1.00 27.82
ATOM 1471 CD  LYS A 193  0 31.739 18.261 13.199 1.00 30.02
ATOM 1472 CE  LYS A 193  0 33.060 19.001 12.990 1.00 31.93
ATOM 1473 NZ  LYS A 193  0 33.392 18.906 11.540 1.00 33.14
ATOM 1474 N   LYS A 194  0 30.067 17.626 18.169 1.00 19.25
ATOM 1475 CA  LYS A 194  0 29.168 18.115 19.187 1.00 19.49
ATOM 1476 C   LYS A 194  0 28.722 19.523 18.780 1.00 19.40
ATOM 1477 O   LYS A 194  0 29.512 20.285 18.235 1.00 19.29
ATOM 1478 CB  LYS A 194  0 29.771 18.115 20.576 1.00 21.88
ATOM 1479 CG  LYS A 194  0 30.338 16.748 20.999 1.00 25.59
ATOM 1480 CD  LYS A 194  0 31.054 16.902 22.331 1.00 29.48
ATOM 1481 CE  LYS A 194  0 31.455 15.582 22.970 1.00 33.58
ATOM 1482 NZ  LYS A 194  0 30.363 15.049 23.868 1.00 35.93
ATOM 1483 N   TYR A 195  0 27.418 19.818 18.910 1.00 16.92
ATOM 1484 CA  TYR A 195  0 26.858 21.068 18.431 1.00 15.60
ATOM 1485 C   TYR A 195  0 26.143 21.838 19.530 1.00 14.20
ATOM 1486 O   TYR A 195  0 25.394 21.232 20.295 1.00 13.75
ATOM 1487 CB  TYR A 195  0 25.814 20.880 17.300 1.00 16.13
ATOM 1488 CG  TYR A 195  0 26.424 20.225 16.066 1.00 15.41
ATOM 1489 CD1 TYR A 195  0 26.663 18.851 16.091 1.00 15.91
ATOM 1490 CD2 TYR A 195  0 26.786 20.942 14.945 1.00 14.73
ATOM 1491 CE1 TYR A 195  0 27.244 18.204 15.010 1.00 16.55
ATOM 1492 CE2 TYR A 195  0 27.331 20.312 13.839 1.00 15.60
ATOM 1493 CZ  TYR A 195  0 27.570 18.947 13.888 1.00 16.18
ATOM 1494 OH  TYR A 195  0 28.144 18.287 12.831 1.00 15.64
ATOM 1495 N   ARG A 196  0 26.366 23.136 19.561 1.00 12.74
ATOM 1496 CA  ARG A 196  0 25.619 23.980 20.482 1.00 13.63
ATOM 1497 C   ARG A 196  0 24.343 24.369 19.711 1.00 13.86
ATOM 1488 O   ARG A 196  0 24.343 25.218 18.802 1.00 13.81
ATOM 1499 CB  ARG A 196  0 26.379 25.187 20.991 1.00 13.96
ATOM 1500 CG  ARG A 196  0 25.520 26.162 21.796 1.00 14.22
ATOM 1501 CD  ARG A 196  0 26.337 27.238 22.438 1.00 15.27
ATOM 1502 NE  ARG A 196  0 25.649 28.138 23.319 1.00 17.38
ATOM 1503 CZ  ARG A 196  0 26.203 29.034 24.140 1.00 18.86
ATOM 1504 NH1 ARG A 196  0 27.540 29.141 24.217 1.00 16.30
ATOM 1505 NH2 ARG A 196  0 25.377 29.788 24.869 1.00 16.73
ATOM 1506 N   MET A 197  0 23.266 23.624 20.002 1.00 13.86
ATOM 1507 CA  MET A 197  0 21.980 23.932 19.340 1.00 12.98
ATOM 1508 C   MET A 197  0 21.293 25.055 20.127 1.00 12.50
ATOM 1509 O   MET A 197  0 21.285 24.997 21.359 1.00 13.93
ATOM 1510 CB  MET A 197  0 21.118 22.693 19.266 1.00 12.50
ATOM 1511 CG  MET A 197  0 21.762 21.567 18.447 1.00 13.94
ATOM 1512 SD  MET A 197  0 21.860 22.033 16.735 1.00 16.62
ATOM 1513 CE  MET A 197  0 22.157 20.467 15.927 1.00 16.37
ATOM 1514 N   ARG A 198  0 20.768 26.064 19.450 1.00 11.00
ATOM 1515 CA  ARG A 198  0 20.131 27.191 20.137 1.00 11.83
ATOM 1516 C   ARG A 198  0 18.624 27.130 19.868 1.00 12.36
ATOM 1517 O   ARG A 198  0 18.145 27.304 18.731 1.00 10.03
ATOM 1518 CB  ARG A 198  0 20.804 28.460 19.629 1.00 13.98
ATOM 1519 CG  ARG A 198  0 22.282 28.567 20.065 1.00 16.25
ATOM 1520 CD  ARG A 198  0 22.932 29.863 19.626 1.00 16.68
ATOM 1521 NE  ARG A 198  0 24.350 29.957 20.042 1.00 16.91
ATOM 1522 CZ  ARG A 198  0 24.812 30.691 21.055 1.00 15.76
ATOM 1523 NH1 ARG A 198  0 24.031 31.456 21.820 1.00 13.44
ATOM 1524 NH2 ARG A 198  0 26.123 30.721 21.316 1.00 15.41
ATOM 1525 N   LEU A 199  0 17.871 26.807 20.908 1.00 10.44
ATOM 1526 CA  LEU A 199  0 16.426 26.568 20.708 1.00 10.69
ATOM 1527 C   LEU A 199  0 15.598 27.772 21.169 1.00 10.07
ATOM 1528 O   LEU A 199  0 15.682 28.216 22.317 1.00 10.07
ATOM 1529 CB  LEU A 199  0 16.003 25.317 21.491 1.00  8.67
ATOM 1530 CG  LEU A 199  0 14.499 24.942 21.391 1.00 10.33
ATOM 1531 CD1 LEU A 199  0 14.193 24.333 20.023 1.00  8.13
ATOM 1532 CD2 LEU A 199  0 14.170 23.907 22.485 1.00  9.10
ATOM 1533 N   ILE A 200  0 14.857 28.370 20.242 1.00 10.46
ATOM 1534 CA  ILE A 200  0 14.104 29.572 20.585 1.00 11.72
ATOM 1535 C   ILE A 200  0 12.627 29.428 20.310 1.00 13.84
ATOM 1536 O   ILE A 200  0 12.254 29.059 19.192 1.00 13.22
ATOM 1537 CB  ILE A 200  0 14.628 30.755 19.735 1.00 12.89
ATOM 1538 CG1 ILE A 200  0 16.165 30.899 19.824 1.00 12.38
ATOM 1539 CG2 ILE A 200  0 13.998 32.091 20.065 1.00 13.13
```

-continued

```
ATOM   1540  CDI ILE A 200    0  16.811  31.634  18.671  1.00  12.54
ATOM   1541  N   SER A 201    0  11.829  29.825  21.312  1.00  14.64
ATOM   1542  CA  SER A 201    0  10.379  29.849  21.023  1.00  13.89
ATOM   1543  C   SER A 201    0  10.018  31.280  20.608  1.00  11.10
ATOM   1544  O   SER A 201    0  10.250  32.261  21.320  1.00   8.85
ATOM   1545  CB  SER A 201    0   9.539  29.367  22.202  1.00  13.01
ATOM   1546  OG  SER A 201    0   8.313  30.047  22.207  1.00  12.19
ATOM   1547  N   LEU A 202    0   9.428  31.376  19.807  1.00   9.64
ATOM   1548  CA  LEU A 202    0   8.959  32.637  18.881  1.00   9.06
ATOM   1549  C   LEU A 202    0   7.415  32.740  19.046  1.00  10.40
ATOM   1550  O   LEU A 202    0   6.802  33.528  18.351  1.00   9.36
ATOM   1551  CB  LEU A 202    0   9.239  32.618  17.379  1.00   9.09
ATOM   1552  CG  LEU A 202    0  10.691  32.451  16.888  1.00  10.90
ATOM   1553  CD1 LEU A 202    0  10.637  32.470  15.367  1.00  10.05
ATOM   1554  CD2 LEU A 202    0  11.617  33.559  17.414  1.00   8.56
ATOM   1555  N   SER A 203    0   6.821  31.942  19.892  1.00   9.59
ATOM   1556  CA  SER A 203    0   5.414  31.756  20.017  1.00  15.31
ATOM   1557  C   SER A 203    0   4.624  32.960  20.544  1.00  16.67
ATOM   1558  O   SER A 203    0   4.964  33.676  21.483  1.00  16.42
ATOM   1559  CB  SER A 203    0   5.130  30.505  20.867  1.00  15.21
ATOM   1560  OG  SER A 203    0   3.742  30.240  21.004  1.00  17.14
ATOM   1561  N   CYS A 204    0   3.428  33.051  19.984  1.00  17.18
ATOM   1562  CA  CYS A 204    0   2.442  34.018  20.470  1.00  18.43
ATOM   1563  C   CYS A 204    0   1.599  33.316  21.522  1.00  17.02
ATOM   1564  O   CYS A 204    0   0.867  34.039  22.200  1.00  17.27
ATOM   1565  CB  CYS A 204    0   1.524  34.508  19.334  1.00  18.60
ATOM   1566  SG  CYS A 204    0   2.135  36.038  18.612  1.00  20.23
ATOM   1567  N   ASP A 205    0   1.687  31.989  21.665  1.00  16.38
ATOM   1568  CA  ASP A 205    0   0.776  31.392  22.683  1.00  12.26
ATOM   1569  C   ASP A 205    0   1.123  30.002  23.087  1.00  11.34
ATOM   1570  O   ASP A 205    0   1.432  29.687  24.255  1.00  11.40
ATOM   1571  CB  ASP A 205    0  -0.622  31.516  22.076  1.00  14.87
ATOM   1572  CG  ASP A 205    0  -1.729  30.881  22.892  1.00  16.61
ATOM   1573  OD1 ASP A 205    0  -2.884  30.999  22.433  1.00  18.48
ATOM   1574  OD2 ASP A 205    0  -1.534  30.263  23.966  1.00  17.48
ATOM   1575  N   PRO A 206    0   1.036  29.030  22.205  1.00  11.79
ATOM   1576  CA  PRO A 206    0   1.313  27.639  22.542  1.00  11.91
ATOM   1577  C   PRO A 206    0   2.739  27.411  23.045  1.00  14.01
ATOM   1578  O   PRO A 206    0   3.676  28.135  22.661  1.00  14.38
ATOM   1579  CB  PRO A 206    0   1.124  26.816  21.262  1.00  11.87
ATOM   1580  CG  PRO A 206    0   1.112  27.893  20.191  1.00  12.83
ATOM   1581  CD  PRO A 206    0   0.749  29.241  20.766  1.00  11.09
ATOM   1582  N   ASN A 207    0   2.888  26.439  23.911  1.00  13.06
ATOM   1583  CA  ASN A 207    0   4.128  25.919  24.429  1.00  15.01
ATOM   1584  C   ASN A 207    0   4.332  25.323  23.677  1.00  15.84
ATOM   1585  O   ASN A 207    0   3.376  24.095  23.038  1.00  16.22
ATOM   1586  CB  ASN A 207    0   4.144  25.682  25.933  1.00  15.12
ATOM   1587  CG  ASN A 207    0   3.054  24.708  26.395  1.00  19.36
ATOM   1588  OD1 ASN A 207    0   2.062  25.161  27.014  1.00  19.36
ATOM   1589  ND2 ASN A 207    0   3.174  23.408  26.203  1.00  16.49
ATOM   1590  N   TRP A 208    0   5.557  24.077  23.634  1.00  14.46
ATOM   1591  CA  TRP A 208    0   5.827  22.865  22.892  1.00  12.04
ATOM   1592  C   TRP A 208    0   5.149  23.164  21.921  1.00  13.85
ATOM   1593  O   TRP A 208    0   7.482  22.385  24.558  1.00  13.02
ATOM   1594  CB  TRP A 208    0   6.654  23.136  21.628  1.00  11.91
ATOM   1595  CG  TRP A 208    0   5.951  23.769  20.465  1.00  11.27
ATOM   1596  CD1 TRP A 208    0   5.149  23.164  19.561  1.00  10.33
ATOM   1597  CD2 TRP A 208    0   5.988  25.158  20.092  1.00  10.29
ATOM   1598  NE1 TRP A 208    0   4.698  24.078  18.625  1.00  10.91
ATOM   1599  CE2 TRP A 208    0   5.201  25.313  18.954  1.00   9.64
ATOM   1600  CE3 TRP A 208    0   6.634  26.294  20.625  1.00  10.25
ATOM   1601  CZ2 TRP A 208    0   5.011  26.553  18.344  1.00   8.53
ATOM   1602  CZ3 TRP A 208    0   6.494  27.514  20.019  1.00  10.02
ATOM   1603  CH2 TRP A 208    0   5.668  27.633  18.881  1.00  11.79
ATOM   1604  N   GLN A 209    0   6.420  20.620  23.580  1.00  13.82
ATOM   1605  CA  GLN A 209    0   7.240  19.588  24.192  1.00  13.83
ATOM   1606  C   GLN A 209    0   8.251  19.281  23.075  1.00  13.07
ATOM   1607  O   GLN A 209    0   7.848  18.968  21.948  1.00  14.18
ATOM   1608  CB  GLN A 209    0   6.441  18.319  24.487  1.00  15.65
ATOM   1609  CG  GLN A 209    0   5.449  18.481  25.649  1.00  17.26
ATOM   1610  CD  GLN A 209    0   6.177  18.514  26.975  1.00  18.17
ATOM   1611  OE1 GLN A 209    0   7.414  18.471  27.002  1.00  20.00
ATOM   1612  NE2 GLN A 209    0   5.462  18.570  28.085  1.00  16.89
ATOM   1613  N   PHE A 210    0   9.538  19.461  23.351  1.00  11.26
ATOM   1614  CA  PHE A 210    0  10.526  19.329  22.287  1.00  10.01
ATOM   1615  C   PHE A 210    0  11.457  18.153  22.585  1.00   9.18
ATOM   1616  O   PHE A 210    0  11.894  17.999  23.732  1.00  10.07
ATOM   1617  CB  PHE A 210    0  11.370  20.629  22.292  1.00  10.86
ATOM   1618  CG  PHE A 210    0  12.489  20.581  21.292  1.00   9.63
ATOM   1619  CD  PHE A 210    0  13.760  20.179  21.674  1.00   9.95
ATOM   1620  CD2 PHE A 210    0  12.251  20.922  19.984  1.00   8.54
ATOM   1621  CE1 PHE A 210    0  14.778  20.150  20.738  1.00   9.23
ATOM   1622  CE2 PHE A 210    0  13.243  20.862  19.023  1.00   7.93
ATOM   1623  CZ  PHE A 210    0  14.520  20.491  19.426  1.00   8.71
ATOM   1624  N   SER A 211    0  11.741  17.384  21.545  1.00   8.62
ATOM   1625  CA  SER A 211    0  12.645  16.255  21.716  1.00  10.71
ATOM   1626  C   SER A 211    0  13.142  15.844  20.347  1.00  11.36
ATOM   1627  O   SER A 211    0  12.661  16.323  19.315  1.00   9.99
ATOM   1628  CB  SER A 211    0  11.970  15.070  22.427  1.00  10.56
ATOM   1629  OG  SER A 211    0  10.899  14.731  21.513  1.00  12.92
ATOM   1630  N   ILE A 212    0  14.268  15.122  20.390  1.00  13.67
ATOM   1631  CA  ILE A 212    0  14.883  14.680  19.131  1.00  14.79
ATOM   1632  C   ILE A 212    0  15.013  13.166  19.220  1.00  15.44
ATOM   1633  O   ILE A 212    0  15.624  12.689  20.177  1.00  15.98
ATOM   1634  CB  ILE A 212    0  16.255  15.341  18.887  1.00  17.04
ATOM   1635  CG1 ILE A 212    0  16.082  16.859  18.756  1.00  15.64
ATOM   1636  CG2 ILE A 212    0  16.935  14.722  17.648  1.00  15.24
ATOM   1637  CD1 ILE A 212    0  17.352  17.648  18.553  1.00  16.57
ATOM   1638  N   ASP A 213    0  14.453  12.418  18.281  1.00  15.53
ATOM   1639  CA  ASP A 213    0  14.549  10.952  18.401  1.00  16.50
ATOM   1640  C   ASP A 213    0  16.004  10.469  18.541  1.00  16.69
ATOM   1641  O   ASP A 213    0  16.948  10.902  17.851  1.00  14.36
ATOM   1642  CB  ASP A 213    0  13.884  10.359  17.173  1.00  17.15
ATOM   1643  CG  ASP A 213    0  12.369  10.467  17.144  1.00  18.12
ATOM   1644  OD1 ASP A 213    0  11.751  10.995  18.092  1.00  16.90
ATOM   1645  OD2 ASP A 213    0  11.801   9.990  16.129  1.00  17.35
ATOM   1646  N   GLY A 214    0  16.198   9.559  19.477  1.00  15.76
ATOM   1647  CA  GLY A 214    0  17.457   8.900  19.747  1.00  17.22
ATOM   1648  C   GLY A 214    0  18.548   9.757  20.368  1.00  18.54
ATOM   1649  O   GLY A 214    0  19.680   9.277  20.404  1.00  18.20
ATOM   1650  N   HIS A 215    0  18.341  11.024  20.738  1.00  18.17
ATOM   1651  CA  HIS A 215    0  19.422  11.880  21.229  1.00  17.59
ATOM   1652  C   HIS A 215    0  19.096  12.505  22.577  1.00  17.92
ATOM   1653  O   HIS A 215    0  17.917  12.696  22.898  1.00  20.45
ATOM   1654  CB  HIS A 215    0  19.705  13.008  20.221  1.00  15.73
ATOM   1655  CG  HIS A 215    0  20.309  12.543  18.936  1.00  16.90
ATOM   1656  ND1 HIS A 215    0  19.589  11.864  17.963  1.00  17.35
ATOM   1657  CD2 HIS A 215    0  21.574  12.658  18.444  1.00  16.15
ATOM   1658  CE1 HIS A 215    0  20.376  11.576  16.933  1.00  17.63
ATOM   1659  NE2 HIS A 215    0  21.599  12.046  17.216  1.00  17.73
ATOM   1660  N   GLU A 216    0  20.104  12.815  23.382  1.00  17.22
ATOM   1661  CA  GLU A 216    0  19.876  13.479  24.665  1.00  15.86
ATOM   1662  C   GLU A 216    0  20.070  14.976  24.456  1.00  15.61
ATOM   1663  O   GLU A 216    0  20.684  15.386  23.453  1.00  14.96
ATOM   1664  CB  GLU A 216    0  20.817  12.901  25.694  1.00  15.38
ATOM   1665  CG  GLU A 216    0  20.440  11.520  26.166  1.00  16.53
ATOM   1666  CD  GLU A 216    0  21.242  11.058  27.357  1.00  17.23
ATOM   1667  OE1 GLU A 216    0  22.378  10.619  27.129  1.00  20.31
ATOM   1668  OE2 GLU A 216    0  20.813  11.119  28.519  1.00  16.06
ATOM   1669  N   LEU A 217    0  19.623  15.792  25.394  1.00  14.64
ATOM   1670  CA  LEU A 217    0  19.738  17.243  25.251  1.00  14.91
ATOM   1671  C   LEU A 217    0  20.512  17.792  26.446  1.00  14.71
ATOM   1672  O   LEU A 217    0  19.950  17.734  27.539  1.00  15.67
ATOM   1673  CB  LEU A 217    0  18.362  17.931  25.229  1.00  14.75
ATOM   1674  CG  LEU A 217    0  17.276  17.349  24.306  1.00  15.40
ATOM   1675  CD1 LEU A 217    0  15.939  18.075  24.505  1.00  15.08
ATOM   1676  CD2 LEU A 217    0  17.723  17.453  22.849  1.00  15.22
ATOM   1677  N   THR A 218    0  21.732  18.278  26.229  1.00  13.65
ATOM   1678  CA  THR A 218    0  22.507  18.714  27.402  1.00  13.26
ATOM   1679  C   THR A 218    0  22.427  20.232  27.505  1.00  13.27
ATOM   1680  O   THR A 218    0  23.142  20.955  26.805  1.00  12.91
ATOM   1681  CB  THR A 218    0  23.955  18.216  27.304  1.00  12.08
ATOM   1682  OG1 THR A 218    0  23.935  16.782  27.331  1.00  15.48
ATOM   1683  CG2 THR A 218    0  24.767  18.721  28.470  1.00  11.46
ATOM   1684  N   ILE A 219    0  21.522  20.649  28.385  1.00  13.30
ATOM   1685  CA  ILE A 219    0  21.259  22.068  28.547  1.00  14.53
ATOM   1686  C   ILE A 219    0  22.420  22.818  29.180  1.00  12.72
ATOM   1687  O   ILE A 219    0  22.795  22.492  30.292  1.00  13.08
ATOM   1688  CB  ILE A 219    0  19.930  22.268  29.323  1.00  14.74
ATOM   1689  CG1 ILE A 219    0  18.761  21.699  28.441  1.00  17.33
ATOM   1690  CG2 ILE A 219    0  19.666  23.717  29.656  1.00  13.40
ATOM   1691  CD1 ILE A 219    0  17.597  21.481  29.412  1.00  19.42
ATOM   1692  N   ILE A 220    0  22.898  23.869  28.510  1.00  12.55
ATOM   1693  CA  ILE A 220    0  23.994  24.696  29.019  1.00  13.25
ATOM   1694  C   ILE A 220    0  23.686  26.193  29.085  1.00  15.11
ATOM   1695  O   ILE A 220    0  24.477  27.001  29.618  1.00  14.73
ATOM   1696  CB  ILE A 220    0  25.239  24.507  28.125  1.00  11.80
ATOM   1697  CG1 ILE A 220    0  24.954  24.871  26.671  1.00  10.93
ATOM   1698  CG2 ILE A 220    0  25.770  23.072  28.291  1.00   9.59
ATOM   1699  CD1 ILE A 220    0  26.249  25.231  25.928  1.00  12.07
```

-continued

```
ATOM 1700 N   GLU A 221  0 22.490 26.573 28.597 1.00 13.30
ATOM 1701 CA  GLU A 221  0 22.048 27.951 28.624 1.00 12.96
ATOM 1702 C   GLU A 221  0 20.522 28.066 28.727 1.00 13.77
ATOM 1703 O   GLU A 221  0 19.799 27.301 28.068 1.00 14.06
ATOM 1704 CB  GLU A 221  0 22.436 28.666 27.318 1.00 12.73
ATOM 1705 CG  GLU A 221  0 22.280 30.178 27.325 1.00 12.94
ATOM 1706 CD  GLU A 221  0 22.018 30.783 25.969 1.00 13.84
ATOM 1707 OE1 GLU A 221  0 22.345 30.269 24.887 1.00 12.66
ATOM 1708 OE2 GLU A 221  0 21.386 31.862 25.936 1.00 14.80
ATOM 1709 N   VAL A 222  0 20.062 29.091 29.434 1.00 13.89
ATOM 1710 CA  VAL A 222  0 18.632 29.350 29.534 1.00 14.13
ATOM 1711 C   VAL A 222  0 18.409 30.853 29.493 1.00 13.87
ATOM 1712 O   VAL A 222  0 18.900 31.657 30.300 1.00 11.55
ATOM 1713 CB  VAL A 222  0 18.003 28.649 30.737 1.00 16.86
ATOM 1714 CG1 VAL A 222  0 18.730 28.941 32.017 1.00 19.16
ATOM 1715 CG2 VAL A 222  0 16.575 29.120 31.033 1.00 18.45
ATOM 1716 N   ASP A 223  0 17.631 31.267 28.481 1.00 11.69
ATOM 1717 CA  ASP A 223  0 17.245 32.673 28.386 1.00 13.60
ATOM 1718 C   ASP A 223  0 18.472 33.598 28.548 1.00 14.44
ATOM 1719 O   ASP A 223  0 18.423 34.552 29.336 1.00 12.75
ATOM 1720 CB  ASP A 223  0 16.161 33.033 29.417 1.00 12.59
ATOM 1721 CG  ASP A 223  0 14.845 32.279 29.364 1.00 14.64
ATOM 1722 OD1 ASP A 223  0 14.697 31.397 28.493 1.00 13.34
ATOM 1723 OD2 ASP A 223  0 13.858 32.463 30.156 1.00 13.85
ATOM 1724 N   GLY A 224  0 19.544 33.372 27.767 1.00 13.49
ATOM 1725 CA  GLY A 224  0 20.728 34.213 27.770 1.00 12.85
ATOM 1726 C   GLY A 224  0 21.562 34.112 29.049 1.00 13.00
ATOM 1727 O   GLY A 224  0 22.326 35.040 29.317 1.00 13.97
ATOM 1728 N   GLU A 225  0 21.370 33.105 29.875 1.00 11.78
ATOM 1729 CA  GLU A 225  0 22.068 32.888 31.114 1.00 14.97
ATOM 1730 C   GLU A 225  0 22.609 31.447 31.106 1.00 16.73
ATOM 1731 O   GLU A 225  0 21.858 30.498 30.849 1.00 15.88
ATOM 1732 CB  GLU A 225  0 21.174 33.062 32.358 1.00 16.54
ATOM 1733 CG  GLU A 225  0 20.509 34.424 32.534 1.00 16.30
ATOM 1734 CD  GLU A 225  0 21.492 35.546 32.823 1.00 17.57
ATOM 1735 OE1 GLU A 225  0 22.450 35.254 33.561 1.00 18.76
ATOM 1736 OE2 GLU A 225  0 21.360 36.711 32.360 1.00 17.77
ATOM 1737 N   LEU A 226  0 23.922 31.285 31.324 1.00 16.90
ATOM 1738 CA  LEU A 226  0 24.526 29.955 31.318 1.00 15.50
ATOM 1739 C   LEU A 226  0 24.183 29.127 32.540 1.00 15.04
ATOM 1740 O   LEU A 226  0 24.002 29.648 33.652 1.00 15.17
ATOM 1741 CB  LEU A 226  0 26.062 30.008 31.216 1.00 15.36
ATOM 1742 CG  LEU A 226  0 26.567 30.741 29.958 1.00 17.95
ATOM 1743 CD1 LEU A 226  0 28.076 30.876 29.979 1.00 18.77
ATOM 1744 CD2 LEU A 226  0 26.111 30.029 28.687 1.00 17.36
ATOM 1745 N   THR A 227  0 24.119 27.799 32.332 1.00 13.62
ATOM 1746 CA  THR A 227  0 23.848 26.930 33.479 1.00 13.72
ATOM 1747 C   THR A 227  0 24.936 25.851 33.528 1.00 14.30
ATOM 1748 O   THR A 227  0 25.732 25.629 32.592 1.00 14.28
ATOM 1749 CB  THR A 227  0 22.478 26.217 33.352 1.00 14.35
ATOM 1750 OG1 THR A 227  0 22.506 25.385 32.178 1.00 13.68
ATOM 1751 CG2 THR A 227  0 21.284 27.161 33.180 1.00 12.29
ATOM 1752 N   GLU A 228  0 24.960 25.136 34.625 1.00 14.73
ATOM 1753 CA  GLU A 228  0 25.765 23.907 34.714 1.00 17.32
ATOM 1754 C   GLU A 228  0 25.110 22.971 33.680 1.00 17.30
ATOM 1755 O   GLU A 228  0 23.917 23.035 33.472 1.00 16.97
ATOM 1756 CB  GLU A 228  0 25.617 23.315 36.114 1.00 16.58
ATOM 1757 CG  GLU A 228  0 26.493 23.979 37.186 1.00 18.10
ATOM 1758 CD  GLU A 228  0 26.236 23.458 38.575 1.00 20.92
ATOM 1759 OE1 GLU A 228  0 25.469 22.470 38.755 1.00 23.38
ATOM 1760 OE2 GLU A 228  0 26.769 23.997 39.564 1.00 21.26
ATOM 1761 N   PRO A 229  0 25.867 22.158 32.984 1.00 16.91
ATOM 1762 CA  PRO A 229  0 25.369 21.207 31.992 1.00 16.37
ATOM 1763 C   PRO A 229  0 24.351 20.275 32.599 1.00 16.24
ATOM 1764 O   PRO A 229  0 24.624 19.652 33.619 1.00 15.76
ATOM 1765 CB  PRO A 229  0 26.612 20.469 31.419 1.00 15.97
ATOM 1766 CG  PRO A 229  0 27.701 21.509 31.741 1.00 15.92
ATOM 1767 CD  PRO A 229  0 27.337 22.141 33.083 1.00 14.86
ATOM 1768 N   HIS A 230  0 23.140 20.164 32.038 1.00 15.58
ATOM 1769 CA  HIS A 230  0 22.090 19.325 32.618 1.00 15.01
ATOM 1770 C   HIS A 230  0 21.354 18.610 31.488 1.00 13.55
ATOM 1771 O   HIS A 230  0 20.756 19.192 30.590 1.00 13.47
ATOM 1772 CB  HIS A 230  0 21.172 20.164 33.510 1.00 15.89
ATOM 1773 CG  HIS A 230  0 20.045 19.341 34.064 1.00 18.32
ATOM 1774 ND1 HIS A 230  0 20.252 18.347 35.004 1.00 18.14
ATOM 1775 CD2 HIS A 230  0 18.713 19.328 33.791 1.00 17.75
ATOM 1776 CE1 HIS A 230  0 19.121 17.768 35.310 1.00 16.33
ATOM 1777 NE2 HIS A 230  0 18.173 18.344 34.609 1.00 17.85
ATOM 1778 N   THR A 231  0 21.496 17.304 31.458 1.00 12.94
ATOM 1779 CA  THR A 231  0 20.995 16.474 30.346 1.00 14.15
ATOM 1780 C   THR A 231  0 19.620 15.890 30.547 1.00 13.41
ATOM 1781 O   THR A 231  0 19.293 15.401 31.616 1.00 14.89
ATOM 1782 CB  THR A 231  0 22.040 15.364 30.060 1.00 13.73
ATOM 1783 OG1 THR A 231  0 23.314 16.023 29.852 1.00 14.77
ATOM 1784 CG2 THR A 231  0 21.655 14.600 28.818 1.00 13.06
ATOM 1785 N   VAL A 232  0 18.776 15.954 29.549 1.00 12.86
ATOM 1786 CA  VAL A 232  0 17.374 15.505 29.665 1.00 13.44
ATOM 1787 C   VAL A 232  0 16.999 14.966 28.319 1.00 14.96
ATOM 1788 O   VAL A 232  0 17.790 15.258 27.390 1.00 14.12
ATOM 1789 CB  VAL A 232  0 16.771 16.910 30.000 1.00 17.41
ATOM 1790 CG1 VAL A 232  0 16.075 17.587 28.856 1.00 14.66
ATOM 1791 CG2 VAL A 232  0 16.158 16.935 31.371 1.00 15.66
ATOM 1792 N   ASP A 233  0 15.874 14.277 28.153 1.00 14.01
ATOM 1793 CA  ASP A 233  0 15.405 13.803 26.874 1.00 14.73
ATOM 1794 C   ASP A 233  0 14.353 14.718 26.245 1.00 14.74
ATOM 1795 O   ASP A 233  0 14.187 14.731 25.027 1.00 13.41
ATOM 1796 CB  ASP A 233  0 14.640 12.465 27.046 1.00 16.54
ATOM 1797 CG  ASP A 233  0 15.637 11.417 27.536 1.00 19.27
ATOM 1798 OD1 ASP A 233  0 16.543 11.145 26.732 1.00 20.98
ATOM 1799 OD2 ASP A 233  0 15.536 10.945 28.667 1.00 19.27
ATOM 1800 N   ARG A 234  0 13.595 15.386 27.122 1.00 13.79
ATOM 1801 CA  ARG A 234  0 12.514 16.199 26.598 1.00 16.36
ATOM 1802 C   ARG A 234  0 12.258 17.426 27.472 1.00 15.17
ATOM 1803 O   ARG A 234  0 12.418 17.390 28.686 1.00 13.96
ATOM 1804 CB  ARG A 234  0 11.265 15.330 26.482 1.00 19.23
ATOM 1805 CG  ARG A 234  0 10.104 16.036 25.788 1.00 22.25
ATOM 1806 CD  ARG A 234  0 8.981 15.023 25.506 1.00 24.68
ATOM 1807 NE  ARG A 234  0 8.157 14.983 26.705 1.00 28.27
ATOM 1808 CZ  ARG A 234  0 6.845 14.828 26.719 1.00 28.66
ATOM 1809 NH1 ARG A 234  0 6.291 14.833 27.909 1.00 30.08
ATOM 1810 NH2 ARG A 234  0 6.191 14.662 25.587 1.00 30.24
ATOM 1811 N   LEU A 235  0 11.874 18.524 26.816 1.00 13.90
ATOM 1812 CA  LEU A 235  0 11.619 19.742 27.607 1.00 13.15
ATOM 1813 C   LEU A 235  0 10.390 20.430 27.041 1.00 11.49
ATOM 1814 O   LEU A 235  0 10.025 20.304 25.873 1.00 11.08
ATOM 1815 CB  LEU A 235  0 12.825 20.630 27.695 1.00 14.39
ATOM 1816 CG  LEU A 235  0 13.459 21.645 26.801 1.00 17.19
ATOM 1817 CD1 LEU A 235  0 14.795 21.218 26.197 1.00 16.98
ATOM 1818 CD2 LEU A 235  0 12.586 22.219 25.685 1.00 18.24
ATOM 1819 N   GLN A 236  0 9.769 21.152 27.949 1.00 12.74
ATOM 1820 CA  GLN A 236  0 8.576 21.944 27.616 1.00 13.45
ATOM 1821 C   GLN A 236  0 9.005 23.390 27.459 1.00 12.21
ATOM 1822 O   GLN A 236  0 9.606 23.939 28.406 1.00 13.90
ATOM 1823 CB  GLN A 236  0 7.525 21.770 28.741 1.00 12.06
ATOM 1824 CG  GLN A 236  0 6.197 22.276 28.238 1.00 14.12
ATOM 1825 CD  GLN A 236  0 5.025 22.108 29.205 1.00 13.35
ATOM 1826 OE1 GLN A 236  0 3.893 22.215 28.721 1.00 15.61
ATOM 1827 NE2 GLN A 236  0 5.226 21.912 30.463 1.00 12.00
ATOM 1828 N   ILE A 237  0 8.748 24.011 26.311 1.00 12.17
ATOM 1829 CA  ILE A 237  0 9.213 25.390 26.156 1.00 12.41
ATOM 1830 C   ILE A 237  0 8.061 26.376 25.953 1.00 13.14
ATOM 1831 O   ILE A 237  0 7.283 26.310 24.990 1.00 13.64
ATOM 1832 CB  ILE A 237  0 10.255 25.437 25.022 1.00 11.03
ATOM 1833 CG1 ILE A 237  0 10.947 26.793 24.960 1.00 11.84
ATOM 1834 CG2 ILE A 237  0 9.615 25.086 23.662 1.00 10.02
ATOM 1835 CD1 ILE A 237  0 12.041 26.953 23.902 1.00 11.23
ATOM 1836 N   PHE A 238  0 8.037 27.414 26.765 1.00 12.83
ATOM 1837 CA  PHE A 238  0 6.979 28.431 26.714 1.00 13.23
ATOM 1838 C   PHE A 238  0 7.382 29.683 25.957 1.00 13.99
ATOM 1839 O   PHE A 238  0 8.530 29.848 25.545 1.00 13.87
ATOM 1840 CB  PHE A 238  0 6.592 28.848 28.145 1.00 12.72
ATOM 1841 CG  PHE A 238  0 6.176 27.691 28.993 1.00 14.51
ATOM 1842 CD1 PHE A 238  0 7.098 26.957 29.710 1.00 14.84
ATOM 1843 CD2 PHE A 238  0 4.836 27.314 29.078 1.00 15.50
ATOM 1844 CE1 PHE A 238  0 6.748 25.882 30.497 1.00 13.87
ATOM 1845 CE2 PHE A 238  0 4.468 26.236 29.862 1.00 14.62
ATOM 1846 CZ  PHE A 238  0 5.423 25.528 30.568 1.00 15.15
ATOM 1847 N   THR A 239  0 6.388 30.494 25.604 1.00 14.16
ATOM 1848 CA  THR A 239  0 6.543 31.678 24.806 1.00 13.44
ATOM 1849 C   THR A 239  0 7.832 32.453 25.106 1.00 11.74
ATOM 1850 O   THR A 239  0 8.012 32.950 26.218 1.00 10.47
ATOM 1851 CB  THR A 239  0 5.381 32.695 24.978 1.00 15.55
ATOM 1852 OG1 THR A 239  0 5.258 33.008 26.359 1.00 17.88
ATOM 1853 CG2 THR A 239  0 4.055 32.131 24.478 1.00 16.75
ATOM 1854 N   GLY A 240  0 8.672 32.593 24.078 1.00 7.94
ATOM 1855 CA  GLY A 240  0 9.877 33.348 24.193 1.00 10.08
ATOM 1856 C   GLY A 240  0 11.039 32.865 25.041 1.00 11.34
ATOM 1857 O   GLY A 240  0 11.977 33.650 25.216 1.00 11.02
ATOM 1858 N   GLN A 241  0 10.990 31.646 25.592 1.00 9.73
ATOM 1859 CA  GLN A 241  0 12.067 31.090 26.364 1.00 9.59
```

-continued

```
ATOM 1860 C   GLN A 241 0 13.114 30.587 25.342 1.00 10.56
ATOM 1861 O   GLN A 241 0 12.823 30.467 24.126 1.00  8.44
ATOM 1862 CB  GLN A 241 0 11.604 29.965 27.285 1.00 10.57
ATOM 1863 CG  GLN A 241 0 10.820 30.363 28.523 1.00 10.54
ATOM 1864 CD  GLN A 241 0 10.341 29.190 29.341 1.00 12.22
ATOM 1865 OE1 GLN A 241 0 10.118 28.077 28.815 1.00 13.21
ATOM 1866 NE2 GLN A 241 0 10.220 29.466 30.639 1.00 11.74
ATOM 1867 N   ARG A 242 0 14.372 30.492 25.774 1.00  9.00
ATOM 1868 CA  ARG A 242 0 15.388 29.992 24.834 1.00 11.01
ATOM 1869 C   ARG A 242 0 16.210 28.966 25.609 1.00 11.30
ATOM 1870 O   ARG A 242 0 16.292 29.133 26.816 1.00  9.51
ATOM 1871 CB  ARG A 242 0 16.324 31.043 24.265 1.00 12.77
ATOM 1872 CG  ARG A 242 0 15.694 32.128 23.364 1.00 12.52
ATOM 1873 CD  ARG A 242 0 15.066 33.249 24.138 1.00 10.81
ATOM 1874 NE  ARG A 242 0 15.957 34.126 24.892 1.00 10.80
ATOM 1875 CZ  ARG A 242 0 15.630 34.761 26.002 1.00 11.36
ATOM 1876 NH1 ARG A 242 0 16.486 35.548 26.648 1.00  7.98
ATOM 1877 NH2 ARG A 242 0 14.365 34.589 26.489 1.00 12.78
ATOM 1878 N   TYR A 243 0 16.717 27.934 24.942 1.00 11.61
ATOM 1879 CA  TYR A 243 0 17.631 27.009 25.610 1.00 12.54
ATOM 1880 C   TYR A 243 0 18.819 26.762 24.650 1.00 14.46
ATOM 1881 O   TYR A 243 0 18.568 26.656 23.435 1.00 16.11
ATOM 1882 CB  TYR A 243 0 17.015 25.638 25.934 1.00 11.09
ATOM 1883 CG  TYR A 243 0 16.007 25.667 27.054 1.00 12.11
ATOM 1884 CD1 TYR A 243 0 14.641 25.825 26.843 1.00 12.88
ATOM 1885 CD2 TYR A 243 0 16.440 25.575 28.371 1.00 12.11
ATOM 1886 CE1 TYR A 243 0 13.748 25.869 27.915 1.00 12.71
ATOM 1887 CE2 TYR A 243 0 15.560 25.582 29.436 1.00 12.50
ATOM 1888 CZ  TYR A 243 0 14.205 25.738 29.188 1.00 12.29
ATOM 1889 OH  TYR A 243 0 13.379 25.789 30.286 1.00 13.65
ATOM 1890 N   SER A 244 0 20.059 26.734 25.144 1.00 12.78
ATOM 1891 CA  SER A 244 0 21.117 26.212 24.268 1.00 13.22
ATOM 1892 C   SER A 244 0 21333 24.779 24.814 1.00 11.06
ATOM 1893 O   SER A 244 0 21.377 24.604 26.018 1.00 11.27
ATOM 1894 CB  SER A 244 0 22.485 26.907 24.308 1.00 14.46
ATOM 1895 OG  SER A 244 0 22.551 28.029 23.463 1.00 13.59
ATOM 1896 N   PHE A 245 0 21.484 23.780 23.983 1.00 11.89
ATOM 1897 CA  PHE A 245 0 21.772 22.437 24.452 1.00 13.14
ATOM 1898 C   PHE A 245 0 22.867 21.857 23.546 1.00 12.32
ATOM 1899 O   PHE A 245 0 22.890 22.128 22.354 1.00 11.11
ATOM 1900 CB  PHE A 245 0 20.554 21.495 24.526 1.00 11.40
ATOM 1901 CG  PHE A 245 0 19.915 21.236 23.195 1.00 11.98
ATOM 1902 CD1 PHE A 245 0 18.815 21.993 22.813 1.00 13.38
ATOM 1903 CD2 PHE A 245 0 20.349 20.236 22.351 1.00 11.45
ATOM 1904 CE1 PHE A 245 0 18.216 21.773 21.588 1.00 12.60
ATOM 1905 CE2 PHE A 245 0 19.759 20.000 21.129 1.00 11.48
ATOM 1906 CZ  PHE A 245 0 18.705 20.796 20.743 1.00 12.65
ATOM 1907 N   VAL A 246 0 23.742 21.073 24.169 1.00 13.51
ATOM 1908 CA  VAL A 246 0 24.775 20.427 23.341 1.00 13.37
ATOM 1909 C   VAL A 246 0 24.096 19.177 22.783 1.00 12.47
ATOM 1910 O   VAL A 246 0 23.505 18.425 23.540 1.00 11.41
ATOM 1911 CB  VAL A 246 0 25.990 19.984 24.190 1.00 14.96
ATOM 1912 CG1 VAL A 246 0 26.995 19.186 23.364 1.00 13.75
ATOM 1913 CG2 VAL A 246 0 26.681 21.165 24.841 1.00 15.92
ATOM 1914 N   LEU A 247 0 24.160 18.996 21.490 1.00 12.97
ATOM 1915 CA  LEU A 247 0 23.766 17.833 20.785 1.00 14.32
ATOM 1916 C   LEU A 247 0 25.071 17.077 20.395 1.00 14.22
ATOM 1917 O   LEU A 247 0 25.954 17.529 19.664 1.00 12.45
ATOM 1918 CB  LEU A 247 0 22.980 18.109 19.505 1.00 16.00
ATOM 1919 CG  LEU A 247 0 22.514 16.786 18.835 1.00 16.80
ATOM 1920 CD1 LEU A 247 0 21.266 16.306 19.513 1.00 18.30
ATOM 1921 CD2 LEU A 247 0 22.207 16.988 17.373 1.00 18.70
ATOM 1922 N   ASP A 248 0 25.144 15.886 20.926 1.00 13.56
ATOM 1923 CA  ASP A 248 0 26.278 14.980 20.727 1.00 16.65
ATOM 1924 C   ASP A 248 0 25.916 14.072 19.581 1.00 16.18
ATOM 1925 O   ASP A 248 0 25.095 13.166 19.813 1.00 17.60
ATOM 1926 CB  ASP A 248 0 26.536 14.229 22.036 1.00 17.83
ATOM 1927 CG  ASP A 248 0 27.798 13.359 22.024 1.00 21.77
ATOM 1928 OD1 ASP A 248 0 28.231 12.967 23.140 1.00 24.11
ATOM 1929 OD2 ASP A 248 0 28.345 13.060 20.950 1.00 21.25
ATOM 1930 N   ALA A 249 0 26414 14.277 18.369 1.00 15.85
ATOM 1931 CA  ALA A 249 0 25.982 13.416 17.255 1.00 17.99
ATOM 1932 C   ALA A 249 0 26.698 12.049 17.306 1.00 20.21
ATOM 1933 O   ALA A 249 0 27.569 11.766 16.485 1.00 19.11
ATOM 1934 CB  ALA A 249 0 26.165 14.126 15.930 1.00 14.57
ATOM 1935 N   ASN A 250 0 26.273 11.223 18.253 1.00 21.66
ATOM 1936 CA  ASN A 250 0 26.861  9.961 18.581 1.00 25.53
ATOM 1937 C   ASN A 250 0 26.061  8.721 18.202 1.00 27.30
ATOM 1938 O   ASN A 250 0 26.344  7.645 18.756 1.00 29.42
ATOM 1939 CB  ASN A 250 0 27.108  9.912 20.104 1.00 25.83
ATOM 1940 CG  ASN A 250 0 25.888  9.968 20.978 1.00 28.76
ATOM 1941 OD1 ASN A 250 0 24.757 10.156 20.527 1.00 29.90
ATOM 1942 ND2 ASN A 250 0 26.042  9.826 22.306 1.00 29.52
ATOM 1943 N   GLN A 251 0 25.089  8.841 17.302 1.00 26.74
ATOM 1944 CA  GLN A 251 0 24.239  7.712 16.934 1.00 23.48
ATOM 1945 C   GLN A 251 0 24.583  7.311 15.510 1.00 21.73
ATOM 1946 O   GLN A 251 0 25.333  8.009 14.843 1.00 19.39
ATOM 1947 CB  GLN A 251 0 22.757  8.104 17.022 1.00 24.79
ATOM 1948 CG  GLN A 251 0 22.333  8.701 18.360 1.00 25.14
ATOM 1949 CD  GLN A 251 0 22.430  7.693 19.480 1.00 26.76
ATOM 1950 OE1 GLN A 251 0 21.762  6.654 19.405 1.00 28.78
ATOM 1951 NE2 GLN A 251 0 23.202  7.986 20.514 1.00 26.02
ATOM 1952 N   PRO A 252 0 24.058  6.177 15.076 1.00 20.53
ATOM 1953 CA  PRO A 252 0 24.293  5.637 13.755 1.00 20.06
ATOM 1954 C   PRO A 252 0 23.940  6.671 12.702 1.00 21.83
ATOM 1955 O   PRO A 252 0 22.973  7.424 12.940 1.00 22.51
ATOM 1956 CB  PRO A 252 0 23.417  4.367 13.647 1.00 19.98
ATOM 1957 CG  PRO A 252 0 23.288  3.997 15.096 1.00 19.94
ATOM 1958 CD  PRO A 252 0 23.223  5.289 15.902 1.00 19.68
ATOM 1959 N   VAL A 253 0 24.663  6.728 11.584 1.00 20.85
ATOM 1960 CA  VAL A 253 0 24.302  7.741 10.604 1.00 22.29
ATOM 1961 C   VAL A 253 0 22.897  7.414 10.108 1.00 23.02
ATOM 1962 O   VAL A 253 0 22.593  6.289  9.753 1.00 21.37
ATOM 1963 CB  VAL A 253 0 25.298  8.065  9.494 1.00 23.22
ATOM 1964 CG1 VAL A 253 0 26.696  7.582  9.827 1.00 22.25
ATOM 1965 CG2 VAL A 253 0 24.859  7.680  8.101 1.00 22.26
ATOM 1966 N   ASP A 254 0 22.012  8.422 10.159 1.00 24.32
ATOM 1967 CA  ASP A 254 0 20.613  8.176  9.786 1.00 22.09
ATOM 1968 C   ASP A 254 0 19.782  9.448  9.821 1.00 20.71
ATOM 1969 O   ASP A 254 0 20.365 10.481 10.099 1.00 18.92
ATOM 1970 CB  ASP A 254 0 20.048  7.211 10.830 1.00 23.39
ATOM 1971 CG  ASP A 254 0 18.964  6.331 10.251 1.00 24.43
ATOM 1972 OD1 ASP A 254 0 18.355  6.663  9.239 1.00 23.21
ATOM 1973 OD2 ASP A 254 0 18.736  5.244 10.816 1.00 28.26
ATOM 1974 N   ASN A 255 0 18.485  9.338  9.496 1.00 18.97
ATOM 1975 CA  ASN A 255 0 17.583 10.479  9.599 1.00 17.69
ATOM 1976 C   ASN A 255 0 16.785 10.335 10.889 1.00 17.64
ATOM 1977 O   ASN A 255 0 16.390  9.204 11.249 1.00 17.75
ATOM 1978 CB  ASN A 255 0 16.663 10.554  8.386 1.00 17.19
ATOM 1979 CG  ASN A 255 0 17.467 10.882  7.143 1.00 17.33
ATOM 1980 OD1 ASN A 255 0 17.891 12.023  6.932 1.00 18.05
ATOM 1981 ND2 ASN A 255 0 17.649  9.913  6.263 1.00 15.98
ATOM 1982 N   TYR A 256 0 16.657 11.403 11.684 1.00 14.89
ATOM 1983 CA  TYR A 256 0 15.983 11.364 12.961 1.00 12.56
ATOM 1984 C   TYR A 256 0 14.966 12.520 12.991 1.00 15.02
ATOM 1985 O   TYR A 256 0 15.208 13.637 12.509 1.00 14.49
ATOM 1986 CB  TYR A 256 0 16.867 11.479 14.216 1.00 14.85
ATOM 1987 CG  TYR A 256 0 17.883 10.349 14.316 1.00 13.96
ATOM 1988 CD1 TYR A 256 0 19.030 10.427 13.529 1.00 13.97
ATOM 1989 CD2 TYR A 256 0 17.712  9.245 15.129 1.00 14.62
ATOM 1990 CE1 TYR A 256 0 19.986  9.422 13.534 1.00 13.83
ATOM 1991 CE2 TYR A 256 0 18.667  8.224 15.170 1.00 15.31
ATOM 1992 CZ  TYR A 256 0 19.795  8.336 14.346 1.00 15.90
ATOM 1993 OH  TYR A 256 0 20.763  7.341 14.337 1.00 17.15
ATOM 1994 N   TRP A 257 0 13.801 12.198 13.564 1.00 13.58
ATOM 1995 CA  TRP A 257 0 12.742 13.196 13.657 1.00 14.21
ATOM 1996 C   TRP A 257 0 13.041 14.198 14.769 1.00 12.04
ATOM 1997 O   TRP A 257 0 13.382 13.811 15.878 1.00 10.46
ATOM 1998 CB  TRP A 257 0 11.363 12.592 13.988 1.00 12.49
ATOM 1999 CG  TRP A 257 0 10.648 11.906 12.865 1.00 13.06
ATOM 2000 CD1 TRP A 257 0 10.315 10.568 12.879 1.00 12.86
ATOM 2001 CD2 TRP A 257 0 10.161 12.437 11.633 1.00 12.33
ATOM 2002 NE1 TRP A 257 0  9.640 10.267 11.720 1.00 13.75
ATOM 2003 CE2 TRP A 257 0  9.530 11.388 10.940 1.00 13.78
ATOM 2004 CE3 TRP A 257 0 10.173 13.691 11.035 1.00 14.13
ATOM 2005 CZ2 TRP A 257 0  8.940 11.538  9.681 1.00 13.24
ATOM 2006 CZ3 TRP A 257 0  9.590 13.868  9.786 1.00 14.34
ATOM 2007 CH2 TRP A 257 0  8.963 12.789  9.127 1.00 13.64
ATOM 2008 N   ILE A 258 0 12.790 15.463 14.454 1.00 12.29
ATOM 2009 CA  ILE A 258 0 12.886 16.498 15.508 1.00 12.44
ATOM 2010 C   ILE A 258 0 11.391 16.840 15.769 1.00 12.40
ATOM 2011 O   ILE A 258 0 10.629 17.039 14.812 1.00 12.43
ATOM 2012 CB  ILE A 258 0 13.617 17.777 15.048 1.00 13.32
ATOM 2013 CG1 ILE A 258 0 15.107 17.477 14.854 1.00 14.52
ATOM 2014 CG2 ILE A 258 0 13.365 18.888 16.052 1.00 12.32
ATOM 2015 CD1 ILE A 258 0 15.839 18.474 13.994 1.00 14.35
ATOM 2016 N   ARG A 259 0 11.017 16.764 17.013 1.00 11.51
ATOM 2017 CA  ARG A 259 0  9.610 16.832 17.407 1.00 13.43
ATOM 2018 C   ARG A 259 0  9.254 18.019 18.274 1.00 12.74
ATOM 2019 O   ARG A 259 0  9.931 18.246 19.280 1.00 12.62
```

```
ATOM 2020 CB  ARG A 259  0   9.326 15.567 18.253 1.00 12.43
ATOM 2021 CG  ARG A 259  0   9.308 14.290 17.414 1.00 15.81
ATOM 2022 CD  ARG A 259  0   8.910 13.054 18.244 1.00 16.58
ATOM 2023 NE  ARG A 259  0   9.204 11.818 17.528 1.00 16.91
ATOM 2024 CZ  ARG A 259  0   8.475 11.187 16.616 1.00 18.43
ATOM 2025 NH1 ARG A 259  0   7.285 11.657 16.239 1.00 19.39
ATOM 2026 NH2 ARG A 259  0   8.907 10.070 16.045 1.00 17.95
ATOM 2027 N   ALA A 260  0   8.226 18.764 17.884 1.00 13.12
ATOM 2028 CA  ALA A 260  0   7.768 19.882 18.727 1.00 12.65
ATOM 2029 C   ALA A 260  0   6.237 19.763 18.802 1.00 14.47
ATOM 2030 O   ALA A 260  0   5.545 20.140 17.868 1.00 14.73
ATOM 2031 CB  ALA A 260  0   8.281 21.188 18.165 1.00  9.58
ATOM 2032 N   GLN A 261  0   5.690 19.225 19.870 1.00 14.78
ATOM 2033 CA  GLN A 261  0   4.272 19.004 20.060 1.00 16.99
ATOM 2034 C   GLN A 261  0   3.606 20.154 20.803 1.00 15.01
ATOM 2035 O   GLN A 261  0   3.914 20.389 21.961 1.00 13.86
ATOM 2036 CB  GLN A 261  0   4.118 17.747 20.924 1.00 20.94
ATOM 2037 CG  GLN A 261  0   2.717 17.131 20.940 1.00 27.53
ATOM 2038 CD  GLN A 261  0   2.721 15.991 21.947 1.00 29.63
ATOM 2039 OE1 GLN A 261  0   3.15214.887 21.682 1.00 31.60
ATOM 2040 NE2 GLN A 261  0   2.331 16.255 23.188 1.00 34.91
ATOM 2041 N   PRO A 262  0   2.663 20.820 20.167 1.00 14.60
ATOM 2042 CA  PRO A 262  0   1.974 21.969 20.739 1.00 15.72
ATOM 2043 C   PRO A 262  0   0.921 21.568 21.757 1.00 16.25
ATOM 2044 O   PRO A 262  0   0.498 20.409 21.814 1.00 15.61
ATOM 2045 CB  PRO A 262  0   1.401 22.752 19.539 1.00 13.88
ATOM 2046 CG  PRO A 262  0   1.168 21.608 18.563 1.00 13.62
ATOM 2047 CD  PRO A 262  0   2.257 20.570 18.772 1.00 13.23
ATOM 2048 N   ASN A 263  0   0.570 22.481 22.665 1.00 17.25
ATOM 2049 CA  ASN A 263  0  -0.471 22.203 23.648 1.00 17.50
ATOM 2050 C   ASN A 263  0  -1.834 22.460 22.981 1.00 18.43
ATOM 2051 O   ASN A 263  0  -2.810 22.121 23.608 1.00 19.35
ATOM 2052 CB  ASN A 263  0  -0.422 22.990 24.954 1.00 16.12
ATOM 2053 CG  ASN A 263  0  -0.333 24.493 24.728 1.00 16.97
ATOM 2054 OD1 ASN A 263  0   0.236 25.002 23.751 1.00 15.54
ATOM 2055 ND2 ASN A 263  0  -0.905 25.269 25.653 1.00 16.31
ATOM 2056 N   LYS A 264  0  -1.947 23.055 21.818 1.00 20.51
ATOM 2057 CA  LYS A 264  0  -3.256 23.208 21.180 1.00 24.76
ATOM 2058 C   LYS A 264  0  -3.055 23.395 19.683 1.00 23.64
ATOM 2059 O   LYS A 264  0  -1.909 23.572 19.267 1.00 24.23
ATOM 2060 CB  LYS A 264  0  -4.038 24.393 21.775 1.00 25.87
ATOM 2061 CG  LYS A 264  0  -3.266 25.702 21.602 1.00 28.62
ATOM 2062 CD  LYS A 264  0  -3.579 26.624 22.772 1.00 30.65
ATOM 2063 CE  LYS A 264  0  -4.114 27.960 22.283 1.00 32.62
ATOM 2064 NZ  LYS A 264  0  -4.593 28.753 23.459 1.00 34.39
ATOM 2065 N   GLY A 265  0  -4.112 23.386 18.892 1.00 22.60
ATOM 2066 CA  GLY A 265  0  -3.959 23.591 17.452 1.00 22.98
ATOM 2067 C   GLY A 265  0  -5.190 23.002 16.758 1.00 23.95
ATOM 2068 O   GLY A 265  0  -5.904 22.202 17.362 1.00 22.64
ATOM 2069 N   ARG A 266  0  -5.398 23.434 15.537 1.00 24.60
ATOM 2070 CA  ARG A 266  0  -6.527 23.051 14.734 1.00 26.24
ATOM 2071 C   ARG A 266  0  -6.412 21.605 14.272 1.00 27.29
ATOM 2072 O   ARG A 266  0  -5.329 21.074 14.015 1.00 25.41
ATOM 2073 CB  ARG A 266  0  -6.628 23.903 13.469 1.00 30.71
ATOM 2074 CG  ARG A 266  0  -7.065 25.334 13.563 1.00 35.66
ATOM 2075 CD  ARG A 266  0  -8.161 25.673 12.539 1.00 40.48
ATOM 2076 NE  ARG A 266  0  -9.379 25.957 13.286 1.00 45.08
ATOM 2077 CZ  ARG A 266  0 -10.551 25.334 13.319 1.00 47.09
ATOM 2078 NH1 ARG A 266  0 -10.921 24.294 12.577 1.00 48.10
ATOM 2079 NH2 ARG A 266  0 -11.452 25.828 14.165 1.00 47.80
ATOM 2080 N   ASN A 267  0  -7.586 20.983 14.141 1.00 25.17
ATOM 2081 CA  ASN A 267  0  -7.727 19.669 13.602 1.00 23.96
ATOM 2082 C   ASN A 267  0  -6.859 18.625 14.244 1.00 22.35
ATOM 2083 O   ASN A 267  0  -6.306 17.864 13.448 1.00 23.57
ATOM 2084 CB  ASN A 267  0  -7.390 19.695 12.098 1.00 26.46
ATOM 2085 CG  ASN A 267  0  -8.461 20.426 11.309 1.00 29.21
ATOM 2086 OD1 ASN A 267  0  -8.190 21.226 10.405 1.00 30.18
ATOM 2087 ND2 ASN A 267  0  -9.681 20.075 11.701 1.00 28.77
ATOM 2088 N   GLY A 268  0  -6.706 18.594 15.550 1.00 21.85
ATOM 2089 CA  GLY A 268  0  -5.890 17.533 16.121 1.00 22.47
ATOM 2090 C   GLY A 268  0  -4.383 17.760 16.118 1.00 23.29
ATOM 2091 0   GLY A 268  0  -3.652 16.898 16.632 1.00 23.28
ATOM 2092 N   LEU A 269  0  -3.880 18.901 15.676 1.00 22.69
ATOM 2093 CA  LEU A 269  0  -2.454 19.222 15.684 1.00 22;62
ATOM 2094 C   LEU A 269  0  -1.753 18.890 16.990 1.00 23.26
ATOM 2095 O   LEU A 269  0  -0.650 18.335 17.035 1.00 23.42
ATOM 2096 CB  LEU A 269  0  -2.311 20.713 15.472 1.00 22.28
ATOM 2097 CG  LEU A 269  0  -1.183 21.414 14.745 1.00 23.42
ATOM 2098 CD1 LEU A 269  0  -0.508 22.380 15.682 1.00 19.64
ATOM 2099 CD2 LEU A 269  0  -0.213 20.492 14.009 1.00 21.26
ATOM 2100 N   ALA A 270  0  -2.371 19.199 18.135 1.00 21.51
ATOM 2101 CA  ALA A 270  0  -1.784 18.899 19.419 1.00 22.26
ATOM 2102 C   ALA A 270  0  -1.612 17.415 19.680 1.00 23.22
ATOM 2103 O   ALA A 270  0  -0.898 17.077 20.637 1.00 21.81
ATOM 2104 CB  ALA A 270  0  -2.632 19.518 20.542 1.00 21.06
ATOM 2105 N   GLY A 271  0  -2.337 16.521 18.996 1.00 23.75
ATOM 2106 CA  GLY A 271  0  -2.190 15.125 19.372 1.00 24.98
ATOM 2107 C   GLY A 271  0  -1.507 14.267 18.328 1.00 26.07
ATOM 2108 O   GLY A 271  0  -1.501 13.045 18.523 1.00 26.26
ATOM 2109 N   THR A 272  0  -0.906 14.825 17.278 1.00 26.48
ATOM 2110 CA  THR A 272  0  -0.327 13.901 16.294 1.00 25.27
ATOM 2111 C   THR A 272  0   0.986 14.362 15.701 1.00 25.58
ATOM 2112 O   THR A 272  0   1.216 15.567 15.701 1.00 24.46
ATOM 2113 CB  THR A 272  0  -1.380 13.759 15.164 1.00 24.40
ATOM 2114 OG1 THR A 272  0  -0.931 12.737 14.275 1.00 26.32
ATOM 2115 CG2 THR A 272  0  -1.575 15.022 14.347 1.00 22.50
ATOM 2116 N   PHE A 273  0   1.714 13.443 15.062 1.00 24.01
ATOM 2117 CA  PHE A 273  0   2.897 13.755 14.271 1.00 23.99
ATOM 2118 C   PHE A 273  0   2.663 13.201 12.858 1.00 24.84
ATOM 2119 O   PHE A 273  0   3.534 13.207 11.987 1.00 24.73
ATOM 2120 CB  PHE A 273  0   4.175 13.094 14.812 1.00 22.16
ATOM 2121 CG  PHE A 273  0   4.550 13.676 16.153 1.00 21.84
ATOM 2122 CD1 PHE A 273  0   4.190 13.037 17.327 1.00 20.67
ATOM 2123 CD2 PHE A 273  0   5.221 14.881 16.216 1.00 20.98
ATOM 2124 CE1 PHE A 273  0   4.538 13.574 18.554 1.00 21.75
ATOM 2125 CE2 PHE A 273  0   5.559 15.428 17.440 1.00 21.65
ATOM 2126 CZ  PHE A 273  0   5.216 14.787 18.616 1.00 22.38
ATOM 2127 N   ALA A 274  0   1.440 12.718 12.647 1.00 24.38
ATOM 2128 CA  ALA A 274  0   1.094 12.053 11.397 1.00 24.29
ATOM 2129 C   ALA A 274  0   1.399 12.920 10.194 1.00 24.15
ATOM 2130 O   ALA A 274  0   0.990 14.078 10.161 1.00 23.07
ATOM 2131 CB  ALA A 274  0  -0.385 11.681 11.387 1.00 23.53
ATOM 2132 N   ASN A 275  0   2.075 12.355  9.204 1.00 23.41
ATOM 2133 CA  ASN A 275  0   2.389 13.068  7.987 1.00 24.88
ATOM 2134 C   ASN A 275  0   3.498 14.093  8.191 1.00 22.73
ATOM 2135 O   ASN A 275  0   3.708 14.947  7.337 1.00 21.57
ATOM 2136 CB  ASN A 275  0   1.138 13.806  7.516 1.00 30.04
ATOM 2137 CG  ASN A 275  0   0.194 13.070  6.633 1.00 35.28
ATOM 2138 OD1 ASN A 275  0  -0.458 12.071  6.985 1.00 36.92
ATOM 2139 ND2 ASN A 275  0   0.156 13.655  5.427 1.00 37.87
ATOM 2140 N   GLY A 276  0   4.185 14.083  9.322 1.00 22.10
ATOM 2141 CA  GLY A 276  0   5.278 15.025  9.503 1.00 20.95
ATOM 2142 C   GLY A 276  0   4.801 16.392  9.962 1.00 19.61
ATOM 2143 O   GLY A 276  0   5.587 17.325  9.816 1.00 19.96
ATOM 2144 N   VAL A 277  0   3.600 16.504 10.540 1.00 16.82
ATOM 2145 CA  VAL A 277  0   3.207 17.796 11.107 1.00 15.06
ATOM 2146 C   VAL A 277  0   4.033 17.942 12.379 1.00 13.80
ATOM 2147 O   VAL A 277  0   4.454 16.912 12.926 1.00 13.80
ATOM 2148 CB  VAL A 277  0   1.676 17.849 11.397 1.00 14.37
ATOM 2149 CG1 VAL A 277  0   0.882 17.824 10.099 1.00 13.37
ATOM 2150 CG2 VAL A 277  0   1.213 16.763 12.330 1.00 11.77
ATOM 2151 N   ASN A 278  0   4.307 19.100 12.936 1.00 14.25
ATOM 2152 CA  ASN A 278  0   5.026 19.262 14.209 1.00 13.80
ATOM 2153 C   ASN A 278  0   6.443 18.640 14.208 1.00 13.80
ATOM 2154 O   ASN A 278  0   7.020 18.228 15.229 1.00 11.81
ATOM 2155 CB  ASN A 278  0   4.216 18.607 15.312 1.00 14.24
ATOM 2156 CG  ASN A 278  0   2.890 19.288 15.659 1.00 15.35
ATOM 2157 OD1 ASN A 278  0   1.952 18.531 16.009 1.00 14.81
ATOM 2158 ND2 ASN A 278  0   2.821 20.591 15.593 1.00 10.69
ATOM 2159 N   SER A 279  0   7.044 18.595 13.025 1.00 12.68
ATOM 2160 CA  SER A 279  0   8.296 17.892 12.860 1.00 15.48
ATOM 2161 C   SER A 279  0   9.323 18.571 11.964 1.00 15.07
ATOM 2162 O   SER A 279  0   8.995 19.309 11.044 1.00 12.20
ATOM 2163 CB  SER A 279  0   7.976 16.549 12.122 1.00 14.76
ATOM 2164 OG  SER A 279  0   7.268 15.722 13.054 1.00 19.57
ATOM 2165 N   ALA A 280  0  10.570 18.152 12.229 1.00 15.67
ATOM 2166 CA  ALA A 280  0  11.664 18.548 11.327 1.00 16.75
ATOM 2167 C   ALA A 280  0  12.620 17.341 11.287 1.00 15.83
ATOM 2168 O   ALA A 280  0  12.438 16.346 11.997 1.00 15.55
ATOM 2169 CB  ALA A 280  0  12.363 19.828 11.745 1.00 16.40
ATOM 2170 N   ILE A 281  0  13.669 17.478 10.485 1.00 14.79
ATOM 2171 CA  ILE A 281  0  14.569 16.346 10.257 1.00 15.55
ATOM 2172 C   ILE A 281  0  16.002 16.610 10.699 1.00 15.92
ATOM 2173 O   ILE A 281  0  16.649 17.577 10.284 1.00 14.96
ATOM 2174 CB  ILE A 281  0  14.557 16.013  8.735 1.00 16.44
ATOM 2175 CG1 ILE A 281  0  13.147 15.573  8.275 1.00 16.42
ATOM 2176 CG2 ILE A 281  0  15.615 14.959  8.421 1.00 15.71
ATOM 2177 CD1 ILE A 281  0  12.981 15.376  6.771 1.00 14.22
ATOM 2178 N   LEU A 282  0  16.505 15.698 11.515 1.00 16.76
ATOM 2179 CA  LEU A 282  0  17.920 15.736 11.912 1.00 15.82
```

```
ATOM 2180 C   LEU A 282  0 18.655 14.747 10.990 1.00 16.16
ATOM 2181 O   LEU A 282  0 18.409 13.530 11.034 1.00 16.41
ATOM 2182 CB  LEU A 282  0 18.129 15.400 13.379 1.00 14.54
ATOM 2183 CG  LEU A 282  0 19.632 15.346 13.773 1.00 16.00
ATOM 2184 CD1 LEU A 282  0 20.100 16.767 14.052 1.00 16.10
ATOM 2185 CD2 LEU A 282  0 19.865 14.469 14.970 1.00 13.21
ATOM 2186 N   ARG A 283  0 19.490 15.254 10.100 1.00 15.20
ATOM 2187 CA  ARG A 283  0 20.160 14.377  9.141 1.00 16.98
ATOM 2188 C   ARG A 283  0 21.683 14.326  9.279 1.00 17.31
ATOM 2189 O   ARG A 283  0 22.398 15.330  9.203 1.00 17.82
ATOM 2190 CB  ARG A 283  0 19.844 14.861  7.736 1.00 17.30
ATOM 2191 CG  ARG A 283  0 20.417 13.978  6.641 1.00 19.94
ATOM 2192 CD  ARG A 283  0 19.860 14.446  5.301 1.00 20.04
ATOM 2193 NE  ARG A 283  0 18.474 14.010  5.208 1.00 21.56
ATOM 2194 CZ  ARG A 283  0 17.479 14.530  4.505 1.00 21.81
ATOM 2195 NH1 ARG A 283  0 16.287 13.922  4.564 1.00 21.52
ATOM 2196 NH2 ARG A 283  0 17.653 15.634  3.797 1.00 21.84
ATOM 2197 N   TYR A 284  0 22.163 13.136  9.567 1.00 16.79
ATOM 2198 CA  TYR A 284  0 23.581 12.821  9.620 1.00 16.35
ATOM 2199 C   TYR A 284  0 24.155 12.787  8.198 1.00 16.52
ATOM 2200 O   TYR A 284  0 23.556 12.226  7.271 1.00 16.33
ATOM 2201 CB  TYR A 284  0 23.730 11.444 10.252 1.00 16.51
ATOM 2202 CG  TYR A 284  0 23.727 11.460 11.755 1.00 17.09
ATOM 2203 CD1 TYR A 284  0 24.910 11.178 12.437 1.00 17.37
ATOM 2204 CD2 TYR A 284  0 22.601 11.753 12.504 1.00 17.15
ATOM 2205 CE1 TYR A 284  0 24.937 11.163 13.817 1.00 17.64
ATOM 2206 CE2 TYR A 284  0 22.623 11.770 13.892 1.00 15.66
ATOM 2207 CZ  TYR A 284  0 23.796 11.476 14.542 1.00 15.99
ATOM 2208 OH  TYR A 284  0 23.873 11.448 15.919 1.00 14.03
ATOM 2209 N   ALA A 285  0 25.276 13.463  7.992 1.00 17.42
ATOM 2210 CA  ALA A 285  0 25.950 13.461  6.692 1.00 19.35
ATOM 2211 C   ALA A 285  0 26.186 11.994  6.328 1.00 19.20
ATOM 2212 O   ALA A 285  0 26.692 11.237  7.146 1.00 17.18
ATOM 2213 CB  ALA A 285  0 27.293 14.194  6.770 1.00 19.86
ATOM 2214 N   GLY A 286  0 25.724 11.614  5.153 1.00 20.01
ATOM 2215 CA  GLY A 286  0 25.851 10.224  4.747 1.00 21.88
ATOM 2216 C   GLY A 286  0 24.507  9.510  4.754 1.00 22.87
ATOM 2217 O   GLY A 286  0 24.406  8.418  4.197 1.00 23.06
ATOM 2218 N   ALA A 287  0 23.504 10.076  5.423 1.00 22.81
ATOM 2219 CA  ALA A 287  0 22.176  9.449  5.364 1.00 21.50
ATOM 2220 C   ALA A 287  0 21.482  9.880  4.079 1.00 20.58
ATOM 2221 O   ALA A 287  0 21.647 11.032  3.629 1.00 19.44
ATOM 2222 CB  ALA A 287  0 21.340  9.890  6.562 1.00 21.34
ATOM 2223 N   ALA A 288  0 20.632  9.041  3.523 1.00 21.20
ATOM 2224 CA  ALA A 288  0 19.899  9.450  2.310 1.00 23.46
ATOM 2225 C   ALA A 288  0 18.965 10.629  2.513 1.00 24.70
ATOM 2226 O   ALA A 288  0 18.494 10.929  3.621 1.00 25.30
ATOM 2227 CB  ALA A 288  0 19.012  8.298  1.827 1.00 24.84
ATOM 2228 N   ASN A 289  0 18.638 11.300  1.411 1.00 25.98
ATOM 2229 CA  ASN A 289  0 17.674 12.398  1.439 1.00 27.16
ATOM 2230 C   ASN A 289  0 16.303 11.707  1.505 1.00 27.36
ATOM 2231 O   ASN A 289  0 15.761 11.330  0.477 1.00 27.56
ATOM 2232 CB  ASN A 289  0 17.784 13.250  0.189 1.00 29.01
ATOM 2233 CG  ASN A 289  0 18.808 14.364  0.299 1.00 30.44
ATOM 2234 OD1 ASN A 289  0 20.005 14.168  0.545 1.00 30.40
ATOM 2235 ND2 ASN A 289  0 18.340 15.591  0.121 1.00 31.98
ATOM 2236 N   ALA A 290  0 15.837 11.426  2.703 1.00 25.22
ATOM 2237 CA  ALA A 290  0 14.600 10.727  2.955 1.00 25.09
ATOM 2238 C   ALA A 290  0 14.087 11.057  4.363 1.00 22.98
ATOM 2239 O   ALA A 290  0 14.830 11.555  5.205 1.00 22.02
ATOM 2240 CB  ALA A 290  0 14.764  9.210  2.823 1.00 24.89
ATOM 2241 N   ASP A 291  0 12.822 10.718  4.597 1.00 21.88
ATOM 2242 CA  ASP A 291  0 12.223 10.985  5.907 1.00 21.71
ATOM 2243 C   ASP A 291  0 12.724  9.965  6.916 1.00 18.93
ATOM 2244 O   ASP A 291  0 12.911  8.814  6.596 1.00 19.66
ATOM 2245 CB  ASP A 291  0 10.695 10.862  5.834 1.00 22.63
ATOM 2246 CG  ASP A 291  0 10.088 12.005  5.076 1.00 25.41
ATOM 2247 OD1 ASP A 291  0 10.781 12.988  4.735 1.00 27.11
ATOM 2248 OD2 ASP A 291  0  8.885 11.932  4.812 1.00 27.47
ATOM 2249 N   PRO A 292  0 12.863 10.362  8.164 1.00 16.14
ATOM 2250 CA  PRO A 292  0 13.229  9.473  9.230 1.00 15.27
ATOM 2251 C   PRO A 292  0 12.087  8.484  9.389 1.00 19.40
ATOM 2252 O   PRO A 292  0 10.925  8.785  9.063 1.00 20.36
ATOM 2253 CB  PRO A 292  0 13.257 10.335 10.511 1.00 14.68
ATOM 2254 CG  PRO A 292  0 13.291 11.739  9.941 1.00 14.39
ATOM 2255 CD  PRO A 292  0 12.606 11.735  8.593 1.00 14.02
ATOM 2256 N   THR A 293  0 12.357  7.361 10.024 1.00 19.91
ATOM 2257 CA  THR A 293  0 11.360  6.379 10.373 1.00 20.62
ATOM 2258 C   THR A 293  0 11.589  6.055 11.847 1.00 20.83
ATOM 2259 O   THR A 293  0 11.323  4.943 12.287 1.00 23.91
ATOM 2260 CB  THR A 293  0 11.556  5.088  9.557 1.00 23.41
ATOM 2261 OG1 THR A 293  0 12.874  4.577  9.836 1.00 24.50
ATOM 2262 CG2 THR A 293  0 11.438  5.341  8.058 1.00 23.72
ATOM 2263 N   THR A 294  0 12.172  6.958 12.624 1.00 19.30
ATOM 2264 CA  THR A 294  0 12.440  6.634 14.017 1.00 19.42
ATOM 2265 C   THR A 294  0 11.214  6.896 14.878 1.00 20.66
ATOM 2266 O   THR A 294  0 10.240  7.485 14.411 1.00 19.89
ATOM 2267 CB  THR A 294  0 13.565  7.548 14.553 1.00 19.28
ATOM 2268 OG1 THR A 294  0 13.174  8.889 14.251 1.00 17.55
ATOM 2269 CG2 THR A 294  0 14.860  7.214 13.822 1.00 19.27
ATOM 2270 N   SER A 295  0 11.359  6.576 16.159 1.00 23.85
ATOM 2271 CA  SER A 295  0 10.274  6.851 17.095 1.00 27.18
ATOM 2272 C   SER A 295  0 10.781  7.484 18.375 1.00 27.92
ATOM 2273 O   SER A 295  0 11.900  7.292 18.844 1.00 27.09
ATOM 2274 CB  SER A 295  0  9.513  5.546 17.367 1.00 28.92
ATOM 2275 OG  SER A 295  0 10.389  4.761 18.160 1.00 33.04
ATOM 2276 N   ALA A 296  0  9.930  8.331 18.965 1.00 30.04
ATOM 2277 CA  ALA A 296  0 10.295  9.003 20.207 1.00 29.82
ATOM 2278 C   ALA A 296  0 10.552  8.011 21.327 1.00 30.83
ATOM 2279 O   ALA A 296  0 10.114  6.861 21.328 1.00 30.67
ATOM 2280 CB  ALA A 296  0  9.187  9.968 20.599 1.00 30.16
ATOM 2281 N   ASN A 297  0 11.286  8.489 22.328 1.00 31.65
ATOM 2282 CA  ASN A 297  0 11.543  7.750 23.549 1.00 32.16
ATOM 2283 C   ASN A 297  0 10.200  7.650 24.285 1.00 32.80
ATOM 2284 O   ASN A 297  0  9.492  8.616 24.565 1.00 31.30
ATOM 2285 CB  ASN A 297  0 12.522  8.497 24.443 1.00 33.07
ATOM 2286 CG  ASN A 297  0 12.869  7.742 25.706 1.00 35.21
ATOM 2287 OD1 ASN A 297  0 12.116  6.965 26.284 1.00 35.45
ATOM 2288 ND2 ASN A 297  0 14.106  7.982 26.162 1.00 37.10
ATOM 2289 N   PRO A 298  0  9.865  6.430 24.647 1.00 33.40
ATOM 2290 CA  PRO A 298  0  8.626  6.116 25.331 1.00 33.89
ATOM 2291 C   PRO A 298  0  8.580  6.685  26.690 26.732 1.00 32.60
ATOM 2292 O   PRO A 298  0  7.522  7.155 27.173 1.00 32.72
ATOM 2293 CB  PRO A 298  0  8.505  4.576 25.358 1.00 35.13
ATOM 2294 CG  PRO A 298  0  9.932  4.147 25.128 1.00 34.52
ATOM 2295 CD  PRO A 298  0 10.630  5.222 24.323 1.00 34.10
ATOM 2296 N   ASN A 299  0  9.689  6.721 27.461 1.00 29.60
ATOM 2297 CA  ASN A 299  0  9.701  7.229 28.834 1.00 28.47
ATOM 2298 C   ASN A 299  0 10.818  8.251 29.006 1.00 27.18
ATOM 2299 O   ASN A 299  0 11.906  7.96729.528 1.00 25.69
ATOM 2300 CB  ASN A 299  0  9.964  6.017 29.747 1.00 29.50
ATOM 2301 CG  ASN A 299  0  8.907  4.935 29.673 1.00 32.34
ATOM 2302 OD1 ASN A 299  0  9.090  3.873 29.075 1.00 33.50
ATOM 2303 ND2 ASN A 299  0  7.735  5.182 30.251 1.00 33.04
ATOM 2304 N   PRO A 300  0 10.629  9.450 28.498 1.00 26.02
ATOM 2305 CA  PRO A 300  0 11.668 10.486 28.498 1.00 23.99
ATOM 2306 C   PRO A 300  0 11.987 11.054 29.860 1.00 21.16
ATOM 2307 O   PRO A 300  0 11.051 11.174 30.649 1.00 20.81
ATOM 2308 CB  PRO A 300  0 11.137 11.623 27.594 1.00 23.33
ATOM 2309 CG  PRO A 300  0  9.645 11.422 27.729 1.00 24.68
ATOM 2310 CD  PRO A 300  0  9.387  9.918 27.882 1.00 25.22
ATOM 2311 N   ALA A 301  0 13.242 11.361 30.179 1.00 19.17
ATOM 2312 CA  ALA A 301  0 13.538 12.139 31.410 1.00 17.57
ATOM 2313 C   ALA A 301  0 13.159 13.588 31.084 1.00 16.53
ATOM 2314 O   ALA A 301  0 13.613 14.235 30.131 1.00 16.24
ATOM 2315 CB  ALA A 301  0 15.006 11.982 31.774 1.00 17.17
ATOM 2316 N   GLN A 302  0 12.139 14.131 31.723 1.00 18.15
ATOM 2317 CA  GLN A 302  0 11.580 15.446 31.441 1.00 19.34
ATOM 2318 C   GLN A 302  0 12.335 16.580 32.124 1.00 19.16
ATOM 2319 O   GLN A 302  0 12.577 16.444 33.324 1.00 19.07
ATOM 2320 CB  GLN A 302  0 10.122 15.483 31.937 1.00 19.10
ATOM 2321 CG  GLN A 302  0  9.304 16.666 31.478 1.00 20.55
ATOM 2322 CD  GLN A 302  0  8.960 16.738 30.009 1.00 20.18
ATOM 2323 OE1 GLN A 302  0  8.843 15.721 29.331 1.00 22.29
ATOM 2324 NE2 GLN A 302  0  8.813 17.936 29.436 1.00 18.46
ATOM 2325 N   LEU A 303  0 12.629 17.681 31.444 1.00 17.92
ATOM 2326 CA  LEU A 303  0 13.241 18.824 32.139 1.00 17.32
ATOM 2327 C   LEU A 303  0 12.316 19.357 33.232 1.00 17.65
ATOM 2328 O   LEU A 303  0 11.140 19.664 33.021 1.00 17.55
ATOM 2329 CB  LEU A 303  0 13.489 19.988 31.168 1.00 15.14
ATOM 2330 CG  LEU A 303  0 13.919 21.317 31.797 1.00 16.94
ATOM 2331 CD1 LEU A 303  0 15.262 21.146 32.504 1.00 17.30
ATOM 2332 CD2 LEU A 303  0 13.988 22.432 30.764 1.00 12.82.
ATOM 2333 N   ASN A 304  0 12.868 19.580 34.399 1.00 17.34
ATOM 2334 CA  ASN A 304  0 12.199 20.212 35.531 1.00 19.12
ATOM 2335 C   ASN A 304  0 13.071 21.435 35.833 1.00 19.06
ATOM 2336 O   ASN A 304  0 14.265 21.349 36.122 1.00 20.37
ATOM 2337 CB  ASN A 304  0 12.073 19.244 36.704 1.00 22.16
ATOM 2338 CG  ASN A 304  0 11.748 19.900 38.024 1.00 25.02
ATOM 2339 OD1 ASN A 304  0 11.506 21.111 38.146 1.00 26.72
```

-continued

```
ATOM   2340  ND2 ASN A 304    0  11.766 19.133 39.114 1.00 25.99
ATOM   2341  N   GLU A 305    0  12.541 22.629 35.662 1.00 17.64
ATOM   2342  CA  GLU A 305    0  13.204 23.890 35.840 1.00 16.64
ATOM   2343  C   GLU A 305    0  13.884 23.977 37.194 1.00 16.06
ATOM   2344  O   GLU A 305    0  14.965 24.564 37.208 1.00 14.78
ATOM   2345  CB  GLU A 305    0  12.286 25.085 35.567 1.00 15.91
ATOM   2346  CG  GLU A 305    0  12.898 26.484 35.831 1.00 14.81
ATOM   2347  CD  GLU A 305    0  11.794 27.546 35.666 1.00 15.72
ATOM   2348  OE1 GLU A 305    0  11.584 28.026 34.527 1.00 14.63
ATOM   2349  OE2 GLU A 305    0  11.154 27.861 36.685 1.00 13.05
ATOM   2350  N   ALA A 306    0  13.416 23.432 38.298 1.00 15.83
ATOM   2351  CA  ALA A 306    0  14.131 23.509 39.565 1.00 17.92
ATOM   2352  C   ALA A 306    0  15.437 22.682 39.532 1.00 18.62
ATOM   2353  O   ALA A 306    0  16.213 22.867 40.464 1.00 18.37
ATOM   2354  CB  ALA A 306    0  13.283 22.993 40.711 1.00 16.23
ATOM   2355  N   ASP A 307    0  15.721 21.860 38.523 1.00 18.04
ATOM   2356  CA  ASP A 307    0  16.988 21.164 38.409 1.00 18.68
ATOM   2357  C   ASP A 307    0  18.035 22.039 37.707 1.00 19.89
ATOM   2358  O   ASP A 307    0  19.239 21.695 37.739 1.00 20.36
ATOM   2359  CB  ASP A 307    0  16.904 19.863 37.592 1.00 17.64
ATOM   2360  CG  ASP A 307    0  15.980 18.873 38.290 1.00 18.17
ATOM   2361  OD1 ASP A 307    0  15.918 18.919 39.535 1.00 18.27
ATOM   2362  OD2 ASP A 307    0  15.311 18.094 37.592 1.00 17.32
ATOM   2363  N   LEU A 308    0  17.583 23.157 37.052 1.00 16.43
ATOM   2364  CA  LEU A 308    0  18.581 23.962 36.377 1.00 16.80
ATOM   2365  C   LEU A 308    0  19.327 24.827 37.384 1.00 16.94
ATOM   2366  O   LEU A 308    0  18.784 25.320 38.380 1.00 17.28
ATOM   2367  CB  LEU A 308    0  17.925 24.775 35.257 1.00 12.52
ATOM   2368  CG  LEU A 308    0  17.436 23.936 34.073 1.00 12.15
ATOM   2369  CD1 LEU A 308    0  16.692 24.834 33.101 1.00 11.67
ATOM   2370  CD2 LEU A 308    0  18.547 23.186 33.341 1.00 12.23
ATOM   2371  N   HIS A 309    0  20.640 24.968 37.243 1.00 18.01
ATOM   2372  CA  HIS A 309    0  21.430 25.802 38.158 1.00 18.47
ATOM   2373  C   HIS A 309    0  22.328 26.770 37.394 1.00 17.36
ATOM   2374  O   HIS A 309    0  23.015 26.378 36.459 1.00 17.82
ATOM   2375  CB  HIS A 309    0  22.267 24.997 39.140 1.00 18.51
ATOM   2376  CG  HIS A 309    0  21.470 24.052 39.965 1.00 20.71
ATOM   2377  ND1 HIS A 309    0  21.526 22.684 39.790 1.00 21.77
ATOM   2378  CD2 HIS A 309    0  20.578 24.285 40.956 1.00 22.07
ATOM   2379  CE1 HIS A 309    0  20.701 22.115 40.657 1.00 22.85
ATOM   2380  NE2 HIS A 309    0  20.120 23.059 41.377 1.00 22.67
ATOM   2381  N   ALA A 310    0  22.352 28.005 37.837 1.00 17.27
ATOM   2382  CA  ALA A 310    0  23.173 29.068 37.228 1.00 17.74
ATOM   2383  C   ALA A 310    0  24.663 28.775 37.342 1.00 18.13
ATOM   2384  O   ALA A 310    0  25.103 28.233 38.369 1.00 19.61
ATOM   2385  CB  ALA A 310    0  22.869 30.356 37.985 1.00 16.92
ATOM   2386  N   LEU A 311    0  25.427 29.021 36.304 1.00 19.30
ATOM   2387  CA  LEU A 311    0  26.856 28.762 36.277 1.00 20.71
ATOM   2388  C   LEU A 311    0  27.655 29.922 36.881 1.00 22.67
ATOM   2389  O   LEU A 311    0  28.581 29.788 37.682 1.00 23.06
ATOM   2390  CB  LEU A 311    0  27.305 28.591 34.817 1.00 20.57
ATOM   2391  CG  LEU A 311    0  28.796 28.196 34.684 1.00 21.52
ATOM   2392  CD1 LEU A 311    0  28.993 26.783 35.229 1.00 20.80
ATOM   2393  CD2 LEU A 311    0  29.319 28.282 33.254 1.00 20.17
ATOM   2394  N   ILE A 312    0  27.333 31.142 36.449 1.00 23.42
ATOM   2395  CA  ILE A 312    0  28.092 32.311 36.899 1.00 24.86
ATOM   2396  C   ILE A 312    0  27.337 33.157 37.914 1.00 26.54
ATOM   2397  O   ILE A 312    0  26.154 33.467 37.739 1.00 25.31
ATOM   2398  CB  ILE A 312    0  28.397 33.179 35.670 1.00 24.45
ATOM   2399  CG1 ILE A 312    0  28.998 32.330 34.576 1.00 25.60
ATOM   2400  CG2 ILE A 312    0  29.261 34.373 36.075 1.00 26.44
ATOM   2401  CD1 ILE A 312    0  30.462 32.026 34.512 1.00 24.51
ATOM   2402  N   ASP A 313    0  28.008 33.523 39.003 1.00 28.70
ATOM   2403  CA  ASP A 313    0  27.432 34.339 40.071 1.00 30.99
ATOM   2404  C   ASP A 313    0  26.065 33.763 40.417 1.00 29.83
ATOM   2405  O   ASP A 313    0  25.024 34.385 40.235 1.00 28.51
ATOM   2406  CB  ASP A 313    0  27.266 35.777 39.576 1.00 35.88
ATOM   2407  CG  ASP A 313    0  28.532 36.505 39.187 1.00 40.21
ATOM   2408  OD1 ASP A 313    0  29.577 36.243 39.847 1.00 42.99
ATOM   2409  OD2 ASP A 313    0  28.525 37.346 38.252 1.00 40.95
ATOM   2410  N   PRO A 314    0  26.041 32.517 40.863 1.00 28.77
ATOM   2411  CA  PRO A 314    0  24.841 31.743 41.074 1.00 27.80
ATOM   2412  C   PRO A 314    0  23.865 32.198 42.137 1.00 26.49
ATOM   2413  O   PRO A 314    0  22.671 31.857 42.032 1.00 27.17
ATOM   2414  CB  PRO A 314    0  25.297 30.311 41.479 1.00 27.61
ATOM   2415  CG  PRO A 314    0  26.711 30.573 41.929 1.00 29.37
ATOM   2416  CD  PRO A 314    0  27.248 31.726 41.111 1.00 28.10
ATOM   2417  N   ALA A 315    0  24.364 32.818 43.206 1.00 23.45
ATOM   2418  CA  ALA A 315    0  23.505 33.092 44.336 1.00 22.34
ATOM   2419  C   ALA A 315    0  22.414 34.111 44.008 1.00 22.46
ATOM   2420  O   ALA A 315    0  22.678 35.127 43.370 1.00 22.52
ATOM   2421  CB  ALA A 315    0  24.294 33.617 45.532 1.00 21.68
ATOM   2422  N   ALA A 316    0  21.226 33.838 44.534 1.00 20.85
ATOM   2423  CA  ALA A 316    0  20.133 34.805 44.422 1.00 20.78
ATOM   2424  C   ALA A 316    0  20.547 36.010 45.271 1.00 20.55
ATOM   2425  O   ALA A 316    0  21.143 35.846 46.333 1.00 21.47
ATOM   2426  CB  ALA A 316    0  18.897 34.166 45.043 1.00 18.32
ATOM   2427  N   PRO A 317    0  20.237 37.212 44.864 1.00 20.84
ATOM   2428  CA  PRO A 317    0  20.539 38.410 45.634 1.00 20.82
ATOM   2429  C   PRO A 317    0  19.766 38.449 46.945 1.00 20.96
ATOM   2430  O   PRO A 317    0  18.668 37.885 47.030 1.00 21.42
ATOM   2431  CB  PRO A 317    0  20.064 39.590 44.758 1.00 21.64
ATOM   2432  CG  PRO A 317    0  19.178 38.938 43.746 1.00 21.69
ATOM   2433  CD  PRO A 317    0  19.517 37.466 43.619 1.00 20.10
ATOM   2434  N   GLY A 318    0  20.269 39.080 47.988 1.00 20.69
ATOM   2435  CA  GLY A 318    0  19.533 39.282 49.225 1.00 21.68
ATOM   2436  C   GLY A 318    0  19.631 38.218 50.283 1.00 22.93
ATOM   2437  O   GLY A 318    0  20.344 37.221 50.101 1.00 23.87
ATOM   2438  N   ILE A 319    0  18.895 38.398 51.368 1.00 22.20
ATOM   2439  CA  ILE A 319    0  18.879 37.432 52.454 1.00 24.16
ATOM   2440  C   ILE A 319    0  18.169 36.189 51.956 1.00 25.28
ATOM   2441  O   ILE A 319    0  17.071 36.271 51.405 1.00 26.26
ATOM   2442  CB  ILE A 319    0  18.208 38.030 53.704 1.00 24.54
ATOM   2443  CG  I1LE A 319   0  19.075 39.176 54.213 1.00 25.08
ATOM   2444  CG2 ILE A 319    0  17.944 37.012 54.793 1.00 24.03
ATOM   2445  CD1 ILE A 319    0  18.262 40.183 55.006 1.00 27.56
ATOM   2446  N   PRO A 320    0  18.762 35.030 52.159 1.00 26.23
ATOM   2447  CA  PRO A 320    0  18.273 33.748 51.684 1.00 26.64
ATOM   2448  C   PRO A 320    0  17.105 33.172 52.453 1.00 26.74
ATOM   2449  O   PRO A 320    0  17.140 32.025 52.896 1.00 27.54
ATOM   2450  CB  PRO A 320    0  19.501 32.801 51.772 1.00 27.16
ATOM   2451  CG  PRO A 320    0  20.216 33.388 52.985 1.00 25.20
ATOM   2452  CD  PRO A 320    0  20.061 34.891 52.837 1.00 25.62
ATOM   2453  N   THR A 321    0  16.022 33.909 52.611 1.00 27.35
ATOM   2454  CA  THR A 321    0  14.820 33.550 53.329 1.00 28.07
ATOM   2455  C   THR A 321    0  13.632 34.190 52.603 1.00 27.48
ATOM   2456  O   THR A 321    0  13.597 35.383 52.321 1.00 27.13
ATOM   2457  CB  THR A 321    0  14.824 34.085 54.780 1.00 29.87
ATOM   2458  OG1 THR A 321    0  15.957 33.582 55.511 1.00 31.85
ATOM   2459  CG2 THR A 321    0  13.548 33.687 55.507 1.00 31.06
ATOM   2460  N   PRO A 322    0  12.630 33.378 52.326 1.00 26.63
ATOM   2461  CA  PRO A 322    0  11.428 33.824 51.637 1.00 25.91
ATOM   2462  C   PRO A 322    0  10.892 35.072 52.313 1.00 25.37
ATOM   2463  O   PRO A 322    0  10.945 35.194 53.542 1.00 25.02
ATOM   2464  CB  PRO A 322    0  10.456 32.638 51.661 1.00 26.11
ATOM   2465  CG  PRO A 322    0  11.370 31.477 51.931 1.00 26.67
ATOM   2466  CD  PRO A 322    0  12.592 31.961 52.691 1.00 26.21
ATOM   2467  N   GLY A 323    0  10.432 36.075 51.573 1.00 24.30
ATOM   2468  CA  GLY A 323    0   9.943 37.288 52.197 1.00 24.13
ATOM   2469  C   GLY A 323    0  11.013 38.161 52.842 1.00 25.48
ATOM   2470  O   GLY A 323    0  10.603 39.128 53.512 1.00 25.28
ATOM   2471  N   ALA A 324    0  12.320 37.959 52.688 1.00 24.80
ATOM   2472  CA  ALA A 324    0  13.278 38.831 53.377 1.00 24.61
ATOM   2473  C   ALA A 324    0  14.034 39.773 52.451 1.00 23.92
ATOM   2474  O   ALA A 324    0  15.148 40.225 52.748 1.00 24.53
ATOM   2475  CB  ALA A 324    0  14.255 38.012 54.204 1.00 23.79
ATOM   2476  N   ALA A 325    0  13.423 40.081 51.315 1.00 22.22
ATOM   2477  CA  ALA A 325    0  14.033 40.985 50.341 1.00 20.42
ATOM   2478  C   ALA A 325    0  13.825 42.423 50.803 1.00 19.97
ATOM   2479  O   ALA A 325    0  12.987 42.648 51.677 1.00 18.14
ATOM   2480  CB  ALA A 325    0  13.272 40.763 49.018 1.00 19.40
ATOM   2481  N   ASP A 326    0  14.422 43.421 50.161 1.00 20.69
ATOM   2482  CA  ASP A 326    0  14.141 44.804 50.529 1.00 22.54
ATOM   2483  C   ASP A 326    0  12.702 45.158 50.220 1.00 22.83
ATOM   2484  O   ASP A 326    0  12.015 45.754 51.030 1.00 23.68
ATOM   2485  CB  ASP A 326    0  15.089 45.767 49.789 1.00 22.32
ATOM   2486  CG  ASP A 326    0  16.494 45.378 50.238 1.00 23.83
ATOM   2487  OD1 ASP A 326    0  16.650 45.284 51.475 1.00 24.78
ATOM   2488  OD2 ASP A 326    0  17.393 45.171 49.409 1.00 24.90
ATOM   2489  N   VAL A 327    0  12.254 44.821 49.026 1.00 24.29
ATOM   2490  CA  VAL A 327    0  10.914 45.064 48.503 1.00 23.57
ATOM   2491  C   VAL A 327    0  10.246 43.721 48.170 1.00 23.46
ATOM   2492  O   VAL A 327    0  10.785 42.933 47.386 1.00 22.62
ATOM   2493  CB  VAL A 327    0  10.946 45.898 47.220 1.00 24.70
ATOM   2494  CG1 VAL A 327    0   9.554 46.274 46.751 1.00 24.11
ATOM   2495  CG2 VAL A 327    0  11.773 47.173 47.420 1.00 26.30
ATOM   2496  N   ASN A 328    0   9.113 43.463 48.811 1.00 21.44
ATOM   2497  CA  ASN A 328    0   8.390 42.212 48.717 1.00 23.21
ATOM   2498  C   ASN A 328    0   6.986 42.410 48.158 1.00 23.12
ATOM   2499  O   ASN A 328    0   6.140 43.030 48.799 1.00 22.76
```

```
ATOM  2500  CB  ASN A 328   0    8.223  41.603  50.121  1.00  23.09
ATOM  2501  CG  ASN A 328   0    9.569  41.204  50.693  1.00  24.61
ATOM  2502  OD1 ASN A 328   0   10.181  40.188  50.295  1.00  25.87
ATOM  2503  ND2 ASN A 328   0   10.017  42.029  51.617  1.00  21.47
ATOM  2504  N   LEU A 329   0    6.776  42.000  46.923  1.00  23.14
ATOM  2505  CA  LEU A 329   0    5.497  42.179  46.268  1.00  24.23
ATOM  2506  C   LEU A 329   0    4.859  40.822  45.953  1.00  25.21
ATOM  2507  O   LEU A 329   0    5.489  39.876  45.469  1.00  24.20
ATOM  2508  CB  LEU A 329   0    5.622  42.963  44.948  1.00  24.33
ATOM  2509  CG  LEU A 329   0    6.369  44.279  45.082  1.00  26.30
ATOM  2510  CD1 LEU A 329   0    6.778  44.884  43.757  1.00  26.24
ATOM  2511  CD2 LEU A 329   0    5.550  45.249  45.913  1.00  27.07
ATOM  2512  N   ARG A 330   0    3.562  40.806  46.204  1.00  25.13
ATOM  2513  CA  ARG A 330   0    2.740  39.641  45.899  1.00  27.48
ATOM  2514  C   ARG A 330   0    1.628  40.116  44.965  1.00  27.52
ATOM  2515  O   ARG A 330   0    0.988  41.132  45.257  1.00  27.17
ATOM  2516  CB  ARG A 330   0    2.200  39.017  47.166  1.00  29.82
ATOM  2517  CG  ARG A 330   0    1.351  37.794  46.932  1.00  33.18
ATOM  2518  CD  ARG A 330   0    0.880  37.251  48.284  1.00  37.06
ATOM  2519  NE  ARG A 330   0    0.305  35.914  48.038  1.00  40.34
ATOM  2520  CZ  ARG A 330   0    1.00 9  34.803  48.298  1.00  40.82
ATOM  2521  NH1 ARG A 330   0    2.229  34.903  48.812  1.00  40.36
ATOM  2522  NH2 ARG A 330   0    0.415  33.642  48.040  1.00  41.33
ATOM  2523  N   PHE A 331   0    1.507  39.481  43.795  1.00  25.88
ATOM  2524  CA  PHE A 331   0    0.475  39.937  42.855  1.00  25.87
ATOM  2525  C   PHE A 331   0   -0.657  38.919  42.779  1.00  25.94
ATOM  2526  O   PHE A 331   0   -0.441  37.697  42.824  1.00  24.61
ATOM  2527  CB  PHE A 331   0    1.102  40.269  41.511  1.00  25.94
ATOM  2528  CG  PRE A 331   0    1.884  41.565  41.496  1.00  28.66
ATOM  2529  CD1 PHE A 331   0    1.282  42.782  41.759  1.00  28.04
ATOM  2530  CD2 PHE A 331   0    3.246  41.569  41.214  1.00  29.71
ATOM  2531  CE1 PHE A 331   0    1.988  43.963  41.744  1.00  29.21
ATOM  2532  CE2 PHE A 331   0    3.975  42.753  41.181  1.00  30.61
ATOM  2533  CZ  PHE A 331   0    3.348  43.965  41.453  1.00  30.66
ATOM  2534  N   GLN A 332   0   -1.873  39.446  42.676  1.00  25.58
ATOM  2535  CA  GLN A 332   0   -3.085  38.628  42.608  1.00  26.60
ATOM  2536  C   GLN A 332   0   -3.672  38.698  41.203  1.00  23.61
ATOM  2537  O   GLN A 332   0    4.136  39.739  40.755  1.00  21.73
ATOM  2538  CB  GLN A 332   0   -4.110  39.094  43.630  1.00  30.32
ATOM  2539  CG  GLN A 332   0   -5.412  38.299  43.642  1.00  35.72
ATOM  2540  CD  GLN A 332   0   -5.199  36.961  44.325  1.00  39.98
ATOM  2541  OE1 GLN A 332   0   -5.859  35.961  44.007  1.00  42.32
ATOM  2542  NE2 GLN A 332   0   -4.257  36.915  45.270  1.00  42.27
ATOM  2543  N   LEU A 333   0   -3.612  37.576  40.504  1.00  23.60
ATOM  2544  CA  LEU A 333   0   -4.105  37.565  39.118  1.00  26.25
ATOM  2545  C   LEU A 333   0   -5.627  37.373  39.123  1.00  26.55
ATOM  2546  O   LEU A 333   0   -6.107  36.655  39.998  1.00  25.70
ATOM  2547  CB  LEU A 333   0   -3.424  36.465  38.304  1.00  25.25
ATOM  2548  CG  LEU A 333   0   -1.919  36.608  38.052  1.00  25.72
ATOM  2549  CD1 LEU A 333   0   -1.431  35.565  37.067  1.00  23.66
ATOM  2550  CD2 LEU A 333   0   -1.551  38.000  37.558  1.00  25.25
ATOM  2551  N   GLY A 334   0   -6.327  37.976  38.188  1.00  27.85
ATOM  2552  CA  GLY A 334   0   -7.770  37.782  38.118  1.00  29.96
ATOM  2553  C   GLY A 334   0   -8.253  37.802  36.672  1.00  32.36
ATOM  2554  O   GLY A 334   0   -7.559  38.175  35.719  1.00  30.74
ATOM  2555  N   PHE A 335   0   -9.502  37.377  36.544  1.00  34.76
ATOM  2556  CA  PHE A 335   0  -10.181  37.360  35.260  1.00  38.54
ATOM  2557  C   PHE A 335   0  -11.625  37.806  35.514  1.00  41.05
ATOM  2558  O   PHE A 335   0  -12.443  37.028  36.021  1.00  41.53
ATOM  2559  CB  PHE A 335   0  -10.183  36.003  34.586  1.00  39.00
ATOM  2560  CG  PHE A 335   0  -10.772  36.105  33.197  1.00  40.61
ATOM  2561  CD1 PHE A 335   0  -10.052  36.686  32.175  1.00  40.45
ATOM  2562  CD2 PHE A 335   0  -12.045  35.614  32.942  1.00  41.39
ATOM  2563  CE1 PHE A 335   0  -10.580  36.778  30.901  1.00  40.81
ATOM  2564  CE2 PHE A 335   0  -12.588  35.697  31.671  1.00  41.51
ATOM  2565  CZ  PHE A 335   0  -11.849  36.281  30.652  1.00  41.87
ATOM  2566  N   SER A 336   0  -11.861  39.075  35.193  1.00  42.39
ATOM  2567  CA  SER A 336   0  -13.203  39.582  35.445  1.00  44.12
ATOM  2568  C   SER A 336   0  -13.704  40.525  34.370  1.00  44.31
ATOM  2569  O   SER A 336   0  -13.028  41.440  33.903  1.00  44.49
ATOM  2570  CB  SER A 336   0  -13.214  40.206  36.842  1.00  45.46
ATOM  2571  OG  SER A 336   0  -13.727  39.233  37.758  1.00  47.11
ATOM  2572  N   GLY A 337   0  -14.963  40.267  33.983  1.00  44.12
ATOM  2573  CA  GLY A 337   0  -15.630  41.067  32.959  1.00  41.89
ATOM  2574  C   GLY A 337   0  -14.963  40.920  31.608  1.00  40.08
ATOM  2575  O   GLY A 337   0  -14.712  41.891  30.888  1.00  41.35
ATOM  2576  N   GLY A 338   0  -14.583  39.699  31.263  1.00  39.12
ATOM  2577  CA  GLY A 338   0  -13.899  39.364  30.034  1.00  36.11
ATOM  2578  C   GLY A 338   0  -12.503  39.970  29.929  1.00  34.97
ATOM  2579  O   GLY A 338   0  -12.005  40.116  28.806  1.00  33.64
ATOM  2580  N   ARG A 339   0  -11.885  40.355  31.048  1.00  33.21
ATOM  2581  CA  ARG A 339   0  -10.538  40.916  30.982  1.00  32.04
ATOM  2582  C   ARG A 339   0   -9.724  40.397  32.164  1.00  29.23
ATOM  2583  O   ARG A 339   0  -10.260  40.053  33.210  1.00  26.38
ATOM  2584  CB  ARG A 339   0  -10.495  42.419  30.845  1.00  36.52
ATOM  2585  CG  ARG A 339   0  -11.291  43.281  31.790  1.00  42.08
ATOM  2586  CD  ARG A 339   0  -11.895  44.502  31.127  1.00  45.03
ATOM  2587  NE  ARG A 339   0  -11.046  45.380  30.351  1.00  47.77
ATOM  2588  CZ  ARG A 339   0  -10.635  46.616  30.664  1.00  49.55
ATOM  2589  NH1 ARG A 339   0  -10.935  47.242  31.799  1.00  49.60
ATOM  2590  NH2 ARG A 339   0   -9.862  47.295  29.805  1.00  49.96
ATOM  2591  N   PHE A 340   0   -8.425  40.181  31.900  1.00  25.50
ATOM  2592  CA  PHE A 340   0   -7.526  39.713  32.938  1.00  22.68
ATOM  2593  C   PHE A 340   0   -7.171  40.945  33.774  1.00  22.15
ATOM  2594  O   PHE A 340   0   -7.069  42.069  33.266  1.00  21.26
ATOM  2595  CB  PHE A 340   0   -6.210  39.135  32.397  1.00  22.39
ATOM  2596  CG  PHE A 340   0   -6.333  37.792  31.736  1.00  20.74
ATOM  2597  CD1 PHE A 340   0   -6.338  37.710  30.357  1.00  20.97
ATOM  2598  CD2 PHE A 340   0   -6.448  36.644  32.468  1.00  21.19
ATOM  2599  CE1 PHE A 340   0   -6.449  36.488  29.721  1.00  21.61
ATOM  2600  CE2 PHE A 340   0   -6.585  35.408  31.826  1.00  22.99
ATOM  2601  CZ  PHE A 340   0   -6.578  35.334  30.444  1.00  19.90
ATOM  2602  N   THR A 341   0   -7.000  40.736  35.069  1.00  20.76
ATOM  2603  CA  THR A 341   0   -6.605  41.879  35.889  1.00  21.55
ATOM  2604  C   THR A 341   0   -5.400  41.509  36.759  1.00  21.00
ATOM  2605  O   THR A 341   0   -5.236  40.329  37.089  1.00  20.70
ATOM  2606  CB  THR A 341   0   -7.757  42.255  36.853  1.00  21.12
ATOM  2607  OG1 THR A 341   0   -8.014  41.102  37.668  1.00  21.26
ATOM  2608  CG2 THR A 341   0   -9.050  42.630  36.150  1.00  21.74
ATOM  2609  N   ILE A 342   0   -4.750  42.529  37.308  1.00  20.28
ATOM  2610  CA  ILE A 342   0   -3.739  42.273  38.333  1.00  20.34
ATOM  2611  C   ILE A 342   0   -4.026  43.212  39.496  1.00  18.92
ATOM  2612  O   ILE A 342   0   -4.004  44.437  39.327  1.00  16.42
ATOM  2613  CB  ILE A 342   0   -2.306  42.439  37.820  1.00  21.04
ATOM  2614  CG1 ILE A 342   0   -1.337  42.721  38.988  1.00  21.39
ATOM  2615  CG2 ILE A 342   0   -2.250  43.540  36.800  1.00  24.57
ATOM  2616  CD1 ILE A 342   0   -0.260  41.661  38.949  1.00  24.53
ATOM  2617  N   ASN A 343   0   -4.282  42.601  40.650  1.00  17.77
ATOM  2618  CA  ASN A 343   0   -4.702  43.413  41.782  1.00  21.51
ATOM  2619  C   ASN A 343   0   -5.881  44.287  41.394  1.00  21.43
ATOM  2620  O   ASN A 343   0   -5.903  45.495  41.598  1.00  20.26
ATOM  2621  CB  ASN A 343   0   -3.513  44.231  42.356  1.00  22.34
ATOM  2622  CG  ASN A 343   0   -2.685  43.190  43.073  1.00  25.38
ATOM  2623  OD1 ASN A 343   0   -2.075  42.218  42.598  1.00  26.90
ATOM  2624  ND2 ASN A 343   0   -2.652  43.238  44.425  1.00  25.34
ATOM  2625  N   GLY A 344   0   -6.875  43.703  40.730  1.00  23.77
ATOM  2626  CA  GLY A 344   0   -8.078  44.406  40.324  1.00  25.28
ATOM  2627  C   GLY A 344   0   -7.954  45.280  39.111  1.00  26.82
ATOM  2628  O   GLY A 344   0   -9.029  45.728  38.672  1.00  29.56
ATOM  2629  N   THR A 345   0   -6.798  45.561  38.527  1.00  26.28
ATOM  2630  CA  THR A 345   0   -6.766  46.440  37.366  1.00  25.48
ATOM  2631  C   THR A 345   0   -6.343  45.703  36.109  1.00  26.49
ATOM  2632  O   THR A 345   0   -5.385  44.925  36.122  1.00  28.22
ATOM  2633  CB  THR A 345   0   -5.829  47.648  37.589  1.00  26.17
ATOM  2634  OG1 THR A 345   0   -6.191  48.334  38.788  1.00  25.32
ATOM  2635  CG2 THR A 345   0   -5.867  48.677  36.462  1.00  24.83
ATOM  2636  N   ALA A 346   0   -7.017  46.012  35.008  1.00  24.80
ATOM  2637  CA  ALA A 346   0   -6.768  45.491  33.688  1.00  23.82
ATOM  2638  C   ALA A 346   0   -5.862  46.511  32.997  1.00  23.77
ATOM  2639  O   ALA A 346   0   -6.098  47.711  33.088  1.00  22.93
ATOM  2640  CB  ALA A 346   0   -8.031  45.353  32.841  1.00  24.13
ATOM  2641  N   TYR A 347   0   -4.793  46.023  32.392  1.00  22.69
ATOM  2642  CA  TYR A 347   0   -3.862  46.949  31.792  1.00  22.75
ATOM  2643  C   TYR A 347   0   -4.483  47.532  30.527  1.00  23.42
ATOM  2644  O   TYR A 347   0   -4.954  46.753  29.709  1.00  22.19
ATOM  2645  CB  TYR A 347   0   -2.521  46.274  31.455  1.00  21.25
ATOM  2646  CG  TYR A 347   0   -1.584  47.221  30.732  1.00  18.93
ATOM  2647  CD1 TYR A 347   0   -0.819  48.137  31.442  1.00  18.17
ATOM  2648  CD2 TYR A 347   0   -1.473  47.176  29.353  1.00  19.30
ATOM  2649  CE1 TYR A 347   0    0.034  49.003  30.763  1.00  18.37
ATOM  2650  CE2 TYR A 347   0   -0.650  48.063  28.664  1.00  18.40
ATOM  2651  CZ  TYR A 347   0    0.102  48.962  29.394  1.00  18.99
ATOM  2652  OH  TYR A 347   0    0.947  49.802  28.706  1.00  19.65
ATOM  2653  N   6LU A 348   0   -4.378  48.833  30.359  1.00  25.22
ATOM  2654  CA  6LU A 348   0   -4.769  49.453  29.098  1.00  28.77
ATOM  2655  C   GLU A 348   0   -3.659  50.470  28.805  1.00  27.38
ATOM  2656  O   GLU A 348   0   -3.297  51.229  29.704  1.00  28.49
ATOM  2657  CB  GLU A 348   0   -6.114  50.134  29.110  1.00  32.95
ATOM  2658  CG  GLU A 348   0   -7.391  49.302  29.072  1.00  39.29
ATOM  2659  CD  GLU A 348   0   -8.562  50.170  29.559  1.00  43.20
```

```
ATOM 2660 OE1 GLU A 348 0 -8.825 51.211 28.900 1.00 45.31
ATOM 2661 OE2 GLU A 348 0 -9.175 49.855 30.601 1.00 44.11
ATOM 2662 N SER A 349 0 -3.168 50.541 27.621 1.00 25.73
ATOM 2663 CA SER A 349 0 -2.080 51.410 27.201 1.00 28.25
ATOM 2664 C SER A 349 0 -2.401 52.887 27.194 1.00 28.71
ATOM 2665 O SER A 349 0 -3.279 53.399 26.526 1.00 29.13
ATOM 2666 CB SER A 349 0 -1.743 50.818 25.838 1.00 28.54
ATOM 2667 OG SER A 349 0 -0.850 51.499 25.026 1.00 33.31
ATOM 2668 N PRO A 350 0 -1.623 53.700 27.898 1.00 29.56
ATOM 2669 CA PRO A 350 0 -1.770 55.145 27.997 1.00 28.53
ATOM 2670 C PRO A 350 0 -1.480 55.825 26.679 1.00 28.01
ATOM 2671 O PRO A 350 0 -0.787 55.217 25.856 1.00 26.93
ATOM 2672 CB PRO A 350 0 -0.752 55.632 29.063 1.00 27.91
ATOM 2673 CG PRO A 350 0 0.309 54.560 28.863 1.00 28.03
ATOM 2674 CD PRO A 350 0 -0.461 53.245 28.688 1.00 28.76
ATOM 2675 N SER A 351 0 -1.951 57.066 26.485 1.00 28.89
ATOM 2676 CA SER A 351 0 -1.630 57.718 25.206 1.00 29.67
ATOM 2677 C SER A 351 0 -0.213 58.287 25.257 1.00 27.67
ATOM 2678 O SER A 351 0 0.320 58.524 24.177 1.00 28.18
ATOM 2679 CB SER A 351 0 -2.566 58.860 24.790 1.00 31.71
ATOM 2680 OG SER A 351 0 -2.793 59.679 25.938 1.00 34.19
ATOM 2681 N VAL A 352 0 0.316 58.529 26.449 1.00 25.32
ATOM 2682 CA VAL A 352 0 1.703 58.997 26.534 1.00 25.27
ATOM 2683 C VAL A 352 0 2.503 57.872 27.211 1.00 23.63
ATOM 2684 O VAL A 352 0 2.181 57.493 28.323 1.00 23.26
ATOM 2685 CB VAL A 352 0 1.934 60.300 27.303 1.00 24.91
ATOM 2686 CG1 VAL A 352 0 1.129 61.436 26.658 1.00 24.41
ATOM 2687 CG2 VAL A 352 0 3.424 60.635 27.281 1.00 23.35
ATOM 2688 N PRO A 353 0 3.498 57.375 26.510 1.00 22.39
ATOM 2689 CA PRO A 353 0 4.342 56.300 26.983 1.00 21.86
ATOM 2690 C PRO A 353 0 4.978 56.699 28.300 1.00 20.91
ATOM 2691 O PRO A 3S3 0 5.393 57.852 28.483 1.00 21.91
ATOM 2692 CB PRO A 353 0 5.417 56.054 25.916 1.00 23.95
ATOM 2693 CG PRO A 353 0 5.181 57.123 24.878 1.00 23.79
ATOM 2694 CD PRO A 353 0 3.882 57.848 25.180 1.00 23.03
ATOM 2695 N THR A 354 0 5.043 55.778 29.234 1.00 18.66
ATOM 2696 CA THR A 354 0 5.646 56.015 30.530 1.00 18.05
ATOM 2697 C THR A 354 0 6.981 56.739 30.478 1.00 18.33
ATOM 2698 O THR A 354 0 7.168 57.630 31.319 1.00 19.46
ATOM 2699 CB THR A 354 0 5.871 54.661 31.242 1.00 17.10
ATOM 2700 OG1 THR A 354 0 4.903 53.710 30.797 1.00 17.24
ATOM 2701 CG2 THR A 354 0 5.772 54.852 32.741 1.00 16.43
ATOM 2702 N LEU A 355 0 7.940 56.380 29.618 1.00 17.49
ATOM 2703 CA LEU A 355 0 9.215 57.076 29.604 1.00 18.84
ATOM 2704 C LEU A 355 0 9.013 58.579 29.284 1.00 19.80
ATOM 2705 O LEU A 355 0 9.722 59.417 29.849 1.00 17.13
ATOM 2706 CB LEU A 355 0 10.200 56.498 28.622 1.00 17.89
ATOM 2707 CG LEU A 355 0 11.703 56.488 28.819 1.00 18.66
ATOM 2708 CD1 LEU A 355 0 12.436 56.851 27.547 1.00 18.37
ATOM 2709 CD2 LEU A 355 0 12.199 57.204 30.056 1.00 16.79
ATOM 2710 N LEU A 356 0 8.134.58.883 28.328 1.00 20.48
ATOM 2711 CA LEU A 356 0 7.812 60.274 27.993 1.00 21.62
ATOM 2712 C LEU A 356 0 7.085 60.932 29.163 1.00 21.29
ATOM 2713 O LEU A 356 0 7.497 62.042 29.506 1.00 22.01
ATOM 2714 CB LEU A 356 0 7.028 60.474 26.700 1.00 22.08
ATOM 2715 CG LEU A 356 0 6.850 61.939 26.239 1.00 23.98
ATOM 2716 CD1 LEU A 356 0 8.157 62.709 26.207 1.00 23.11
ATOM 2717 CD2 LEU A 356 0 6.191 61.985 24.864 1.00 24.74
ATOM 2718 N GLN A 357 0 6.219 60.267 29.922 1.00 21.37
ATOM 2719 CA GLN A 357 0 5.669 60.893 31.120 1.00 21.87
ATOM 2720 C GLN A 357 0 6.759 61.254 32.128 1.00 24.12
ATOM 2721 O GLN A 357 0 6.674 62.277 32.811 1.00 24.92
ATOM 2722 CB GLN A 357 0 4.636 60.015 31.822 1.00 20.63
ATOM 2723 CG GLN A 357 0 3.447 59.674 30.906 1.00 19.17
ATOM 2724 CD GLN A 357 0 2.547 58.643 31.540 1.00 18.85
ATOM 2725 OE1 GLN A 357 0 2.162 58.748 32.713 1.00 19.06
ATOM 2726 NE2 GLN A 357 0 2.262 57.600 30.742 1.00 18.49
ATOM 2727 N ILE A 358 0 7.735 60.371 32.346 1.00 25.66
ATOM 2728 CA ILE A 358 0 8.822 60.651 33.263 1.00 26 19
ATOM 2729 C ILE A 358 0 9.699 61.800 32.762 1.00 27.66
ATOM 2730 O ILE A 358 0 9.940 62.725 33.551 1.00 26.65
ATOM 2731 CB ILE A 358 0 9.692 59.420 33.578 1.00 24.79
ATOM 2732 CG1 ILE A 358 0 8.807 58.395 34.304 1.00 24.09
ATOM 2733 CG2 ILE A 358 0 10.865 59.841 34.451 1.00 23.78
ATOM 2734 CD1 ILE A 358 0 9.251 56.954 34.234 1.00 23.34
ATOM 2735 N MET A 359 0 10.054 61.844 31.486 1.00 29.63
ATOM 2736 CA MET A 359 0 10.893 62.910 30.965 1.00 33.02
ATOM 2737 C MET A 359 0 10.174 64.260 31.027 1.00 34.46
ATOM 2738 O MET A 359 0 10.801 65.324 31.026 1.00 33.77
ATOM 2739 CB MET A 359 0 11.346 62.664 29.537 1.00 35.67
ATOM 2740 CG MET A 359 0 12.065 61.403 29.138 1.00 40.75
ATOM 2741 SD MET A 359 0 13.764 61.153 29.671 1.00 44.90
ATOM 2742 CE MET A 359 0 14.594 62.592 29.007 1.00 44.24
ATOM 2743 N SER A 360 0 8.835 64.238 31.070 1.00 33.43
ATOM 2744 CA SER A 360 0 8.024 65.430 31.088 1.00 32.92
ATOM 2745 C SER A 360 0 7.761 65.995 32.474 1.00 33.24
ATOM 2746 O SER A 360 0 6.989 66.966 32.556 1.00 34.08
ATOM 2747 CB SER A 360 0 6.678 65.134 30.393 1.00 31.34
ATOM 2748 OG SER A 360 0 6.928 65.109 28.996 1.00 31.06
ATOM 2749 N GLY A 361 0 8.288 65.360 33.517 1.00 32.06
ATOM 2750 CA GLY A 361 0 8.072 65.868 34.847 1.00 31.80
ATOM 2751 C GLY A 361 0 7.487 64.955 35.880 1.00 32.48
ATOM 2752 O GLY A 361 0 7.420 65.377 37.043 1.00 33.20
ATOM 2753 N ALA A 362 0 6.991 63.769 35.535 1.00 33.69
ATOM 2754 CA ALA A 362 0 6.406 62.926 36.601 1.00 35.10
ATOM 2755 C ALA A 362 0 7.475 62.615 37.650 1.00 34.45
ATOM 2756 O ALA A 362 0 8.598 62.306 37.286 1.00 33.60
ATOM 2757 CB ALA A 362 0 5.789 61.658 36.043 1.00 34.88
ATOM 2758 N GLN A 363 0 7.146 62.676 38.920 1.00 36.22
ATOM 2759 CA GLN A 363 0 8.083 62.458 40.007 1.00 37.87
ATOM 2760 C GLN A 363 0 7.776 61.189 40.787 1.00 37.20
ATOM 2761 O GLN A 363 0 8.620 60.777 41.587 1.00 36.79
ATOM 2762 CB GLN A 363 0 8.012 63.619 41.022 1.00 40.41
ATOM 2763 CG GLN A 363 0 8.986 64.740 40.721 1.00 44.07
ATOM 2764 CD GLN A 363 0 8.586 66.154 41.092 1.00 45.77
ATOM 2765 OE1 GLN A 363 0 7.697 66.473 41.901 1.00 46.53
ATOM 2766 NE2 GLN A 363 0 9.294 67.089 40.435 1.00 46.12
ATOM 2767 N SER A 364 0 6.579 60.632 40.610 1.00 35.74
ATOM 2768 CA SER A 364 0 6.249 59.434 41.381 1.00 34.54
ATOM 2769 C SER A 364 0 5.225 58.588 40.653 1.00 34.32
ATOM 2770 O SER A 364 0 4.605 59.037 39.692 1.00 33.71
ATOM 2771 CB SER A 364 0 5.774 59.835 42.769 1.00 35.68
ATOM 2772 OG SER A 364 0 4.396 60.095 42.928 1.00 35.86
ATOM 2773 N ALA A 365 0 5.015 57.372 41.146 1.00 33.95
ATOM 2774 CA ALA A 365 0 4.017 56.486 40.564 1.00 34.62
ATOM 2775 C ALA A 365 0 2.637 57.148 40.560 1.00 34.46
ATOM 2776 O ALA A 365 0 1.906 56.995 39.582 1.00 34.37
ATOM 2777 CB ALA A 365 0 3.963 55.155 41.301 1.00 33.51
ATOM 2778 N ASN A 366 0 2.261 57.916 41.571 1.00 34.45
ATOM 2779 CA ASN A 366 0 1.00 3 58.619 41.632 1.00 36.37
ATOM 2780 C ASN A 366 0 0.708 59.524 40.447 1.00 35.60
ATOM 2781 O ASN A 366 0 -0.462 59.719 40.131 1.00 36.50
ATOM 2782 CB ASN A 366 0 0.904 59.464 42.918 1.00 38.72
ATOM 2783 CG ASN A 366 0 0.794 58.558 44.126 1.00 41.08
ATOM 2784 OD1 ASN A 366 0 0.863 58.966 45.284 1.00 43.39
ATOM 2785 ND2 ASN A 366 0 0.646 57.256 43.914 1.00 42.72
ATOM 2786 N ASP A 367 0 1.694 60.046 39.752 1.00 34.06
ATOM 2787 CA ASP A 367 0 1.571 60.899 38.610 1.00 33.37
ATOM 2788 C ASP A 367 0 1.566 60.122 37.293 1.00 32.09
ATOM 2789 O ASP A 367 0 1.430 60.762 36.247 1.00 31.74
ATOM 2790 CB ASP A 367 0 2.768 61.841 38.483 1.00 35.96
ATOM 2791 CG ASP A 367 0 3.048 62.818 39.602 1.00 37.69
ATOM 2792 OD1 ASP A 367 0 2.123 63.209 40.336 1.00 37.23
ATOM 2793 OD2 ASP A 367 0 4.258 63.194 39.705 1.00 39.62
ATOM 2794 N LEU A 368 0 1.791 58.814 37.371 1.00 30.39
ATOM 2795 CA LEU A 368 0 1.897 58.055 36.123 1.00 28.74
ATOM 2796 C LEU A 368 0 0.586 57.386 35.745 1.00 28.85
ATOM 2797 O LEU A 368 0 -0.214 56.947 36.555 1.00 28.17
ATOM 2798 CB LEU A 368 0 3.043 57.046 36.194 1.00 26.94
ATOM 2799 CG LEU A 368 0 4.436 57.668 36.422 1.00 27.05
ATOM 2800 CD1 LEU A 368 0 5.455 56.581 36.765 1.00 25.41
ATOM 2801 CD2 LEU A 368 0 4.882 58.499 35.236 1.00 24.44
ATOM 2802 N LEU A 369 0 0.392 57.332 34.446 1.00 28.81
ATOM 2803 CA LEU A 369 0 -0.753 56.671 33.834 1.00 29.65
ATOM 2804 C LEU A 369 0 0238 55.398 33.162 1.00 28.29
ATOM 2805 O LEU A 369 0 0.875 55.356 32.660 1.00 25.59
ATOM 2806 CB LEU A 369 0 -1.333 57.668 32.821 1.00 30.27
ATOM 2807 CG LEU A 369 0 -1.800 58.998 33.456 1.00 32.06
ATOM 2808 CD1 LEU A 369 0 -2.220 59.979 32.370 1.00 31.87
ATOM 2809 CD2 LEU A 369 0 -2.932 58.787 34.455 1.00 30.89
ATOM 2810 N PRO A 370 0 -1.054 54.361 33.157 1.00 27.87
ATOM 2811 CA PRO A 370 0 -2.396 54.379 33.688 1.00 26.71
ATOM 2812 C PRO A 370 0 -2.513 54.112 35.169 1.00 26.73
ATOM 2813 O PRO A 370 0 -1.872 53.184 35.668 1.00 26.55
ATOM 2814 CB PRO A 370 0 -3.126 53.222 32.958 1.00 27.28
ATOM 2815 CG PRO A 370 0 -2.003 52.317 32.557 1.00 27.38
ATOM 2816 CD PRO A 370 0 -0.720 53.102 32.482 1.00 27.24
ATOM 2817 N ALA A 371 0 -3.414 54.810 35.870 1.00 26.16
ATOM 2818 CA ALA A 371 0 -3.581 54.556 37.302 1.00 25.73
ATOM 2819 C ALA A 371 0 -3.892 53.103 37.616 1.00 24.59
```

| | |
|---|---|
| ATOM 2820 O ALA A 371 0 -4.758 52.533 36.946 1.00 25.05 | ATOM 2900 CD GLN A 381 0 16.065 49.297 48.792 1.00 30.24 |
| ATOM 2821 CB ALA A 371 0 -4.718 55.394 37.903 1.00 26.42 | ATOM 2901 OE1 GLN A 381 0 15.067 49.917 49.171 1.00 34.48 |
| ATOM 2822 N GLY A 372 0 -3.261 52.524 38.625 1.00 22.47 | ATOM 2902 NE2 GLN A 381 0 16.929 48.742 49.611 1.00 30.80 |
| ATOM 2823 CA GLY A 372 0 -3.519 51.187 39.087 1.00 21.06 | ATOM 2903 N VAL A 382 0 17.046 44.825 46.594 1.00 18.67 |
| ATOM 2824 C GLY A 372 0 -2.691 50.096 38.427 1.00 23.01 | ATOM 2904 CA VAL A 382 0 16.665 43.472 46.248 1.00 18.98 |
| ATOM 2825 O GLY A 372 0 -2.758 48.928 38.831 1.00 23.85 | ATOM 2905 C VAL A 382 0 15.139 43.327 46.212 1.00 19.75 |
| ATOM 2826 N SER A 373 0 -1.910 50.428 37.421 1.00 23.30 | ATOM 2906 O VAL A 382 0 14.443 43.550 47.225 1.00 18.76 |
| ATOM 2827 CA SER A 373 0 -1.054 49.459 36.736 1.00 24.36 | ATOM 2907 CB VAL A 382 0 17.252 42.491 47.278 1.00 19.03 |
| ATOM 2828 C SER A 373 0 0.429 49.746 36.919 1.00 24.76 | ATOM 2908 CG1 VAL A 382 0 16.811 41.065 46.960 1.00 18.87 |
| ATOM 2829 O SER A 373 0 1.257 49.103 36.270 1.00 25.75 | ATOM 2909 CG2 VAL A 382 0 18.779 42.637 47.344 1.00 17.54 |
| ATOM 2830 CB SER A 373 0 -1.371 49.584 35.233 1.00 23.25 | ATOM 2910 N VAL A 383 0 14.601 42.954 45.046 1.00 17.58 |
| ATOM 2831 OG SER A 373 0 -2.638 49.014 34.952 1.00 23.80 | ATOM 2911 CA VAL A 383 0 13.151 42.715 45.037 1.00 17.76 |
| ATOM 2832 N VAL A 374 0 0.779 50.799 37.657 1.00 23.87 | ATOM 2912 C VAL A 383 0 12.777 41.254 44.883 1.00 17.50 |
| ATOM 2833 CA VAL A 374 0 2.176 51.255 37.706 1.00 22.95 | ATOM 2913 O VAL A 383 0 13.348 40.472 44.153 1.00 16.42 |
| ATOM 2834 C VAL A 374 0 2.739 51.109 39.105 1.00 21.72 | ATOM 2914 CB VAL A 383 0 12.306 43.626 44.145 1.00 17.69 |
| ATOM 2835 O VAL A 374 0 2.093 51.518 40.059 1.00 21.03 | ATOM 2915 CG1 VAL A 383 0 13.111 44.759 43.585 1.00 15.33 |
| ATOM 2836 CB VAL A 374 0 2.317 52.687 37.169 1.00 23.05 | ATOM 2916 CG2 VAL A 383 0 11.400 43.009 43.126 1.00 17.79 |
| ATOM 2837 CG1 VAL A 374 0 3.720 53.273 37.323 1.00 24.13 | ATOM 2917 N GLU A 384 0 11.743 40.861 45.638 1.00 18.47 |
| ATOM 2838 CG2 VAL A 374 0 1.945 52.771 35.698 1.00 21.58 | ATOM 2918 CA GLU A 384 0 11.173 39.529 45.542 1.00 18.27 |
| ATOM 2839 N TYR A 375 0 3.862 50.402 39.246 1.00 20.52 | ATOM 2919 C GLU A 384 0 9.711 39.683 45.096 1.00 18.94 |
| ATOM 2840 CA TYR A 375 0 4.445 50.184 40.573 1.00 22.02 | ATOM 2920 O GLU A 384 0 8.956 40.311 45.816 1.00 19.06 |
| ATOM 2841 C TYR A 375 0 5.873 50.743 40.549 1.00 22.56 | ATOM 2921 CB GLU A 384 0 11.253 38.764 46.852 1.00 17.12 |
| ATOM 2842 O TYR A 375 0 6.665 50.524 39.639 1.00 21.82 | ATOM 2922 CG GLU A 384 0 10.717 37.345 46.738 1.00 17.52 |
| ATOM 2843 CB TYR A 375 0 4.467 48.729 41.067 1.00 21.98 | ATOM 2923 CD GLU A 384 0 10.979 36.551 47.998 1.00 19.10 |
| ATOM 2844 CG TYR A 375 0 3.042 48.217 41.226 1.00 24.04 | ATOM 2924 OE1 GLU A 384 0 12.101 36.050 48.218 1.00 20.69 |
| ATOM 2845 CD1 TYR A 375 0 2.398 48.261 42.445 1.00 23.57 | ATOM 2925 OE2 GLU A 384 0 10.018 36.405 48.773 1.00 21.22 |
| ATOM 2846 CD2 TYR A 375 0 2.339 47.760 40.115 1.00 24.92 | ATOM 2926 N LEU A 385 0 9.326 39.182 43.948 1.00 19.78 |
| ATOM 2847 CE1 TYR A 375 0 1.100 47.831 42.575 1.00 25.65 | ATOM 2927 CA LEU A 385 0 7.966 39.153 43.463 1.00 21.07 |
| ATOM 2848 CE2 TYR A 375 0 1.034 47.327 40.220 1.00 25.89 | ATOM 2928 C LEU A 385 0 7.391 37.738 43.591 1.00 20.91 |
| ATOM 2849 CZ TYR A 375 0 0.429 47.352 41.464 1.00 26.65 | ATOM 2929 O LEU A 385 0 8.043 36.790 43.113 1.00 21.40 |
| ATOM 2850 OH TYR A 375 0 -0.869 46.916 41.593 1.00 27.26 | ATOM 2930 CB LEU A 385 0 7.881 39.466 41.959 1.00 20.92 |
| ATOM 2851 N GLU A 376 0 6.130 51.563 41.546 1.00 22.36 | ATOM 2931 CG LEU A 385 0 8.393 40.795 41.457 1.00 23.75 |
| ATOM 2852 CA GLU A 376 0 7.403 52.214 41.718 1.00 23.62 | ATOM 2932 CD1 LEU A 385 0 8.118 40.984 39.962 1.00 23.01 |
| ATOM 2853 C GLU A 376 0 8.411 51.289 42.387 1.00 22.40 | ATOM 2933 CD2 LEU A 385 0 7.827 41.977 42.244 1.00 22.40 |
| ATOM 2854 O GLU A 376 0 8.062 50.578 43.324 1.00 21.88 | ATOM 2934 N VAL A 386 0 6.182 37.574 44.099 1.00 20.91 |
| ATOM 2855 CB GLU A 376 0 7.211 53.465 42.614 1.00 25.13 | ATOM 2935 CA VAL A 386 0 5.510 36.274 44.189 1.00 19.03 |
| ATOM 2856 CG GLU A 376 0 8.500 54.255 42.720 1.00 27.91 | ATOM 2936 C VAL A 386 0 4.228 36.334 43.356 1.00 21.11 |
| ATOM 2857 CD GLU A 376 0 8.376 55.725 43.046 1.00 29.20 | ATOM 2937 O VAL A 386 0 3.465 37.326 43.516 1.00 20.56 |
| ATOM 2858 OE1 GLU A 376 0 7.247 56.268 43.109 1.00 30.01 | ATOM 2938 CB VAL A 386 0 5.159 35.967 45.654 1.00 20.91 |
| ATOM 2859 OE2 GLU A 376 0 9.458 56.336 43.219 1.00 28.05 | ATOM 2939 CG1 VAL A 386 0 4.518 34.575 45.739 1.00 20.40 |
| ATOM 2860 N LEU A 377 0 9.669 51.353 41.954 1.00 21.23 | ATOM 2940 CG2 VAL A 386 0 6.321 36.044 46.625 1.00 19.89 |
| ATOM 2861 CA LEU A 377 0 10.705 50.535 42.626 1.00 19.95 | ATOM 2941 N VAL A 387 0 4.011 35.469 42.358 1.00 20.02 |
| ATOM 2862 C LEU A 377 0 11.838 51.478 42.982 1.00 20.30 | ATOM 2942 CA VAL A 387 0 2.817 35.515 41.491 1.00 20.83 |
| ATOM 2863 O LEU A 377 0 12.220 52.350 42.197 1.00 20.12 | ATOM 2943 C VAL A 387 0 2.119 34.152 41.385 1.00 21.15 |
| ATOM 2864 CB LEU A 377 0 11.129 49.419 41.692 1.00 20.77 | ATOM 2944 O VAL A 387 0 2.369 33.285 40.528 1.00 19.97 |
| ATOM 2865 CG LEU A 377 0 10.668 47.964 41.818 1.00 20.49 | ATOM 2945 CB VAL A 387 0 3.163 36.076 40.104 1.00 20.91 |
| ATOM 2866 CD1 LEU A 377 0 9.439 47.739 42.629 1.00 17.77 | ATOM 2946 CG1 VAL A 387 0 1.917 36.472 39.297 1.00 22.49 |
| ATOM 2867 CD2 LEU A 377 0 10.617 47.242 40.483 1.00 19.28 | ATOM 2947 CG2 VAL A 387 0 3.959 37.393 40.171 1.00 22.24 |
| ATOM 2868 N PRO A 378 0 12.407 51.334 44.162 1.00 19.69 | ATOM 2948 N PRO A 388 0 1.262 33.832 42.358 1.00 20.55 |
| ATOM 2869 CA PRO A 378 0 13.523 52.117 44.631 1.00 19.91 | ATOM 2949 CA PRO A 388 0 0.570 32.548 42.483 1.00 20.93 |
| ATOM 2870 C PRO A 378 0 14.797 51.650 43.937 1.00 19.81 | ATOM 2950 C PRO A 388 0 -0.271 32.226 41.264 1.00 20.76 |
| ATOM 2871 O PRO A 378 0 14.795 50.645 43.241 1.00 17.74 | ATOM 2951 O PRO A 388 0 -0.928 33.118 40.715 1.00 19.53 |
| ATOM 2872 CB PRO A 378 0 13.611 51.893 46.157 1.00 20.21 | ATOM 2952 CB PRO A 388 0 -0.310 32.559 43.757 1.00 20.54 |
| ATOM 2873 CG PRO A 378 0 12.957 50.546 46.291 1.00 20.73 | ATOM 2953 CG PRO A 388 0 0.280 33.766 44.482 1.00 21.86 |
| ATOM 2874 CD PRO A 378 0 12.050 50.292 45.114 1.00 19.74 | ATOM 2954 CD PRO A 388 0 0.841 34.707 43.438 1.00 20.83 |
| ATOM 2875 N ARG A 379 0 15.877 52.410 44.059 1.00 19.68 | ATOM 2955 N ALA A 389 0 -0.160 30.986 40.807 1.00 21.68 |
| ATOM 2876 CA ARG A 379 0 17.172 52.135 43.449 1.00 18.58 | ATOM 2956 CA ALA A 389 0 -0.983 30.617 39.640 1.00 24.20 |
| ATOM 2877 C ARG A 379 0 18.027 51.129 44.193 1.00 18.68 | ATOM 2957 C ALA A 389 0 -2.394 30.320 40.148 1.00 25.02 |
| ATOM 2878 O ARG A 379 0 18.151 51.126 45.432 1.00 17.60 | ATOM 2958 O ALA A 389 0 -2.619 30.162 41.350 1.00 24.19 |
| ATOM 2879 CB ARG A 379 0 17.946 53.487 43.431 1.00 18.33 | ATOM 2959 CB ALA A 389 0 -0.383 29.403 38.968 1.00 23.67 |
| ATOM 2880 CG ARG A 379 0 19.406 53.348 43.030 1.00 19.33 | ATOM 2960 N GLY A 390 0 -3.309 30.143 39.222 1.00 28.43 |
| ATOM 2881 CD ARG A 379 0 20.026 54.710 42.729 1.00 19.06 | ATOM 2961 CA GLY A 390 0 -4.713 29.811 39.539 1.00 28.47 |
| ATOM 2882 NE ARG A 379 0 21.413 54.561 42.295 1.00 16.65 | ATOM 2962 C GLY A 390 0 -5.624 30.325 38.431 1.00 28.63 |
| ATOM 2883 CZ ARG A 379 0 21.794 54.681 41.031 1.00 15.60 | ATOM 2963 O GLY A 390 0 -6.512 29.630 37.937 1.00 31.26 |
| ATOM 2884 NH1 ARG A 379 0 20.964 54.904 40.038 1.00 14.29 | ATOM 2964 N VAL A 391 0 -5.402 31.531 37.961 1.00 27.11 |
| ATOM 2885 NH2 ARG A 379 0 23.096 54.505 40.783 1.00 17.29 | ATOM 2965 CA VAL A 391 0 -6.234 32.164 36.962 1.00 26.51 |
| ATOM 2886 N ASN A 380 0 18.701 50.263 43.441 1.00 20.11 | ATOM 2966 C VAL A 391 0 -6.246 31.377 35.666 1.00 29.59 |
| ATOM 2887 CA ASN A 380 0 19.658 49.328 44.011 1.00 21.97 | ATOM 2967 O VAL A 391 0 -5.274 30.775 35.181 1.00 30.61 |
| ATOM 2888 C ASN A 380 0 19.129 48.604 45.227 1.00 22.44 | ATOM 2968 CB VAL A 391 0 -5.835 33.634 36.788 1.00 25.83 |
| ATOM 2889 O ASN A 380 0 19.712 48.630 46.317 1.00 22.53 | ATOM 2969 CG1 VAL A 391 0 -4.584 33.787 35.937 1.00 24.18 |
| ATOM 2890 CB ASN A 380 0 20.995 50.045 44.345 1.00 23.30 | ATOM 2970 CG2 VAL A 391 0 -7.017 34.419 36.219 1.00 24.11 |
| ATOM 2891 CG ASN A 380 0 21.860 50.231 43.107 1.00 25.83 | ATOM 2971 N LEU A 392 0 -7.439 31.392 35.058 1.00 30.83 |
| ATOM 2892 OD1 ASN A 380 0 22.636 51.186 42.877 1.00 27.14 | ATOM 2972 CA LEU A 392 0 -7.705 30.604 33.867 1.00 30.29 |
| ATOM 2893 ND2 ASN A 380 0 21.767 49.271 42.185 1.00 24.91 | ATOM 2973 C LEU A 392 0 -6.809 31.00 4 32.710 1.00 27.38 |
| ATOM 2894 N GLN A 381 0 17.974 47.936 45.097 1.00 21.39 | ATOM 2974 O LEU A 392 0 -6.316 32.113 32.665 1.00 24.62 |
| ATOM 2895 CA GLN A 381 0 17.468 47.162 46.220 1.00 20.88 | ATOM 2975 CB LEU A 392 0 -9.173 30.726 33.436 1.00 32.58 |
| ATOM 2896 C GLN A 381 0 17.169 45.760 45.679 1.00 19.96 | ATOM 2976 CG LEU A 392 0 -9.711 32.126 33.189 1.00 33.97 |
| ATOM 2897 O GLN A 381 0 17.000 45.635 44.471 1.00 19.90 | ATOM 2977 CD1 LEU A 392 0 -9.411 32.626 31.786 1.00 34.78 |
| ATOM 2898 CB GLN A 381 0 16.219 47.722 46.871 1.00 22.84 | ATOM 2978 CD2 LEU A 392 0 -11.225 32.122 33.463 1.00 36.03 |
| ATOM 2899 CG GLN A 381 0 16.326 49.172 47.318 1.00 27.28 | ATOM 2979 N GLY A 393 0 -6.725 30.074 31.754 1.00 26.24 |

-continued

```
ATOM 2980 CA GLY A 393 0 -5.936 30.302 30.554 1.00 25.54
ATOM 2981 C GLY A 393 0 -4.458 29.994 30.710 1.00 25.81
ATOM 2982 O GLY A 393 0 -3.686 30.361 29.820 1.00 26.67
ATOM 2983 N GLY A 394 0 -4.033 29.379 31.803 1.00 25.84
ATOM 2984 CA GLY A 394 0 -2.615 29.112 32.035 1.00 25.94
ATOM 2985 C GLY A 394 0 -2.140 27.844 31.348 1.00 26.00
ATOM 2986 O GLY A 394 0 -2.884 27.193 30.625 1.00 25.18
ATOM 2987 N PRO A 395 0 -0.860 27.527 31.517 1.00 24.26
ATOM 2988 CA PRO A 395 0 0.051 28.258 32.364 1.00 21.79
ATOM 2989 C PRO A 395 0 0.517 29.518 31.660 1.00 19.29
ATOM 2990 O PRO A 395 0 0.704 29.597 30.445 1.00 17.41
ATOM 2991 CB PRO A 395 0 1.159 27.279 32.794 1.00 22.52
ATOM 2992 CG PRO A 395 0 1.062 26.223 31.758 1.00 24.35
ATOM 2993 CD PRO A 395 0 -0.241 26.312 30.973 1.00 24.87
ATOM 2994 N HIS A 396 0 0.586 30.591 32.451 1.00 16.97
ATOM 2995 CA HIS A 396 0 0.970 31.917 31.980 1.00 15.05
ATOM 2996 C HIS A 396 0 2.477 32.137 32.186 1.00 15.41
ATOM 2997 O HIS A 396 0 3.039 32.025 33.275 1.00 14.21
ATOM 2998 CB HIS A 396 0 0.288 32.989 32.842 1.00 15.40
ATOM 2999 CG HIS A 396 0 -1.224 32.924 32.737 1.00 18.23
ATOM 3000 ND1 HIS A 396 0 -1.942 33.504 31.702 1.00 16.23
ATOM 3001 CD2 HIS A 396 0 -2.109 32.319 33.557 1.00 17.00
ATOM 3002 CE1 HIS A 396 0 -3.218 33.262 31.906 1.00 18.22
ATOM 3003 NE2 HIS A 396 0 -3.343 32.526 33.014 1.00 19.08
ATOM 3004 N PRO A 397 0 3.143 32.403 31.090 1.00 14.69
ATOM 3005 CA PRO A 397 0 4.593 32.617 31.080 1.00 16.91
ATOM 3006 C PRO A 397 0 4.818 34.129 31.202 1.00 17.59
ATOM 3007 O PRO A 397 0 4.524 34.843 30.235 1.00 17.59
ATOM 3008 CB PRO A 397 0 5.076 32.040 29.757 1.00 16.63
ATOM 3009 CG PRO A 397 0 3.785 31.844 28.978 1.00 17.83
ATOM 3010 CD PRO A 397 0 2.620 32.464 29.736 1.00 14.36
ATOM 3011 N PHE A 398 0 5.242 34.590 32.377 1.00 16.39
ATOM 3012 CA PHE A 398 0 5.462 36.019 32.529 1.00 15.95
ATOM 3013 C PHE A 398 0 6.906 36.365 32.168 1.00 15.74
ATOM 3014 O PHE A 398 0 7.846 35.619 32.444 1.00 15.78
ATOM 3015 CB PHE A 398 0 5.173 36.455 33.963 1.00 17.20
ATOM 3016 CG PHE A 398 0 3.817 37.073 34.169 1.00 19.23
ATOM 3017 CD1 PHE A 398 0 2.673 36.299 34.005 1.00 19.58
ATOM 3018 CD2 PHE A 398 0 3.688 38.403 34.537 1.00 19.42
ATOM 3019 CE1 PHE A 398 0 1.409 36.832 34.198 1.00 19.83
ATOM 3020 CE2 PHE A 398 0 2.405 38.933 34.709 1.00 21.46
ATOM 3021 CZ PHE A 398 0 1.260 38.162 34.539 1.00 19.65
ATOM 3022 N HIS A 399 0 7.080 37.562 31.640 1.00 14.77
ATOM 3023 CA HIS A 399 0 8.374 38.089 31.333 1.00 14.75
ATOM 3024 C HIS A 399 0 8.580 39.496 31.872 1.00 17.67
ATOM 3025 O HIS A 399 0 7.635 40.308 31.925 1.00 18.29
ATOM 3026 CB HIS A 399 0 8.582 37.968 29.861 1.00 14.01
ATOM 3027 CG HIS A 399 0 8.747 39.105 28.962 1.00 16.26
ATOM 3028 ND1 HIS A 399 0 9.957 39.511 28.446 1.00 15.35
ATOM 3029 CD2 HIS A 399 0 7.788 39.903 28.386 1.00 17.58
ATOM 3030 CE1 HIS A 399 0 9.764 40.507 27.593 1.00 15.61
ATOM 3031 NE2 HIS A 399 0 8.457 40.770 27.548 1.00 17.52
ATOM 3032 N LEU A 400 0 9.837 39.771 32.201 1.00 15.57
ATOM 3033 CA LEU A 400 0 10.220 41.061 32.745 1.00 16.93
ATOM 3034 C LEU A 400 0 11.207 41.732 31.788 1.00 16.51
ATOM 3035 O LEU A 400 0 12.268 41.175 31.510 1.00 15.77
ATOM 3036 CB LEU A 400 0 10.913 40.825 34.084 1.00 18.17
ATOM 3037 CG LEU A 400 0 10.877 41.741 35.288 1.00 21.27
ATOM 3038 CD1 LEU A 400 0 12.130 41.638 36.151 1.00 19.27
ATOM 3039 CD2 LEU A 400 0 10.536 43.166 34.926 1.00 19.86
ATOM 3040 N HIS A 401 0 10.945 42.916 31.321 1.00 14.34
ATOM 3041 CA HIS A 401 0 11.830 43.707 30.508 1.00 16.06
ATOM 3042 C HIS A 401 0 12.924 44.300 31.428 1.00 16.15
ATOM 3043 O HIS A 401 0 12.644 44.543 32.600 1.00 13.61
ATOM 3044 CB HIS A 401 0 11.105 44.884 29.843 1.00 13.27
ATOM 3045 CG HIS A 401 0 10.184 44.441 28.751 1.00 14.50
ATOM 3046 ND1 HIS A 401 0 10.201 44.973 27.479 1.00 14.96
ATOM 3047 CD2 HIS A 401 0 9.202 43.492 28.750 1.00 12.35
ATOM 3048 CE1 HIS A 401 0 9.263 44.387 26.725 1.00 12.61
ATOM 3049 NE2 HIS A 401 0 8.677 43.507 27.492 1.00 12.41
ATOM 3050 N GLY A 402 0 14.103 44.549 30.855 1.00 15.59
ATOM 3051 CA GLY A 402 0 15.152 45.209 31.598 1.00 15.18
ATOM 3052 C GLY A 402 0 16.009 44.351 32.510 1.00 15.96
ATOM 3053 O GLY A 402 0 16.927 44.898 33.170 1.00 16.30
ATOM 3054 N HIS A 403 0 15.618 43.147 32.893 1.00 12.96
ATOM 3055 CA HIS A 403 0 16.282 42.337 33.873 1.00 15.00
ATOM 3056 C HIS A 403 0 16.226 40.839 33.586 1.00 15.22
ATOM 3057 O HIS A 403 0 15.253 40.381 32.971 1.00 16.16
ATOM 3058 CB HIS A 403 0 15.525 42.478 35.227 1.00 14.13
ATOM 3059 CG HIS A 403 0 15.571 43.829 35.827 1.00 16.69
ATOM 3060 ND1 HIS A 403 0 16.604 44.253 36.649 1.00 16.13
ATOM 3061 CD2 HIS A 403 0 14.744 44.911 35.659 1.00 15.50
ATOM 3062 CE1 HIS A 403 0 16.425 45.520 37.002 1.00 15.02
ATOM 3063 NE2 HIS A 403 0 15.285 45.905 36.430 1.06 16.15
ATOM 3064 N ALA A 404 0 17.138 40.054 34.113 1.00 13.71
ATOM 3065 CA ALA A 404 0 17.039 38.607 34.158 1.00 12.60
ATOM 3066 C ALA A 404 0 16.771 38.370 35.649 1.00 12.31
ATOM 3067 O ALA A 404 0 17.156 39.291 36.373 1.00 13.94
ATOM 3068 CB ALA A 404 0 18.249 37.819 33.721 1.00 13.84
ATOM 3069 N PHE A 405 0 16.085 37.356 36.126 1.00 12.21
ATOM 3070 CA PHE A 405 0 15.813 37.235 37.559 1.00 11.64
ATOM 3071 C PHE A 405 0 16.177 35.821 38.008 1.00 12.55
ATOM 3072 O PHE A 405 0 16.196 34.883 37.201 1.00 12.23
ATOM 3073 CB PHE A 405 0 14.325 37.487 37.907 1.00 11.82
ATOM 3074 CG PHE A 405 0 13.382 36.893 36.879 1.00 11.75
ATOM 3075 CD1 PHE A 405 0 13.030 35.557 36.933 1.00 10.76
ATOM 3076 CD2 PHE A 405 0 12.917 37.663 35.824 1.00 11.55
ATOM 3077 CE1 PHE A 405 0 12.189 35.002 35.978 1.00 11.52
ATOM 3078 CE2 PHE A 405 0 12.087 37.112 34.862 1.00 13.32
ATOM 3079 CZ PHE A 405 0 11.692 35.767 34.946 1.00 11.45
ATOM 3080 N SER A 406 0 16.414 35.625 39.288 1.00 12.86
ATOM 3081 CA SER A 406 0 16.660 34.286 39.796 1.00 13.43
ATOM 3082 C SER A 406 0 15.276 33.712 40.130 1.00 13.49
ATOM 3083 O SER A 406 0 14.518 34.375 40.837 1.00 10.13
ATOM 3084 CB SER A 406 0 17.433 34.290 41.123 1.00 13.78
ATOM 3085 OG SER A 406 0 18.708 34.834 40.938 1.00 16.72
ATOM 3086 N VAL A 407 0 15.100 32.453 39.741 1.00 14.53
ATOM 3087 CA VAL A 407 0 13.853 31.777 40.093 1.00 13.90
ATOM 3088 C VAL A 407 0 14.160 30.943 41.325 1.00 14.53
ATOM 3089 O VAL A 407 0 14.513 29.753 41.262 1.00 14.62
ATOM 3090 CB VAL A 407 0 13.333 30.903 38.941 1.00 16.43
ATOM 3091 CG1 VAL A 407 0 11.969 30.317 39.341 1.00 16.69
ATOM 3092 CG2 VAL A 407 0 13.272 31.682 37.626 1.00 14.90
ATOM 3093 N VAL A 408 0 13.971 31.544 42.485 1.00 14.32
ATOM 3094 CA VAL A 408 0 14.173 30.947 43.780 1.00 15.47
ATOM 3095 C VAL A 408 0 13.115 29.870 44.049 1.00 16.51
ATOM 3096 O VAL A 408 0 13.387 28.92744.812 1.00 17.39
ATOM 3097 CB VAL A 408 0 14.280 31.967 44.932 1.00 15.75
ATOM 3098 CG1 VAL A 408 0 15.345 33.015 44.600 1.00 14.81
ATOM 3099 CG2 VAL A 408 0 12.952 32.693 45.189 1.00 15.99
ATOM 3100 N ARG A 409 0 11.972 29.940 43.387 1.00 16.28
ATOM 3101 CA ARG A 409 0 10.960 28.900 43.570 1.00 17.67
ATOM 3102 C ARG A 409 0 10.217 28.757 42.236 1.00 17.09
ATOM 3103 O ARG A 409 0 9.585 29.698 41.763 1.00 15.25
ATOM 3104 CB ARG A 409 0 9.993 29.143 44.718 1.00 17.87
ATOM 3105 CG ARG A 409 0 8.796 28.188 44.663 1.00 21.12
ATOM 3106 CD ARG A 409 0 8.008 28.181 45.945 1.00 22.10
ATOM 3107 NE ARG A 409 0 6.801 27.370 45.955 1.00 24.80
ATOM 3108 CZ ARG A 409 0 5.918 27.361 46.961 1.00 25.93
ATOM 3109 NH1 ARG A 409 0 4.859 26.569 46.877 1.00 27.14
ATOM 3110 NH2 ARG A 409 0 6.068 28.117 48.046 1.00 25.44
ATOM 3111 N SER A 410 0 10.366 27.576 41.668. 1.00 16.33
ATOM 3112 CA SER A 410 0 9.802 27.245 40.373 1.00 18.33
ATOM 3113 C SER A 410 0 8.406 26.612 40.492 1.00 18.60
ATOM 3114 O SER A 410 0 7.941 26.223 41.566 1.00 16.94
ATOM 3115 CB SER A 410 0 10.724 26.199 39.705 1.00 19.51
ATOM 3116 OG SER A 410 0 11.718 26.865 38.933 1.00 20.28
ATOM 3117 N ALA A 411 0 7.754 26.551 39.343 1.00 18.19
ATOM 3118 CA ALA A 411 0 6.458 25.899 39.231 1.00 19.76
ATOM 3119 C ALA A 411 0 6.667 24.406 39.474 1.00 22.62
ATOM 3120 O ALA A 411 0 7.636 23.759 39.067 1.00 20.97
ATOM 3121 CB ALA A 411 0 5.873 26.075 37.841 1.00 17.13
ATOM 3122 N GLY A 412 0 5.710 23.856 40.229 1.00 26.30
ATOM 3123 CA GLY A 412 0 5.714 22.442 40.558 1.00 27.05
ATOM 3124 C GLY A 412 0 6.692 22.150 41.677 1.00 29.22
ATOM 3125 O GLY A 412 0 6.917 20.959 41.944 1.00 32.10
ATOM 3126 N SER A 413 0 7.293 23.139 42.322 1.00 28.66
ATOM 3127 CA SER A 413 0 8.223 22.871 43.400 1.00 28.58
ATOM 3128 C SER A 413 0 7.757 23.600 44.642 1.00 29.64
ATOM 3129 O SER A 413 0 7.279 24.735 44.524 1.00 30.66
ATOM 3130 CB SER A 413 0 9.610 23.407 43.015 1.00 30.12
ATOM 3131 OG SER A 413 0 10.484 23.233 44.127 1.00 31.74
ATOM 3132 N SER A 414 0 7.902 23.031 45.819 1.00 29.19
ATOM 3133 CA SER A 414 0 7.523 23.753 47.033 1.00 30.71
ATOM 3134 C SER A 414 0 8.762 24.124 47.834 1.00 30.51
ATOM 3135 O SER A 414 0 8.746 24.453 49.017 1.00 31.90
ATOM 3136 CB SER A 414 0 6.612 22.832 47.853 1.00 31.10
ATOM 3137 OG SER A 414 0 7.438 21.764 48.299 1.00 34.24
ATOM 3138 N THR A 415 0 9.919 24.063 47.194 1.00 30.60
ATOM 3139 CA THR A 415 0 11.194 24.336 47.860 1.00 30.60
```

-continued

```
ATOM 3140 C THR A 415 0 11.819 25.614 47.291 1.00 27.71
ATOM 3141 O THR A 415 0 11.582 25.998 46.137 1.00 27.49
ATOM 3142 CB THR A 415 0 12.089 23.095 47.747 1.00 32.16
ATOM 3143 OG1 THR A 415 0 13.411 23.441 47.285 1.00 35.60
ATOM 3144 CG2 THR A 415 0 11.599 22.103 46.710 1.00 34.11
ATOM 3145 N TYR A 416 0 12.662 26.268 48.053 1.00 24.34
ATOM 3146 CA TYR A 416 0 13.288 27.513 47.621 1.00 25.69
ATOM 3147 C TYR A 416 0 14.782 27.297 47.392 1.00 24.69
ATOM 3148 O TYR A 416 0 15.364 26.603 48.211 1.00 25.96
ATOM 3149 CB TYR A 416 0 13.129 28.633 48.659 1.00 23.79
ATOM 3150 CG TYR A 416 0 11.690 29.091 48.794 1.00 24.53
ATOM 3151 CD1 TYR A 416 0 10.789 28.387 49.596 1.00 24.14
ATOM 3152 CD2 TYR A 416 0 11.230 30.219 48.131 1.00 23.99
ATOM 3153 CE1 TYR A 416 0 9.474 28.799 49.713 1.00 23.70
ATOM 3154 CE2 TYR A 416 0 9.922 30.641 48.248 1.00 23.96
ATOM 3155 CZ TYR A 416 0 9.050 29.929 49.054 1.00 23.73
ATOM 3156 OH TYR A 416 0 7.744 30.337 49.152 1.00 23.53
ATOM 3157 N ASN A 417 0 15.360 27.867 46.353 1.00 22.34
ATOM 3158 CA ASN A 417 0 16.810 27.702 46.223 1.00 20.83
ATOM 3159 C ASN A 417 0 17.425 29.089 46.092 1.00 20.43
ATOM 3160 O ASN A 417 0 17.247 29.761 45.082 1.00 20.00
ATOM 3161 CB ASN A 417 0 17.179 26.763 45.086 1.00 19.72
ATOM 3162 CG ASN A 417 0 18.660 26.716 44.758 1.00 19.50
ATOM 3163 OD1 ASN A 417 0 19.485 27.313 45.465 1.00 20.18
ATOM 3164 ND2 ASN A 417 0 18.981 26.043 43.660 1.00 17.21
ATOM 3165 N PHE A 418 0 18.153 29.508 47.119 1.00 20.79
ATOM 3166 CA PHE A 418 0 18.831 30.797 47.049 1.00 20.77
ATOM 3167 C PHE A 418 0 20.314 30.613 46.725 1.00 20.47
ATOM 3168 O PHE A 418 0 20.973 31.618 46.517 1.00 19.47
ATOM 3169 CB PHE A 418 0 18.764 31.542 48.384 1.00 20.52
ATOM 3170 CG PHE A 418 0 17.332 31.821 48.753 1.00 22.19
ATOM 3171 CD1 PHE A 418 0 16.644 30.947 49.578 1.00 21.64
ATOM 3172 CD2 PHE A 418 0 16.697 32.951 48.244 1.00 21.95
ATOM 3173 CE1 PHE A 418 0 15.320 31.208 49.919 1.00 21.64
ATOM 3174 CE2 PHE A 418 0 15.386 33.198 48.599 1.00 22.81
ATOM 3175 CZ PHE A 418 0 14.694 32.325 49.419 1.00 22.57
ATOM 3176 N VAL A 419 0 20.816 29.380 46.732 1.00 19.72
ATOM 3177 CA VAL A 419 0 22.272 29.235 46.564 1.00 19.96
ATOM 3178 C VAL A 419 0 22.682 29.261 45.114 1.00 20.65
ATOM 3179 O VAL A 419 0 23.634 29.875 44.671 1.00 21.02
ATOM 3180 CB VAL A 419 0 22.708 27.888 47.200 1.00 21.81
ATOM 3181 CG1 VAL A 419 0 23.954 27.291 46.588 1.00 21.97
ATOM 3182 CG2 VAL A 419 0 22.885 28.098 48.713 1.00 21.55
ATOM 3183 N ASN A 420 0 21.867 28.585 44.327 1.00 19.77
ATOM 3184 CA ASN A 420 0 22.076 28.232 42.967 1.00 21.81
ATOM 3185 C ASN A 420 0 21.028 28.263 41.891 1.00 20.21
ATOM 3186 O ASN A 420 0 21.046 27.407 41.00 4 1.00 20.13
ATOM 3187 CB ASN A 420 0 22.166 26.587 43.207 1.00 21.91
ATOM 3188 CG ASN A 420 0 23.441 26.231 42.589 1.00 24.12
ATOM 3189 OD1 ASN A 420 0 23.933 25.113 42.403 1.00 26.75
ATOM 3190 ND2 ASN A 420 0 24.051 27.318 42.027 1.00 25.42
ATOM 3191 N PRO A 421 0 19.987 29.034 42.038 1.00 20.27
ATOM 3192 CA PRO A 421 0 18.808 28.951 41.183 1.00 17.57
ATOM 3193 C PRO A 421 0 19.100 29.369 39.778 1.00 15.76
ATOM 3194 O PRO A 421 0 19.907 30.281 39.586 1.00 15.13
ATOM 3195 CB PRO A 421 0 17.769 29.850 41.894 1.00 19.52
ATOM 3196 CG PRO A 421 0 18.674 30.863 42.589 1.00 19.88
ATOM 3197 CD PRO A 421 0 19.847 30.057 43.095 1.00 20.45
ATOM 3198 N VAL A 422 0 18.385 28.803 38.820 1.00 15.28
ATOM 3199 CA VAL A 422 0 18.502 29.239 37.420 1.00 13.48
ATOM 3200 C VAL A 422 0 18.157 30.721 37.397 1.00 14.53
ATOM 3201 O VAL A 422 0 17.340 31.208 38.183 1.00 14.44
ATOM 3202 CB VAL A 422 0 17.498 28.435 36.585 1.00 15.23
ATOM 3203 CG1 VAL A 422 0 16.032 28.747 36.937 1.00 13.85
ATOM 3204 CG2 VAL A 422 0 17.681 28.514 35.089 1.00 13.26
ATOM 3205 N LYS A 423 0 18.691 31.447 36.451 1.00 15.35
ATOM 3206 CA LYS A 423 0 18.366 32.831 36.189 1.00 17.23
ATOM 3207 C LYS A 423 0 17.759 32.891 34.784 1.00 16.55
ATOM 3208 O LYS A 423 0 18.284 32.189 33.909 1.00 16.92
ATOM 3209 CB LYS A 423 0 19.627 33.681 36.174 1.00 19.33
ATOM 3210 CG LYS A 423 0 20.118 33.985 37.565 1.00 24.09
ATOM 3211 CD LYS A 423 0 21.065 35.206 37.466 1.00 27.32
ATOM 3212 CE LYS A 423 0 22.470 34.596 37.263 1.00 28.78
ATOM 3213 NZ LYS A 423 0 23.128 34.482 38.595 1.00 29.50
ATOM 3214 N ARG A 424 0 16.630 33.570 34.617 1.00 15.85
ATOM 3215 CA ARG A 424 0 16.016 33.592 33.294 1.00 16.20
ATOM 3216 C ARG A 424 0 15.235 34.890 33.105 1.00 14.86
ATOM 3217 O ARG A 424 0 15.354 35.771 33.959 1.00 14.64
ATOM 3218 CB ARG A 424 0 15.158 32.367 32.994 1.00 16.11
ATOM 3219 CG ARG A 424 0 14.036 31.864 33.849 1.00 14.06
ATOM 3220 CD ARG A 424 0 13.447 30.506 33.427 1.00 11.65
ATOM 3221 NE ARG A 424 0 13.422 30.395 31.961 1.00 9.03
ATOM 3222 CZ ARG A 424 0 13.312 29.234 31.319 1.00 10.63
ATOM 3223 NH1 ARG A 424 0 13.185 28.133 32.082 1.00 11.02
ATOM 3224 NH2 ARG A 424 0 13.403 29.213 29.988 1.00 8.52
ATOM 3225 N ASP A 425 0 14.519 34.975 31.995 1.00 13.83
ATOM 3226 CA ASP A 425 0 13.751 36.209 31.752 1.00 15.00
ATOM 3227 C ASP A 425 0 12.298 35.929 31.359 1.00 15.65
ATOM 3228 O ASP A 425 0 11.474 36.850 31.271 1.00 15.11
ATOM 3229 CB ASP A 425 0 14.499 37.130 30.797 1.00 12.96
ATOM 3230 CG ASP A 425 0 14.609 36.652 29.371 1.00 14.32
ATOM 3231 OD1 ASP A 425 0 13.697 35.957 28.818 1.00 13.30
ATOM 3232 OD2 ASP A 425 0 15.632 37.003 28.729 1.00 13.76
ATOM 3233 N VAL A 426 0 11.883 34.675 31.206 1.00 15.21
ATOM 3234 CA VAL A 426 0 10.530 34.229 30.984 1.00 13.92
ATOM 3235 C VAL A 426 0 10.247 33.000 31.865 1.00 13.98
ATOM 3236 O VAL A 426 0 10.891 31.965 31.696 1.00 15.56
ATOM 3237 CB VAL A 426 0 10.128 33.807 29.567 1.00 12.49
ATOM 3238 CG1 VAL A 426 0 8.629 33.473 29.531 1.00 13.99
ATOM 3239 CG2 VAL A 426 0 10.390 34.874 28.536 1.00 12.37
ATOM 3240 N VAL A 427 0 9.274 33.090 32.766 1.00 12.82
ATOM 3241 CA VAL A 427 0 8.979 31.969 33.639 1.00 12.27
ATOM 3242 C VAL A 427 0 7.495 31.589 33.651 1.00 14.14
ATOM 3243 O VAL A 427 0 6.594 32.426 33.083 1.00 14.10
ATOM 3244 CB VAL A 427 0 9.458 32.315 35.056 1.00 11.46
ATOM 3245 CG1 VAL A 427 0 8.732 33.549 35.594 1.oo 9.39
ATOM 3246 CG2 VAL A 427 0 9.353 31.116 35.982 1.00 10.53
ATOM 3247 N SER A 428 0 7.229 30.282 33.622 1.00 13.74
ATOM 3248 CA SER A 428 0 5.889 29.766 33.721 1.00 15.16
ATOM 3249 C SER A 428 0 5.445 29.878 35.171 1.00 15.48
ATOM 3250 O SER A 428 0 6.186 29.505 36.087 1.00 15.38
ATOM 3251 CB SER A 428 0 5.776 28.323 33.206 1.00 16.37
ATOM 3252 OG SER A 428 0 4.464 27.821 33.484 1.00 17.00
ATOM 3253 N LEU A 429 0 4.246 30.376 35.399 1.00 15.74
ATOM 3254 CA LEU A 429 0 3.686 30.489 36.744 1.00 15.73
ATOM 3255 C LEU A 429 0 3.035 29.184 37.198 1.00 16.41
ATOM 3256 O LEU A 429 0 2.741 29.041 38.390 1.00 15.74
ATOM 3257 CB LEU A 429 0 2.669 31.627 36.886 1.00 14.99
ATOM 3258 CG LEU A 429 0 3.155 33.027 36.540 1.00 16.60
ATOM 3259 CD1 LEU A 429 0 2.043 34.042 36.862 1.00 17.78
ATOM 3260 CD2 LEU A 429 0 4.438 33.386 37.281 1.00 16.26
ATOM 3261 N GLY A 430 0 2.913 28.218 36.295 1.00 17.70
ATOM 3262 CA GLY A 430 0 2.419 26.904 36.701 1.00 19.84
ATOM 3263 C GLY A 430 0 0.894 26.836 36.778 1.00 20.72
ATOM 3264 O GLY A 430 0 0.178 27.498 36.029 1.00 20.89
ATOM 3265 N VAL A 431 0 0.428 26.056 37.729 1.00 22.04
ATOM 3266 CA VAL A 431 0 -0.956 25.713 37.966 1.00 22.61
ATOM 3267 C VAL A 431 0 -1.337 26.028 39.409 1.00 23.06
ATOM 3268 O VAL A 431 0 -0.476 26.392 40.218 1.00 22.42
ATOM 3269 CB VAL A 431 0 -1.245 24.193 37.768 1.00 23.03
ATOM 3270 CG1 VAL A 431 0 -0.795 23.672 36.416 1.00 22.74
ATOM 3271 CG2 VAL A 431 0 -0.574 23.315 38.820 1.00 22.77
ATOM 3272 N THR A 432 0 -2.615 25.835 39.704 1.00 23.88
ATOM 3273 CA THR A 432 0 -3.168 26.067 41.041 1.00 24.18
ATOM 3274 C THR A 432 0 -2.324 25.401 42.092 1.00 23.94
ATOM 3275 O THR A 432 0 -1.915 24.249 41.909 1.00 24.69
ATOM 3276 CB THR A 432 0 -4.625 25.565 41.069 1.00 25.75
ATOM 3277 OG1 THR A 432 0 -5.336 26.344 40.087 1 .00 25.87
ATOM 3278 CG2 THR A 432 0 -5.319 25.800 42.398 1.00 26.65
ATOM 3279 N GLY A 433 0 -1.924 26.136 43.124 1.00 24.45
ATOM 3280 CA GLY A 433 0 -1.035 25.589 44.159 1.00 22.27
ATOM 3281 C GLY A 433 0 0.394 26.120 43.983 1.00 23.26
ATOM 3282 O GLY A 433 0 1.103 26.212 45.000 1.00 23.30
ATOM 3283 N ASP A 434 0 0.833 26.481 42.776 1.00 21.12
ATOM 3284 CA ASP A 434 0 2.192 26.986 42.586 1.00 20.62
ATOM 3285 C ASP A 434 0 2.360 28.408 43.126 1.00 22.36
ATOM 3286 O ASP A 434 0 1.425 29.225 43.076 1.00 21.24
ATOM 3287 CB ASP A 434 0 2.548 27.024 41.087 1.00 18.78
ATOM 3288 CG ASP A 434 0 2.827 25.616 40.597 1.00 19.71
ATOM 3289 OD1 ASP A 434 0 3.304 24.828 41.409 1.00 20.43
ATOM 3290 OD2 ASP A 434 0 2.596 25.242 39.432 1.00 21.58
ATOM 3291 N GLU A 435 0 3.585 28.721 43.562 1.00 22.08
ATOM 3292 CA GLU A 435 0 3.853 30.077 44.068 1.00 23.24
ATOM 3293 C GLU A 435 0 5.244 30.512 43.612 1.00 20.24
ATOM 3294 O GLU A 435 0 6.201 30.611 44.372 1.00 19.50
ATOM 3295 CB GLU A 435 0 3.659 30.068 45.572 1.00 25.56
ATOM 3296 CG GLU A 435 0 3.739 31.409 46.258 1.00 30.52
ATOM 3297 CD GLU A 435 0 3.107 31.350 47.657 1.00 35.00
ATOM 3298 OE1 GLU A 435 0 2.093 30.603 47.760 1.00 35.71
ATOM 3299 OE2 GLU A 435 0 3.658 32.020 48.579 1.00 35.91
```

```
ATOM 3300 N VAL A 436 0 5.344 30.690 42.297 1.00 17.80
ATOM 3301 CA VAL A 436 0 6.564 31.083 41.640 1.00 15.30
ATOM 3302 C VAL A 436 0 7.049 32.416 42.221 1.00 17.15
ATOM 3303 O VAL A 436 0 6.326 33.402 42.275 1.00 17.48
ATOM 3304 CB VAL A 436 0 6.360 31.219 40.129 1.00 14.63
ATOM 3305 CG1 VAL A 436 0 7.463 32.009 39.454 1.00 10.79
ATOM 3306 CG2 VAL A 436 0 6.238 29.806 39.536 1.00 14.13
ATOM 3307 N THR A 437 0 8.290 32.391 42.691 1.00 16.51
ATOM 3308 CA THR A 437 0 8.940 33.505 43.364 1.00 16.19
ATOM 3309 C THR A 437 0 10.254 33.817 42.668 1.00 15.24
ATOM 3310 O THR A 437 0 11.100 32.940 42.419 1.00 15.47
ATOM 3311 CB THR A 437 0 9.190 33.067 44.827 1.00 14.95
ATOM 3312 OG1 THA 437 0 7.969 32.499 45.308 1.00 13.50
ATOM 3313 CG2 THR A 437 0 9.599 34.232 45.697 1.00 13.41
ATOM 3314 N ILE A 438 0 10.413 35.059 42.251 1.00 13.38
ATOM 3315 CA ILE A 438 0 11.597 35.471 41.510 1.00 15.78
ATOM 3316 C ILE A 438 0 12.292 36.590 42.264 1.00 15.86
ATOM 3317 O ILE A 438 0 11.617 37.270 43.048 1.00 17.32
ATOM 3318 CB ILE A 438 0 11.249 35.848 40.053 1.00 15.40
ATOM 3319 CG1 ILE A 438 0 10.340 37.055 39.985 1.00 15.85
ATOM 3320 CG2 ILE A 438 0 10.602 34.653 39.346 1.00 17.11
ATOM 3321 CD1 ILE A 438 0 9.971 37.607 38.632 1.00 17.49
ATOM 3322 N ARG A 439 0 13.599 36.789 42.055 1.00 16.02
ATOM 3323 CA ARG A 439 0 14.315 37.896 42.671 1.00 13.90
ATOM 3324 C ARG A 439 0 15.181 38.645 41.676 1.00 13.52
ATOM 3325 O ARG A 439 0 15.748 38.056 40.762 1.00 14.74
ATOM 3326 CB ARG A 439 0 15.193 37.501 43.850 1.00 15.15
ATOM 3327 CG ARG A 439 0 14.457 37.235 45.147 1.00 14.83
ATOM 3328 CD ARG A 439 0 15.367 37.337 46.355 1.00 14.08
ATOM 3329 NE ARG A 439 0 14.613 37.000 47.566 1.00 17.06
ATOM 3330 CZ ARG A 439 0 15.192 36.922 48.767 1.00 18.01
ATOM 3331 NH1 ARG A 439 0 16.487 37.176 48.908 1.00 17.76
ATOM 3332 NH2 ARG A 439 0 14.459 36.604 49.818 1.00 18.55
ATOM 3333 N PHE A 440 0 15.314 39.957 41.853 1.00 14.44
ATOM 3334 CA PHE A 440 0 16.204 40.737 40.993 1.00 15.97
ATOM 3335 C PHE A 440 0 16.645 41.986 41.761 1.00 15.86
ATOM 3336 O PHE A 440 0 16.113 42.313 42.801 1.00 15.79
ATOM 3337 CB PHE A 440 0 15.638 41.081 39.620 1.00 15.17
ATOM 3338 CG PHE A 440 0 14.416 41.948 39.647 1.00 16.95
ATOM 3339 CD1 PHE A 440 0 14.525 43.333 39.528 1.00 17.23
ATOM 3340 CD2 PHE A 440 0 13.158 41.377 39.798 1.00 16.35
ATOM 3341 CE1 PHE A 440 0 13.397 44.152 39.566 1.00 17.07
ATOM 3342 CE2 PHE A 440 0 12.026 42.180 39.841 1.00 17.12
ATOM 3343 CZ PHE A 440 0 12.144 43.575 39.719 1.00 18.30
ATOM 3344 N VAL A 441 0 17.676 42.648 41.268 1.00 16.10
ATOM 3345 CA VAL A 441 0 18.172 43.874 41.879 1.00 16.29
ATOM 3346 C VAL A 441 0 17.776 45.035 40.972 1.00 14.00
ATOM 3347 O VAL A 441 0 17.866 44.924 39.736 1.00 12.72
ATOM 3348 CB VAL A 441 0 19.675 43.769 42.144 1.00 18.13
ATOM 3349 CG1 VAL A 441 0 20.195 45.040 42.794 1.00 18.53
ATOM 3350 CG2 VAL A 441 0 19.969 42.583 43.065 1.00 18.55
ATOM 3351 N THR A 442 0 17.328 46.125 41.579 1.00 11.73
ATOM 3352 CA THR A 442 0 16.905 47.291 40.801 1.00 13.02
ATOM 3353 C THR A 442 0 18.055 48.208 40.432 1.00 14.83
ATOM 3354 0 THR A 442 0 18.218 49.323 40.947 1.00 15.17
ATOM 3355 CB THR A 442 0 15.840 48.127 41.558 1.00 14.62
ATOM 3356 OG1 THR A 442 0 16.314 48.463 42.864 1.00 14.34
ATOM 3357 CG2 THR A 442 0 14.552 47.299 41.727 1.00 13.82
ATOM 3358 N ASP A 443 0 18.818 47.764 39.437 1.00 15.48
ATOM 3359 CA ASP A 443 0 20.004 48.449 38.964 1.00 16.57
ATOM 3360 C ASP A 443 0 19.807 49.010 37.569 1.00 15.38
ATOM 3361 O ASP A 443 0 20.788 49.208 36.858 1.00 15.57
ATOM 3362 CB ASP A 443 0 21.133 47.391 38.962 1.00 19.75
ATOM 3363 CG ASP A 443 0 20.877 46.264 37.990 1.00 22.78
ATOM 3364 OD1 ASP A 443 0 21.711 45.353 37.789 1.00 25.70
ATOM 3365 OD2 ASP A 443 0 19.836 46.161 37.313 1.00 23.88
ATOM 3366 N ASN A 444 0 18.593 49.278 37.144 1.00 13.71
ATOM 3367 CA ASN A 444 0 18.388 49.721 35.752 1.00 15.87
ATOM 3368 C ASN A 444 0 17.245 50.728 35.702 1.00 17.00
ATOM 3369 O ASN A 444 0 16.052 50.419 35.614 1.00 16.83
ATOM 3370 CB ASN A 444 0 18.198 48.453 34.930 1.00 15.78
ATOM 3371 CG ASN A 444 0 18.225 48.675 33.442 1.00 18.49
ATOM 3372 OD1 ASN A 444 0 18.505 49.809 33.047 1.00 19.42
ATOM 3373 ND2 ASN A 444 0 17.925 47.689 32.588 1.00 15.91
ATOM 3374 N PRO A 445 0 17.598 52.003 35.890 1.00 17.59
ATOM 3375 CA PRO A 445 0 16.683 53.137 35.938 1.00 16.56
ATOM 3376 C PRO A 445 0 15.788 53.217 34.721 1.00 16.99
ATOM 3377 O PRO A 445 0 16.293 53.246 33.594 1.00 17.02
ATOM 3378 CB PRO A 445 0 17.552 54.418 35.951 1.00 18.28
ATOM 3379 CG PRO A 445 0 18.870 53.871 36.474 1.00 18.09
ATOM 3380 CD PRO A 445 0 19.002 52.409 36.084 1.00 16.05
ATOM 3381 N GLY A 446 0 14.462 53.194 34.918 1.00 17.16
ATOM 3382 CA GLY A 446 0 13.560 53.281 33.743 1.00 15.84
ATOM 3383 C GLY A 446 0 12.297 52.453 33.984 1.00 14.24
ATOM 3384 O GLY A 446 0 12.192 51.797 35.005 1.00 12.22
ATOM 3385 N PRO A 447 0 11.285 52.697 33.181 1.00 15.53
ATOM 3386 CA PRO A 447 0 9.999 52.048 33.195 1.00 15.24
ATOM 3387 C PRO A 447 0 10.101 50.737 32.401 1.00 13.82
ATOM 3388 O PRO A 447 0 10.514 50.733 31.240 1.00 13.85
ATOM 3389 CB PRO A 447 0 9.013 52.976 32.473 1.00 16.21
ATOM 3390 CG PRO A 447 0 9.933 53.729 31.554 1.00 16.19
ATOM 3391 CD PRO A 447 0 11.347 53.707 32.096 1.00 17.15
ATOM 3392 N TRP A 448 0 9.787 49.623 33.021 1.00 11.83
ATOM 3393 CA TRP A 448 0 9.898 48.317 32.371 1.00 14.30
ATOM 3394 C TRP A 448 0 8.610 47.493 32.427 1.00 13.12
ATOM 3395 O TRP A 448 0 8.013 47.355 33.502 1.00 11.63
ATOM 3396 CB TRP A 448 0 10.985 47.483 33.095 1.00 13.17
ATOM 3397 CG TRP A 448 0 12.321 48.160 33.124 1.00 14.54
ATOM 3398 CD1 TRP A 448 0 12.897 48.728 34.239 1.00 14.19
ATOM 3399 CD2 TRP A 448 0 13.211 48.382 32.029 1.00 14.38
ATOM 3400 NE1 TRP A 448 0 14.083 49.290 33.873 1.00 15.02
ATOM 3401 CE2 TRP A 448 0 14.308 49.095 32.527 1.00 14.41
ATOM 3402 CE3 TRP A 448 0 13.193 48.053 30.672 1.00 15.39
ATOM 3403 CZ2 TRP A 448 0 15.388 49.467 31.729 1.00 14.57
ATOM 3404 CZ3 TRP A 448 0 14.250 48.446 29.867 1.00 14.92
ATOM 3405 CH2 TRP A 448 0 15.355 49.135 30.399 1.00 14.93
ATOM 3406 N PHE A 449 0 8.231 46.884 31.315 1.00 14.03
ATOM 3407 CA PHE A 449 0 7.023 46.039 31.297 1.00 13.60
ATOM 3408 C PHE A 449 0 7.231 44.712 32.016 1.00 15.32
ATOM 3409 O PHE A 449 0 8.312 44.093 31.993 1.00 13.66
ATOM 3410 CB PHE A 449 0 6.627 45.773 29.845 1.00 16.19
ATOM 3411 CG PHE A 449 0 5.221 46.033 29.380 1.00 18.26
ATOM 3412 CD1PHE A 449 0 4.165 46.288 30.226 1.00 17.95
ATOM 3413 CD2 PHE A 449 0 4.962 46.027 28.011 1.00 20.73
ATOM 3414 CE1 PHE A 449 0 2.899 46.565 29.745 1.00 18.55
ATOM 3415 CE2 PHE A 449 0 3.701 46.293 27.503 1.00 20.13
ATOM 3416 CZ PHE A 449 0 2.664 46.543 28.387 1.00 18.59
ATOM 3417 N PHE A 450 0 6.195 44.245 32.715 1.00 12.79
ATOM 3418 CA PHE A 450 0 6.119 42.963 33.359 1.00 14.38
ATOM 3419 C PHE A 450 0 4.775 42.323 32.952 1.00 15.45
ATOM 3420 O PHE A 450 0 3.743 42.812 33.423 1.00 15.30
ATOM 3421 CB PHE A 450 0 6.186 43.041 34.879 1.00 15.06
ATOM 3422 CG PHE A 450 0 6.210 41.693 35.555 1.00 15.95
ATOM 3423 CD1 PHE A 450 0 7.157 40.734 35.204 1.00 16.36
ATOM 3424 CD2 PHE A 450 0 5.325 41.398 36.570 1.00 15.45
ATOM 3425 CE1 PHE A 450 0 7.222 39.518 35.855 1.00 13.87
ATOM 3426 CE2 PHE A 450 0 5.386 40.187 37.224 1.00 16.10
ATOM 3427 CZ PHE A 450 0 6.317 39.236 36.854 1.00 15.90
ATOM 3428 N HIS A 451 0 4.737 41.301 32.122 1.00 15.54
ATOM 3429 CA HIS A 451 0 3.443 40.841 31.610 1.00 16.24
ATOM 3430 C HIS A 451 0 3.461 39.426 31.073 1.00 16.95
ATOM 3431 O HIS A 451 0 4.526 38.860 30.812 1.00 17.42
ATOM 3432 CB HIS A 451 0 2.996 41.743 30.435 1.00 14.01
ATOM 3433 CG HIS A 451 0 3.921 41.696 29.281 1.00 16.98
ATOM 3434 ND1 HIS A 451 0 3.791 40.844 28.201 1.00 18.14
ATOM 3435 CD2 HIS A 451 0 5.058 42.435 29.046 1.00 17.88
ATOM 3436 CE1 HIS A 451 0 4.759 41.060 27.337 1.00 17.83
ATOM 3437 NE2 HIS A 451 0 5.554 42.011 27.842 1.00 18.98
ATOM 3438 N CYS A 452 0 2.261 38.863 30.951 1.00 16.78
ATOM 3439 CA CYS A 452 0 2.167 37.537 30.388 1.00 16.34
ATOM 3440 C CYS A 452 0 2.604 37.623 28.924 1.00 14.77
ATOM 3441 O CYS A 452 0 2.167 38.514 28.188 1.00 13.61
ATOM 3442 CB CYS A 452 0 0.727 36.983 30.451 1.00 18.22
ATOM 3443 SG CYS A 452 0 0.701 35.325 29.692 1.00 19.80
ATOM 3444 N HIS A 453 0 3.388 36.640 28.474 1.00 13.29
ATOM 3445 CA HIS A 453 0 3.867 36.716 27.100 1.00 13.19
ATOM 3446 C HIS A 453 0 2.983 35.987 26.099 1.00 13.47
ATOM 3447 O HIS A 453 0 3.296 35.974 24.906 1.00 11.93
ATOM 3448 CB HIS A 453 0 5.314 36.251 27.033 1.00 13.98
ATOM 3449 CG HIS A 453 0 6.124 36.860 25.945 1.00 11.89
ATOM 3450 ND1 HIS A 453 0 5.835 36.763 24.612 1.00 10.68
ATOM 3451 CD2 HIS A 453 0 7.270 37.594 26.072 1.00 12.71
ATOM 3452 CE1 HIS A 453 0 6.776 37.418 23.923 1.00 12.37
ATOM 3453 NE2 HIS A 453 0 7.663 37.930 24.793 1.00 13.20
ATOM 3454 N ILE A 454 0 1.860 35.429 26.549 1.00 15.35
ATOM 3455 CA ILE A 454 0 0.849 34.937 25.600 1.00 15.85
ATOM 3456 C ILE A 454 0 0.214 36.238 25.089 1.00 18.65
ATOM 3457 O ILE A 454 0 -0.452 36.997 25.824 1.00 17.92
ATOM 3458 CB ILE A 454 0 -0.156 34.001 26.280 1.00 16.46
ATOM 3459 CG1 ILE A 454 0 0.456 32.598 26.512 1.00 15.26
```

-continued

```
ATOM 3460 CG2 ILE A 454 0 -1.402 33.898 25.419 1.00 14.21
ATOM 3461 CD1 ILE A 454 0 -0.249 31.804 27.592 1.00 16.26
ATOM 3462 N GLU A 455 0 0.448 36.607 23.832 1.00 21.02
ATOM 3463 CA GLU A 455 0 -0.024 37.856 23.289 1.00 23.78
ATOM 3464 C GLU A 455 0 -1.526 38.042 23.422 1.00 24.40
ATOM 3465 O GLU A 455 0 -1.953 39.161 23.700 1.00 24.30
ATOM 3466 CB GLU A 455 0 0.399 38.090 21.830 1.00 27.20
ATOM 3467 CG GLU A 455 0 0.602 39.599 21.595 1.00 33.86
ATOM 3468 CD GLU A 455 0 1.783 40.205 22.309 1.00 37.49
ATOM 3469 OE1 GLU A 455 0 2.311 39.657 23.320 1.00 41.51
ATOM 3470 OE2 GLU A 455 0 2.303 41.284 21.907 1.00 41.22
ATOM 3471 N PHE A 456 0 -2.347 37.005 23.334 1.00 23.97
ATOM 3472 CA PHE A 456 0 377537.163 23.516 1.00 24.68
ATOM 3473 C PHE A 456 0 -4.084 37.533 24.959 1.00 25.11
ATOM 3474 O PHE A 456 0 -5.181 38.092 25.170 1.00 27.37
ATOM 3475 CB PHE A 456 0 -4.552 35.919 23.023 1.00 24.76
ATOM 3476 CG PHE A 456 0 -4.098 35.614 21.606 1.00 24.98
ATOM 3477 CD1 PHE A 456 0 -4.392 36.500 20.590 1.00 24.98
ATOM 3478 CD2 PHE A 456 0 -3.331 34.506 21.320 1.00 24.42
ATOM 3479 CE1 PHE A 456 0 -3.988 36.292 19.291 1.00 25.44
ATOM 3480 CE2 PHE A 456 0 -2.913 34.293 20.015 1.00 26.40
ATOM 3481 CZ PHE A 456 0 -3.226 35.171 18.997 1.00 25.10
ATOM 3482 N HIS A 457 0 -3.205 37.294 25.922 1.00 22.35
ATOM 3483 CA HIS A 457 0 -3.508 37.682 27.291 1.00 22.55
ATOM 3484 C HTSA 457 0 -3.053 39.121 27.561 1.00 23.81
ATOM 3485 O HIS A 457 0 -3.756 39.832 28.262 1.00 21.33
ATOM 3486 CB HIS A 457 0 -2.912 36.766 28.336 1.00 20.96
ATOM 3487 CG HIS A 457 0 -3.345 35.346 28.201 1.00 22.51
ATOM 3488 ND1 HIS A 457 0 -2.745 34.329 28.905 1.00 21.40
ATOM 3489 CD2 HIS A 457 0 -4.291 34.771 27.404 1.00 22.50
ATOM 3490 CE1 HIS A 457 0 -3.320 33.184 28.575 1.00 22.51
ATOM 3491 NE2 HIS A 457 0 -4.237 33.428 27.666 1.00 23.19
ATOM 3492 N LEU A 458 0 -1.876 39.481 27.028 1.00 23.74
ATOM 3493 CA LEU A 458 0 -1.357 40.817 27.125 1.00 24.76
ATOM 3494 C LEU A 458 0 -2.411 41.828 26.616 1.00 26.52
ATOM 3495 O LEU A 458 0 -2.757 42.751 27.351 1.00 25.18
ATOM 3496 CB LEU A 458 0 -0.108 40.986 26.252 1.00 23.81
ATOM 3497 CG LEU A 458 0 0.898 42.062 26.624 1.00 24.09
ATOM 3498 CD1 LEU A 458 0 1.619 42.606 25.390 1.00 24.28
ATOM 3499 CD2 LEU A 458 0 0.351 43.195 27.462 1.00 23.72
ATOM 3500 N MET A 459 0 -2.896 41.611 25.388 1.00 28.19
ATOM 3501 CA MET A 459 0 -3.914 42.458 24.785 1.00 31.98
ATOM 3502 C MET A 459 0 -5.207 42.436 25.603 1.00 29.95
ATOM 3503 O MET A 459 0 -5.886 43.439 25.520 1.00 29.10
ATOM 3504 CB MET A 459 0 -4.148 42.226 23.284 1.00 35.99
ATOM 3505 CG MET A 459 0 -5.056 41.103 22.852 1.00 42.66
ATOM 3506 SD MET A 459 0 -5.296 40.817 21.069 1.00 49.28
ATOM 3507 CE MET A 459 0 -6.238 39.291 21.119 1.00 47.39
ATOM 3508 N ASN A 460 0 -5.523 41.486 26.464 1.00 29.07
ATOM 3509 CA ASN A 460 0 -6.706 41.539 27.296 1.00 29.41
ATOM 3510 C ASN A 460 0 -6.407 41.908 28.746 1.00 28.46
ATOM 3511 O ASN A 460 0 -7.183 41.577 29.645 1.00 26.89
ATOM 3512 CB ASN A 460 0 -7.537 40.253 27.120 1.00 31.34
ATOM 3513 CG ASN A 460 0 -8.325 40.243 25.9001.00 33.82
ATOM 3514 OD1 ASN A 460 0 -7.909 39.609 24.926 1.00 34.29
ATOM 3515 ND2 ASN A 460 0 -9.437 40.971 25.861 1.00 34.55
ATOM 3516 N GLY A 461 0 -5.320 42.655 28.981 1.00 26.30
ATOM 3517 CA GLY A 461 0 -5.020 43.198 30.268 1.00 24.99
ATOM 3518 C GLY A 461 0 -4.043 42.601 31.235 1.00 24.75
ATOM 3519 O GLY A 461 0 -3.879 43.228 32.304 1.00 22.69
ATOM 3520 N LEU A 462 0 -3.375 41.478 30.914 1.00 22.85
ATOM 3521 CA LEU A 462 0 -2.478 40.872 31.913 1.00 22.10
ATOM 3522 C LEU A 462 0 -1.071 41.485 31.890 1.00 21.56
ATOM 3523 O LEU A 462 0 -0.116 40.876 31.415 1.00 20.28
ATOM 3524 CB LEU A 462 0 -2.477 39.376 31.669 1.00 20.03
ATOM 3525 CG LEU A 462 0 -2.010 38.393 32.720 1.00 20.74
ATOM 3526 CD1 LEU A 462 0 -2.603 38.608 34.093 1.00 20 35
ATOM 3527 CD2 LEU A 462 0 -2.385 36.983 32.229 1.00 21.01
ATOM 3528 N ALA A 463 0 -0.908 42.695 32.408 1.00 20.00
ATOM 3529 CA ALA A 463 0 0.350 43.432 32.381 1.00 20.74
ATOM 3530 C ALA A 463 0 0.398 44.511 33.481 1.00 21.85
ATOM 3531 O ALA A 463 0 -0.667 44.965 33.934 1.00 22.85
ATOM 3532 CB ALA A 463 0 0.559 44.179 31.060 1.00 15.13
ATOM 3533 N ILE A 464 0 1.605 44.810 33.950 1.00 19.91
ATOM 3534 CA ILE A 464 0 1.852 45.905 34.850 1.00 19.81
ATOM 3535 C ILE A 464 0 3.180 46.579 34.434 1.00 19.41
ATOM 3536 O ILE A 464 0 3.938 46.003 33.660 1.00 18.24
ATOM 3537 CB ILE A 464 0 1.910 45.678 36.347 1.00 19.13
ATOM 3538 CG1 ILE A 464 0 2.867 44.546 36.697 1.00 19.39
ATOM 3539 CG2 ILE A 464 0 0.520 45.455 36.924 1.00 18.48
ATOM 3540 CD1 ILE A 464 0 3.205 44.549 38.179 1.00 21.00
ATOM 3541 N VAL A 465 0 3.380 47.791 34.924 1.00 18.95
ATOM 3542 CA VAL A 465 0 4.579 48.570 34.637 1.00 18.36
ATOM 3543 C VAL A 465 0 5.327 48.928 35.931 1.00 18.07
ATOM 3544 O VAL A 465 0 4.787 49.424 36.931 1.00 15.19
ATOM 3545 CB VAL A 465 0 4.329 49.913 33.918 1.00 19.73
ATOM 3546 CG1 VAL A 465 0 5.659 50.605 33.602 1.00 18.34
ATOM 3547 CG2 VAL A 465 0 3.522 49.766 32.629 1.00 18.74
ATOM 3548 N PHE A 466 0 6.649 48.655 35.879 1.00 17.55
ATOM 3549 CA PHE A 466 0 7.499 49.051 37.013 1.00 14.72
ATOM 3550 C PHE A 466 0 8.251 50.344 36.653 1.00 12.68
ATOM 3551 O PHE A 466 0 9.007 50.420 35.679 1.00 12.23
ATOM 3552 CB PHE A 466 0 8.484 47.978 37.381 1.00 15.19
ATOM 3553 CG PHE A 466 0 7.962 46.770 38.080 1.00 15.90
ATOM 3554 CD1 PHE A 466 0 7.328 46.856 39.299 1.00 16.23
ATOM 3555 CD2 PHE A 466 0 8.153 45.533 37.492 1.00 16.23
ATOM 3556 CE1 PHE A 466 0 6.861 45.720 39.936 1.00 15.97
ATOM 3557 CE2 PHE A 466 0 7.665 44.389 38.133 1.00 18.27
ATOM 3558 CZ PHE A 466 0 7.018 44.480 39.352 1.00 16.74
ATOM 3559 N ALA A 467 0 8.045 S1.361 37.443 1.00 10.60
ATOM 3560 CA ALA A 467 0 8.788 52.648 37.194 1.00 12.27
ATOM 3561 C ALA A 467 0 10.007 52.526 38.111 1.00 12.02
ATOM 3562 O ALA A 467 0 9.905 52.728 39.325 1.00 12.43
ATOM 3563 CB ALA A 467 0 7.845 53.790 37.501 1.00 10.50
ATOM 3564 N GLU A 468 0 11.126 51.989 37.625 1.00 12.62
ATOM 3565 CA GLU A 468 0 12.263 51.683 38.515 1.00 14.63
ATOM 3566 C GLU A 468 0 13.195 52.883 38.685 1.00 13.91
ATOM 3567 O GLU A 468 0 13.631 53.369 37.651 1.00 13.05
ATOM 3568 CB GLU A 468 0 13.049 50.546 37.843 1.00 14.51
ATOM 3569 CG GLU A 468 0 14.256 50.035 38.629 1.00 16.84
ATOM 3570 CD GLU A 468 0 14.805 48.779 37.975 1.00 17.96
ATOM 3571 OE1 GLU A 468 0 15.985 48.479 38.124 1.00 16.98
ATOM 3572 OE2 GLU A 468 0 14.086 48.043 37.260 1.00 18.42
ATOM 3573 N ASP A 469 0 13.546 53.286 39.886 1.00 15.17
ATOM 3574 CA ASP A 469 0 14.491 54.371 40.116 1.00 16.85
ATOM 3575 C ASP A 469 0 14.134 55.630 39.333 1.00 16.33
ATOM 3576 O ASP A 469 0 14.851 56.046 38.437 1.00 16.59
ATOM 3577 CB ASP A 469 0 15.899 53.920 39.748 1.00 19.86
ATOM 3578 CG ASP A 469 0 17.040 54.766 40.289 1.00 21.40
ATOM 3579 OD1 ASP A 469 0 16.811 55.793 40.943 1.00 22.21
ATOM 3580 OD2 ASP A 469 0 18.216 54.403 40.069 1.00 22.21
ATOM 3581 N MET A 470 0 13.007 56.246 39.635 1.00 16.12
ATOM 3582 CA MET A 470 0 12.522 57.373 38.853 1.00 18.77
ATOM 3583 C MET A 470 0 13.451 58.576 38.950 1.00 16.31
ATOM 3584 O MET A 470 0 13.591 59.208 37.925 1.00 13.55
ATOM 3585 CB MET A 470 0 11.116 57.847 39.302 1.00 20.06
ATOM 3586 CG MET A 470 0 10.041 56.941 38.684 1.00 23.99
ATOM 3587 SD MET A 470 0 8.375 57.337 39.283 1.00 26.08
ATOM 3588 CE MET A 470 0 8.030 58.581 38.020 1.00 24.40
ATOM 3589 N ALA A 471 0 14.046 58.793 40.117 1.00 14.69
ATOM 3590 CA ALA A 471 0 14.953 59.906 40.287 1.00 16.97
ATOM 3591 C ALA A 471 0 16.141 59.864 39.335 1.00 18.79
ATOM 3592 O ALA A 471 0 16.602 60.956 38.945 1.00 21.08
ATOM 3593 CB ALA A 471 0 15.471 59.927 41.728 1.00 17.62
ATOM 3594 N ASN A 472 0 16.623 58.695 38.912 1.00 17.28
ATOM 3595 CA ASN A 472 0 17.788 58.675 38.015 1.00 16.56
ATOM 3596 C ASN A 472 0 17.457 58.355 36.572 1.00 16.99
ATOM 3597 O ASN A 472 0 18.407 58.143 35.795 1.00 18.74
ATOM 3598 CB ASN A 472 0 18.811 57.645 38.548 1.00 14.60
ATOM 3599 CG ASN A 472 0 19.417 58.132 39.887 1.00 14.00
ATOM 3600 OD1 ASN A 472 0 18.895 57.830 40.967 1.00 12.71
ATOM 3601 ND2 ASN A 472 0 20.468 58.916 39.775 1.00 10.80
ATOM 3602 N THR A 473 0 16.174 58.284 36.239 1.00 14.26
ATOM 3603 CA THR A 473 0 15.789 57.885 34.882 1.00 15.82
ATOM 3604 C THR A 473 0 16.150 58.891 33.812 1.00 16.81
ATOM 3605 O THR A 473 0 16.599 58.455 32.746 1.00 15.89
ATOM 3606 CB THR A 473 0 14.267 57.576 34.826 1.00 16.10
ATOM 3607 OG1 THR A 473 0 14.001 56.416 35.609 1.00 15.41
ATOM 3608 CG2 THR A 473 0 13.750 57.337 33.427 1.00 15.24
ATOM 3609 N VAL A 474 0 16.000 60.195 34.081 1.00 18.57
ATOM 3610 CA VAL A 474 0 16.355 61.192 33.050 1.00 21.06
ATOM 3611 C VAL A 474 0 17.859 61.209 32.817 1.00 19.12
ATOM 3612 O VAL A 474 0 18.339 61.234 31.688 1.00 19.95
ATOM 3613 CB VAL A 474 0 15.860 62.616 33.424 1.00 22.91
ATOM 3614 CG1 VAL A 474 0 16.467 63.702 32.538 1.00 23.06
ATOM 3615 CG2 VAL A 474 0 14.346 62.721 33.334 1.00 23.04
ATOM 3616 N ASP A 475 0 18.647 61.175 33.886 1.00 19.20
ATOM 3617 CA ASP A 475 0 20.109 61.168 33.741 1.00 18.98
ATOM 3618 C ASP A 475 0 20.578 59.899 33.047 1.00 17.52
ATOM 3619 O ASP A 475 0 21.386 60.028 32.130 1.00 18.31
```

```
ATOM 3620 CB  ASP A 475 0  20.780 61.273 35.119 1.00 20.27
ATOM 3621 CG  ASP A 475 0  22.283 61.075 35.107 1.00 20.18
ATOM 3622 OD1 ASP A 475 0  22.950 61.889 34.431 1.00 21.73
ATOM 3623 OD2 ASP A 475 0  22.798 60.139 35.750 1.00 18.03
ATOM 3624 N   ALA A 476 0  20.062 58.725 33.392 1.00 18.26
ATOM 3625 CA  ALA A 476 0  20.539 57.486 32.793 1.00 18.93
ATOM 3626 C   ALA A 476 0  20.165 57.269 31.343 1.00 20.62
ATOM 3627 O   ALA A 476 0  20.845 56.502 30.661 1.00 22.64
ATOM 3628 CB  ALA A 476 0  19.966 56.298 33.551 1.00 18.48
ATOM 3629 N   ASN A 477 0  19.047 57.787 30.858 1.00 22.66
ATOM 3630 CA  ASN A 477 0  18.605 57.512 29.491 1.00 25.22
ATOM 3631 C   ASN A 477 0  18.578 58.782 28.683 1.00 28.55
ATOM 3632 O   ASN A 477 0  17.969 59.755 29.143 1.00 30.20
ATOM 3633 CB  ASN A 477 0  17.172 56.948 29.560 1.00 24.22
ATOM 3634 CG  ASN A 477 0  17.114 55.666 30.380 1.00 23.73
ATOM 3635 OD1 ASN A 477 0  16.747 55.672 31.570 1.00 21.83
ATOM 3636 ND2 ASN A 477 0  17.512 54.575 29.736 1.00 20.87
ATOM 3637 N   ASN A 478 0  19.208 58.878 27.514 1.00 31.69
ATOM 3638 CA  ASN A 478 0  19.036 60.131 26.776 1.00 33.61
ATOM 3639 C   ASN A 478 0  18.758 59.770 25.331 1.00 32.22
ATOM 3640 O   ASN A 478 0  19.602 59.478 24.508 1.00 32.16
ATOM 3641 CB  ASN A 478 0  20.086 61.194 27.017 1.00 38.57
ATOM 3642 CG  ASN A 478 0  21.426 60.602 27.370 1.00 40.94
ATOM 3643 OD1 ASN A 478 0  21.928 59.903 26.484 1.00 44.60
ATOM 3644 ND2 ASN A 478 0  21.866 60.861 28.578 1.00 41.32
ATOM 3645 N   PRO A 479 0  17.461 59.733 25.075 1.00 32.37
ATOM 3646 CA  PRO A 479 0  16.890 59.381 23.790 1.00 31.84
ATOM 3647 C   PRO A 479 0  17.268 60.448 22.776 1.00 32.35
ATOM 3648 O   PRO A 479 0  17.422 61.609 23.136 1.00 32.66
ATOM 3649 CB  PRO A 479 0  15.364 59.385 23.931 1.00 31.68
ATOM 3650 CG  PRO A 479 0  15.126 59.724 25.373 1.00 31.69
ATOM 3651 CD  PRO A 479 0  16.416 60.071 26.064 1.00 32.23
ATOM 3652 N   PRO A 48O 0  17.399 60.036 21.537 1.00 31.62
ATOM 3653 CA  PRO A 48O 0  17.670 60.939 20.422 1.00 30.72
ATOM 3654 C   PRO A 48O 0  16.452 61.827 20.225 1.00 30.37
ATOM 3655 O   PRO A 48O 0  15.362 61.525 20.733 1.00 29.47
ATOM 3656 CB  PRO A 48O 0  17.935 60.035 19.203 1.00 29.87
ATOM 3657 CG  PRO A 48O 0  17.111 58.811 19.590 1.00 30.44
ATOM 3658 CD  PRO A 48O 0  17.161 58.657 21.093 1.00 30.35
ATOM 3659 N   VAL A 481 0  16.559 62.906 19.458 1.00 31.72
ATOM 3660 CA  VAL A 481 0  15.398 63.788 19.268 1.00 30.68
ATOM 3661 C   VAL A 481 0  14.335 63.090 18.446 1.00 29.51
ATOM 3662 O   VAL A 481 0  13.134 63.284 18.648 1.00 27.97
ATOM 3663 CB  VAL A 48I 0  15.818 65.132 18.648 1.00 33.04
ATOM 3664 CG1 VAL A 481 0  16.126 65.010 17.161 1.00 31.91
ATOM 3665 CG2 VAL A 481 0  14.717 66.171 18.907 1.00 33.32
ATOM 3666 N   GLU A 482 0  14.746 62.167 17.562 1.00 28.90
ATOM 3667 CA  GLU A 482 0  13.755 61.402 16.803 1.00 29.62
ATOM 3668 C   GLU A 482 0  12.839 60.565 17.691 1.00 28.33
ATOM 3669 O   GLU A 482 0  11.704 60.287 17.280 1.00 28.36
ATOM 3670 CB  GLU A 482 0  14.449 60.498 15.788 1.00 30.63
ATOM 3671 CG  GLU A 482 0  15.143 61.256 14.666 1.00 32.78
ATOM 3672 CD  GLU A 482 0  16.522 61.784 14.990 1.00 34.96
ATOM 3673 OE1 GLU A 482 0  17.021 61.746 16.141 1.00 34.62
ATOM 3674 OE2 GLU A 482 0  17.170 62.297 14.033 1.00 37.13
ATOM 3675 N   TRP A 483 0  13.311 60.124 18.857 1.00 25.91
ATOM 3676 CA  TRP A 483 0  12.496 59.280 19.711 1.00 25.49
ATOM 3677 C   TRP A 483 0  11.224 60.011 20.125 1.00 26.47
ATOM 3678 O   TRP A 483 0  10.155 59.405 20.116 1.00 26.95
ATOM 3679 CB  TRP A 483 0  13.216 58.807 20.974 1.00 21.98
ATOM 3680 CG  TRP A 483 0  12.378 58.144 22.013 1.00 21.49
ATOM 3681 CD1 TRP A 483 0  11.960 56.827 22.003 1.00 20.81
ATOM 3682 CD2 TRP A 483 0  11.818 58.730 23.194 1.00 20.14
ATOM 3683 NE1 TRP A 483 0  11.187 56.575 23.143 1.00 20.29
ATOM 3684 CE2 TRP A 483 0  11.097 57.736 23.868 1.00 20.29
ATOM 3685 CE3 TRP A 483 0  11.875 60.006 23.754 1.00 21.32
ATOM 3686 CZ2 TRP A 483 0  10.422 57.973 25.062 1.00 20.89
ATOM 3687 CZ3 TRP A 483 0  11.217 60.248 24.946 1.00 20.78
ATOM 3688 CH2 TRP A 483 0  10.495 59.227 25.596 1.00 21.44
ATOM 3689 N   ALA A 484 0  11.342 61.261 20.560 1.00 28.59
ATOM 3690 CA  ALA A 484 0  10.165 62.003 21.029 1.00 30.73
ATOM 3691 C   ALA A 484 0  9.226  62.350 19.869 1.00 30.42
ATOM 3692 O   ALA A 484 0  8.024  62.337 20.071 1.00 31.34
ATOM 3693 CB  ALA A 484 0  10.583 63.244 21.806 1.00 31.05
ATOM 3694 N   GLN A 485 0  9.702  62.488 18.653 1.00 30.79
ATOM 3695 CA  GLN A 485 0  8.927  62.742 17.466 1.00 33.16
ATOM 3696 C   GLN A 485 0  8.026  61.608 17.017 1.00 32.81
ATOM 3697 O   GLN A 485 0  7.044  61.847 16.302 1.00 32.74
ATOM 3698 CB  GLN A 485 0  9.859  63.113 16.290 1.00 34.56
ATOM 3699 CG  GLN A 485 0  10.631 64.361 16.686 1.00 39.67
ATOM 3700 CD  GLN A 485 0  11.559 64.919 15.640 1.00 42.86
ATOM 3701 OE1 GLN A 485 0  11.528 66.145 15.434 1.00 45.48
ATOM 3702 NE2 GLN A 485 0  12.375 64.103 14.982 1.00 44.07
ATOM 3703 N   LEU A 486 0  8.328  60.380 17.443 1.00 30.46
ATOM 3704 CA  LEU A 486 0  7.500  59.231 17.095 1.00 27.76
ATOM 3705 C   LEU A 486 0  6.051  59.510 17.509 1.00 28.23
ATOM 3706 O   LEU A 486 0  5.100  59.331 16.752 1.00 26.71
ATOM 3707 CB  LEU A 486 0  8.043  58.034 17.838 1.00 25.03
ATOM 3708 CG  LEU A 486 0  8.988  57.012 17.226 1.00 24.18
ATOM 3709 CD1 LEU A 486 0  9.780  57.416 16.011 1.00 21.41
ATOM 3710 CD2 LEU A 486 0  9.864  56.464 18.342 1.00 23.28
ATOM 3711 N   CYS A 487 0  5.870  59.974 18.739 1.00 28.05
ATOM 3712 CA  CYS A 487 0  4.560  60.263 19.279 1.00 30.77
ATOM 3713 C   CYS A 487 0  3..823 61.350 18.499 1.00 33.19
ATOM 3714 O   CYS A 487 0  2.627  61.170 18.263 1.00 33.69
ATOM 3715 CB  CYS A 487 0  4.643  60.637 20.752 1.00 27.94
ATOM 3716 SG  CYS A 487 0  5.214  59.280 21.781 1.00 27.23
ATOM 3717 N   GLU A 488 0  4.543  62.373 18.064 1.00 35.80
ATOM 3718 CA  GLU A 488 0  3.871  63.458 17.334 1.00 39.12
ATOM 3719 C   GLU A 488 0  3.384  62.928 15.995 1.00 37.78
ATOM 3720 O   GLU A 488 0  2.186  63.025 15.711 1.00 37.61
ATOM 3721 CB  GLU A 488 0  4.737  64.697 17.257 1.00 42.04
ATOM 3722 CG  GLU A 488 0  5.667  64.822 16.064 1.00 47.75
ATOM 3723 CD  GLU A 488 0  5.634  66.239 15.500 1.00 51.36
ATOM 3724 OE1 GLU A 488 0  5.501  66.422 14.266 1.00 52.66
ATOM 3725 OE2 GLU A 488 0  5.743  67.154 16.358 1.00 53.40
ATOM 3726 N   ILE A 489 0  4.263  62.253 15.267 1.00 36.63
ATOM 3727 CA  ILE A 489 0  3.906  61.647 14.004 1.00 36.74
ATOM 3728 C   ILE A 489 0  2.754  60.662 14.113 1.00 36.98
ATOM 3729 O   ILE A 489 0  1.847  60.664 13.276 1.00 38.60
ATOM 3730 CB  ILE A 489 0  5.089  60.903 13.361 1.00 36.57
ATOM 3731 CG1 ILE A 489 0  6.267  61.853 13.148 1.00 36.46
ATOM 3732 CG2 ILE A 489 0  4.651  60.305 12.030 1.00 36.90
ATOM 3733 CD1 ILE A 489 0  7.535  61.194 12.654 1.00 35.62
ATOM 3734 N   TYR A 490 0  2.758  59.808 15.105 1.00 36.22
ATOM 3735 CA  TYR A 490 0  1.771  58.765 15.298 1.00 35.95
ATOM 3736 C   TYR A 490 0  0.413  59.314 15.692 1.00 37.83
ATOM 3737 O   TYR A 490 0  -0.581 58.816 15.165 1.00 39.24
ATOM 3738 CB  TYR A 490 0  2.206  57.817 16.409 1.00 32.47
ATOM 3739 CG  TYR A 490 0  1.314  56.641 16.663 1.00 30.55
ATOM 3740 CD1 TYR A 490 0  1.176  55.623 15.726 1.00 29.96
ATOM 3741 CD2 TYR A 490 0  0.610  56.536 17.849 1.00 29.79
ATOM 3742 CE1 TYR A 490 0  0.378  54.528 15.975 1.00 29.51
ATOM 3743 CE2 TYR A 490 0  -0.192 55.441 18.114 1.00 29.64
ATOM 3744 CZ  TYR A 490 0  -0.288 54.445 17.171 1.00 29.51
ATOM 3745 OH  TYR A 490 0  -1.101 53.363 17.437 1.00 32.06
ATOM 3746 N   ASP A 491 0  0.369  60.302 16.564 1.00 40.86
ATOM 3747 CA  ASP A 491 0  -0.909 60.887 16.963 1.00 43.97
ATOM 3748 C   ASP A 491 0  -1.586 61.633 15.811 1.00 45.30
ATOM 3749 O   ASP A 491 0  -2.809 61.752 15.820 1.00 45.60
ATOM 3750 CB  ASP A 491 0  -0.764 61.800 18.170 1.00 44.67
ATOM 3751 CG  ASP A 491 0  -0.441 61.101 19.475 1.00 45.90
ATOM 3752 OD1 ASP A 491 0  0.149  61.761 20.364 1.00 46.32
ATOM 3753 OD2 ASP A 491 0  -0.763 59.911 19.669 1.00 46.04
ATOM 3754 N   ASP A 492 0  -0.871 62.107 14.817 1.00 46.75
ATOM 3755 CA  ASP A 492 0  -1.323 62.804 13.653 1.00 48.98
ATOM 3756 C   ASP A 492 0  -1.702 61.936 12.460 1.00 49.48
ATOM 3757 O   ASP A 492 0  -2.002 62.458 11.378 1.00 50.24
ATOM 3758 CB  ASP A 492 0  -0.155 63.649 13.107 1.00 51.54
ATOM 3759 CG  ASP A 492 0  -0.168 65.081 13.587 1.00 53.57
ATOM 3760 OD1 ASP A 492 0  -0.886 65.375 14.570 1.00 54.07
ATOM 3761 OD2 ASP A 492 0  0.576  65.857 12.939 1.00 55.04
ATOM 3762 N   LEU A 493 0  -1.554 60.630 12.584 1.00 49.01
ATOM 3763 CA  LEU A 493 0  -1.896 59.732 11.483 1.00 47.63
ATOM 3764 C   LEU A 493 0  -3.377 59.872 11.137 1.00 47.61
ATOM 3765 O   LEU A 493 0  -4.209 60.018 12.027 1.00 47.02
ATOM 3766 CB  LEU A 493 0  -1.661 58.296 11.940 1.00 46.08
ATOM 3767 CG  LEU A 493 0  -0.485 57.463 11.464 1.00 45.24
ATOM 3768 CD1 LEU A 493 0  0.616  58.224 10.756 1.00 43.57
ATOM 3769 CD2 LEU A 493 0  0.075  56.710 12.669 1.00 44.62
ATOM 3770 N   PRO A 494 0  -3.694 59.763 9.866  1.00 48.01
ATOM 3771 CA  PRO A 494 0  -5.049 59.734 9.353  1.00 49.11
ATOM 3772 C   PRO A 494 0  -5.617 58.339 9.570  1.00 51.21
ATOM 3773 O   PRO A 494 0  -4.919 57.325 9.495  1.00 50.61
ATOM 3774 CB  PRO A 494 0  -4.938 59.995 7.843  1.00 48.94
ATOM 3775 CG  PRO A 494 0  -3.559 59.463 7.544  1.00 48.47
ATOM 3776 CD  PRO A 494 0  -2.714 59.538 8.797  1.00 48.22
ATOM 3777 N   PRO A 495 0  -6.915 58.238 9.796  1.00 53.24
ATOM 3778 CA  PRO A 495 0  -7.630 57.006 10.055 1.00 53.93
ATOM 3779 C   PRO A 495 0  -7.404 55.890 9.058  1.00 54.84
```

-continued

```
ATOM 3780 O PRO A 495 0 -7.348 54.705 9.423 1.00 55.08
ATOM 3781 CB PRO A 495 0 -9.126 57.362 10.146 1.00 54.40
ATOM 3782 CG PRO A 495 0 -9.090 58.848 10.391 1.00 54.17
ATOM 3783 CD PRO A 495 0 -7.787 59.420 9.895 1.00 53.58
ATOM 3784 N GLU A 496 0 -7.190.56.198 7.784 1.00 55.36
ATOM 3785 CA GLU A 496 0 -6.936 55.187 6.763 1.00 55.83
ATOM 3786 C GLU A 496 0 -5.582 54.521 6.971 1.00 54.09
ATOM 3787 O GLU A 496 0 -5.345 53.406 6.505 1.00 53.29
ATOM 3788 CB GLU A 496 0 -7.091 55.805 5.378 1.00 57.96
ATOM 3789 CG GLU A 496 0 -6.030 55.604 4.339 1.00 61.30
ATOM 3790 CD GLU A 496 0 -6.448 54.984 3.025 1.00 63.68
ATOM 3791 OE1 GLU A 496 0 -7.449 55.411 2.388 1.00 65.15
ATOM 3792 OE2 GLU A 496 0 -5.747 54.034 2.586 1.00 64.91
ATOM 3793 N ALA A 497 0 -4.665 55.217 7.630 1.00 52.35
ATOM 3794 CA ALA A 497 0 -3.326 54.738 7.886 1.00 50.83
ATOM 3795 C ALA A 497 0 -3.245 53.626 8.924 1.00 49.08
ATOM 3796 O ALA A 497 0 -2.361 52.773 8.794 1.00 47.61
ATOM 3797 CB ALA A 497 0 -2.443 55.910 8.317 1.00 51.23
ATOM 3798 N THR A 498 0 -4.113 53.630 9.926 1.00 48.01
ATOM 3799 CA THR A 498 0 -4.086 52.617 10.964 1.00 48.73
ATOM 3800 C THR A 498 0 -5.271 51.656 10.938 1.00 48.99
ATOM 3801 O THR A 498 0 -5.425 50.852 11.862 1.00 47.81
ATOM 3802 CB THR A 498 0 -4.055 53.223 12.388 1.00 49.04
ATOM 3803 OG1 THR A 498 0 -5.315 53.816 12.752 1.00 47.95
ATOM 3804 CG2 THR A 498 0 -2.919 54.223 12.514 1.00 48.94
ATOM 3805 N SER A 499 0 -6.101 51.756 9.911 1.00 49.78
ATOM 3806 CA SER A 499 0 -7.307 50.933 9.814 1.00 51.20
ATOM 3807 C SER A 499 0 -7.048 49.470 9.494 1.00 49.98
ATOM 3808 O SER A 499 0 -6.257 49.143 8.617 1.00 48.80
ATOM 3809 CB SER A 499 0 -8.223 51.606 8.800 1.00 52.62
ATOM 3810 OG SER A 499 0 -8.428 50.827 7.596 1.00 55.22
ATOM 3811 N ILE A 500 0 -7.706 48.585 10.230 1.00 50.08
ATOM 3812 CA ILE A 500 0 -7.563 47.151 10.077 1.00 51.25
ATOM 3813 C ILE A 500 0 -8.642 46.518 9.207 1.00 53.08
ATOM 3814 O ILE A 500 0 -9.785 46.351 9.639 1.00 54.00
ATOM 3815 CB ILE A 500 0 -7.631 46.428 11.436 1.00 50.61
ATOM 3816 CG1 ILE A 500 0 -6.475 46.866 12.336 1.00 50.22
ATOM 3817 CG2 ILE A 500 0 -7.619 44.907 11.302 1.00 50.34
ATOM 3818 CD1 ILE A 500 0 -6.806 46.617 13.800 1.00 50.52
ATOM 3819 N GLN A 501 0 -8.263 46.074 8.024 1.00 54.35
ATOM 3820 CA GLN A 501 0 -9.177 45.360 7.129 1.00 55.14
ATOM 3821 C GLN A 501 0 -9.298 43.904 7.564 1.00 55.85
ATOM 3822 O GLN A 501 0 -8.335 43.130 7.556 1.00 55.59
ATOM 3823 CB GLN A 501 0 -8.594 45.485 5.732 1.00 55.56
ATOM 3824 CG GLN A 501 0 -9.262 44.736 4.604 1.00 56.32
ATOM 3825 CD GLN A 501 0 -8.874 45.369 3.271 1.00 57.46
ATOM 3826 OE1 GLN A 501 0 -8.480 44.667 2.336 1.00 57.35
ATOM 3827 NE2 GLN A 501 0 -8.998 46.697 3.219 1.00 57.61
ATOM 3828 N THR A 502 0 -10.493 43.506 7.968 1.00 57.08
ATOM 3829 CA THR A 502 0 -10.788 42.146 8.401 1.00 58.28
ATOM 3830 C THR A 502 0 -10.966 41.205 7.216 1.00 58.80
ATOM 3831 O THR A 502 0 -11.199 41.604 6.074 1.00 58.71
ATOM 3832 CB THR A 502 0 -12.046 42.108 9.293 1.00 58.99
ATOM 3833 OG1 THR A 502 0 -11.794 42.909 10.464 1.00 59.62
ATOM 3834 CG2 THR A 502 0 -12.421 40.707 9.749 1.00 58.74
ATOM 3835 N VAL A 503 0 -10.746 39.922 7.471 1.00 59.20
ATOM 3836 CA VAL A 503 0 -10.904 38.877 6.468 1.00 60.27
ATOM 3837 C VAL A 503 0 -11.687 37.736 7.119 1.00 61.11
ATOM 3838 O VAL A 503 0 -11.606 37.563 8.341 1.00 61.03
ATOM 3839 CB VAL A 503 0 -9.589 38.430 5.823 1.00 59.97
ATOM 3840 CG1 VAL A 503 0 -8.337 38.964 6.507 1.00 59.65
ATOM 3841 CG2 VAL A 503 0 -9.467 36.914 5.722 1.00 59.97
ATOM 3842 N VAL A 504 0 -12.478 37.002 6.341 1.00 61.77
ATOM 3843 CA VAL A 504 0 -13.203 35.863 6.911 1.00 62.40
ATOM 3844 C VAL A 504 0 -12.673 34.579 6.259 1.00 62.99
ATOM 3845 O VAL A 504 0 -11.811 33.894 6.803 1.00 63.13
ATOM 3846 CB VAL A 504 0 -14.730 35.882 6.756 1.00 62.39
ATOM 3847 CG1 VAL A 504 0 -15.392 36.931 7.635 1.00 61.89
ATOM 3848 CG2 VAL A 504 0 -15.127 36.068 5.297 1.00 62.17
ATOM 3849 C1 NAG A 800 0 -2.401 42.835 45.802 1.00 30.44
ATOM 3850 C2 NAG A 800 0 -1.327 43.232 46.780 1.00 31.80
ATOM 3851 N2 NAG A 800 0 -0.119 43.561 45.983 1.00 31.37
ATOM 3852 C7 NAG A 800 0 0.179 44.844 45.683 1.00 32.37
ATOM 3853 O7 NAG A 800 0 -0.549 45.688 45.982 1.00 34.61
ATOM 3854 C8 NAG A 800 0 1.457 45.094 44.983 1.00 31.67
ATOM 3855 C3 NAG A 800 0 -1.015 42.187 47.801 1.00 32.94
ATOM 3856 O3 NAG A 800 0 -0.264 42.838 48.796 1.00 34.46
ATOM 3857 C4 NAG A 800 0 -2.351 41.662 48.377 1.00 34.05
ATOM 3858 O4 NAG A 800 0 -2.097 40.644 49.344 1.00 35.62
ATOM 3859 CS NAG A 800 0 -3.128 41.025 47.202 1.00 35.11
ATOM 3860 O5 NAG A 800 0 -3.466 42.046 46.295 1.00 33.06
ATOM 3861 C6 NAG A 800 0 -4.444 40.420 47.673 1.00 36.66
ATOM 3862 O6 NAG A 800 0 -5.199 41.411 48.288 1.00 39.73
ATOM 3863 C1 GLC A 900 0 -8.957 50.280 6.333 1.00 58.53
ATOM 3864 C2 GLC A 900 0 -8.500 49.605 5.037 1.00 59.25
ATOM 3865 C3 GLC A 900 0 -7.806 50.686 4.219 1.00 59.71
ATOM 3866 C4 GLC A 900 0 -8.691 51.905 3.987 1.00 60.13
ATOM 3867 CS GLC A 900 0 -9.595 52.289 5.142 1.00 59.22
ATOM 3868 O5 GLC A 900 0 -10.004 51.177 5.937 1.00 59.71
ATOM 3869 CU IUM B 1 0 -1.332 34.401 30.132 1.00 29.47
ATOM 3870 CU IUM B 2 0 7.297 42.245 26.618 1.00 27.01
ATOM 3871 CU IUM B 3 0 9.569 38.786 23.923 1.00 21.38
ATOM 3872 O IUM B 5 0 7.445 40.703 25.162 1.00 26.99
ATOM 3873 OW0 WAT W 1 0 19.509 36.893 30.054 1.00 13.07
ATOM 3874 OW0 WAT W 2 0 24.726 29.672 16.651 1.00 7.67
ATOM 3875 OW0 WAT W 3 0 15.295 17.988 35.061 1.00 8.65
ATOM 3876 OW0 WAT W 4 0 6.481 28.311 23.427 1.00 8.00
ATOM 3877 OW0 WAT W 5 0 14.921 45.178 24.306 1.00 17.04
ATOM 3878 OW0 WAT W 6 0 14.413 44.401 28.162 1.00 10.12
ATOM 3879 OW0 WAT W 7 0 9.967 21.576 9.620 1.00 11.43
ATOM 3880 OW0 WAT W 8 0 10.088 28.675 13.038 1.00 9.27
ATOM 3881 OW0 WAT W 9 0 9.808 47.902 28.959 1.00 12.71
ATOM 3882 OW0 WAT W 10 0 21.976 23.052 35.604 1.00 11.72
ATOM 3883 OW0 WAT W 11 0 10.862 25.744 29.928 1.00 10.21
ATOM 3884 OW0 WAT W 12 0 26.087 32.996 23.097 1.00 14.21
ATOM 3885 OW0 WAT W 13 0 22.256 58.745 37.931 1.00 17.85
ATOM 3886 OW0 WAT W 14 0 -0.104 29.831 35.249 1.00 16.36
ATOM 3887 OW0 WAT W 15 0 18.153 61.857 36.641 1.00 14.38
ATOM 3888 OW0 WAT W 16 0 9.426 38.431 9.161 1.00 15.35
ATOM 3889 OW0 WAT W 17 0 7.639 24.371 3.713 1.00 22.18
ATOM 3890 OW0 WAT W 18 0 27.977 11.643 9.481 1.00 19.22
ATOM 3891 OW0 WAT W 19 0 3.140 21.028 24.695 1.00 11.12
ATOM 3892 OW0 WAT W 20 0 9.847 20.701 30.902 1.00 16.16
ATOM 3893 OW0 WAT W 21 0 -1.517 29.009 43.180 1.00 27.18
ATOM 3894 OW0 WAT W 22 0 3.497 29.138 26.088 1.00 17.22
ATOM 3895 OW0 WAT W 23 0 20.614 32.765 40.433 1.00 17.63
ATOM 3896 OW0 WAT W 24 0 19.098 51.778 39.452 1.00 22.33
ATOM 3897 OW0 WAT W 25 0 0.977 21.396 5.064 1.00 18.54
ATOM 3898 OW0 WAT W 26 0 8.546 16.150 21.761 1.00 16.40
ATOM 3899 OW0 WAT W 27 0 6.102 19.858 10.350 1.00 17.79
ATOM 3900 OW0 WAT W 28 0 11.702 55.189 41.955 1.00 18.92
ATOM 3901 OW0 WAT W 29 0 3.360 42.251 18.209 1.00 16.26
ATOM 3902 OW0 WAT W 30 0 6.232 14.672 22.473 1.00 24.49
ATOM 3903 OW0 WAT W 31 0 16.729 26.542 39.731 1.00 15.28
ATOM 3904 OW0 WAT W 32 0 2.834 30.640 40.601 1.00 18.11
ATOM 3905 OW0 WAT W 33 0 21.893 42.837 27.884 1.00 15.08
ATOM 3906 OW0 WAT W 34 0 1.581 28.193 27.914 1.00 17.77
ATOM 3907 OW0 WAT W 35 0 -3.503 21.749 11.578 1.00 15.32
ATOM 3908 OW0 WAT W 36 0 7.131 33.344 11.786 1.00 18.15
ATOM 3909 OW0 WAT W 37 0 17.312 38.603 29.961 1.00 14.75
ATOM 3910 OW0 WAT W 38 0 -6.705 40.723 39.909 1.00 23.49
ATOM 3911 OW0 WAT W 39 0 9.010 31.121 11.736 1.00 19.99
ATOM 3912 OW0 WAT W 40 0 9.376 28.353 33.076 1.00 16.22
ATOM 3913 OW0 WAT W 41 0 30.104 29.895 20.857 1.00 25.77
ATOM 3914 OW0 WAT W 42 0 -6.950 33.663 21.335 1.00 26.62
ATOM 3915 OW0 WAT W 43 0 8.541 27.867 36.827 1.00 12.80
ATOM 3916 OW0 WAT W 44 0 3.590 21.651 11.893 1.00 14.46
ATOM 3917 OW0 WAT W 45 0 23.290 21.665 37.787 1.00 28.75
ATOM 3918 OW0 WAT W 46 0 22.724 11.873 22.270 1.00 23.07
ATOM 3919 OW0 WAT W 47 0 -1.090 42.001 12.877 1.00 19.33
ATOM 3920 OW0 WAT W 48 0 14.091 27.298 40.583 1.00 18.51
ATOM 3921 OW0 WAT W 49 0 2.336 52.026 29.983 1.00 25.66
ATOM 3922 OW0 WAT W 50 0 15.475 14.450 22.853 1.00 20.37
ATOM 3923 OW0 WAT W 51 0 25.945 26.568 40.287 1.00 24.49
ATOM 3924 OW0 WAT W 52 0 19.545 41.598 35.087 1.00 20.70
ATOM 3925 OW0 WAT W 53 0 -3.802 47.942 9.638 1.00 29.98
ATOM 3926 OW0 WAT W 54 0 -7.478 41.160 9.585 1.00 24.26
ATOM 3927 OW0 WAT W 55 0 -2.938 29.733 36.048 1.00 22.93
ATOM 3928 OW0 WAT W 56 0 29.051 32.114 22.680 1.00 22.50
ATOM 3929 OW0 WAT W 57 0 0.360 29.505 5.595 1.00 17.78
ATOM 3930 OW0 WAT W 58 0 8.583 57.422 21.440 1.00 21.90
ATOM 3931 OW0 WAT W 59 0 25.151 31.947 34.812 1.00 22.13
ATOM 3932 OW0 WAT W 60 0 25.133 62.204 32.968 1.00 25.75
ATOM 3933 OW0 WAT W 61 0 14.909 40.770 30.294 1.00 17.25
ATOM 3934 OW0 WAT W 62 0 20.825 30.520 34.676 1.00 16.18
ATOM 3935 OW0 WAT W 63 0 5.509 26.744 43.167 1.00 30.12
ATOM 3936 OW0 WAT W 64 0 5.280 57.279 14.627 1.00 22.66
ATOM 3937 OW0 WAT W 65 0 2.944 53.436 32.359 1.00 22.97
ATOM 3938 OW0 WAT W 66 0 11.266 43.508 3.407 1.00 20.01
ATOM 3939 OW0 WAT W 67 0 21.535 45.549 26.563 1.00 24.47
```

-continued

```
ATOM 3940 OW0 WAT W 68 0 0.412 33.358 11.837 1.00 19.89
ATOM 3941 OW0 WAT W 69 0 26.466 32.305 25.785 1.00 20.19
ATOM 3942 OW0 WAT W 70 0 0.910 45.068 7.829 1.00 22.05
ATOM 3943 OW0 WAT W 71 0 -2.060 46.506 39.381 1.00 23.49
ATOM 3944 OW0 WAT W 72 0 20.236 56.718 25.851 1.00 23.74
ATOM 3945 OW0 WAT W 73 0 3.253 23.017 38.254 1.00 24.83
ATOM 3946 OW0 WAT W 74 0 9.653 22.835 35.143 1.00 25.79
ATOM 3947 OW0 WAT W 75 0 16.877 52.904 47.331 1.00 24.42
ATOM 3948 OW0 WAT W 76 0 14.293 22.021 3.993 1.00 32.28
ATOM 3949 OW0 WAT W 77 0 -5.287 19.835 18.528 1.00 24.65
ATOM 3950 OW0 WAT W 78 0 8.414 38.317 49.069 1.00 28.77
ATOM 3951 OW0 WAT W 79 0 7.070 32.466 47.926 1.00 21.83
ATOM 3952 OW0 WAT W 80 0 -0.452 28.307 25.779 1.00 16.58
ATOM 3953 OW0 WAT W 81 0 14.774 15.006 34.455 1.00 25.63
ATOM 3954 OW0 WAT W 82 0 11.515 54.942 35.962 1.00 14.20
ATOM 3955 OW0 WAT W 83 0 25.643 33.451 32.105 1.00 30.31
ATOM 3956 OW0 WAT W 84 0 11.869 12.221 20.394 1.00 31.37
ATOM 3957 OW0 WAT W 85 0 11.653 51.587 22.411 1.00 16.48
ATOM 3958 OW0 WAT W 86 0 17.334 40.837 51.079 1.00 30.26
ATOM 3959 OW0 WAT W 87 0 4.355 25.208 34.030 1.00 32.26
ATOM 3960 OW0 WAT W 88 0 18.816 52.360 32.512 1.00 21.19
ATOM 3961 OW0 WAT W 89 0 -2.704 46.518 35.364 1.00 21.99
ATOM 3962 OW0 WAT W 90 0 18.793 27.893 49.481 1.00 24.52
ATOM 3963 OW0 WAT W 91 0 22.459 46.584 28.898 1.00 18.99
ATOM 3964 OW0 WAT W 92 0 7.958 34.422 49.370 1.00 26.14
ATOM 3965 OW0 WAT W 93 0 23.972 16.246 6.806 1.00 24.35
ATOM 3966 OW0 WAT W 94 0 1.340 49.185 26.307 1.00 31.64
ATOM 3967 OW0 WAT W 95 0 -1.830 35.291 12.266 1.00 27.28
ATOM 3968 OW0 WAT W 96 0 20.460 17.486 3.589 1.00 33.51
ATOM 3969 OW0 WAT W 97 0 15.177 6.964 9.868 1.00 24.40
ATOM 3970 OW0 WAT W 98 0 18.616 57.927 43.922 1.00 30.76
ATOM 3971 OW0 WAT W 99 0 10.562 32.112 9.972 1.00 28.90
ATOM 3972 OW0 WAT W 100 0 1.630 61.363 10.878 1.00 33.92
ATOM 3973 OW0 WAT W 101 0 -4.939 49.989 33.211 1.00 29.73
ATOM 3974 OW0 WAT W 102 0 19.385 44.813 34.546 1.00 23.52
ATOM 3975 OW0 WAT W 103 0 19.055 43.063 37.581 1.00 30.59
ATOM 3976 OW0 WAT W 105 0 28.703 33.555 27.406 1.00 32.92
ATOM 3977 OW0 WAT W 106 0 28.835 19.646 10.759 1.00 40.44
ATOM 3978 OW0 WAT W 107 0 22.047 22.465 9.758 1.00 29.98
ATOM 3979 OW0 WAT W 108 0 14.689 61.032 36.346 1.00 30.63
ATOM 3980 OW0 WAT W 109 0 16.998 24.042 9.318 1.00 23.90
ATOM 3981 OW0 WAT W 110 0 13.472 30.533 11.848 1.00 34.83
ATOM 3982 OW0 WAT W 111 0 -2.175 35.601 41.496 1.00 28.55
ATOM 3983 OW0 WAT W 112 0 1.528 17.373 -1.396 1.00 38.21
ATOM 3984 OW0 WAT W 113 0 -2.856 29.748 19.681 1.00 30.55
ATOM 3985 OW0 WAT W 114 0 2.377 42.810 47.971 1.00 26.87
ATOM 3986 OW0 WAT W 115 0 10.947 12.820 33.745 1.00 31.60
ATOM 3987 OW0 WAT W 116 0 9.807 58.194 12.442 1.00 29.63
ATOM 3988 OW0 WAT W 117 0 18.488 62.559 29.771 1.00 45.83
ATOM 3989 OW0 WAT W 118 0 11.708 61.566 40.940 1.00 37.19
ATOM 3990 OW0 WAT W 119 0 -10.101 22.257 15.091 1.00 30.48
ATOM 3991 OW0 WAT W 120 0 -1.930 15.913 7.386 1.00 36.63
ATOM 3992 OW0 WAT W 121 0 23.988 43.686 29.319 1.00 32.15
ATOM 3993 OW0 WAT W 122 0 7.354 57.153 12.809 1.00 28.10
ATOM 3994 OW0 WAT W 123 0 24.207 22.101 11.958 1.00 32.83
ATOM 3995 OW0 WAT W 124 0 -1.268 15.083 9.738 1.00 32.53
ATOM 3996 OW0 WAT W 125 0 19.363 5047 13.812 1.00 34.57
ATOM 3997 OW0 WAT W 126 0 4.799 41.145 23.688 1.00 28.33
ATOM 3998 OW0 WAT W 127 0 15.975 23.287 5.889 1.00 30.95
ATOM 3999 OW0 WAT W 128 0 3.698 38.582 -2.369 1.00 36.84
ATOM 4000 OW0 WAT W 129 0 -2.601 49.124 11.710 1.00 28.91
ATOM 4001 OW0 WAT W 130 0 15.779 56.598 43.285 1.00 27.76
ATOM 4002 OW0 WAT W 131 0 26.306 32.724 13.233 1.00 37.94
ATOM 4003 OW0 WAT W 132 0 3.610 46.947 23.991 1.00 35.49
ATOM 4004 OW0 WAT W 133 0 18.354 11.929 29.348 1.00 33.88
ATOM 4005 OW0 WAT W 134 0 13.966 41.517 27.765 1.00 18.02
ATOM 4006 OW0 WAT W 135 0 23.545 49.080 27.785 1.00 25.21
ATOM 4007 OW0 WAT W 136 0 16.876 25.082 41.791 1.00 28.71
ATOM 4008 OW0 WAT W 137 0 15.439 54.809 45.527 1.00 35.30
ATOM 4009 OW0 WAT W 138 0 11.733 25.676 43.264 1.00 38.24
ATOM 4010 OW0 WAT W 139 0 9.795 34.460 11.898 1.00 31.61
ATOM 4011 OW0 WAT W 140 0 13.328 57.569 42.356 1.00 30.66
ATOM 4012 OW0 WAT W 141 0 14.146 7.869 20.604 1.00 35.72
ATOM 4013 OW0 WAT W 142 0 23.330 12.948 3.922 1.00 29.83
ATOM 4014 OW0 WAT W 143 0 16.607 10.575 24.347 1.00 36.47
ATOM 4015 OW0 WAT W 144 0 8.509 25.546 35.012 1.00 35.43
ATOM 4016 OW0 WAT W 145 0 12.597 44457 1.450 1.00 39.54
ATOM 4017 OW0 WAT W 146 0 21.680 51.509 39.154 1.00 40.08
ATOM 4018 OW0 WAT W 147 0 -0.702 52.593 39.700 1.00 29.62
ATOM 4019 OW0 WAT W 148 0 23.269 14.719 22.589 1.00 30.24
ATOM 4020 OW0 WAT W 149 0 27.149 22.972 41.846 1.00 35.00
ATOM 4021 OW0 WAT W 150 0 2.854 9.792 8.923 1.00 46.35
ATOM 4022 OW0 WAT W 151 0 24.831 15.672 24.889 1.00 29.22
ATOM 4023 OW0 WAT W 152 0 24.965 51.606 19.113 1.00 32.19
ATOM 4024 OW0 WAT W 153 0 -4.611 25.034 37.817 1.00 46.51
ATOM 4025 OW0 WAT W 154 0 12.225 39.382 28.864 1.00 25.42
ATOM 4026 OW0 WAT W 155 0 18.332 22.341 43.180 1.00 36.18
ATOM 4027 OW0 WAT W 156 0 36.467 20.701 17.144 1.00 44.13
ATOM 4028 OW0 WAT W 157 0 -4.903 47.901 40.886 1.00 33.97
ATOM 4029 OW0 WAT W 158 0 12.979 13.955 3.208 1.00 33.60
ATOM 4030 OW0 WAT W 159 0 32.383 12.693 24.743 1.00 30.25
ATOM 4031 OW0 WAT W 160 0 30.796 26.296 14.368 1.00 44.37
ATOM 4032 OW0 WAT W 161 0 19.332 37.280 40.057 1.00 31.54
ATOM 4033 OW0 WAT W 162 0 17.625 20.028 41.642 1.00 45.88
ATOM 4034 OW0 WAT W 163 0 19.917 56.115 46.103 1.00 40.37
ATOM 4035 OW0 WAT W 164 0 -4.743 14.204 16.748 1.00 40.86
ATOM 4036 OW0 WAT W 165 0 0.738 46.912 21.790 1.00 38.56
ATOM 4037 OW0 WAT W 166 0 22.648 62.277 30.976 1.00 24.37
ATOM 4038 OW0 WAT W 167 0 -4.322 45.754 26.894 1.00 48.97
ATOM 4039 OW0 WAT W 168 0 -2.386 24.601 0.665 1.00 32.57
ATOM 4040 OW0 WAT W 169 0 -0.459 41.618 35.838 1.00 35.25
ATOM 4041 OW0 WAT W 170 0 26.659 4.722 11.434 1.00 41.25
ATOM 4042 OW0 WAT W 171 0 13.720 11.379 22.121 1.00 39.59
ATOM 4043 OW0 WAT W 172 0 15.266 7.451 6.576 1.00 41.71
ATOM 4044 OW0 WAT W 173 0 0.134 17.450 6.165 1.00 42.12
ATOM 4045 OW0 WAT W 174 0 38.646 32.884 25.247 1.00 41.80
ATOM 4046 OW0 WAT W 175 0 10.591 17.398 3.251 1.00 29.37
ATOM 4047 OW0 WAT W 176 0 22.444 49.424 25.264 1.00 19.51
ATOM 4048 OW0 WAT W 177 0 0.429 23.224 28.598 1.00 33.54
ATOM 4049 OW0 WAT W 178 0 -2.302 27.278 34.780 1.00 44.76
ATOM 4050 OW0 WAT W 179 0 2.054 25.866 16.462 1.00 34.29
ATOM 4051 OW0 WAT W 180 0 30.277 18.006 25.789 1.00 42.28
ATOM 4052 OW0 WAT W 181 0 2.316 18.424 27.884 1.00 47.39
ATOM 4053 OW0 WAT W 182 0 19.401 41.164 39.560 1.00 3968
ATOM 4054 OW0 WAT W 183 0 23.742 10.982 24.879 1.00 43.32
ATOM 4055 OW0 WAT W 184 0 3.926 24.450 44.251 1.00 48.95
ATOM 4056 OW0 WAT W 185 0 25.186 21.211 40.951 1.00 39.05
ATOM 4057 OW0 WAT W 186 0 20.353 34.816 48.799 1.00 34.08
ATOM 4058 OW0 WAT W 187 0 35.782 22.476 21.693 1.00 40.04
ATOM 4059 OW0 WAT W 188 0 27.256 23.617 12.235 1.00 40.85
ATOM 4060 OW0 WAT W 189 0 6.777 12.502 12.641 1.00 53.37
ATOM 4061 OW0 WAT W 190 0 -4.663 38.998 4.159 1.00 39.85
ATOM 4062 OW0 WAT W 191 0 24.398 52.064 24.607 1.00 45.51
ATOM 4063 OW0 WAT W 192 0 1.808 15.541 4.832 1.00 41.06
ATOM 4064 OW0 WAT W 193 0 5.341 36.359 7.569 1.00 39.36
ATOM 4065 OW0 WAT W 194 0 32.192 38.650 21.799 1.00 37.18
ATOM 4066 OW0 WAT W 195 0 -10.782 36.616 38.705 1.00 50.35
ATOM 4067 OW0 WAT W 196 0 4.119 64.116 32.946 1.00 34.51
ATOM 4068 OW0 WAT W 197 0 19.427 22.772 5.898 1.00 37.94
ATOM 4069 OW0 WAT W 198 0 -4.671 33.476 1.652 1.00 43.38
ATOM 4070 OW0 WAT W 199 0 -8.983 23.757 17.693 1.00 57.10
ATOM 4071 OW0 WAT W 290 0 -6.735 22.473 20.432 1.00 38.49
ATOM 4072 OW0 WAT W 201 0 -6.954 26.746 37.309 1.00 55.48
ATOM 4073 OW0 WAT W 202 0 23.418 38.662 33.700 1.00 42.20
ATOM 4074 OW0 WAT W 203 0 9.004 24.070 36.971 1.00 40.06
ATOM 4075 OW0 WAT W 204 0 18.890 42.920 51.502 1.00 46.29
ATOM 4076 OW0 WAT W 205 0 13.301 18.514 3.624 1.00 42.17
ATOM 4077 OW0 WAT W 206 0 31.189 12.995 19.645 1.00 51.92
ATOM 4078 OW0 WAT W 207 0 15.589 57.456 13.738 1.00 38.96
ATOM 4079 OW0 WAT W 208 0 -3.389 12.961 12.738 1.00 46.99
ATOM 4080 OW0 WAT W 209 0 9.321 30.475 6.320 1.00 49.75
ATOM 4081 OW0 WAT W 210 0 1.680 61.379 33.738 1.00 37.48
ATOM 4082 OW0 WAT W 211 0 -3.811 36.417 3.807 1.00 46.01
ATOM 4083 OW0 WAT W 212 0 17.087 46.902 3.830 1.00 45.12
ATOM 4084 OW0 WAT W 213 0 23.702 22.325 43.022 1.00 36.14
ATOM 4085 OW0 WAT W 214 0 10.849 60.003 14.389 1.00 32.05
ATOM 4086 OW0 WAT W 215 0 34.001 25.493 20.855 1.00 40.75
ATOM 4087 OW0 WAT W 216 0 27.422 37.093 28.951 1.00 42.33
ATOM 4088 OW0 WAT W 217 0 2.471 63.256 35.173 1.00 48.36
ATOM 4089 OW0 WAT W 218 0 -0.973 59.086 28.720 1.00 53.14
ATOM 4090 OW0 WAT W 219 0 28.841 9.287 6.463 1.00 39.02
ATOM 4091 OW0 WAT W 220 0 -5.593 21.802 9.619 1.00 44.21
ATOM 4092 OW0 WAT W 221 0 22.109 15.521 1.696 1.00 38.33
ATOM 4093 OW0 WAT W 222 0 13.029 32.860 12.233 1.00 37.63
ATOM 4094 OW0 WAT W 223 0 11.840 33.823 3.800 1.00 42.20
ATOM 4095 OW0 WAT W 224 0 8.476 42.976 -0.104 1.00 40.23
ATOM 4096 OW0 WAT W 225 0 6.607 9.754 13.906 1.00 41.30
ATOM 4097 OW0 WAT W 226 0 22.513 32.613 49.067 1.00 47.26
ATOM 4098 OW0 WAT W 227 0 13.790 4.924 16.718 1.00 38.05
ATOM 4099 OW0 WAT W 228 0 4.578 46.381 2.146 1.00 38.90
```

-continued

```
ATOM 4100 OW0 WAT W 229 0 -0.178 18.054 23.533 1.00 43.42
ATOM 4101 OW0 WAT W 230 0 -5.146 34.010 4.766 1.00 38.90
ATOM 4102 OW0 WAT W 231 0 20.232 28.890 51.507 1.00 44.95
ATOM 4103 OW0 WAT W 232 0 16.083 32.879 10.309 1.00 45.29
ATOM 4104 OW0 WAT W 233 0 22.111 51.333 10.599 1.00 34.03
ATOM 4105 OW0 WAT W 234 0 3.247 15.790 28.046 1.00 50.25
ATOM 4106 OW0 WAT W 235 0 5.547 11.598 9.674 1.00 56.39
ATOM 4107 OW0 WAT W 236 0 -1.085 18.297 -2.265 1.00 45.26
ATOM 4108 OW0 WAT W 237 0 30.994 12.013 22.690 1.00 50.37
ATOM 4109 OW0 WAT W 238 0 24.691 33.260 27.819 1.00 37.65
ATOM 4110 OW0 WAT W 239 0 18.911 40.770 5.815 1.00 44.15
ATOM 4111 OW0 WAT W 240 0 21.532 53.033 33.280 1.00 31.23
ATOM 4112 OW0 WAT W 240 0 19.745 46.029 4.364 1.00 46.38
ATOM 4113 OW0 WAT W 242 0 27.516 16.526 25.474 1.00 51.75
ATOM 4114 OW0 WAT W 243 0 34.171 19.604 8.423 1.00 55.79
ATOM 4115 OW0 WAT W 244 0 23.870 53.512 11.474 1.00 42.01
ATOM 4116 OW0 WAT W 245 0 14.492 23.842 44.882 1.00 52.25
ATOM 4117 OW0 WAT W 246 0 -3.070 63.260 33.189 1.00 40.77
ATOM 4118 OW0 WAT W 247 0 22.185 55.701 37.353 1.00 39.52
ATOM 4119 OW0 WAT W 248 0 14.144 26.239 42.825 1.00 42.50
ATOM 4120 OW0 WAT W 249 0 25.026 36.545 35.213 1.00 58.19
ATOM 4121 OW0 WAT W 250 0 27.072 34.293 43.895 1.00 46.58
ATOM 4122 OW0 WAT W 251 0 11.742 7.192 4.856 1.00 42.78
ATOM 4123 OW0 WAT W 252 0 0.730 46.405 24.947 1.00 39.31
ATOM 4124 OW0 WAT W 253 0 28.346 34.036 30.808 1.00 43.10
ATOM 4125 OW0 WAT W 254 0 -3.838 40.281 1.903 1.00 38.67
ATOM 4126 OW0 WAT W 25S 0 6.837 35.163 51.935 1.00 58.57
ATOM 4127 OW0 WAT W 256 0 19.740 62.853 17.880 1.00 52.39
ATOM 4128 OW0 WAT W 258 0 -0.994 41.755 22.088 0.00 69.57
ATOM 4129 OW0 WAT W 259 0 1.221 10.473 15.458 1.00 54.80
ATOM 4130 OW0 WAT W 260 0 23.445 55.367 31.430 1.00 48.90
ATOM 4131 OW0 WAT W 261 0 23.757 57.854 34.657 1.00 37.69
ATOM 4132 OW0 WAT W 262 0 8.508 19.111 34.572 1.00 55.52
ATOM 4133 OW0 WAT W 263 0 22.806 22.381 3.611 1.00 64.20
ATOM 4134 OW0 WAT W 264 0 0.398 22.602 42.625 1.00 58.86
ATOM 4135 OW0 WAT W 265 0 4.195 52.287 43.465 1.00 36.84
ATOM 4136 OW0 WAT W 266 0 20.211 6.536 4.911 1.00 39.34
ATOM 4137 OW0 WAT W 267 0 14.680 16.117 2.803 1.00 45.76
ATOM 4138 OW0 WAT W 268 0 14.938 25.582 6.850 1.00 41.01
ATOM 4139 OW0 WAT W 269 0 7.763 7.940 31.891 0.00 71.30
ATOM 4140 OW0 WAT W 270 0 -3.459 33.491 39.400 1.00 40.80
ATOM 4141 OW0 WAT W 271 0 23.154 22.897 6.985 1.00 48.25
ATOM 4142 OW0 WAT W 272 0 34.916 25.555 28.092 1.00 52.63
ATOM 4143 OW0 WAT W 273 0 8.332 45.481 50.776 1.00 47.23
ATOM 4144 OW0 WAT W 274 0 -3.441 57.643 28.775 1.00 49.70
ATOM 4145 OW0 WAT W 275 0 23.213 40.573 47.561 1.00 56.02
ATOM 4146 OW0 WAT W 276 0 5.421 55.179 45.172 1.00 52.70
ATOM 4147 OW0 WAT W 277 0 -3.012 21.908 40.933 1.00 41.69
ATOM 4148 OW0 WAT W 278 0 26.328 53.637 17.905 1.00 37.80
ATOM 4149 OW0 WAT W 279 0 9.740 58.922 43.485 1.00 52.06
ATOM 4150 OW0 WAT W 280 0 23.545 15.660 4.258 1.00 41.55
ATOM 4151 OW0 WAT W 281 0 22.652 31.154 51.246 1.00 58.65
ATOM 4152 OW0 WAT W 282 0 22.192 51.135 8.251 1.00 44.76
ATOM 4153 OW0 WAT W 283 0 -6.046 22.886 24.288 1.00 52.40
ATOM 4154 OW0 WAT W 284 0 19.949 45.276 49.516 1.00 54.58
ATOM 4155 OW0 WAT W 285 0 7.388 22.308 32.108 1.00 43.62
ATOM 4156 OW0 WAT W 286 0 15.080 50.452 2.795 1.00 52.20
ATOM 4157 OW0 WAT W 287 0 1.016 62.235 30.878 1.00 56.81
ATOM 4158 OW0 WAT W 288 0 23.803 52.570 27.699 1.00 56.22
ATOM 4159 OW0 WAT W 289 0 -10.525 31.623 13.870 1.00 47.21
ATOM 4160 OW0 WAT W 290 0 1.599 55.502 24.567 1.00 44.50
ATOM 4161 OW0 WAT W 291 0 -15.671 37.251 14.660 1.00 83.62
ATOM 4162 OW0 WAT W 292 0 7.231 7.950 17.754 1.00 50.61
ATOM 4163 OW0 WAT W 293 0 -4.009 34.057 42.492 1.00 78.48
ATOM 4164 OW0 WAT W 294 0 21.00 4 58.371 18.690 1.00 61.15
ATOM 4165 OW0 WAT W 295 0 16.405 48.869 52.211 1.00 53.17
ATOM 4166 OW0 WAT W 296 0 7.329 31.202 1.964 1.00 38.86
ATOM 4167 OW0 WAT W 297 0 9.518 53.886 5.467 1.00 41.62
ATOM 4168 OW0 WAT W 298 0 10.398 48.995 0.335 1.00 49.64
ATOM 4169 OW0 WAT W 299 0 9.889 15.077 3.774 1.00 42.28
ATOM 4170 OW0 WAT W 300 0 15.854 56.731 10.934 1.00 44.02
```

What is claimed is:

1. A variant of a parent *Coprinus laccase,* which comprises a mutation in a position corresponding to at least one of the following positions in SEQ ID No. 1:

> W125,
> Y134,
> Y126,
> Y170,
> M75, and/or
> M477.

2. A detergent additive comprising a laccase variant according to claim 1 in the form of a non-dusting granulate, a stabilised liquid or a protected enzyme.

3. A detergent additive according to claim 2, which additionally includes one or more other enzymes comprising a protease, a lipase, an amylase, and a cellulase.

4. A detergent composition comprising a laccase variant according to claim 1 and a surfactant.

5. A detergent composition according to claim 4 which additionally includes one or more other enzymes comprising a protease, a lipase, an amylase and a cellulase.

* * * * *